(12) United States Patent
Kato et al.

(10) Patent No.: US 6,703,083 B2
(45) Date of Patent: Mar. 9, 2004

(54) SILICON COMPOUND, LIQUID CRYSTAL COMPOSITION AND LIQUID CRYSTAL DISPLAY

(75) Inventors: Takashi Kato, Chiba (JP); Yasuyuki Koizumi, Chiba (JP); Yasuhiro Kubo, Chiba (JP); Kanetsugu Terashima, Chiba (JP)

(73) Assignees: Chisso Corporation, Osaka (JP); Chisso Petrochemical Corporation, Tokyo (JP)

( * ) Notice: Subject to any disclaimer, the term of this patent is extended or adjusted under 35 U.S.C. 154(b) by 0 days.

(21) Appl. No.: 10/084,854

(22) Filed: Feb. 28, 2002

(65) Prior Publication Data
US 2003/0168632 A1 Sep. 11, 2003

(30) Foreign Application Priority Data
Mar. 1, 2001 (JP) ........................................ 2000-057164

(51) Int. Cl.⁷ .................. C09K 19/34; C09K 19/30; C09K 19/12; C09K 19/20; C07F 7/04; C07F 7/08

(52) U.S. Cl. .............. 428/1.1; 252/299.61; 252/299.63; 252/299.64; 252/299.65; 252/299.66; 252/299.67; 556/436; 556/445; 556/465; 556/487; 556/488; 556/489

(58) Field of Search ....................... 428/1.1; 252/299.61, 252/299.63, 299.64, 299.65, 299.66, 299.67; 556/436, 445, 465, 487, 488, 489; 544/298; 549/369

(56) References Cited

U.S. PATENT DOCUMENTS 5,229,481 A * 7/1993 Tilley ........................... 528/10

* cited by examiner

*Primary Examiner*—Shean C Wu
(74) *Attorney, Agent, or Firm*—Wenderoth, Lind & Ponack, L.L.P.

(57) ABSTRACT

Silicon compounds having a low viscosity and a low threshold voltage and improved mutual solubility, a liquid crystal composition comprising the same and a liquid crystal display using the liquid crystal composition. The silicon compound is represented by formula (1):

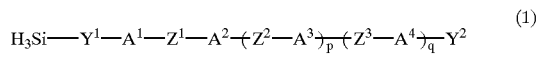

wherein $Y^1$ is, for example, alkylene having 1 to 10 carbon atoms, $Y^2$ is, for example, hydrogen, halogen, —CN, —C≡C—CN, or alkyl having 1 to 10 carbon atoms; $A^1$, $A^2$, $A^3$, and $A^4$ each are, for example, independently 1,4-cyclohexylene, 1,4-cyclohexenylene, 1,4-phenylene, or 1,4-phenylene; $Z^1$, $Z^2$ and $Z^3$ each are independently a single bond, —$(CH_2)_2$—, —$OCH_2$—, —$CH_2O$—, —CH=CH—, —C≡C—, —$(CH_2)_4$—, —$O(CH_2)_3$—, —$(CH_2)_3O$—, —COO—, —OCO—, —$OCF_2$—, or —$CF_2O$—; and p and q each are independently 0 or 1.

24 Claims, No Drawings

SILICON COMPOUND, LIQUID CRYSTAL COMPOSITION AND LIQUID CRYSTAL DISPLAY

BACKGROUND OF THE INVENTION

1. Field of the Invention

The present invention relates to a novel liquid crystalline compound and a liquid crystal composition (hereinafter referred to merely as a composition according to circumstances). More specifically, it relates to a liquid crystalline compound having a $SiH_3$ group at an end, a composition comprising the same and a liquid crystal display constituted using this composition. The term "liquid crystalline compound" used in the present invention is a general term for a compound showing a liquid crystal phase and a compound which does not show a liquid crystal phase but is useful as a component for a liquid crystal composition.

2. Description of the Related Art

A liquid crystal display (LCD) making use of characteristics of a nematic liquid crystal phase is widely used for various uses including monitors for personal computers and portable telephones, and demand therefor has been growing large year by year. In accordance with it, improvement items for performances required for LCD have come to extend over many divergences such as an expansion in an operable temperature range, a shift to a high density and coloring of a display picture plane, an acceleration in response and an expansion in a viewing angle. Various display modes using electro-optical effects, such as a DS (Dynamic Scattering) mode, a TN (Twisted Nematic) mode, a GH (Guest Host) mode, an STN (Super Twisted Nematic) mode, an IPS (In-Plane switching) mode, a VA (Vertical Alignment) mode and OCB (Optically Compensated Bend) have been proposed in order as means for solving them.

In such situation, various characteristics are required to a composition used for LCD according to the respective display modes. First, the physical property values such as a birefringence ($\Delta n$), a dielectric anisotropy ($\Delta\in$), a viscosity ($\eta$), a conductivity and an elastic constant ratio $K_{33}/K_{11}$ ($K_{33}$: bend elastic constant and $K_{11}$: spray elastic constant) of a liquid crystal composition are required to have values which are optimum for a display mode and a form of an element. Further, in order to achieve high-speed response in any of the LCD's shown above, a composition having a low viscosity is required, and a liquid crystalline compound has to be indispensably reduced as well in a viscosity. In addition thereto, given as common items of characteristics required to a composition are stability against moisture, light, heat and air which are usually present under an use environment and stability against an electric field and electromagnetic irradiation. Further, it is important that a liquid crystalline compound constituting a composition is chemically stable under use conditions and that they have a good solubility with each other.

In the existing state, however, it is very difficult to solve these problems only with the existing liquid crystal compounds and compositions, and it is an urgent matter to develop a novel liquid crystalline compound and composition which can meet the various requirements described above.

In recent years, development of various techniques in a liquid crystal display has been tried for the purpose of an enlargement in a picture plane. Especially, liquid crystal compositions which contribute largely to a reduction in power consumption and high speed response are desired to be developed. It is essential for a reduction in power consumption to further reduce a threshold voltage of a composition (E. Jakeman et al., Phys. Lett., 39A. 69 (1972)). Also, a low viscosity is important as well for high speed response. Various compounds have so far been developed in order to achieve these objects. For example, compounds having a silyl group in a molecule represented by the following formulas (a), (b) and (c) are known respectively according to Japanese Patent Application Laid-Open No. 9653/1994, Japanese Patent Application Laid-Open No. 2878/1995 and Japanese Patent Application Laid-Open No. 2879/1995:

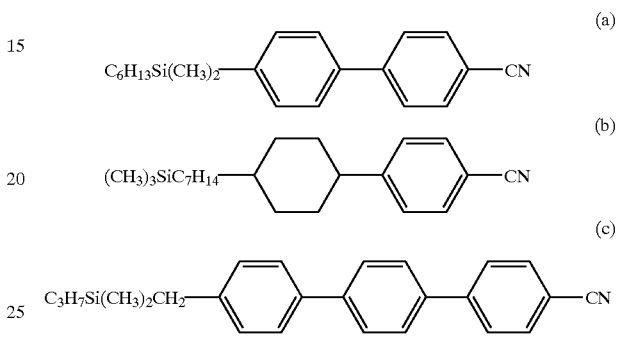

In these compounds, silicon is substituted with three alkyl groups. For example, the present inventors measured the physical property values of a compound having a propyldimethylsilyl group represented by the following formula (d) to find the problem that it had not only a markedly high viscosity but also an unsatisfactory mutual solubility with other components constituting a composition:

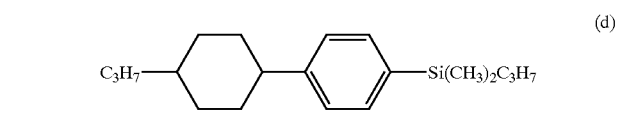

Physical property measurement: a nematic phase-isotropic phase transition temperature (NI) and a viscosity ($\eta$) at 20° C. of a liquid crystal composition ZLI-1132 manufactured by Merck Co., Ltd. were 72.6° C. and 26.7 mPa·s respectively. Then, 15% by weight of the compound represented by the formula (d) was added to 85% by weight of this composition, and NI and $\eta$ of the resulting composition were determined to find that they were 15° C. or lower and 39.7 mPa·s respectively. It has been found from this result that a composition prepared using the compound represented by the formula (d) is not only notably increased in a viscosity but also reduced in NI by 50° C. or lower. Further, the compound represented by the formula (d) was inferior in mutual solubility with the other compositions.

SUMMARY OF THE INVENTION

An object of the present invention is to solve problems on conventional techniques and provide a novel silicon compound which has a low viscosity and a low threshold voltage and which is improved in mutual solubility, a composition comprising the same and a liquid crystal display using the above composition.

In order to achieve the objects described above, the following inventions are claimed for the grant of a patent in the present application.

[1] A silicon compound represented by formula (1):

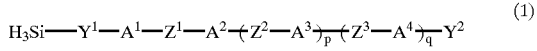

wherein $Y^1$ is alkylene having 1 to 10 carbon, in which any —$CH_2$— in this alkylene may be replaced by —O—, —S—, —CO—, —CH=CH— or —C≡C—, but —O— and —O—, —S— and —S—, —O— and —S—, —O— and $SiH_3$, or —S— and $SiH_3$ are not adjacent, and at least one hydrogen in the alkylene may be replaced by halogen or —CN; $Y^2$ is hydrogen, halogen, —CN, —C≡C—CN, or alkyl having 1 to 10 carbon, in which any —$CH_2$— in the alkyl may be replaced by —O—, —S—, —CO—, —CH=CH—, or —C≡C—, but —O— and —O—, —S— and —S—, or —O— and —S— are not adjacent, and any hydrogen in the alkyl may be replaced by halogen or —CN; $A^1$, $A^2$, $A^3$, and $A^4$ each are independently 1,4-cyclohexylene, 1,4-cyclohexenylene, 1,4-phenylene, or 1,4-phenylene in which any hydrogen is replaced by halogen; in which any hydrogen in 1,4-cyclohexylene or 1,4-cyclohexenylene may be replaced by halogen, any —$CH_2$— in these rings may be replaced by —O—, but —O— and —O— are not adjacent, and any —CH= in 1,4-phenylene may be replaced by —N=; $Z^1$, $Z^2$ and $Z^3$ each are independently a single bond, —$(CH_2)_2$—, —$OCH_2$—, —$CH_2O$—, —CH=CH—, —C≡C—, —$(CH_2)_4$—, —$O(CH_2)_3$—, —$(CH_2)_3O$—, —COO—, —OCO—, —$OCF_2$—, or —$CF_2O$—; and p and q each are independently 0 or 1.

[2] The silicon compound defined in the above item [1], wherein in formula (1) described above, p and q are 0; $A^1$ and $A^2$ each are independently 1,4-cyclohexylene, 1,4-cyclohexylene in which one or more non-adjacent —$CH_2$— are replaced by —O—, 1,4-phenylene, 1,4-phenylene in which any hydrogen is replaced by halogen, or pirimidine-2,5-diyl; and $Z^1$ is a single bond, —$(CH_2)_2$—, —CH=CH—, —C≡C—, —$(CH_2)_4$—, —COO—, —OCO—, —$OCF_2$—, or —$CF_2O$—.

[3] The silicon compound defined in the above item [1], wherein in formula (1) described above, p is 1, and q is 0; $A^1$, $A^2$ and $A^3$ each are independently 1,4-cyclohexylene, 1,4-cyclohexylene in which one or more non-adjacent —$CH_2$— are replaced by —O—, 1,4-phenylene, 1,4-phenylene in which any hydrogen is replaced by halogen, or pirimidine-2,5-diyl; and $Z^1$ and $Z^2$ each are independently a single bond, —$(CH_2)_2$—, —CH=CH—, —C≡C—, —COO—, —OCO—, —$(CH_2)_4$—, —$OCF_2$—, or —$CF_2O$—.

[4] The silicon compound defined in the above item [1], wherein in formula (1) described above, p and q are 1; $A^1$, $A^2$, $A^3$, and $A^4$ each are independently 1,4-cyclohexylene, 1,4-cyclohexylene in which one or more non-adjacent —$CH_2$— are replaced by —O—, 1,4-phenylene, 1,4-phenylene in which any hydrogen is replaced by halogen, or pirimidine-2,5-diyl; and $Z^1$, $Z^2$ and $Z^3$ each are independently a single bond, —$(CH_2)_2$—, —CH=CH—, —C≡C—, —COO—, —OCO—, —$(CH_2)_4$—, —$OCF_2$—, or —$CF_2O$—.

[5] The silicon compound defined in the above item [1], wherein in formula (1) described above, $Y^1$ is alkylene having 1 to 10 carbon, in which any —$CH_2$— in this alkylene may be replaced by —O— or —CH=CH—, but —O— and —O— or —O— and $SiH_3$ are not adjacent; $Y^2$ is alkyl having 1 to 10 carbon, in which any —$CH_2$— in the alkyl may be replaced by —O—, —CH=CH— or —C≡C—, but —O— and —O— are not adjacent; and $A^1$, $A^2$, $A^3$, and $A^4$ each are independently 1,4-cyclohexylene, 1,4-cyclohexylene in which one or more non-adjacent —$CH_2$— are replaced by —O—, 1,4-phenylene, or pirimidine-2,5-diyl.

[6] The silicon compound defined in the above item [1], wherein in formula (1) described above, $Y^1$ is alkylene having 1 to 10 carbon, in which any —$CH_2$— in the alkylene may be replaced by —O— or —CH=CH—, but —O— and —O— or —O— and $SiH_3$ are not adjacent; $Y^2$ is halogen, —CN, —C≡C—CN or alkyl having 1 to 10 carbon, in which any —$CH_2$— in the alkyl may be replaced by —O—, but —O— and —O— are not adjacent, and at least one hydrogen is replaced by halogen; and $A^1$, $A^2$, $A^3$, and $A^4$ each are independently 1,4-cyclohexylene in which one or more non-adjacent —$CH_2$— are replaced by —O—, 1,4-phenylene, 1,4-phenylene in which at least one hydrogen is replaced by halogen, or pirimidine-2,5-diyl.

[7] The silicon compound defined in the above item [1], wherein in formula (1) described above, $Y^1$ is alkylene having 1 to 10 carbon, in which any —$CH_2$— in the alkylene may be replaced by —O— or —CH=CH—, but —O— and —O— or —O— and $SiH_3$ are not adjacent; $Y^2$ is alkyl having 1 to 10 carbon, in which any —$CH_2$— in the alkyl may be replaced by —O—, —S— or —CH=CH—, but —O— and —O—, —S— and —S—, or —O— and —S— are not adjacent; $A^1$, $A^2$, $A^3$, and $A^4$ each are independently 1,4-cyclohexylene, 1,4-cyclohexylene in which one or more non-adjacent —$CH_2$— are replaced by —O—, 1,4-phenylene in which a 2-position is replaced by halogen, 1,4-phenylene in which a 3-position is replaced by halogen, or 1,4-phenylene in which a 2-position and a 3-position are replaced by halogen, and one of $A^1$, $A^2$, $A^3$, and $A^4$ is always 1,4-phenylene in which a 2-position or a 3-position is replaced by halogen or 1,4-phenylene in which a 2-position and a 3-position are replaced by halogen.

[8] A liquid crystal composition comprising at least one silicon compound defined in any one of the items [1] to [7].

[9] The liquid crystal composition defined in the above item [8], comprising at least one silicon compound described in any one of the items [1] to [7] as a first component and at least one compound selected from the group of compounds represented by formulas (2), (3) and (4) as a second component:

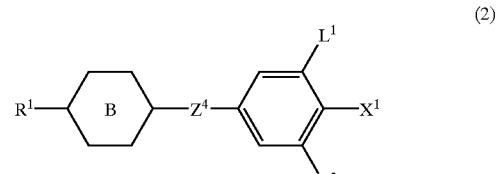

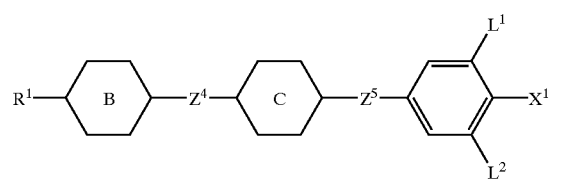

-continued

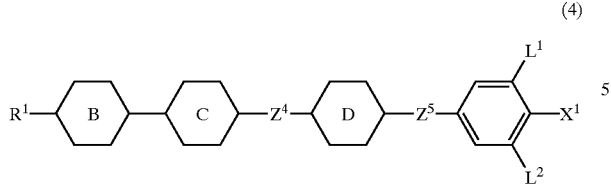
(4)

wherein $R^1$ is alkyl having 1 to 10 carbon, in which any —CH$_2$— in the alkyl may be replaced by —O— or —CH=CH—, but —O— and —O— are not adjacent, and any hydrogen in the group may be replaced by fluorine; $X^1$ is fluorine, Chlorine, —OCF$_3$, —OCF$_2$H, —CF$_3$, —CF$_2$H, —CFH$_2$, —OCF$_2$CF$_2$H, or —OCF$_2$CFHCF$_3$; $L^1$ and $L^2$ each are independently hydrogen or fluorine; $Z^4$ and $Z^5$ each are independently —(CH$_2$)$_2$—, —(CH$_2$)$_4$—, —COO—, —CF$_2$O—, —OCF$_2$—, —CH=CH—, or a single bond; a ring B and a ring C each are independently 1,4-cyclohexylene, 1,3-dioxane-2,5-diyl, 1,4-phenylene, or 1,4-phenylene in which at least one hydrogen is replaced by fluorine; and a ring D is 1,4-cyclohexylene, 1,4-phenylene or 1,4-phenylene in which at least one hydrogen is replaced by fluorine.

[10] The liquid crystal composition defined in the above item [8], comprising at least one silicon compound described in any one of the items [1] to [7] as the first component and at least one compound selected from the group of compounds represented by formulas (5) and (6) as a second component:

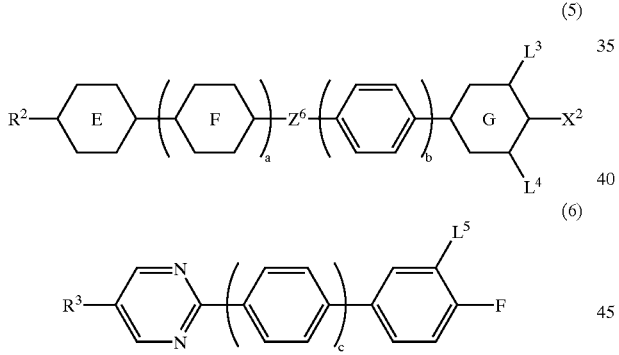
(5)

(6)

wherein $R^2$ and $R^3$ each are independently alkyl having 1 to 10 carbon, in which any —CH$_2$— in the alkyl may be replaced by —O— or —CH=CH—, but —O— and —O— are not adjacent, and any hydrogen in the alkyl may be replaced by fluorine; $X^2$ is —CN or —C≡C—CN; a ring E is 1,4-cyclohexylene, 1,4-phenylene, 1,3-dioxane-2,5-diyl, or pyrimidine-2,5-diyl; a ring F is 1,4-cyclohexylene, 1,4-phenylene, 1,4-phenylene in which hydrogen is replaced by fluorine, or pyrimidine-2,5-diyl; a ring G is 1,4-cyclohexylene or 1,4-phenylene; $Z^6$ is —(CH$_2$)$_2$—, —COO—, —CF$_2$O—, —OCF$_2$—, or a single bond; $L^3$, $L^4$ and $L^5$ each are independently hydrogen or fluorine; and a, b and c each are independently 0 or 1.

[11] The liquid crystal composition defined in the above item [8], comprising at least one silicon compound described in any one of the items [1] to [7] as the first component and at least one compound selected from the group of compounds represented by formulas (7), (8) and (9) as a second component:

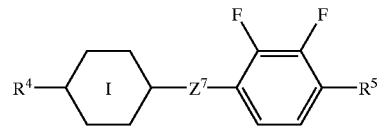
(7)

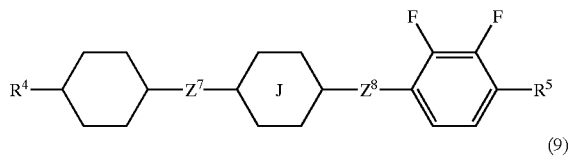
(8)

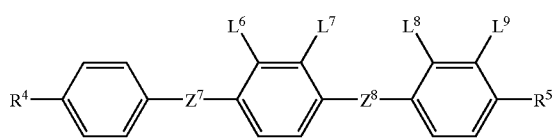
(9)

wherein $R^4$ and $R^5$ each are independently alkyl having 1 to 10 carbon, in which any —CH$_2$— in the alkyl may be replaced by —O— or —CH=CH—, but —O— and —O— are not adjacent, and any hydrogen in the alkyl may be replaced by fluorine; a ring I and a ring J each are independently 1,4-cyclohexylene or 1,4-phenylene; $L^6$, $L^7$, $L^8$ and $L^9$ each are independently hydrogen or fluorine, and all of them are not hydrogen simultaneously; and $Z^7$ and $Z^8$ each are independently —(CH$_2$)$_2$—, —COO— or a single bond.

[12] The liquid crystal composition defined in the above item [8], comprising at least one silicon compound described in any of the items [1] to [7] as the first component, at least one compound selected from the group of the compounds represented by formulas (2), (3) and (4) described in the above item [9] as the second component, and at least one compound selected from the group of compounds represented by formulas (10), (11) and (12) as a third component:

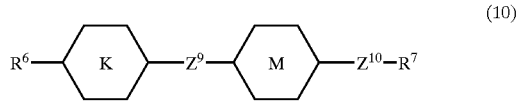
(10)

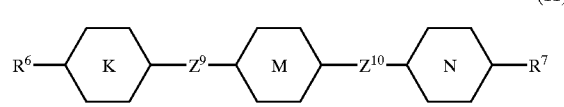
(11)

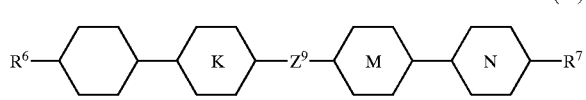
(12)

wherein $R^6$ and $R^7$ each are independently alkyl having 1 to 10 carbon, in which any —CH$_2$— in the alkyl may be replaced by —O— or —CH=CH—, but —O— and —O— are not adjacent, and any hydrogen in the alkyl may be replaced by fluorine; a ring K, a ring M and a ring N each are independently 1,4-cyclohexylene, pyrimidine-2,5-diyl, 1,4-phenylene, or 1,4-phenylene in which hydrogen is replaced by fluorine; and $Z^9$ and $Z^{10}$ each are independently —C≡C—, —COO—, —(CH$_2$)$_2$—, —CH=CH— or a single bond.

[13] The liquid crystal composition defined in the above item [8], comprising at least one silicon compound described in any one of the items [1] to [7] as the first component, at least one compound selected from the group of the compounds represented by formulas (5) and (6) described in the above item [10] as the second component, and at least one compound selected from the group of the compounds represented by formulas (10), (11) and (12) described in the above item [12] as the third component.

[14] The liquid crystal composition defined in the above item [8], comprising at least one silicon compound described in any one of the items [1] to [7] as the first component, at least one compound selected from the group of the compounds represented by formulas (7), (8) and (9) described in the above item [11] as the second component and at least one compound selected from the group of the compounds represented by formulas (10), (11) and (12) described in the above item [12] as the third component.

[15] The liquid crystal composition defined in the above item [8], comprising at least one silicon compound described in any of the items [1] to [7] as the first component, at least one compound selected from the group of the compounds represented by formulas (2), (3) and (4) described in the above item [9] as the second component, at least one compound selected from the group of the compounds represented by formulas (5) and (6) described in the above item [10] as the third component, and at least one compound selected from the group of the compounds represented by formulas (10), (11) and (12) described in the above item [12] as a fourth component.

[16] A liquid crystal composition comprising at least one liquid crystal composition defined in the items [8] and further comprising at least one optically active compound.

[17] A liquid crystal display using the liquid crystal composition defined in any of the items [8] to [15].

The compound (1) of the present invention is a compound having a SiH$_3$ group at an end and 2 to 4 six-membered rings (hereinafter referred to as a bicyclic system to a tetracyclic system), and it is physically and chemically very stable under conditions on which a display is used. Further, six-membered rings, a bonding group and side chains constituting the compound (1) having a good mutual solubility, a low viscosity and a low threshold voltage are suitably selected, whereby the desired physical property values can optionally be controlled. The preferred compounds are shown below.

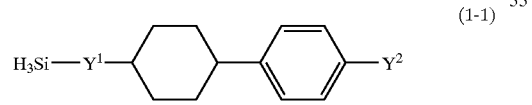
(1-1)

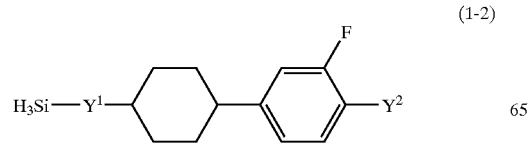
(1-2)

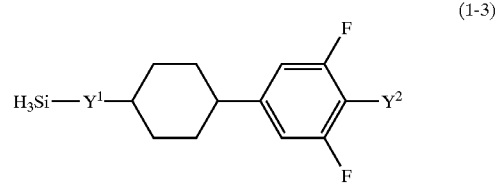
(1-3)

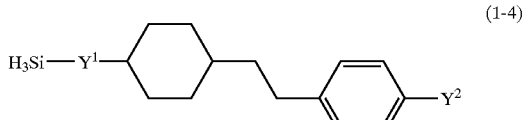
(1-4)

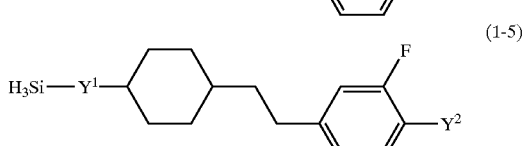
(1-5)

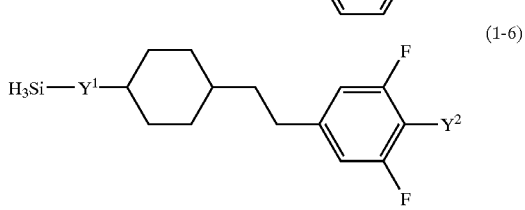
(1-6)

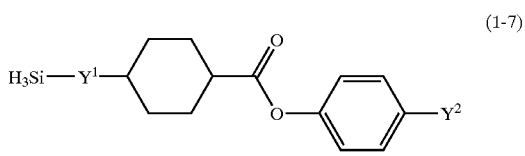
(1-7)

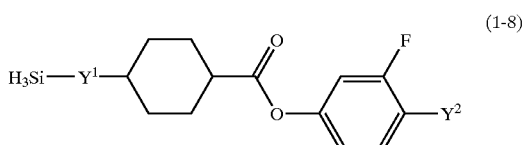
(1-8)

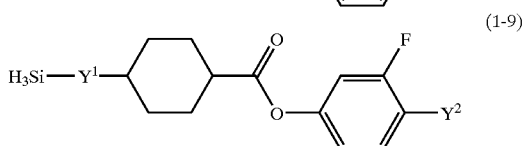
(1-9)

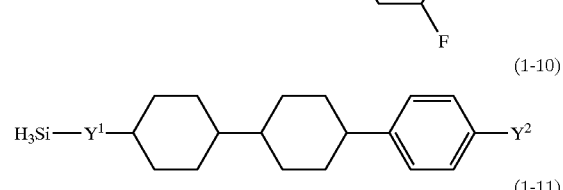
(1-10)

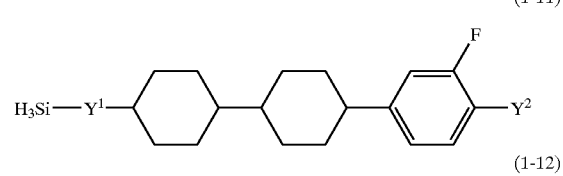
(1-11)

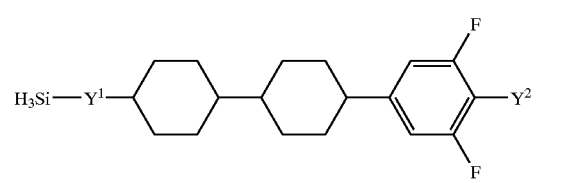
(1-12)

(1-13)
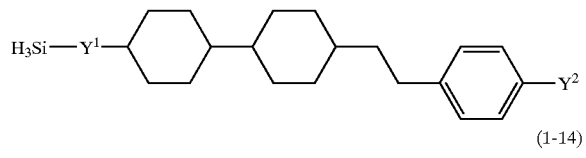
(1-14)
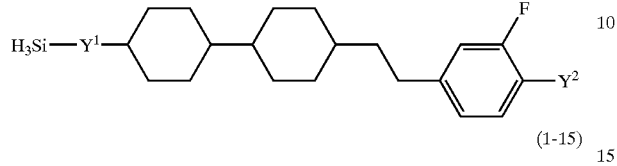
(1-15)
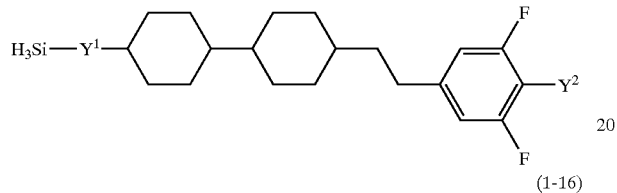
(1-16)
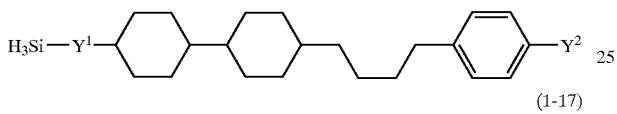
(1-17)
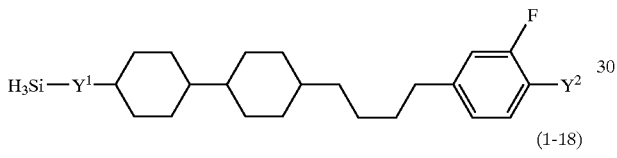
(1-18)
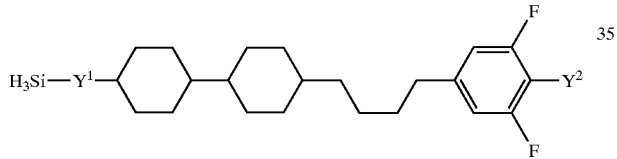
(1-19)
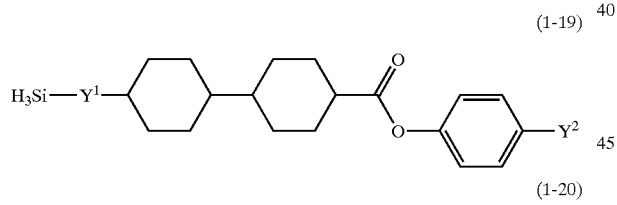
(1-20)
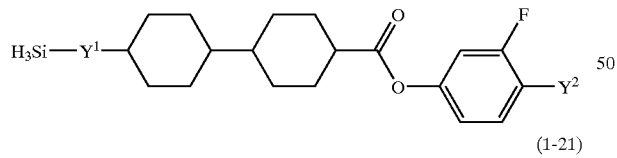
(1-21)
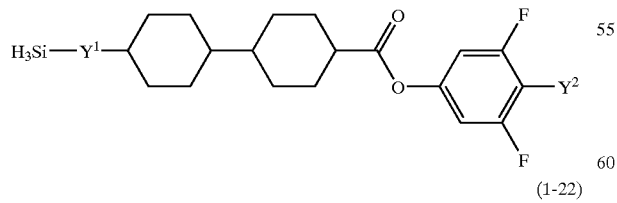
(1-22)
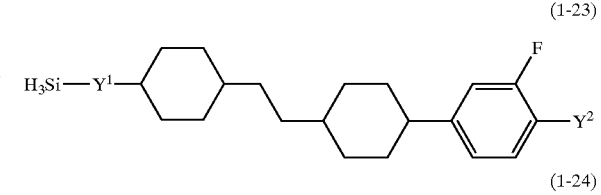
(1-23)
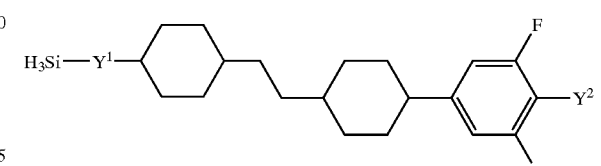
(1-24)
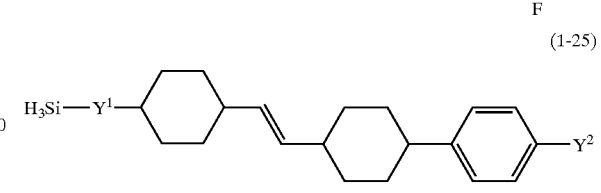
(1-25)
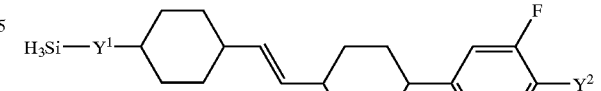
(1-26)
(1-27)
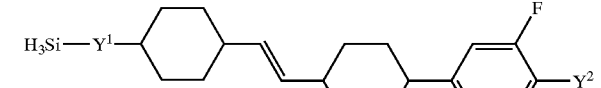
(1-28)
(1-29)
(1-30)
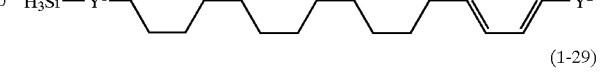
(1-31)
(1-32)
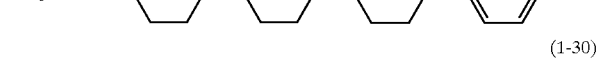

(1-33)
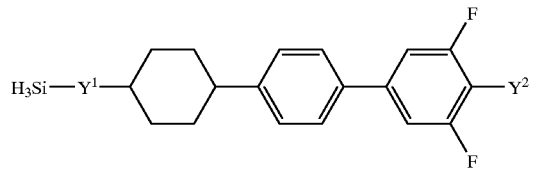
(1-34)
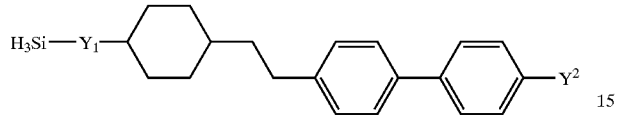
(1-35)
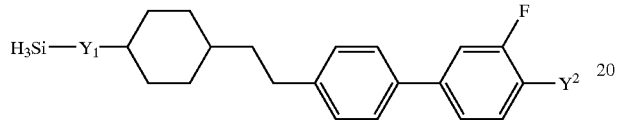
(1-36)
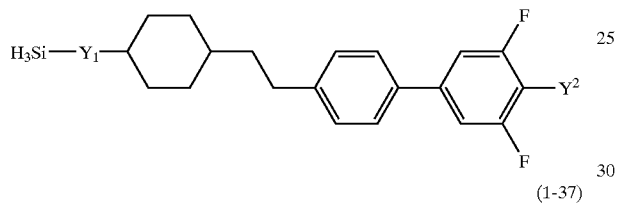
(1-37)
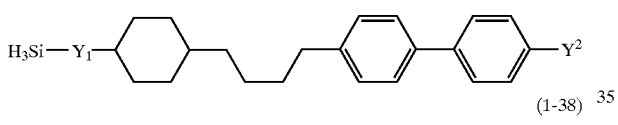
(1-38)
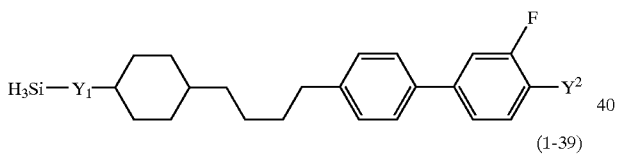
(1-39)
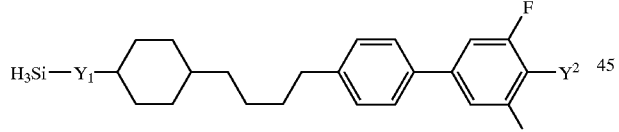
(1-40)
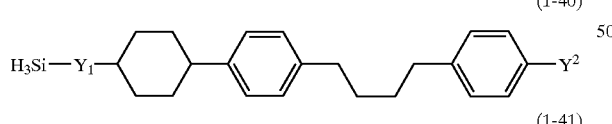
(1-41)
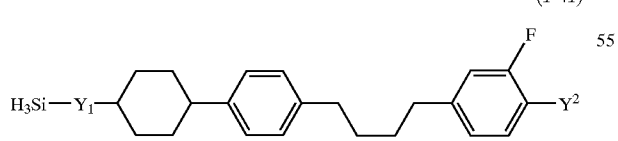
(1-42)
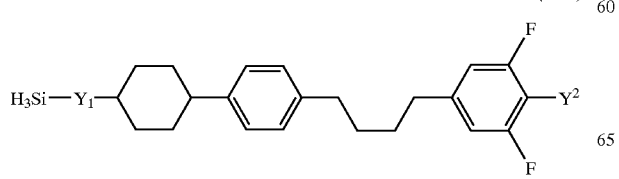
(1-43)
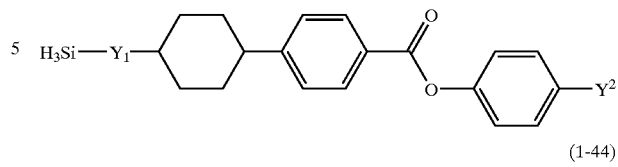
(1-44)
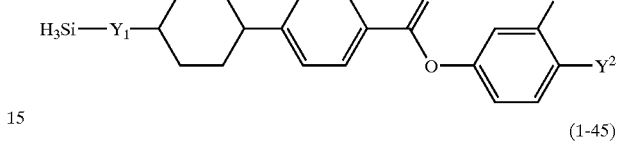
(1-45)
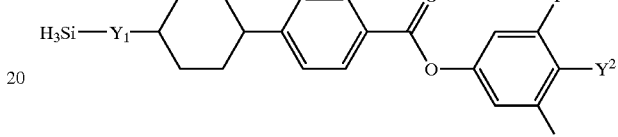
(1-46)
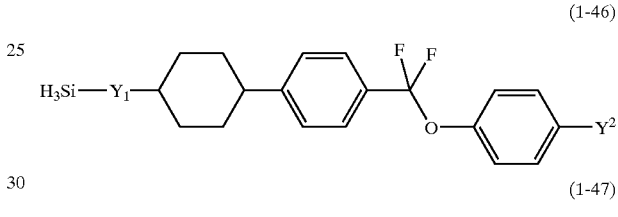
(1-47)
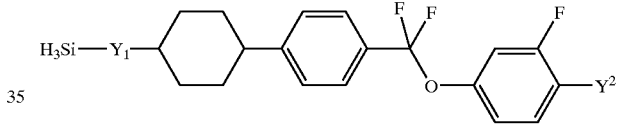
(1-48)
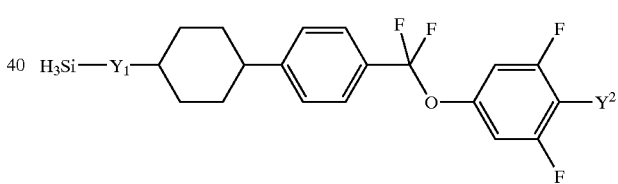
(1-49)
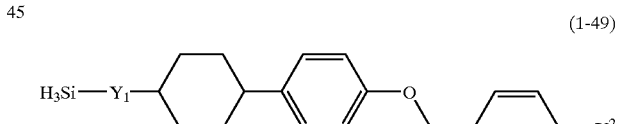
(1-50)
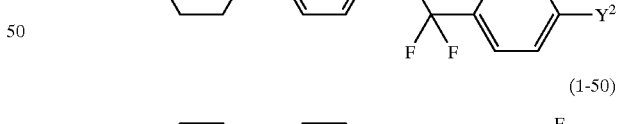
(1-51)
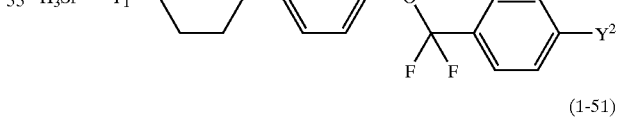
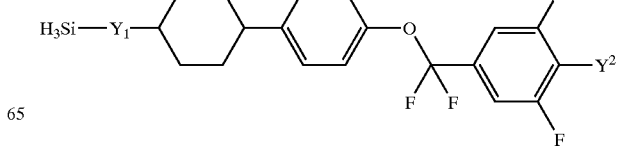

-continued
(1-52)
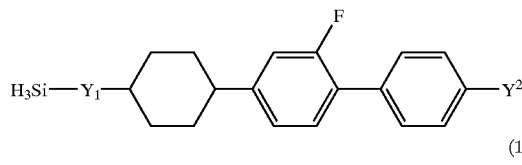
(1-53)
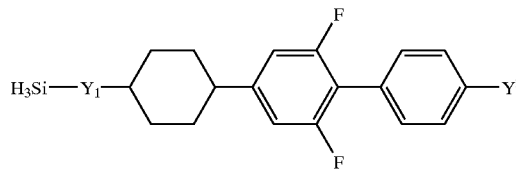
(1-54)
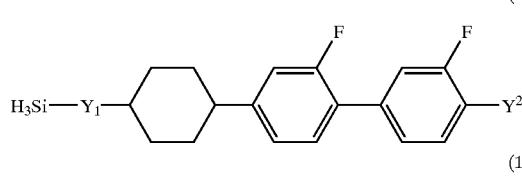
(1-55)
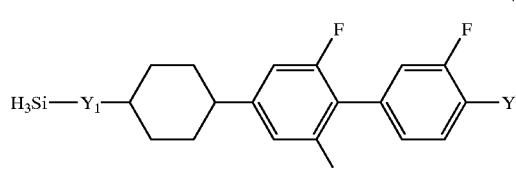
(1-56)
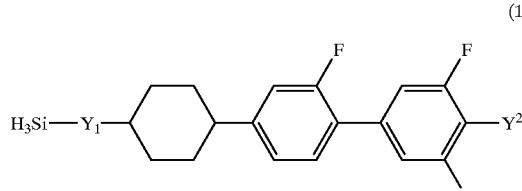
(1-57)
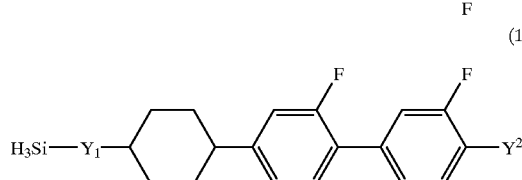
(1-58)
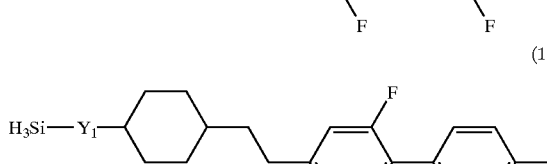
(1-59)
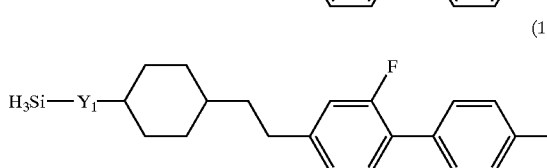
(1-60)
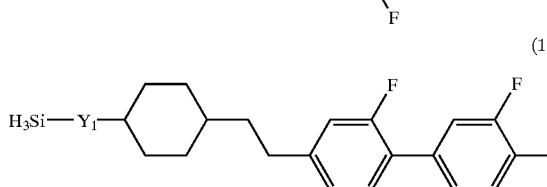
-continued
(1-61)
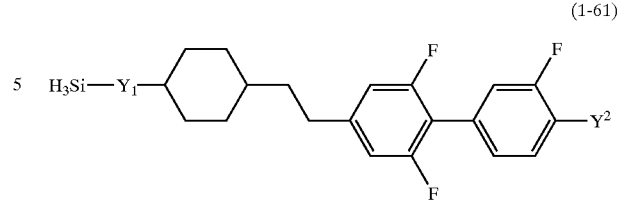
(1-62)
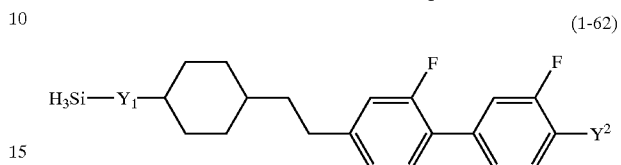
(1-63)
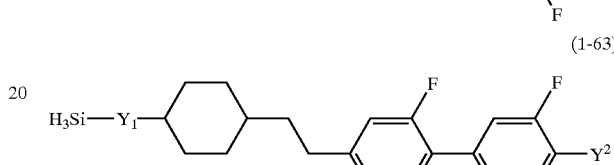
(1-64)
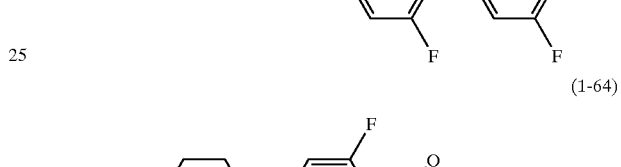
(1-65)
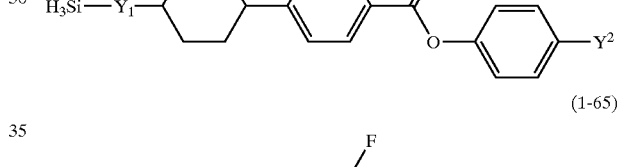
(1-66)
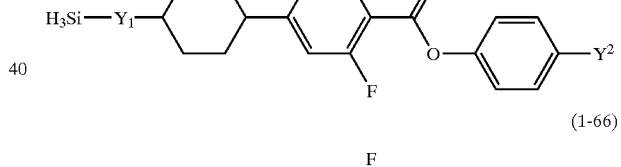
(1-67)
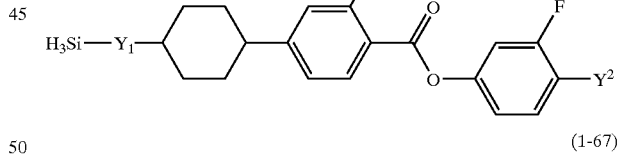
(1-68)
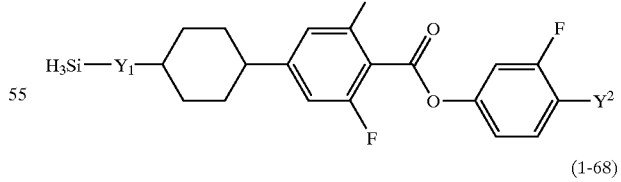
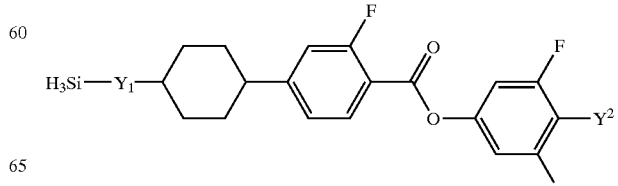

(1-69)
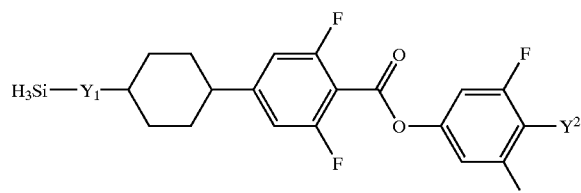
(1-70)
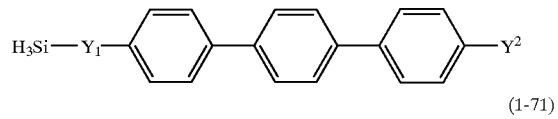
(1-71)
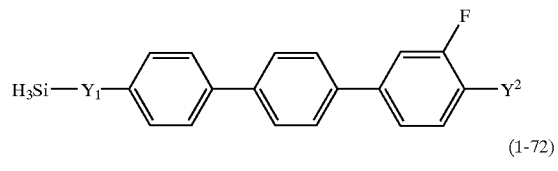
(1-72)
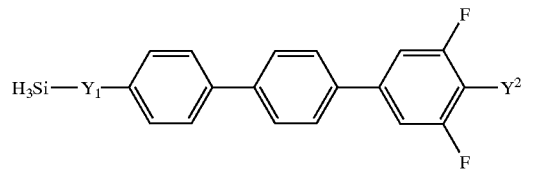
(1-73)
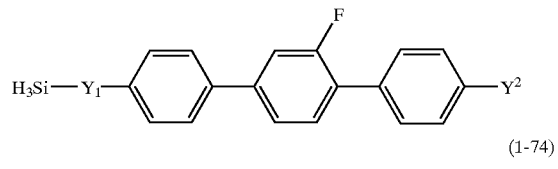
(1-74)
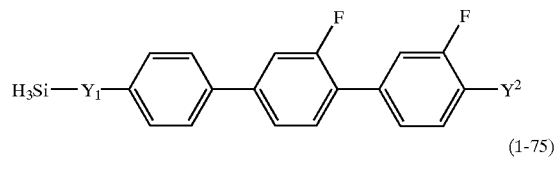
(1-75)
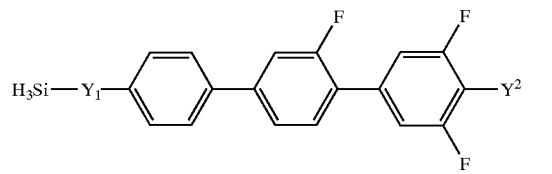
(1-76)
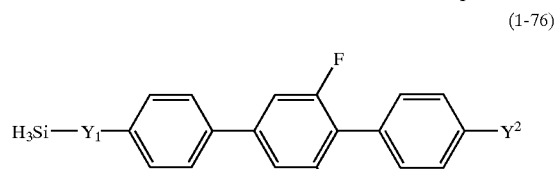
(1-77)
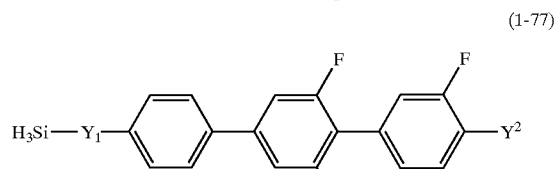
(1-78)
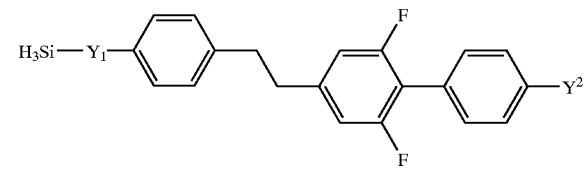
(1-79)
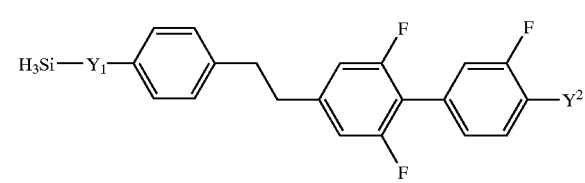
(1-80)
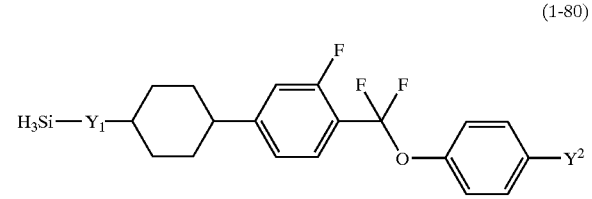
(1-81)
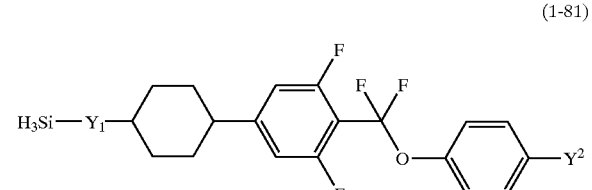
(1-82)
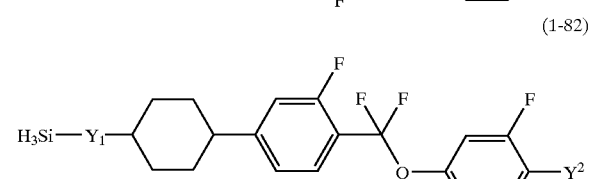
(1-83)
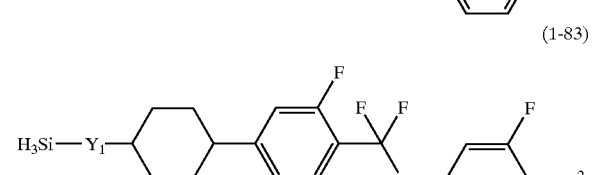
(1-84)
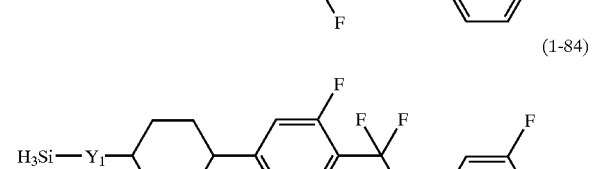
(1-85)
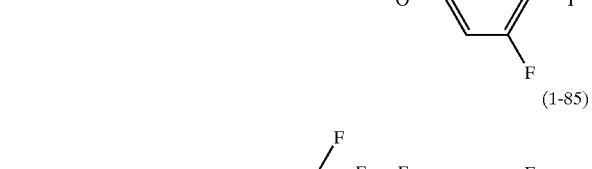
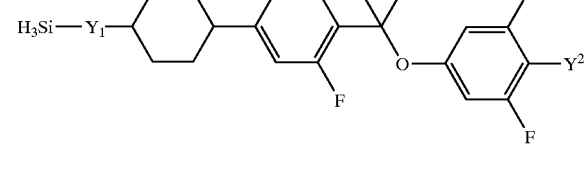

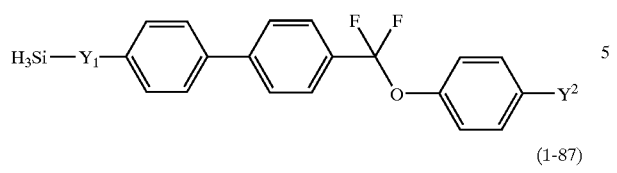 (1-86)
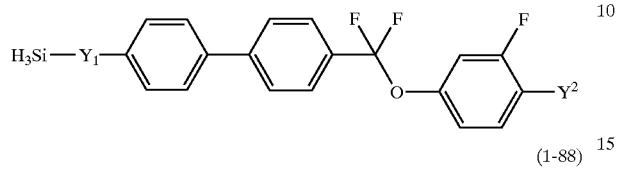 (1-87)
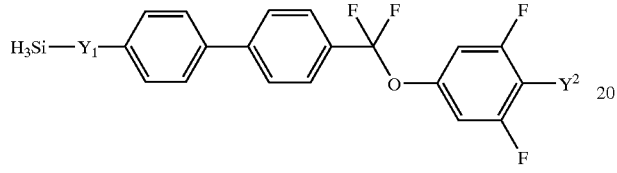 (1-88)
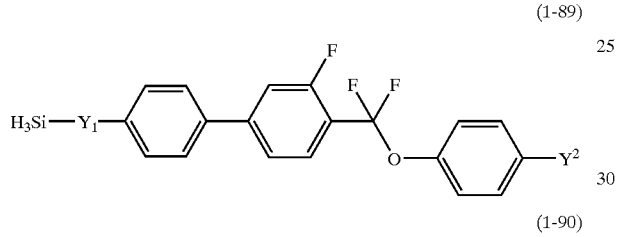 (1-89)
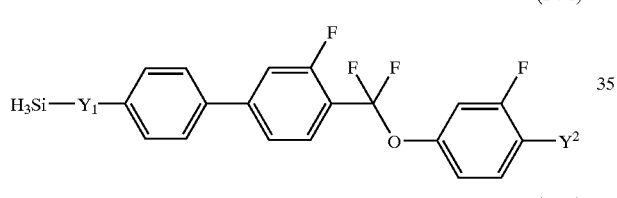 (1-90)
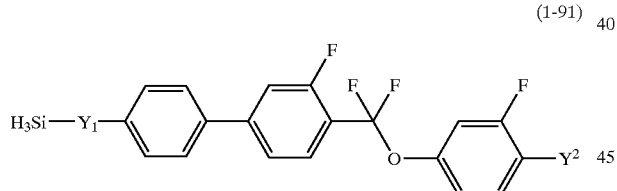 (1-91)
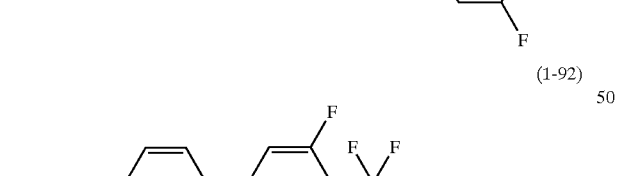 (1-92)
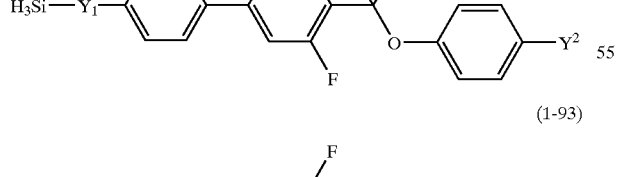 (1-93)
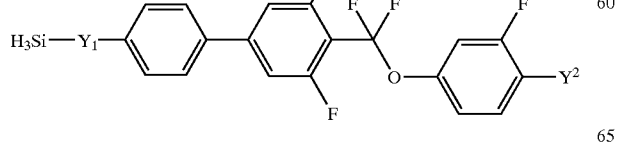
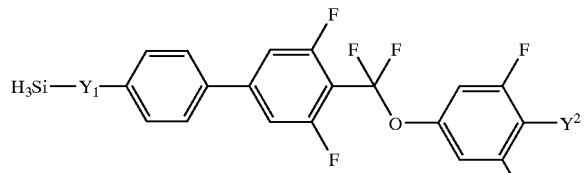 (1-94)
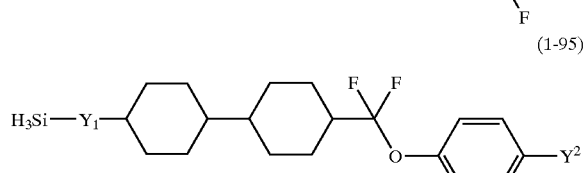 (1-95)
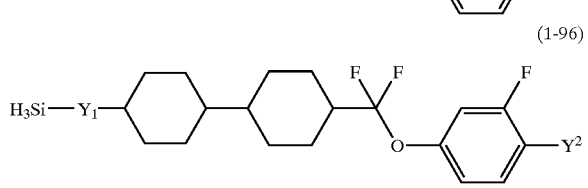 (1-96)
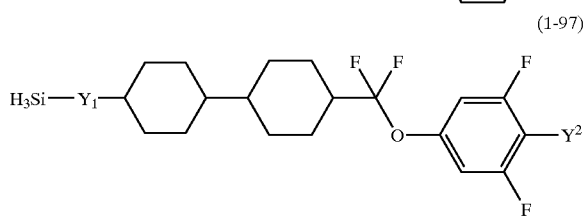 (1-97)
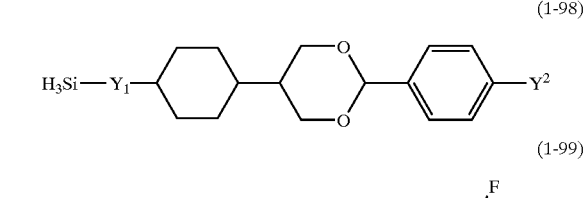 (1-98)
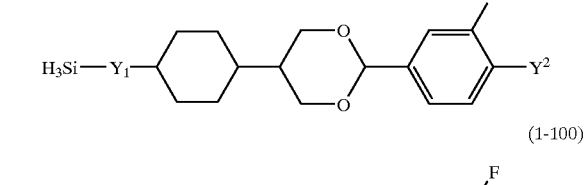 (1-99)
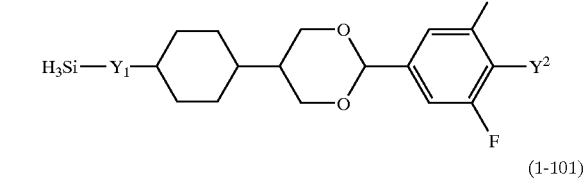 (1-100)
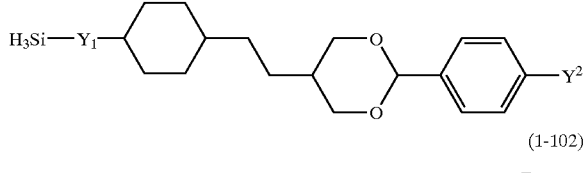 (1-101)
(1-102)

-continued
(1-103)
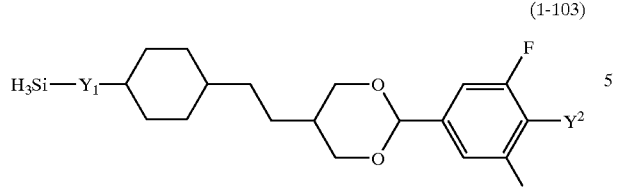
(1-104)
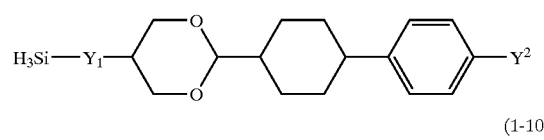
(1-105)
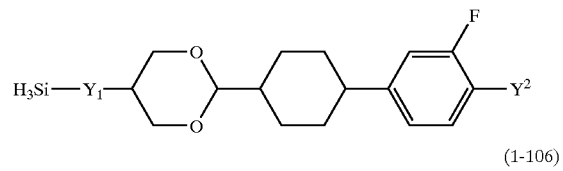
(1-106)
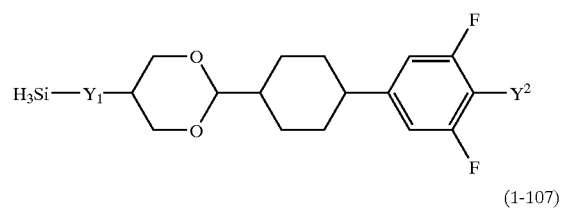
(1-107)
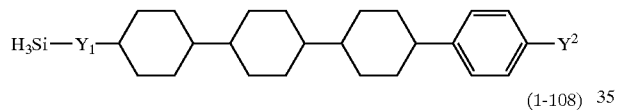
(1-108)
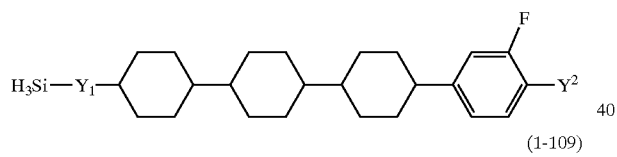
(1-109)
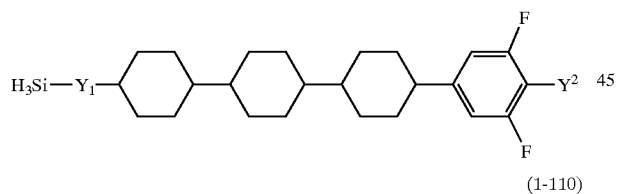
(1-110)
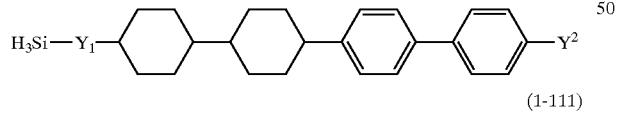
(1-111)
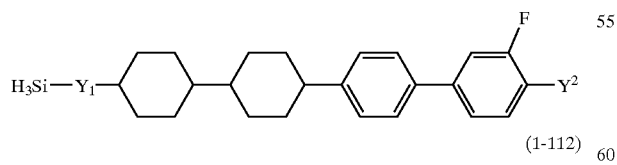
(1-112)
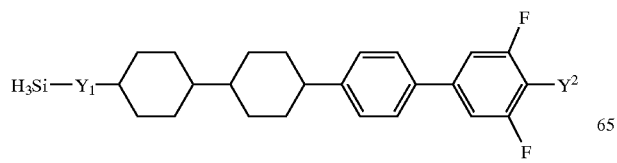
(1-113)
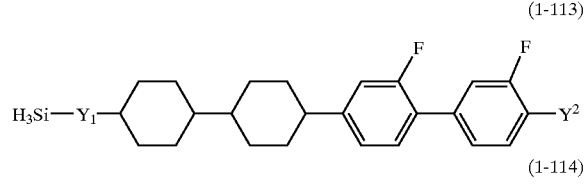
(1-114)
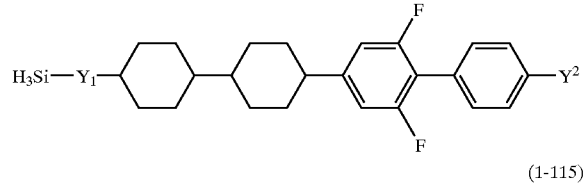
(1-115)
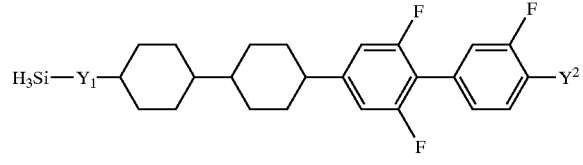
(1-116)
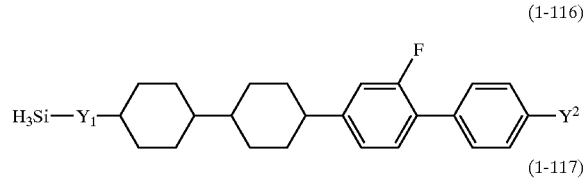
(1-117)
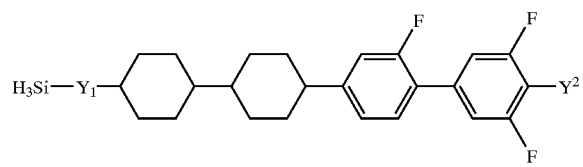
(1-118)
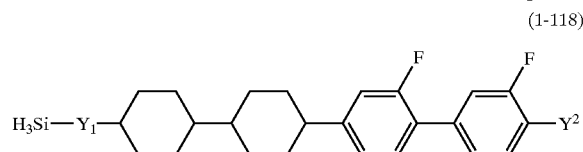
(1-119)
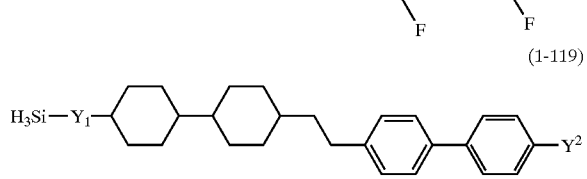
(1-120)
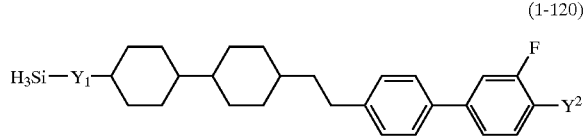
(1-121)
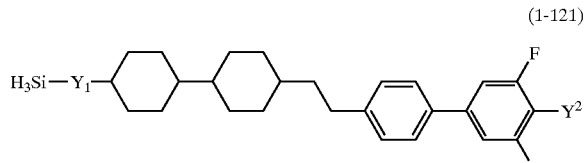
(1-122)
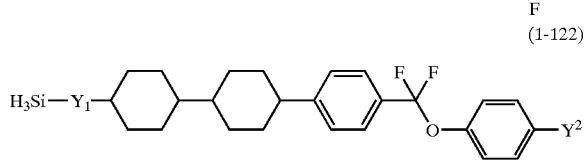

-continued
(1-123)
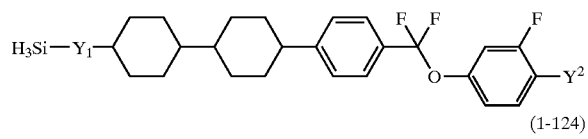
(1-124)
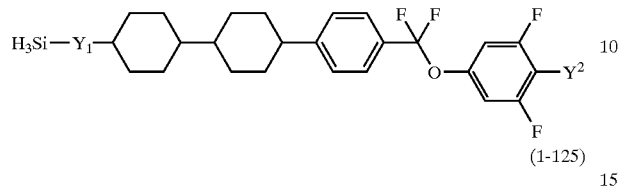
(1-125)
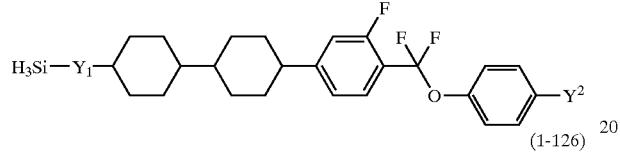
(1-126)
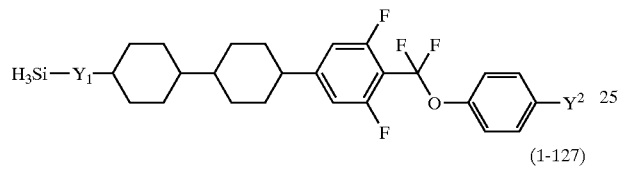
(1-127)
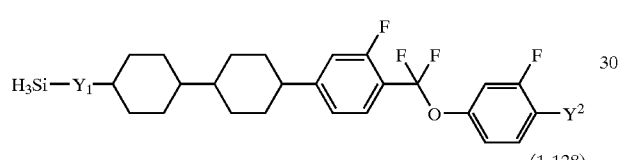
(1-128)
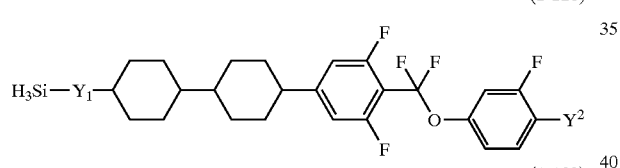
(1-129)
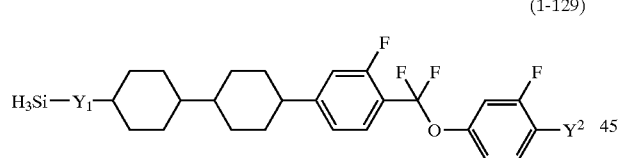
(1-130)
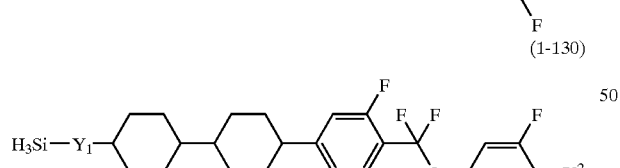
(1-131)
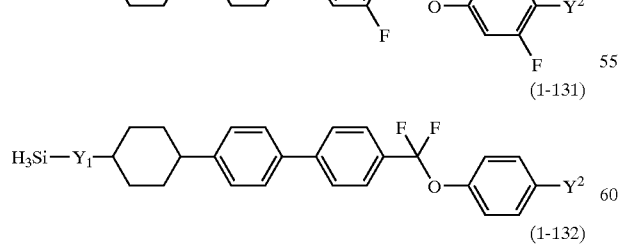
(1-132)
-continued
(1-133)
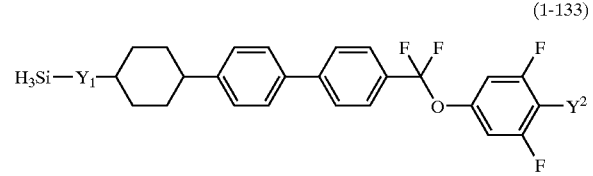
(1-134)
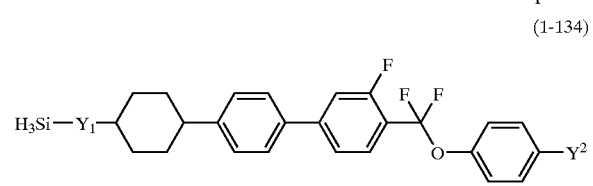
(1-135)
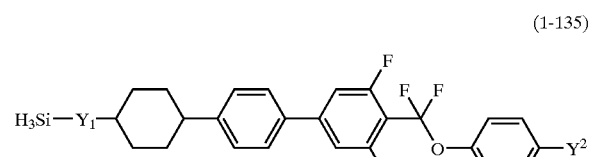
(1-136)
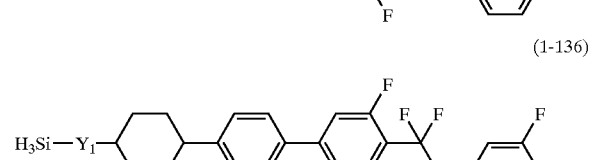
(1-137)
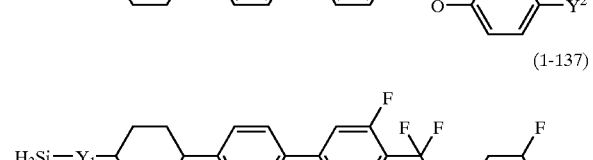
(1-138)
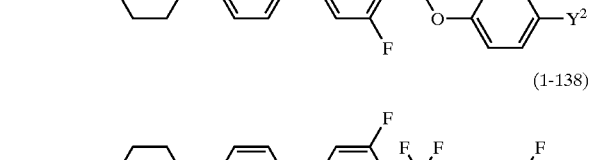
(1-139)
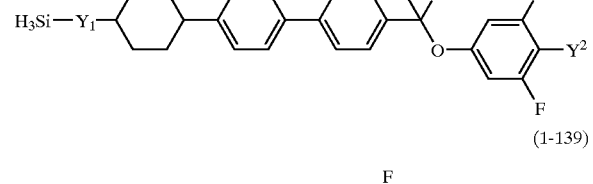
(1-140)
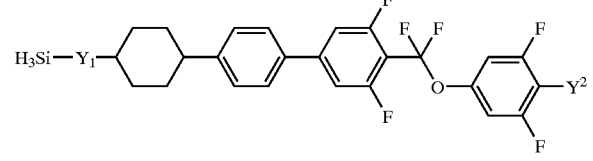
(1-141)
(1-142)
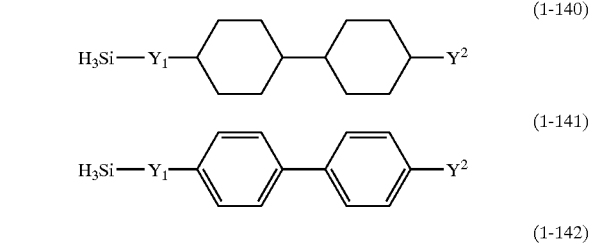

(1-143) 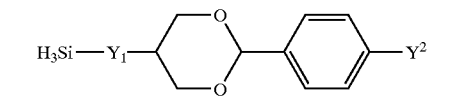
(1-144) 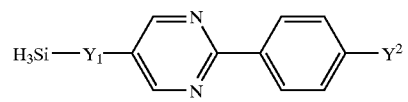
(1-145) 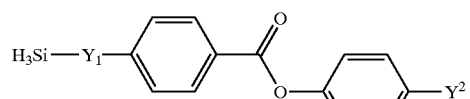
(1-146) 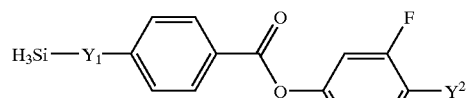
(1-147) 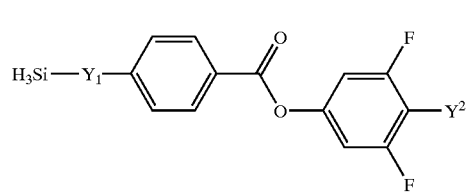
(1-148) 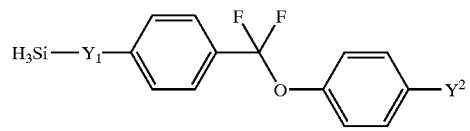
(1-149) 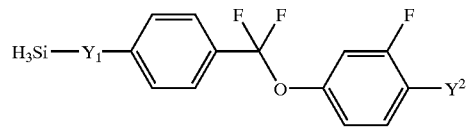
(1-150) 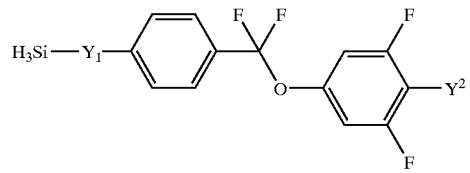
(1-151) 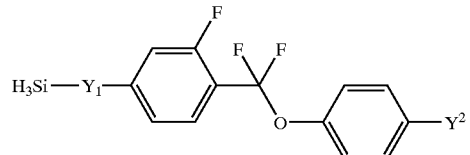
(1-152) 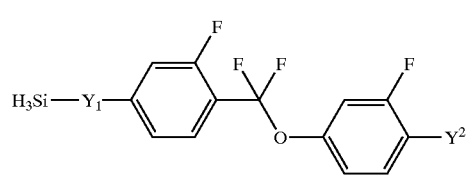
(1-153) 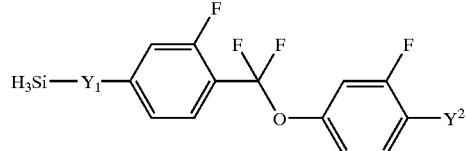
(1-154) 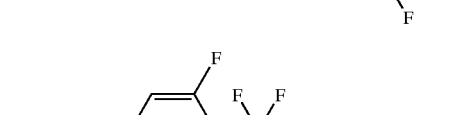
(1-155) 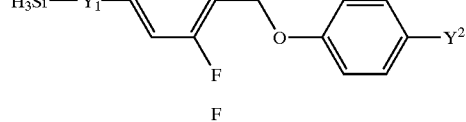
(1-156) 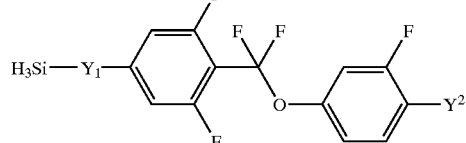
(1-157) 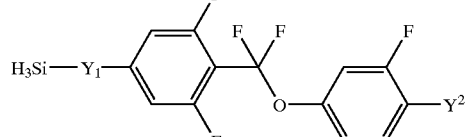
(1-158) 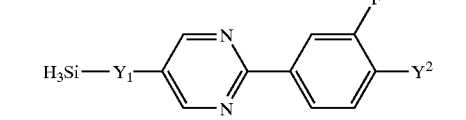
(1-159) 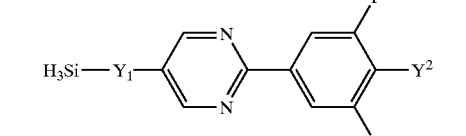
(1-160) 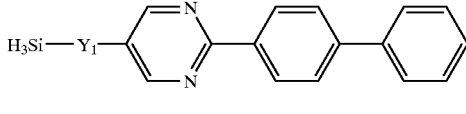
(1-161) 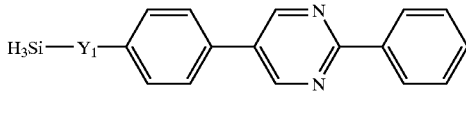
(1-162) 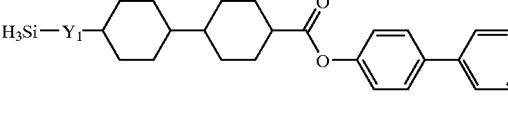
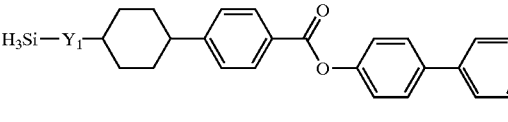

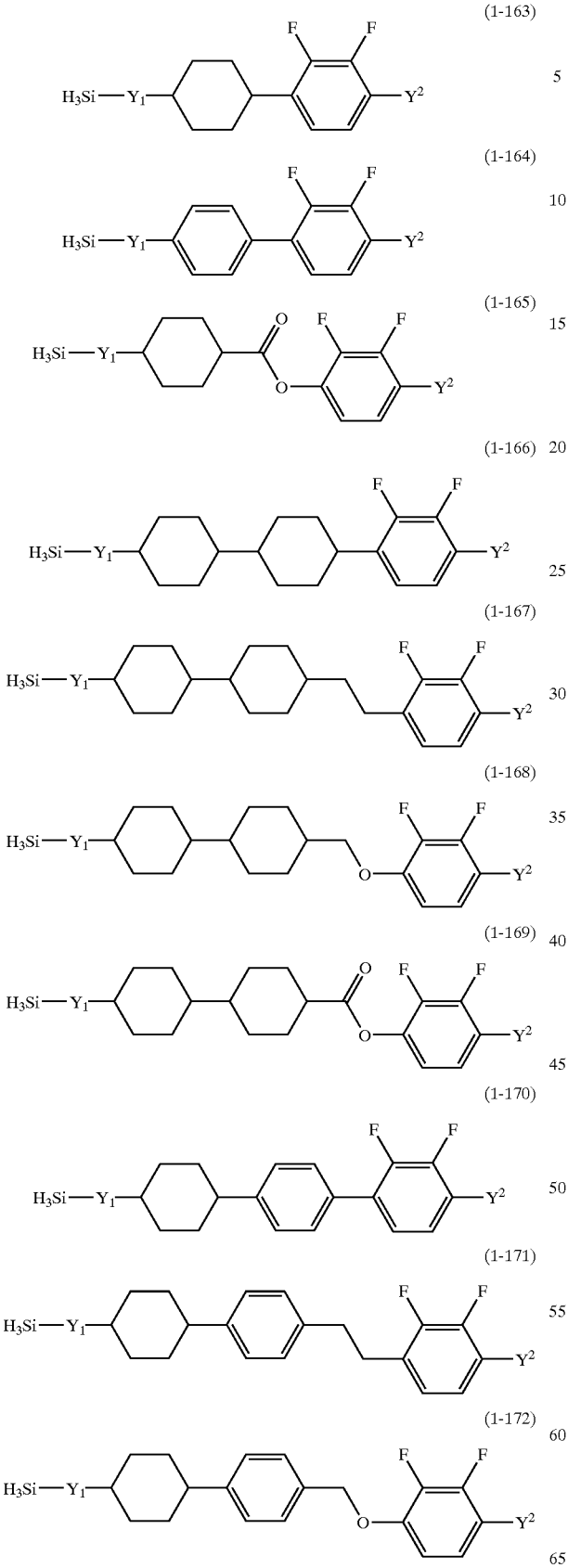

-continued
(1-185)
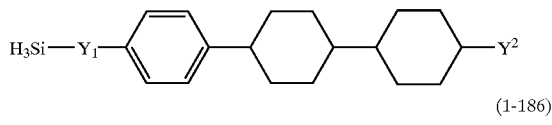
(1-186)
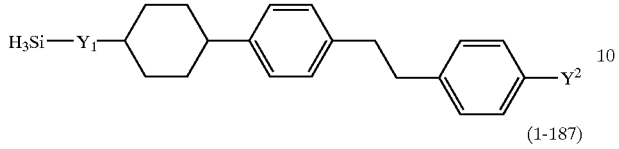
(1-187)
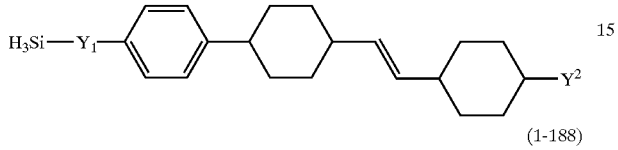
(1-188)
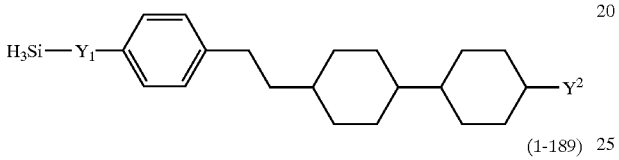
(1-189)
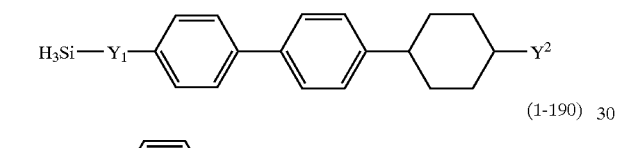
(1-190)
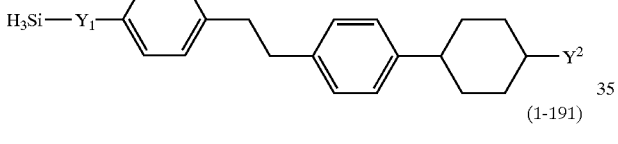
(1-191)
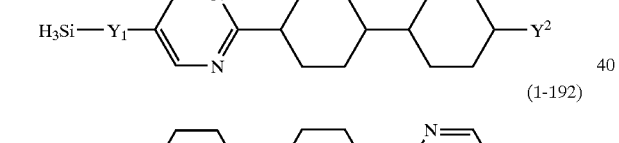
(1-192)
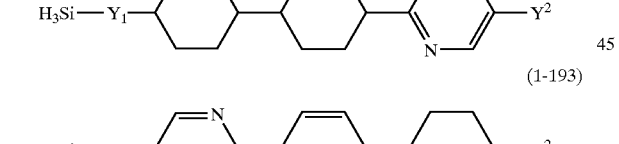
(1-193)
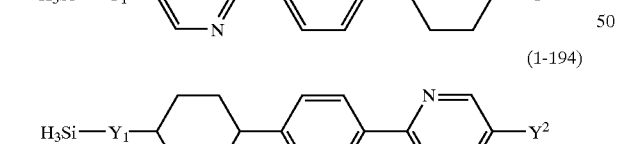
(1-194)
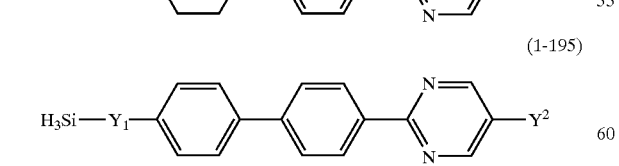
(1-195)
-continued
(1-197)
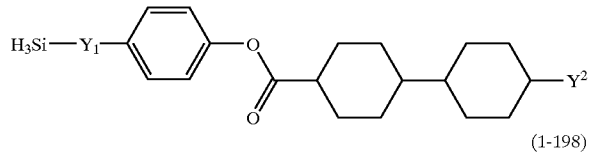
(1-198)
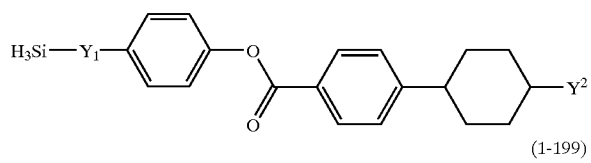
(1-199)
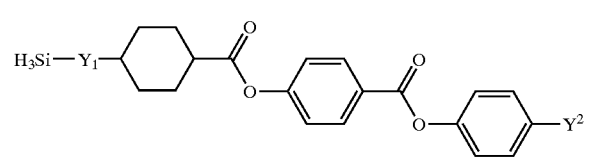
(1-200)
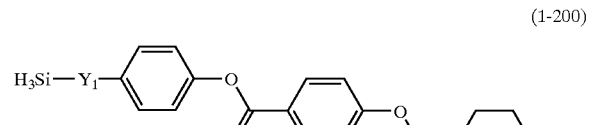
(1-201)
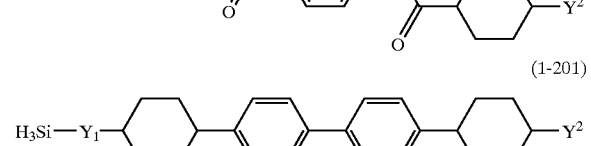
(1-202)
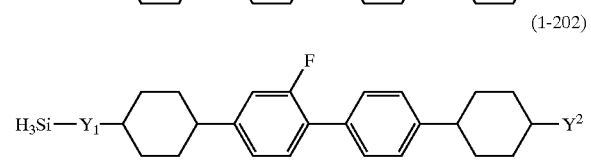
(1-203)
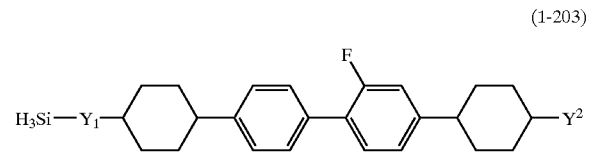
(1-204)
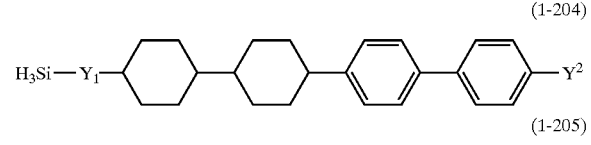
(1-205)
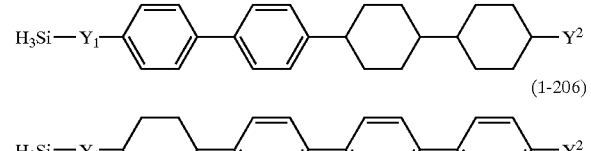
(1-206)
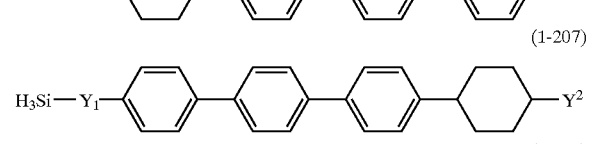
(1-207)
(1-208)
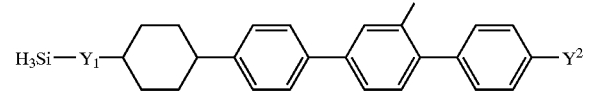

(1-209)

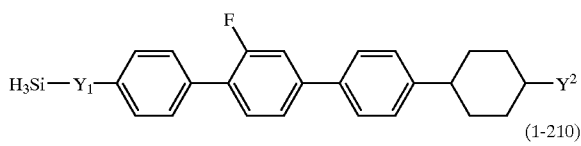

(1-210)

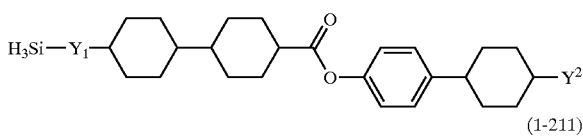

(1-211)

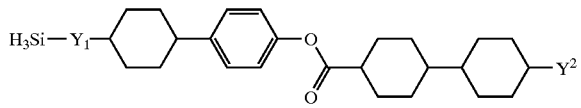

Y[1] and Y[2] mean the same as those described in the item [1] described above.

Capable of being given as preferred Y[1] is alkylene, alkyleneoxy, alkyleneoxyalkylene, alkenylene, alkenyleneoxy, alkenyleneoxyalkylene or alkyleneoxyalkenylene which has 1 to 10 carbon atoms. Among them, the most preferred group includes methylene, ethylene, propylene, butylene, pentylene, hexylene, heptylene, methyleneoxy, ethyleneoxy, propyleneoxy, butyleneoxy, pentyleneoxy, hexyleneoxy, heptyleneoxy, methyleneoxymethylene, ethyleneoxymethylene, propyleneoxymethylene, methyleneoxyethylene, ethyleneoxyethylene, methyleneoxyproeylene, ethyleneoxypropylene, vinylene, 1-propenylene, 2-propenylene, 1-butenylene, 2-butenylene, 3-butenylene, 2-prpenyleneoxy and 2-butenyleneoxy.

Capable of being given as preferred Y[2] is alkyl alkoxy, alkoxyalkyl, alkenyl, alkenyloxy, alkenyloxyalkyl or alkyloxyalkenyl which has 1 to 10 carbon atoms, alkynyl, fluoroalkyl, fluoroalkyloxy, halogen, cyano and cyanoalkynyl. Among them, the particularly preferred groups include methyl, ethyl, propyl, butyl, pentyl, hexyl, heptyl, octyl, methoxy, ethoxy, propoxy, butoxy, pentyloxy, hexyloxy, heptyloxy, octyloxy, methoxymethyl, ethoxymethyl, propoxymethyl, butoxymethyl, methoxyethyl, ethoxyethyl, propoxyethyl, methoxypropyl, ethoxypropyl, propoxypropyl, vinyl, 1-propenyl, 2-propenyl, 1-butenyl, 2-butenyl, 3-butenyl, 1-pentenyl, 2-pentenyl, 3-pentenyl, 4-pentenyl, 2-propenyloxy, 2-butenyloxy, 2-pentenyloxy, 4-pentenyloxy, 2-propenyloxymethyl, 2-propenyloxyethyl, 3-butenyloxymethyl, 3-methoxy-1-propenyl, 3-methoxy-1-pentenyl, 3-methoxy-2-pentenyl, ethynyl, 1-propynyl, 2-propynyl, 1-butynyl, 2-butynyl, 3-butynyl, 1-pentynyl, 2-pentynyl, 3-pentynyl, 4-pentynyl, —F, —Cl, —CN, —C≡C—CN, —CF$_3$, —OCF$_3$ and —OCF$_2$H.

The compound in which one or both of Y[1] and Y[2] are optically active groups is particularly useful as a chiral dopant. Addition thereof to the composition makes it possible to prevent reverse twist domain from being produced.

The compound (1) can suitably be used as a component for a composition used for various displays including a TN type, an STN type, a TFT type and so on. Among the compounds (1), the bicyclic and tricyclic compounds show a low viscosity, and the tricyclic and tetracyclic compounds show a high isotropic phase transition temperature.

The compound (1) having two or more cyclohexane rings in a molecule shows a high isotropic phase transition temperature, a small Δn and a low viscosity. Further, the compound (1) having a dioxane ring or a pyrimidine ring shows a relatively large Δ∈.

The compound (1) having at least one benzene ring in a molecule shows a relatively large Δn and a high liquid crystal orientational parameter and therefore is excellent. In particular, the compound (1) having two or more benzene rings in a molecule shows a particularly large Δn, a broad liquid crystal temperature range and a chemically high stability.

The compound (1) which is substituted with groups such as —F, —CN, —CF$_3$, —OCF$_3$ and —OCF$_2$H so that the dipole moment grows larger in a molecular long axis direction has a large positive Δ∈, a high isotropic phase transition temperature and a relatively low viscosity. The compound in which these groups are substituted on a benzene ring shows an excellent stability and a particularly large positive Δ∈. Further, the compound in which plural groups are substituted on a benzene ring shows a larger Δ∈.

The compound (1) which is substituted with —F so that the dipole moment grows larger in a molecular short axis direction has a large negative Δ∈, a high isotropic phase transition temperature and a relatively low viscosity. The compound in which —F is substituted on a lateral side of a benzene ring shows an excellent chemical stability and a large negative Δ∈. The compound having two or more —F shows a particularly large negative Δ∈.

The compound (1) having double bonds on Z[1], Z[2] or Z[3] shows a broad liquid crystal temperature range and a large elastic constant ratio, and therefore it is suitably used as a composition for STN. The compound (1) having a triple bond shows a large Δ∈.

These matters make it possible to provide a novel liquid crystalline compound having desired physical properties by suitably selecting rings, side chains and/or bonding groups. Further, the compound (1) in which atoms constituting it are substituted with the isotopes shows the same characteristics and therefore can be used as well.

The composition of the present invention shall be explained below. This composition preferably contains 0.1 to 99.9% by weight of at least one compound (1) (hereinafter referred to as a first component) in order to allow excellent characteristics to be revealed. The amount is more preferably 1 to 80% by weight and further preferably 1 to 60% by weight.

The composition may comprise only the first component. It is allowed to be added as the second component, which is at least one compound (hereinafter referred to as a second A component) selected from the compounds (2), (3) and (4) described above or at least one compound (hereinafter referred to as a second B component) selected from the compounds (5) and (6) to the first component. At least one compound selected from the compounds (10), (11) and (12) can also be added as the third component for the purpose of controlling a threshold voltage, a liquid crystal phase temperature range, a birefringence, a dielectric anisotropy and a viscosity.

The compounds which are the respective components for the composition may be the analogues thereof comprising the isotopes of the respective elements since there is no large difference between the physical characteristics thereof.

In the second A component described above, the suitable examples of the compound (2) are (2-1) to (2-9); the suitable examples of the compound (3) are (3-1) to (3-97); and the suitable examples of the compound (4) are (4-1) to (4-33).

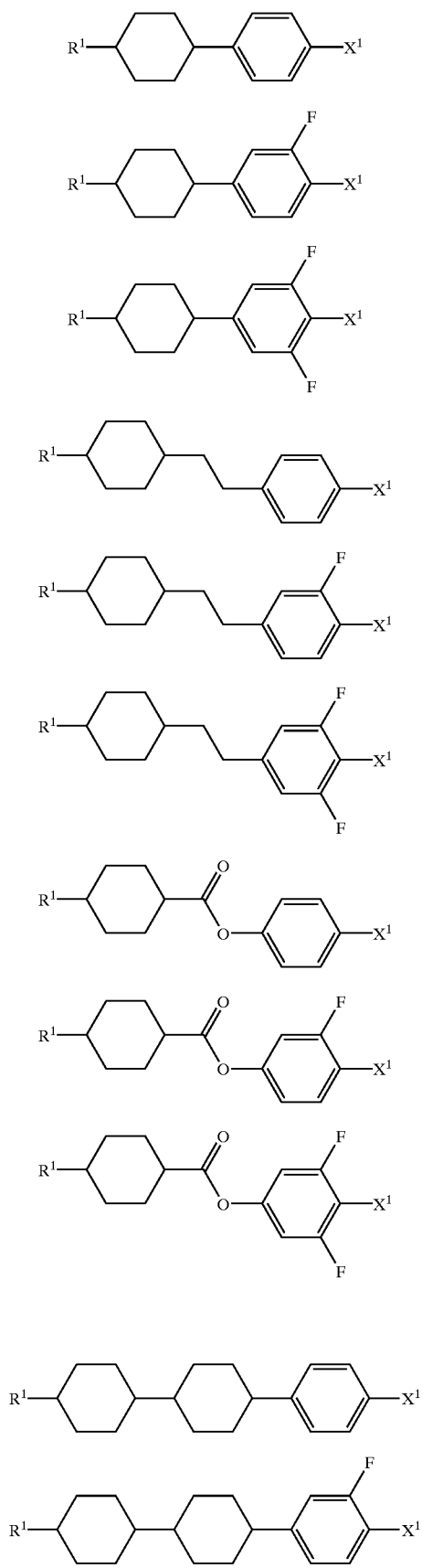
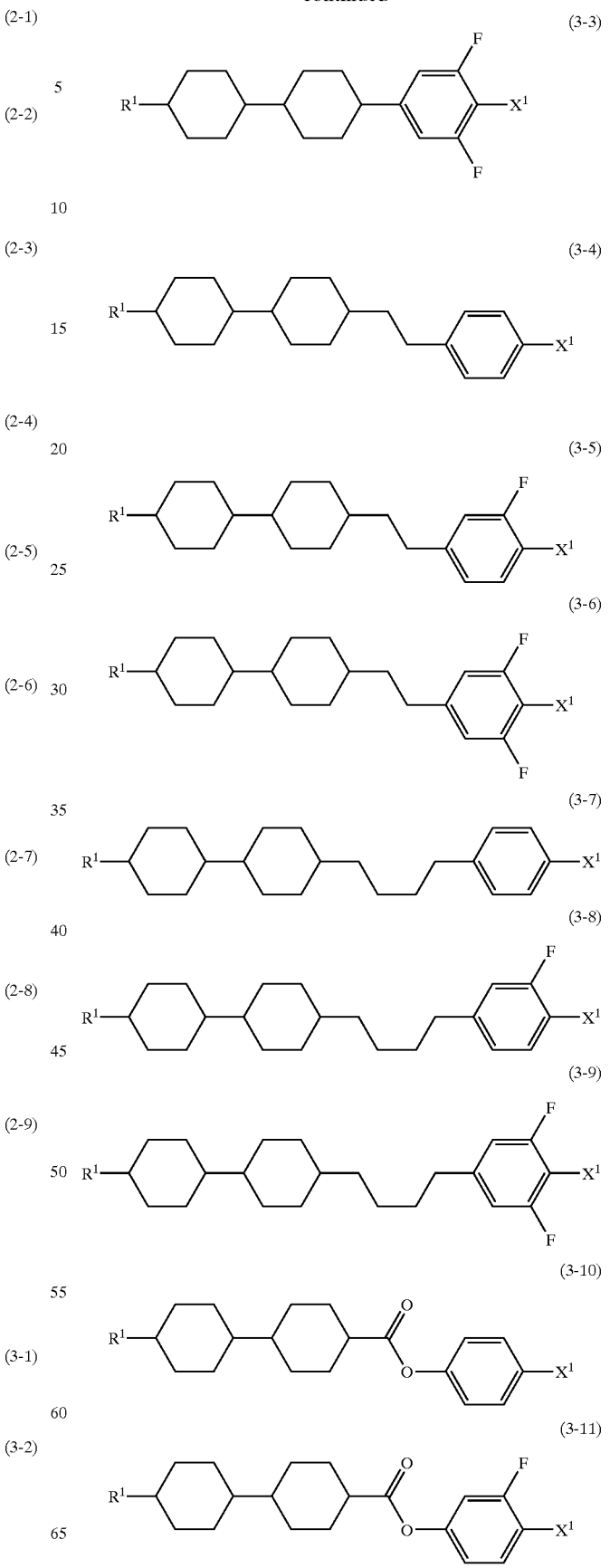

-continued (3-31) 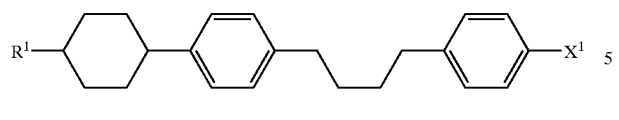
(3-32) 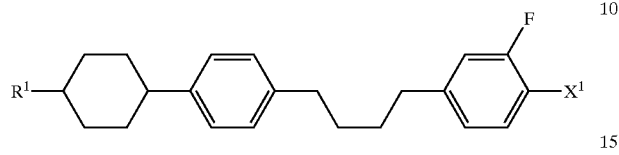
(3-33) 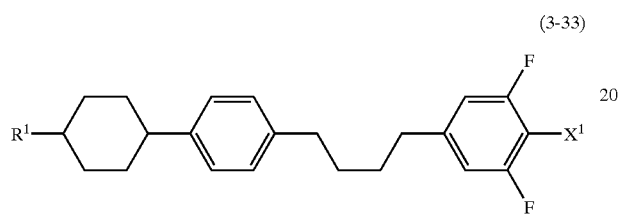
(3-34) 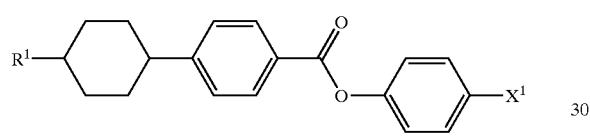
(3-35) 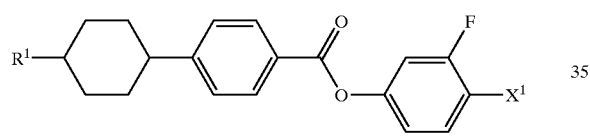
(3-36) 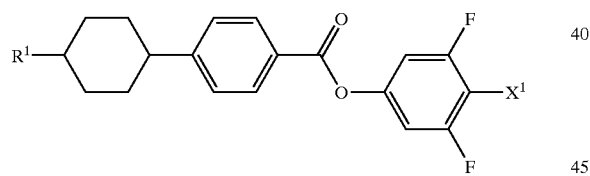
(3-37) 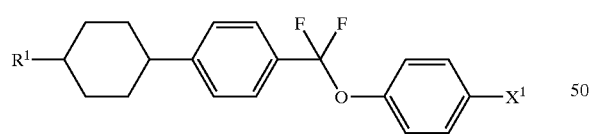
(3-38) 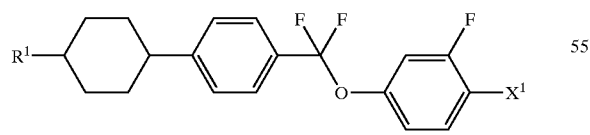
(3-39) 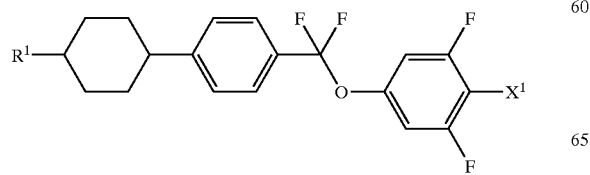
(3-40) 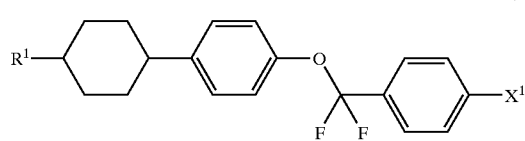
(3-41) 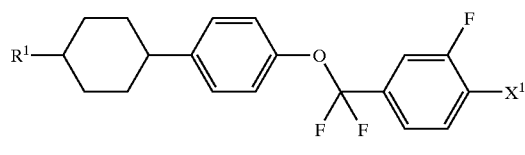
(3-42) 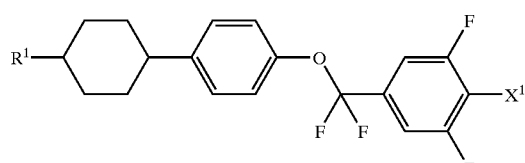
(3-43) 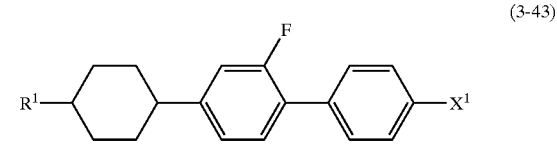
(3-44) 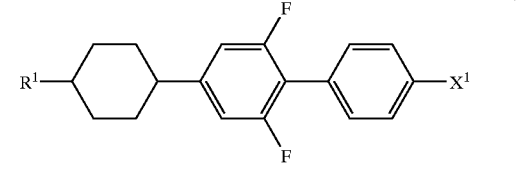
(3-45) 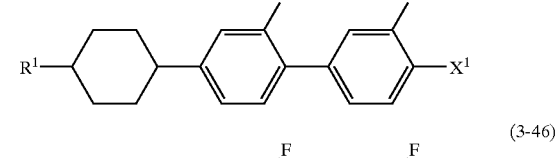
(3-46) 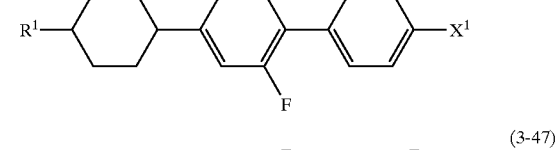
(3-47) 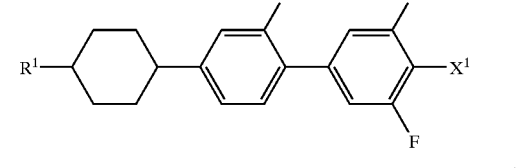
(3-48) 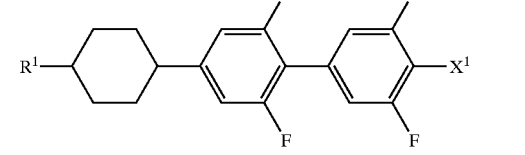

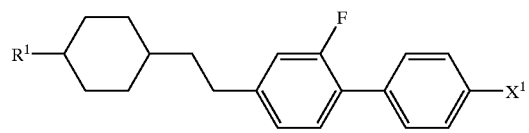
(3-49)
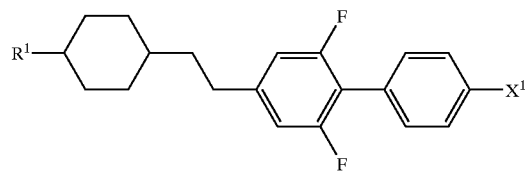
(3-50)
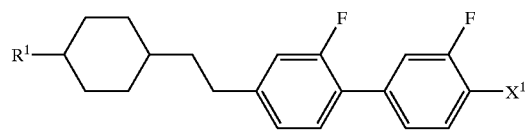
(3-51)
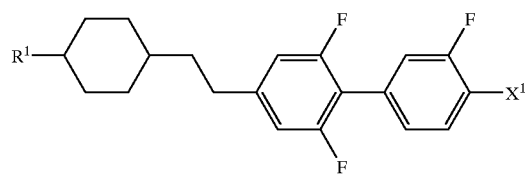
(3-52)
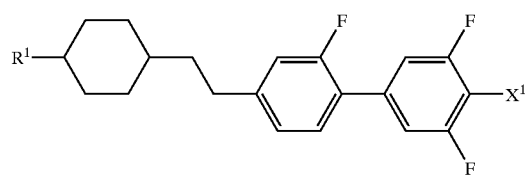
(3-53)
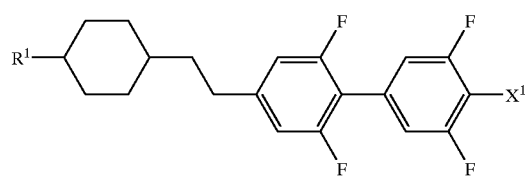
(3-54)
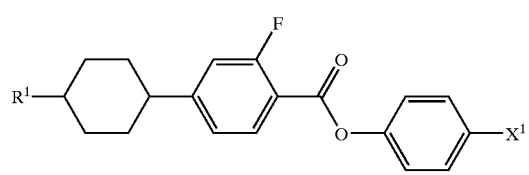
(3-55)
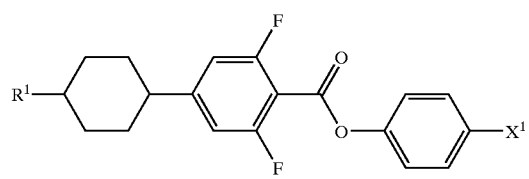
(3-56)
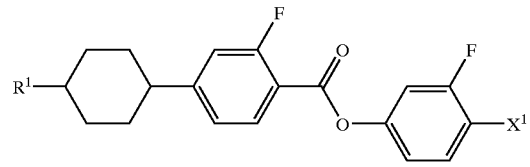
(3-57)
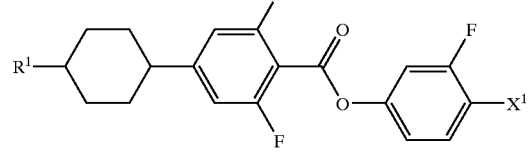
(3-58)
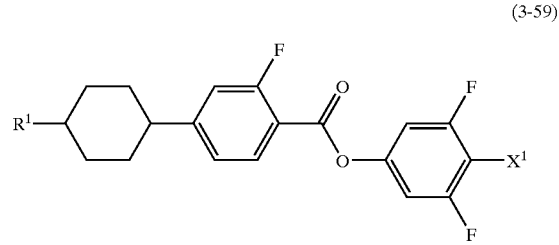
(3-59)
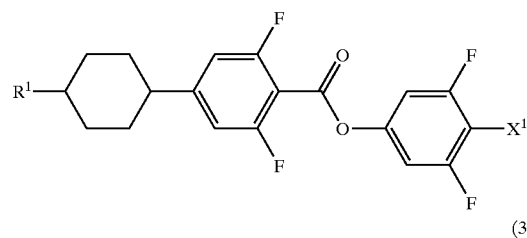
(3-60)
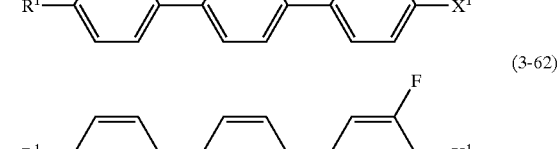
(3-61)
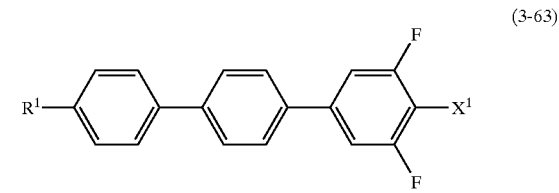
(3-62)
(3-63)
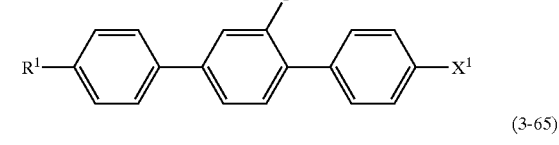
(3-64)
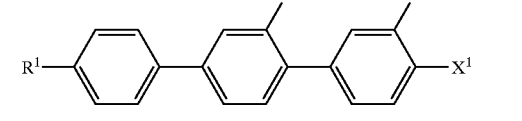
(3-65)

(3-66)
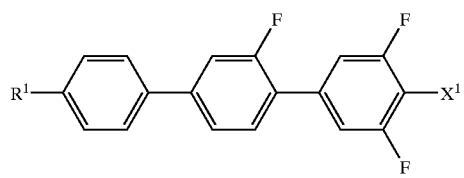
(3-67)
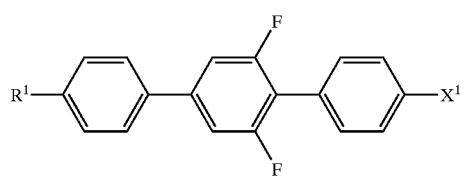
(3-68)
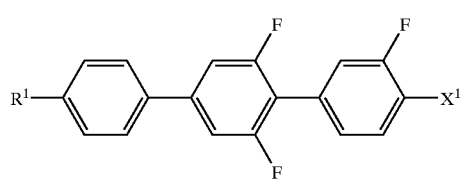
(3-69)
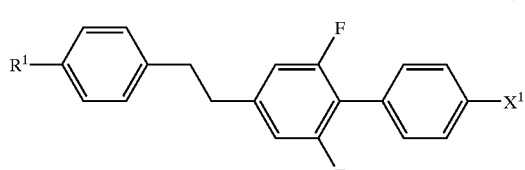
(3-70)
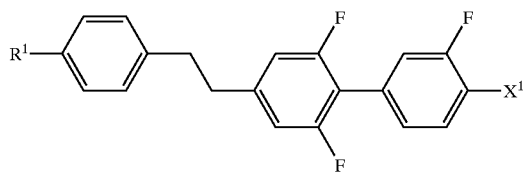
(3-71)
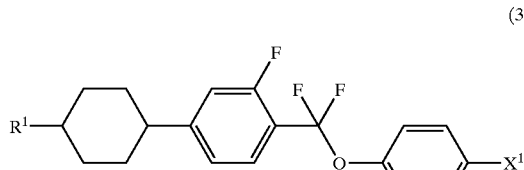
(3-72)
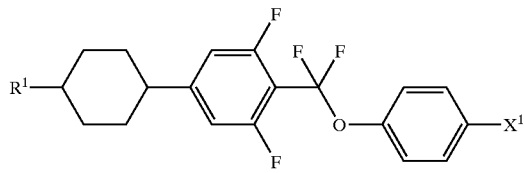
(3-73)
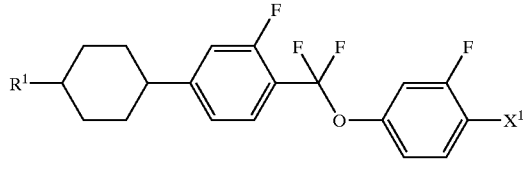
(3-74)
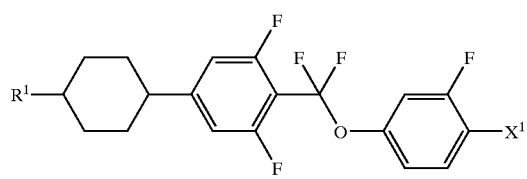
(3-75)
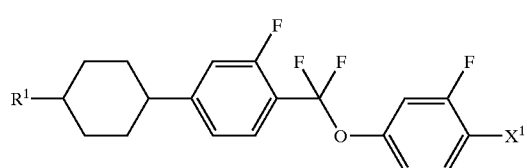
(3-76)
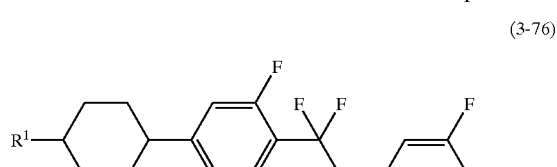
(3-77)
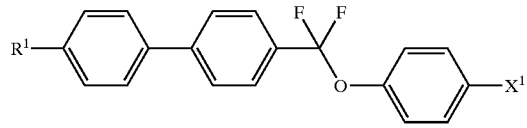
(3-78)
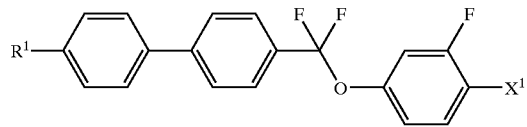
(3-79)
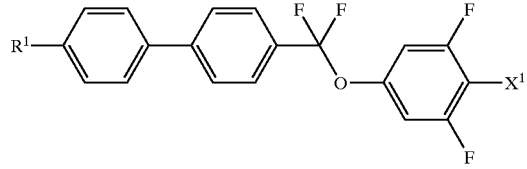
(3-80)
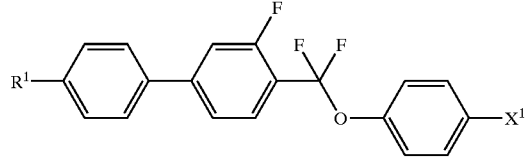
(3-81)
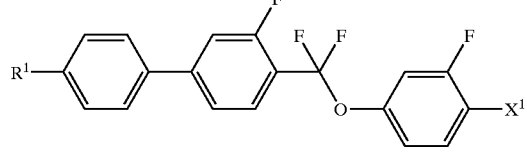

(3-82) 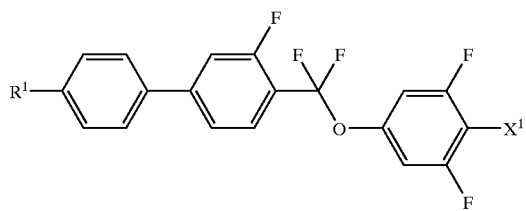
(3-83) 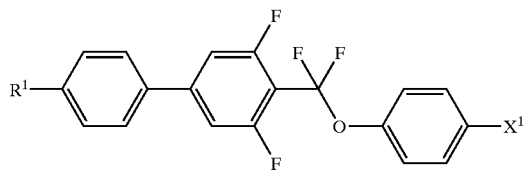
(3-84) 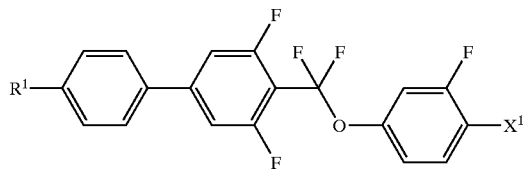
(3-85) 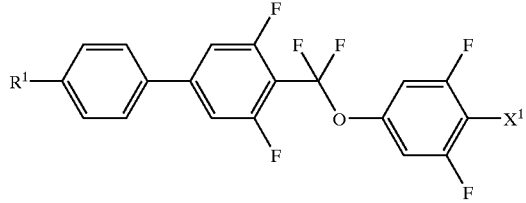
(3-86) 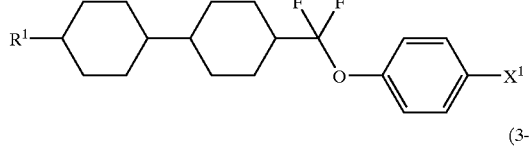
(3-87) 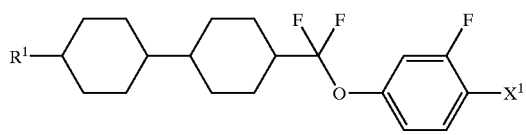
(3-88) 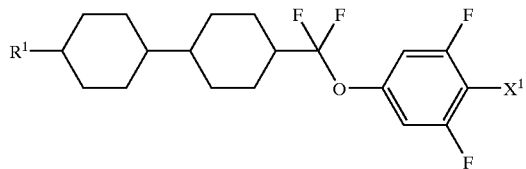
(3-89) 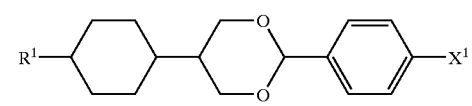
(3-90) 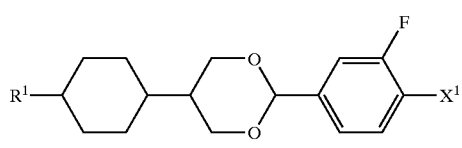
(3-91) 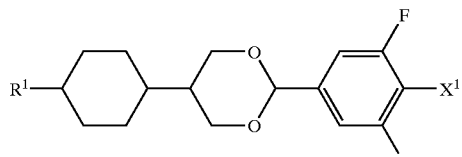
(3-92) 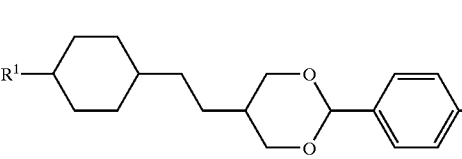
(3-93) 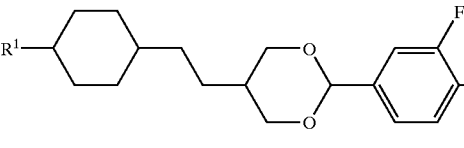
(3-94) 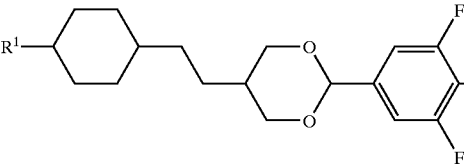
(3-95) 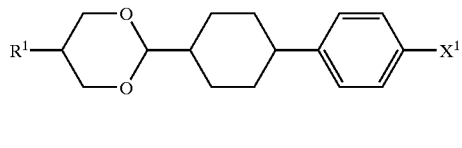
(3-96) 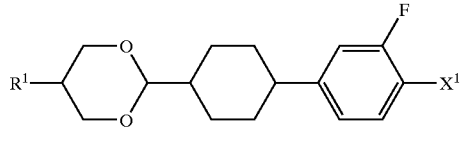
(3-97) 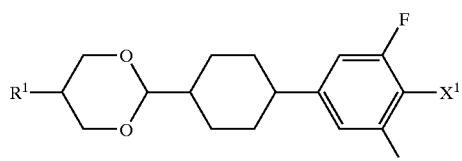
(4-1) 

(4-2) 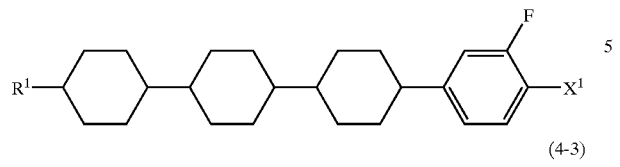
(4-3) 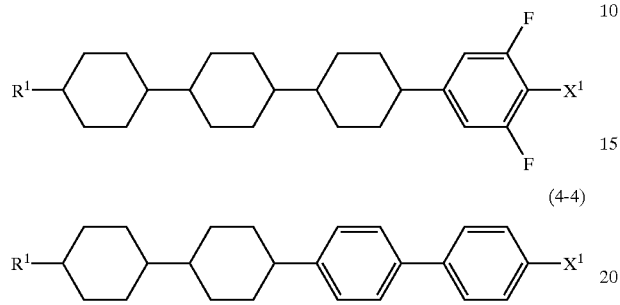
(4-4)
(4-5) 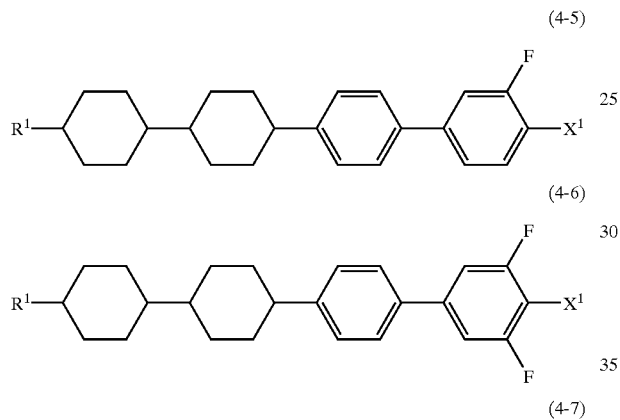
(4-6)
(4-7) 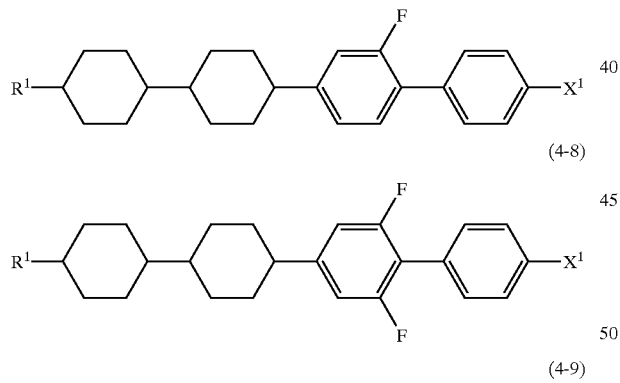
(4-8)
(4-9) 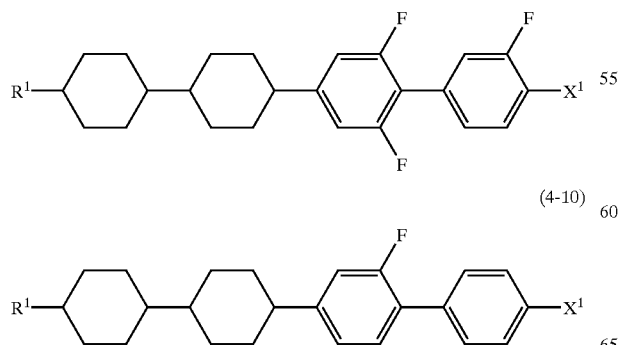
(4-10)
(4-11) 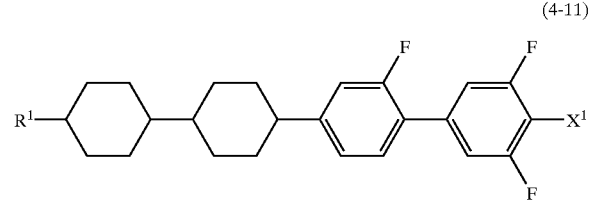
(4-12) 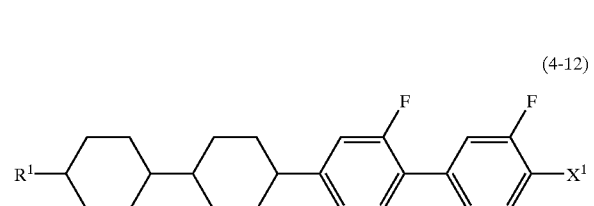
(4-13) 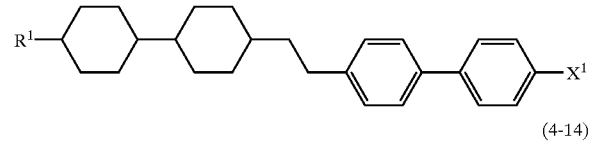
(4-14) 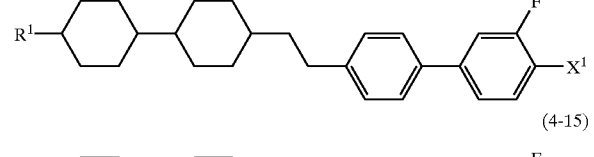
(4-15) 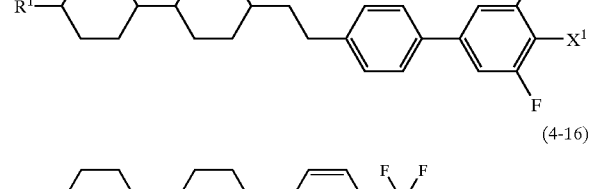
(4-16) 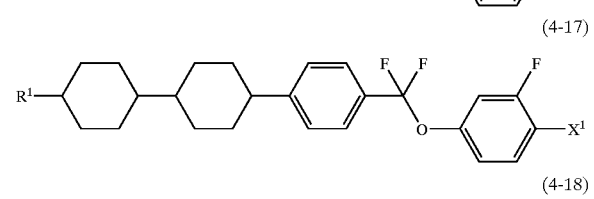
(4-17)
(4-18) 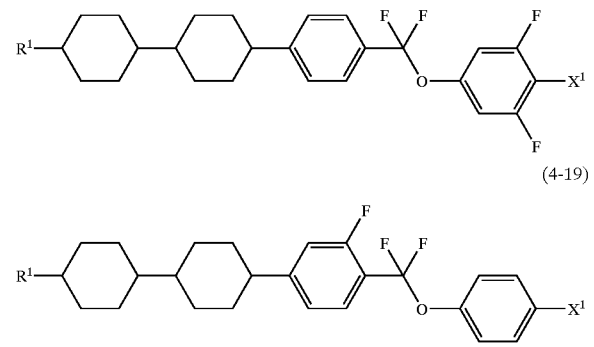
(4-19)

(4-20) 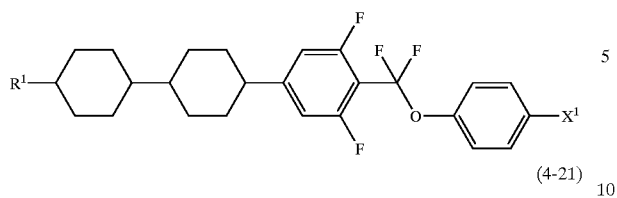

(4-21) 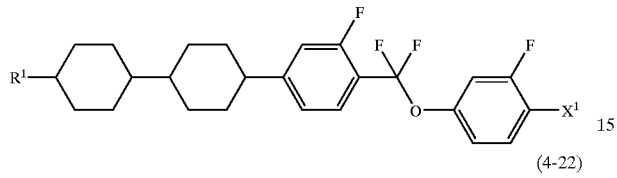

(4-22) 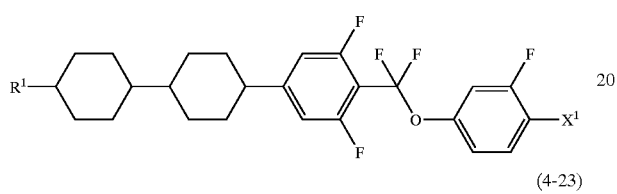

(4-23) 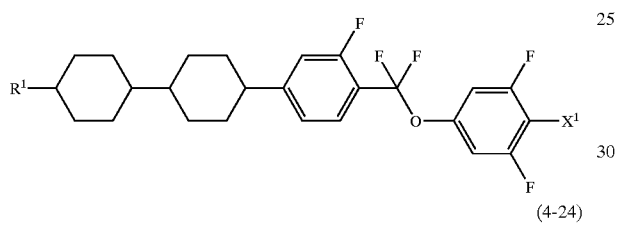

(4-24) 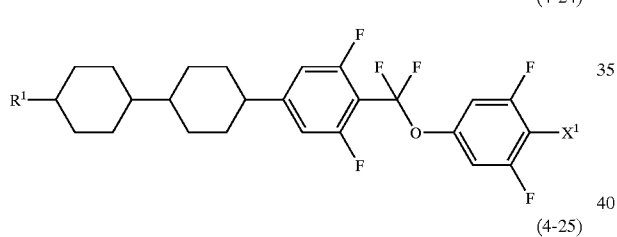

(4-25) 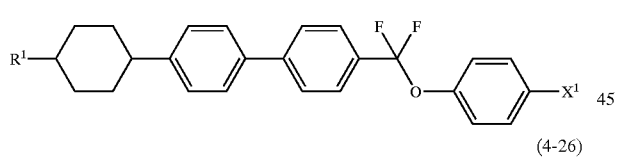

(4-26) 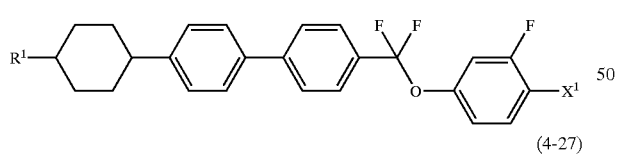

(4-27) 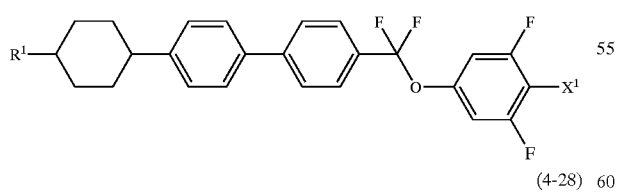

(4-28) 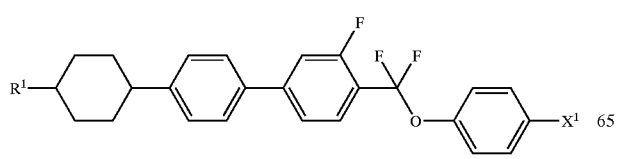

(4-29) 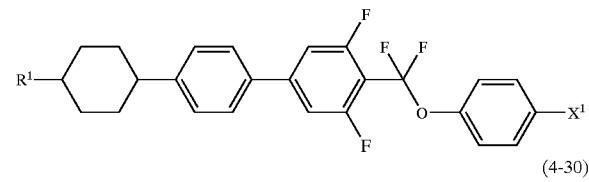

(4-30) 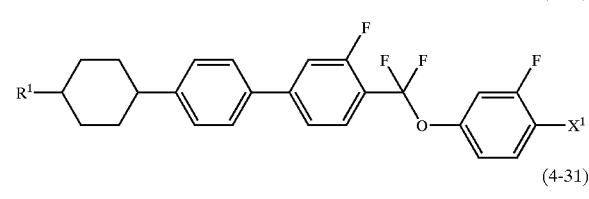

(4-31) 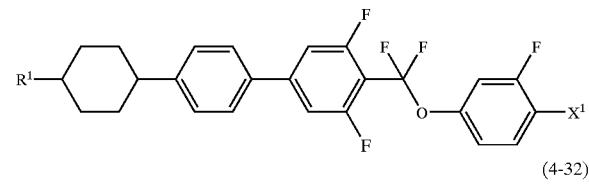

(4-32) 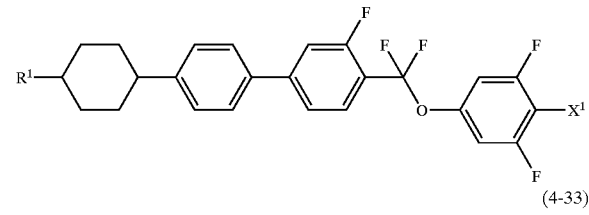

(4-33) 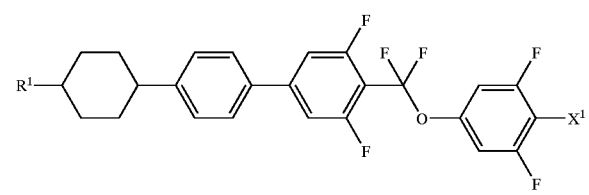

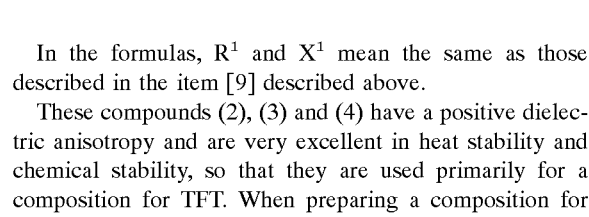

In the formulas, $R^1$ and $X^1$ mean the same as those described in the item [9] described above.

These compounds (2), (3) and (4) have a positive dielectric anisotropy and are very excellent in heat stability and chemical stability, so that they are used primarily for a composition for TFT. When preparing a composition for TFT, an amount of the above compound falls in a range of 0.1 to 99.9% by weight, preferably 10 to 97% by weight and more preferably 40 to 95% by weight based on the whole weight of a composition. The compounds (10) to (12) may further be added to the composition for the purpose of controlling a viscosity.

In the second B component described above, the suitable examples of the compounds (5) to (6) are (5-1) to (5-58) and (6-1) to (6-3) respectively.

(5-1) 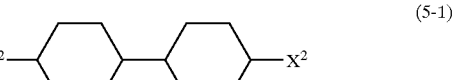

(5-2) 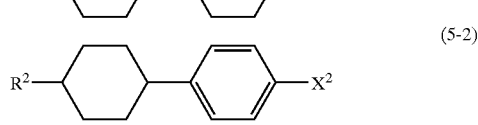

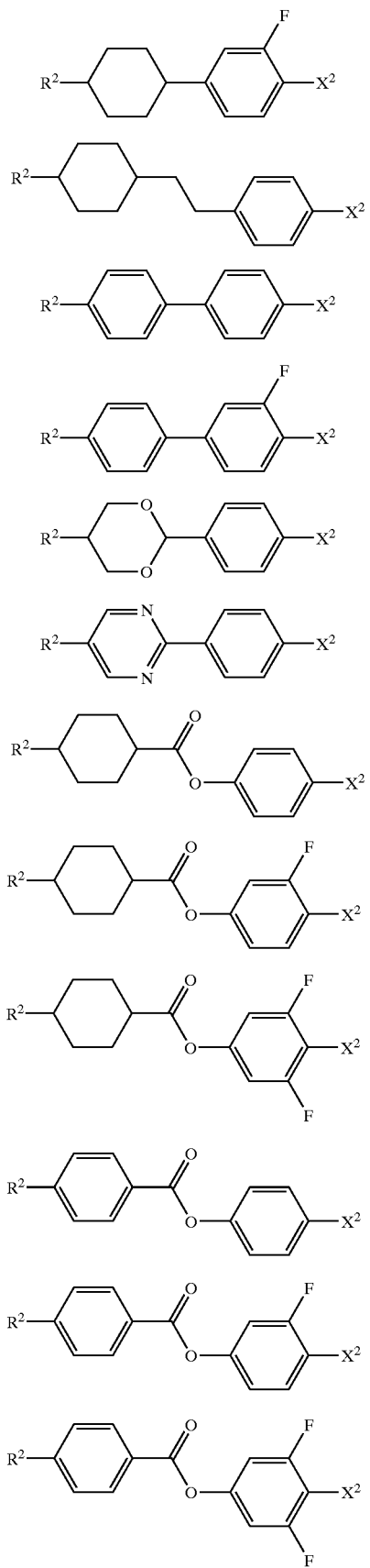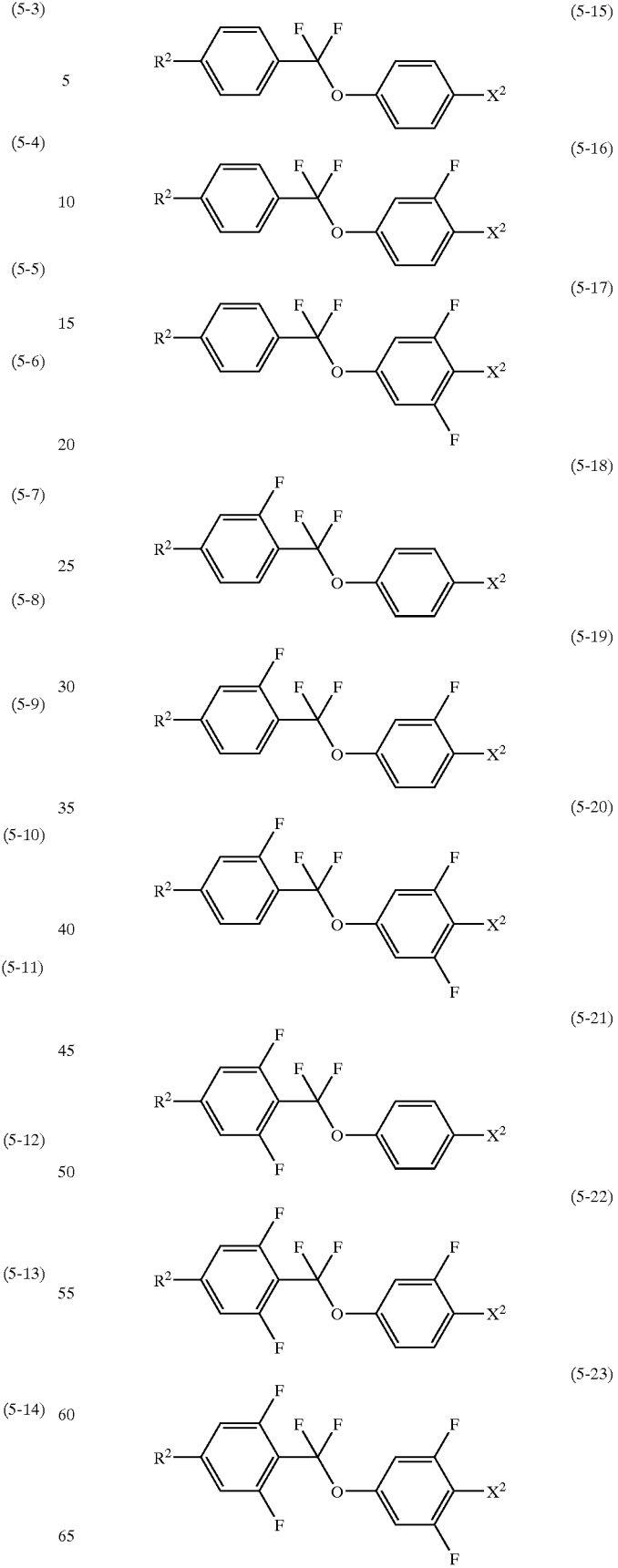

(5-24) through (5-43): chemical structure formulas (5-44)
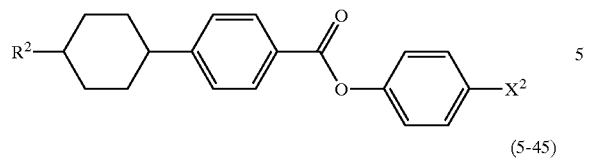
(5-45)
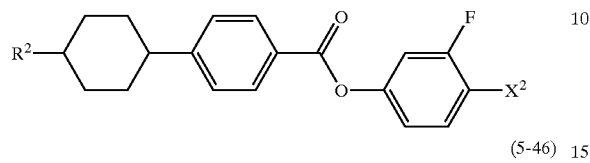
(5-46)
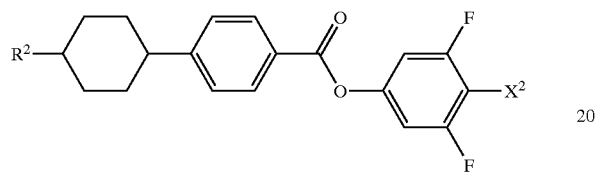
(5-47)
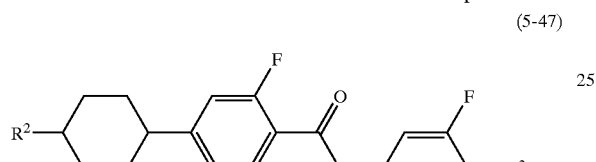
(5-48)
(5-49)
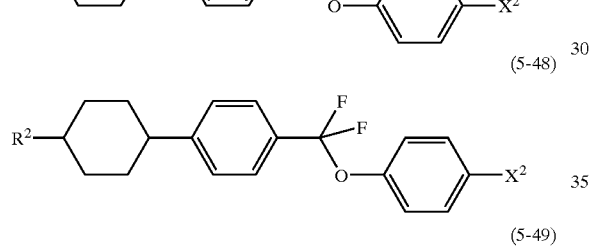
(5-50)
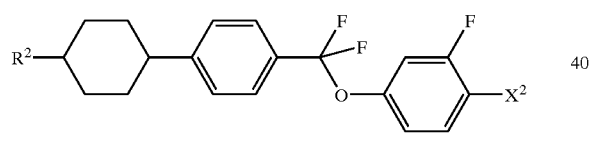
(5-51)
(5-52)
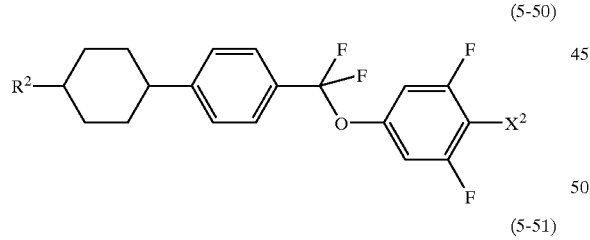
(5-53)
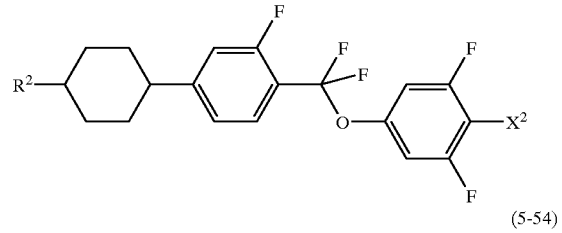
(5-54)
(5-55)
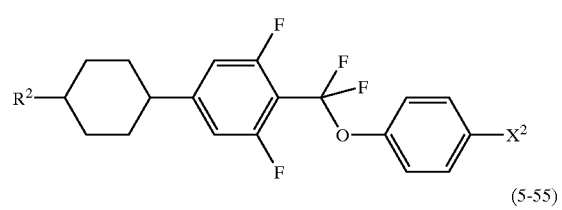
(5-56)
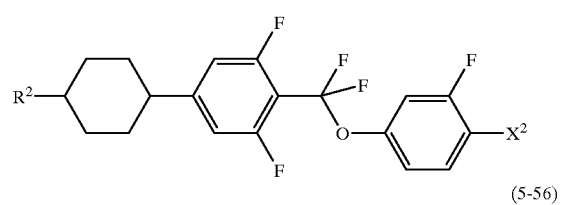
(5-57)
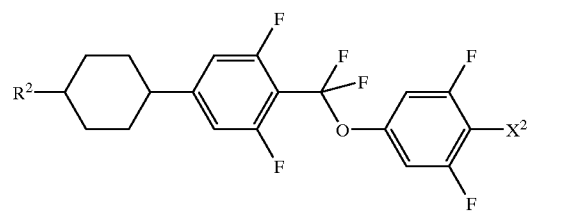
(5-58)
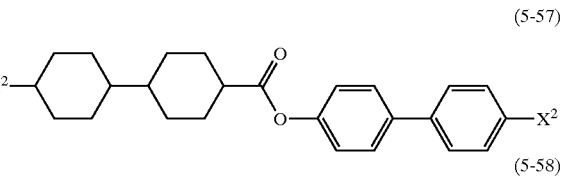
(6-1)
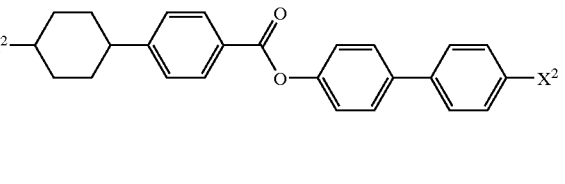
(6-2)
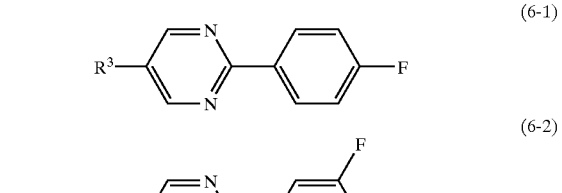
(6-3)
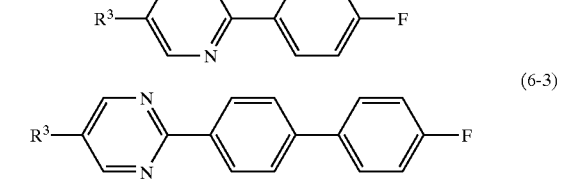
In the formulas, $R^2$, $R^3$ and $X^2$ mean the same as those described in the item [10] described above.

These compounds (5) and (6) have a very large positive dielectric anisotropy, so that they are used mainly for the compositions for STN or TN. These compounds are used particularly for the purpose of reducing a threshold voltage. They are used as well for the purposes of controlling a viscosity and a birefringence and expanding a liquid crystal phase temperature range and also for the purpose of improving steepness. When preparing a composition for STN or TN, a use amount of the compounds (5) and (6) falls in a range of 0.1 to 99.9% by weight, preferably 10 to 97% by weight and more preferably 40 to 95% by weight. A third component described later can further be added for the purpose of controlling a threshold voltage, a liquid crystal phase temperature range, a birefringence, a dielectric anisotropy and a viscosity.

When preparing a composition having a negative dielectric anisotropy which is suited for a vertical aligning mode (VA mode), preferably mixed is at least one compound (hereinafter referred to as a second C component) selected from the compounds (7) to (9). The suitable examples of the compounds (7) to (9) in the second C component are (7-1) to (7-3), (8-1) to (8-5) and (9-1) to (9-3) respectively.

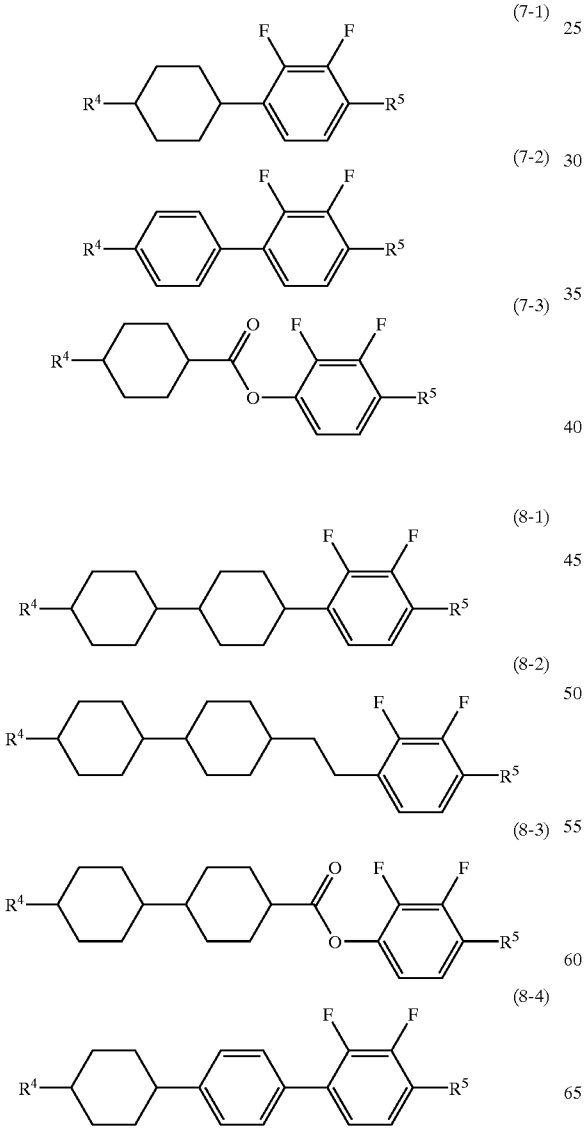

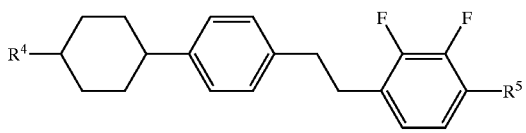

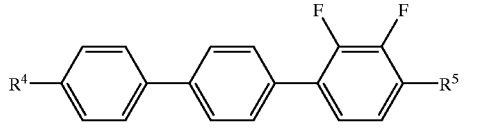

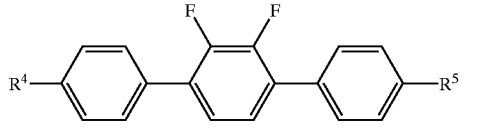

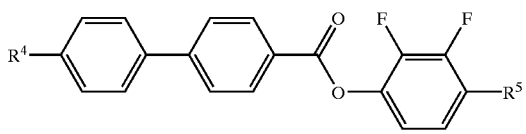

In the formulas, $R^4$ and $R^5$ mean the same as those described in the item [11] described above).

The compounds (7) to (9) have a negative dielectric anisotropy. The compound (7) having two six-membered rings is used mainly for the purpose of controlling a threshold voltage, a viscosity or a dielectric anisotropy. The compound (8) is used for the purpose of elevating the clearing point to expand a nematic range, reducing a threshold voltage and increasing a dielectric anisotropy.

The compounds (7) to (9) are used for a composition for a VA mode having a negative value of the dielectric anisotropy. If an amount thereof is increased, a composition is reduced in a threshold voltage but increased in a viscosity. Accordingly, as small amount as possible is preferred as long as a required value of the threshold voltage is satisfied. An amount of the compounds (7) to (9) is preferably 40% by weight or more, more preferably 50 to 90% by weight in the case of uses for a VA mode.

The compounds (7) to (9) are mixed in a certain case with a composition having a positive dielectric anisotropy for the purpose of controlling an elastic constant and a voltage transmission curve of the composition. An amount thereof is preferably 30% by weight or less.

In the third component described above, the suitable examples of the compounds (10) to (12) are (10-1) to (10-11), (11-1) to (11-12) and (12-1) to (12-6) respectively.

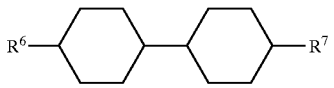

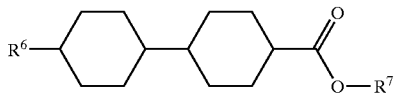

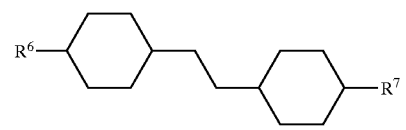 (10-3)
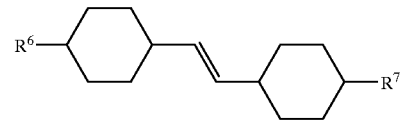 (10-4)
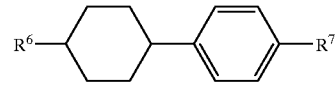 (10-5)
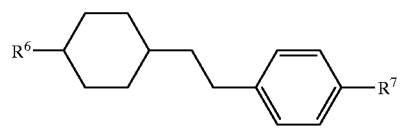 (10-6)
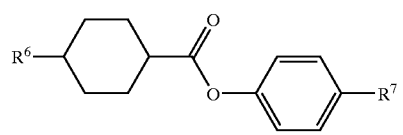 (10-7)
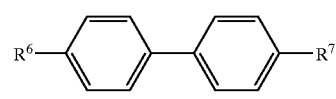 (10-8)
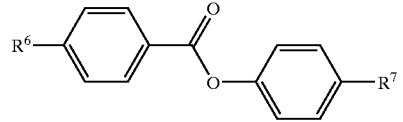 (10-9)
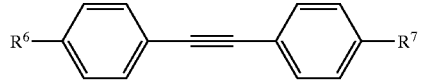 (10-10)
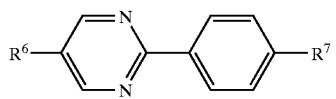 (10-11)
 (11-1)
 (11-4)
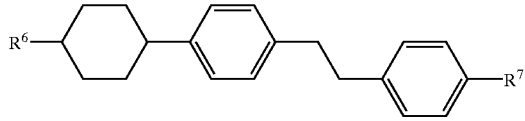 (11-5)
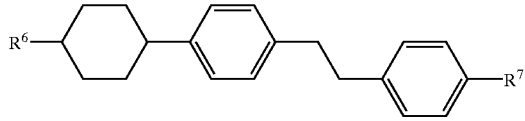 (11-6)
 (11-7)
 (11-8)
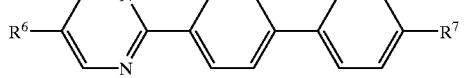 (11-9)
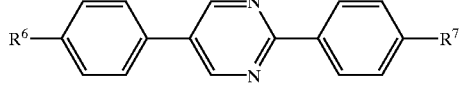 (11-10)
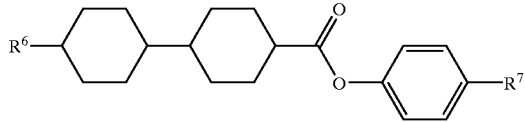 (11-11)
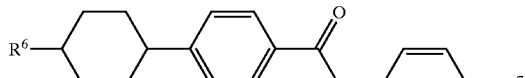 (11-12)
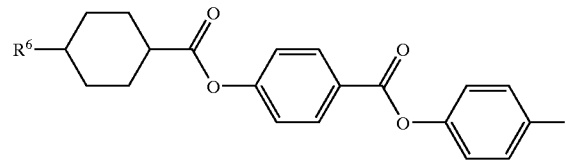 (12-1)
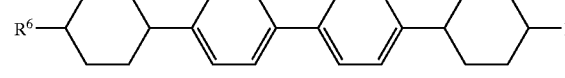 (12-2)
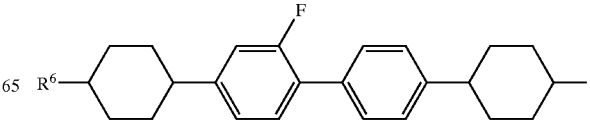

-continued (12-3)
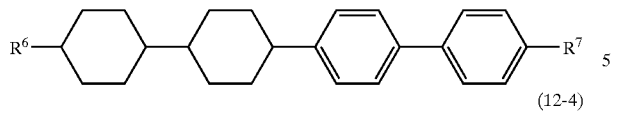

(12-4)
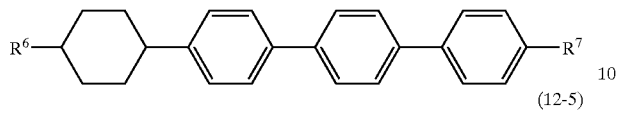

(12-5)
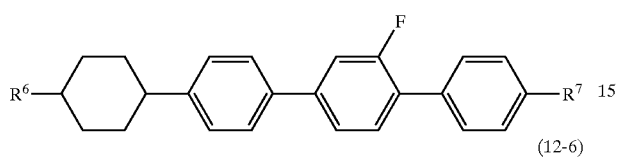

(12-6)
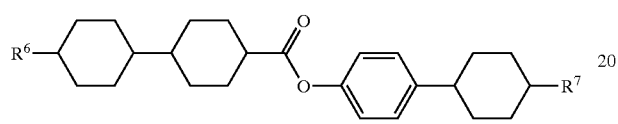

In the formulas, $R^6$ and $R^7$ mean the same as those described in the item [12] described above.

The compounds (10) to (12) have a small absolute value of a dielectric anisotropy and are close to neutrality. The compound (10) is used mainly for the purpose of controlling a viscosity or a dielectric anisotropy. Further, the compounds (11) and (12) are used for the purpose of elevating a clearing point to broaden a nematic range or controlling a dielectric anisotropy. If a use amount of the compounds (10) to (12) is increased, a composition is elevated in a threshold voltage and reduced in a viscosity. Accordingly, they are used preferably in a large amount as long as a required value of the threshold voltage is satisfied. An amount of the compounds (10) to (12) is 40% by weight or less, preferably 35% by weight or less in the case of uses for TFT. An amount in uses for STN or TN is 70% by weight or less, preferably 60% by weight or less.

A composition of the present invention contains 0.1 to 99% by weight of at least one of the compounds (1), whereby the excellent characteristics are revealed.

A composition is prepared by a publicly known method, for example, by dissolving various components by heating. Suitable additives are added if necessary, whereby the composition is optimized according to intended uses. Such additives are well known by a person averagely skilled in the art and described in detail in literatures. A chiral dopant induces a spiral structure of liquid crystal to provide distortion to thereby prevent inverse distortion. The following optically active compounds can be given as the examples of the chiral dopant.

Code: C15
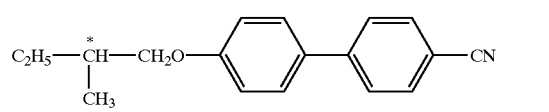

Code: CB15
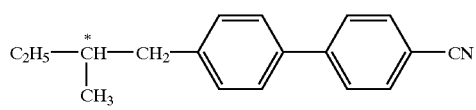

Code: CM21
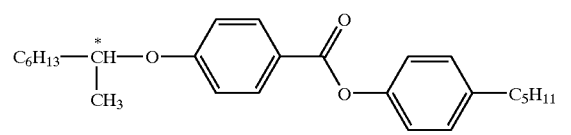

Code: CM33

Code: CM43L
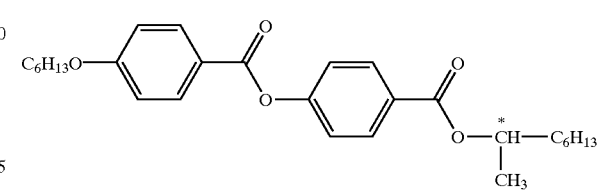

Code: CM45
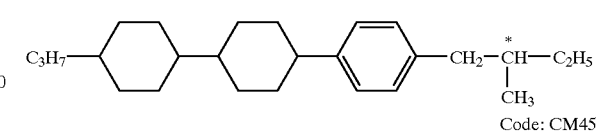

Code: CM47
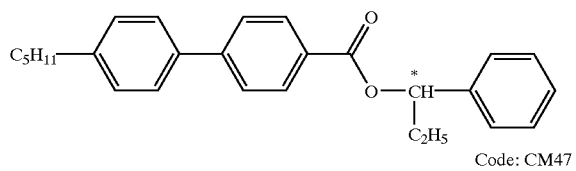

Code: CN
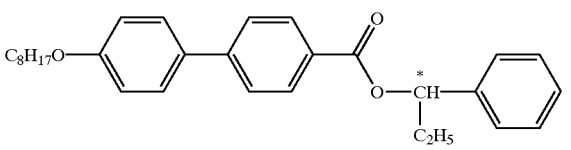

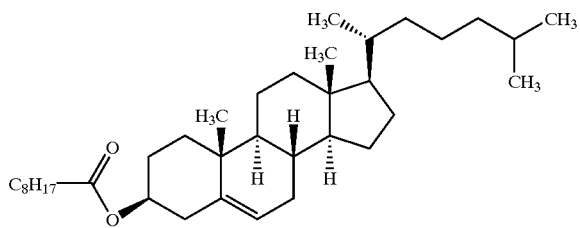

Usually, in the composition of the present invention, these optically active compounds are added to control a pitch in distortion. The pitch in distortion falls preferably in a range of 40 to 200 μm in the case of the compositions for TFT and TN. In the case of the composition for STN, it falls preferably in a range of 6 to 20 μm. Further, in the case of the composition for a bistable TN mode, it falls preferably in a range of 1.5 to 4 μm. Two or more kinds of the optically active compounds may be added for the purpose of controlling a temperature dependency of the pitch.

The composition of the present invention can also be used as a liquid crystal composition for a G-H mode by adding dichroic dyes such as merocyanines, styryls, azo, azomethines, azoxy, quinophthalones, anthraquinones, tetrazines, or the like. The composition according to the present invention can also be used as a composition for NCAP prepared by micro-capsulizing nematic liquid crystal and Polymer Dispersed Liquid Crystal Display (PDLCD) prepared by forming a three-dimensional network polymer in the liquid crystal, for example, Polymer Network Liquid Crystal Display (PNLCD). It can also be used as a composition for Electrically Controlled Birefringence (ECB) mode and a DS mode The compound (1) is produced by a conventional organic synthetic method. Suitably selected and combined are publicly known and conventional synthetic methods described in publications and magazines such as, for example, Organic Synthesis (John Wiley & Sons), Organic Reactions (John Wiley & Sons), Comprehensive Organic Synthesis (Pergamon Press) and Shin-Zikken Kagaku Koza (Maruzen).

Suitably selected and combined for introducing an Si part are publicly known and conventional synthetic methods described in publications and magazines such as, for example, Silicon in Organic Synthesis (Butterworths), Silicon Reagents for Organic Synthesis (Springer-Verlag) and Silicon Reagents in Organic Synthesis (Academic Press).

Routes shown below can be given as the specific examples.

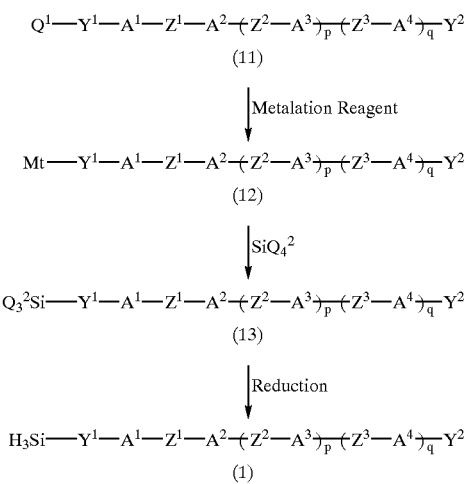

$Y^1, Y^2, A^1, A^2, A^3, A^4, Z^1, Z^2, Z^3$, p and q each described above are the same as those described in the item [1] described above. $Q^1$ is halogen, and $Q^2$ is halogen or alkoxy. Mt is lithium, potassium, halogenated magnesium or halogenated zinc.

First, the compound (11) is reacted with metal such as magnesium and various organic metal reagents such as alkyllithium compounds, alkylzinc compounds, alkylpotassium compounds and alkylcadmium compounds, whereby an organic metal reagent (12) is prepared. This is reacted with tretrasubstituted silane such as tetraalkoxysilane and tetrahalosilane to obtain a silicon compound (13). The compound (13) is subjected to reducing treatment with a suitable reducing agent such as lithium aluminum hydride, diisobutylaluminum hydride, sodium borohydride, sodium cyanoborohydride and diborane-THF, whereby it is derived into a compound (1). When other substituents in the compound (13) are reduced with these reducing agents, suitable additives are used or the reaction conditions are controlled to selectively reduce only $SiQ^2_3$.

EXAMPLES

The present invention shall be explained below in more details with reference to examples, but the present invention shall not be restricted by these examples. The structures of the compounds were confirmed by means of a nuclear magnetic resonance spectrum and a mass spectrum (hereinafter abbreviated as MS). M+ in MS represents a molecular ion peak. C shows a crystal phase; S shows a smectic phase; N shows a nematic phase; and Iso shows an isotropic liquid phase. A unit of a phase transition temperature is ° C. in all examples.

Example 1

Production of trans-1-pentyl-4-(trans-4-silylmethylcyclohexyl)cyclohexane (compound (No. 742) in which in Formula (1), $Y^1$ is methylene; $Y^2$ is pentyl; $A^1$ and $A^2$ are trans-1,4-cyclohexylene; $Z^1$ is a single bond; p and q are 0)

First Step:

A Grignard reagent was prepared from 100 ml of THF, magnesium (120 mmole) and trans-1-pentyl-4-(trans-4-chloromethylcyclohexyl)cyclohexane (100 mmole) under nitrogen atmosphere. A THF 100 ml solution of tetramethoxysilane (150 mmole) was heated to 65° C., and the Grignard reagent was added dropwise thereto. Further, the solution was stirred at the same temperature for 2 hours, and after left standing for cooling, the reaction mixture was filtered. The solvent was distilled off, and then trans-1-pentyl-4-(trans-4-trimethoxysilylmethyl-cyclohexyl)cyclohexane (65 mmole) was obtained by distillation under reduced pressure.

Second Step:

Lithium aluminum hydride (59 mmole) was suspended in 50 ml of THF on an ice bath under nitrogen atmosphere, and a THF 50 ml solution of trans-1-pentyl-4-(trans-4-trimethoxymethylsilylcyclohexyl)cyclohexane (65 mmole), which was obtained in the reaction of the first step, was added dropwise thereto. After stirring for one hour, water was added to the reaction mixture, and insoluble matters were filtered off. The separated organic layer was dried on anhydrous magnesium sulfate, and the solvent was distilled off under reduced pressure. The residue was purified with a silica gel column chromatography (eluent: heptane), and then it was recrystallized from heptane to obtain trans-1-pentyl-4-(trans-4-silylmethylcyclohexyl)cyclohexane (30 mmole).

Phase transition temperature: Cr −0.9 S 74.2 Iso MS: m/e=280 (M+).

Example 2

Production of 1-trifluoromethoxy-4-(trans-4-(trans-4-silylethylcyclohexyl)cyclohexyl)benzene (compound (No. 34) in which in Formula (1), $Y^1$ is ethylene;. $Y^2$ is —$OCF_3$; $A^1$ and $A^2$ are trans-1,4-cyclohexylene; $A^3$ is 1,4-phenylene; $Z^1$ and $Z^2$ are single bonds; p is 1, and q is 0)

First Step:

A Grignard reagent was prepared from 100 ml of THF, magnesium (120 mmole) and 1-trifluoromethoxy-4-(trans-4-(trans-4-chloroethylcyclohexyl)cyclohexyl)benzene (100 mmole) under nitrogen atmosphere. A THF 100 ml solution of tetramethoxysilane (150 mmole) was heated to 65° C., and the Grignard reagent was added dropwise thereto. The solution was stirred at the same temperature for 2 hours, and after left standing for cooling, the reaction mixture was filtered. The solvent was distilled off, and then 1-trifluoromethoxy-4-(trans-4-(trans-4-trimethoxysilylethylcyclohexyl)cyclohexyl)benzene (57 mmole) was obtained by distillation under reduced pressure.

Second Step:

Lithium aluminum hydride (51 mmole) was suspended in 50 ml of THF on an ice bath under nitrogen atmosphere, and a THF 50 ml solution of 1-trifluoromethoxy-4-(trans-4-(trans-4-trimethoxysilylethylcyclohexyl)cyclohexyl)-benzene (57 mmole), which was obtained in the reaction of the first step, was added dropwise thereto. After adding dropwise, the solution was stirred for one hour, and water was added to the reaction mixture, followed by filtering off insoluble matters. The separated organic layer was dried on anhydrous magnesium sulfate, and the solvent was distilled off under reduced pressure. The residue was purified with a silica gel column chromatography (eluent: mixed solvent of heptane/toluene), and it was recrystallized from heptane to obtain 1-trifluoromethoxy-4-(trans-4-(trans-4-silylethylcyclohexyl)cyclohexyl)benzene (26 mmole).

MS: m/e=384 (M+).

Example 3

Production of 1-ethoxy-2,3-difluoro-4-(trans-4-silylbutylcyclohexyl)benzene (compound (No. 676) in which in Formula (1), $Y^1$ is butylene; $Y^2$ is ethoxy; $A^1$ is trans-1,4-cyclohexylene, and $A^2$ is 2,3-difluoro-1,4-phenylene; $Z^1$ is a single bond; p and q are 0)

First Step:

A Grignard reagent was prepared from 100 ml of THF, magnesium (120 mmole) and 1-ethoxy-2,3-difluoro-4-(trans-4-chlorobutylcyclohexyl)benzene (100 mmole) under nitrogen atmosphere. A THF 100 ml solution of tetramethoxysilane (150 mmole) was heated to 65° C., and the Grignard reagent was added dropwise thereto. Further, the solution was stirred at the same temperature for 2 hours, and after left standing for cooling, the reaction mixture was filtered. The solvent was distilled off, and then 1-ethoxy-2,3-difluoro-4-(trans-4-trimethoxysilyl-butylcyclohexyl)benzene (58 mmole) was obtained by distillation under reduced pressure.

Second Step:

Lithium aluminum hydride (52 mmole) was suspended in 50 ml of THF on an ice bath under nitrogen atmosphere, and a THF 50 ml solution of 1-ethoxy-2,3-difluoro-4-(trans-4-trimethoxysilylbutylcyclohexyl)benzene (58 mmole), which was obtained in the reaction of the first step, was added dropwise thereto. After adding dropwise, the solution was stirred for one hour, and water was added to the reaction mixture, followed by filtering off insoluble matters. The separated organic layer was dried on anhydrous magnesium sulfate, and the solvent was distilled off under reduced pressure. The residue was purified with a silica gel column chromatography (eluent: mixed solvent of heptane/toluene), and it was recrystallized from heptane to obtain 1-ethoxy-2,3-difluoro-4-(trans-4-silylbutylcyclohexyl)benzene (25 mmole). MS: m/e=326 (M+).

Example 4

Production of 2-fluoro-1-(4-propylphenyl)-4-(4-silylethylphenyl)benzene (compound (No. 861) in which in Formula (1), $Y^1$ is ethylene; $Y^2$ is propyl; $A^1$ and $A^3$ are 1,4-phenylene; $A^2$ is 2-fluoro-1,4-phenylene; $Z^1$ and $Z^2$ are single bonds; p is 1, and q is 0)

First Step:

A Grignard reagent was prepared from 100 ml of THF, magnesium (120 mmole) and 2-fluoro-1-(4-propylphenyl)-4-(4-chloroethylphenyl)benzene (100 mmole) under nitrogen atmosphere. A THF 100 ml solution of tetramethoxysilane (150 mmole) was heated to 65° C., and the Grignard reagent was added dropwise thereto. Further, the solution was stirred at the same temperature for 2 hours, and after left standing for cooling, the reaction mixture was filtered. The solvent was distilled off, and then 2-fluoro-1-(4-propylphenyl)-4-(4-trimethoxysilyl-ethylphenyl)benzene (59 mmole) was obtained by distillation under reduced pressure.

Second Step:

Lithium aluminum hydride (53 mmole) was suspended in 50 ml of THF on an ice bath under nitrogen atmosphere, and a THF 50 ml solution of 2-fluoro-(4-propylphenyl)-4-1-(4-trimethoxysilylethylphenyl)benzene (59 mmole), which was obtained in the reaction of the first step, was added dropwise thereto. After adding dropwise, the solution was stirred for one hour, and water was added to the reaction mixture, followed by filtering off insoluble matters. The separated organic layer was dried on anhydrous magnesium sulfate, and the solvent was distilled off under reduced pressure. The residue was purified with a silica gel column chromatography (eluent: heptane), and it was recrystallized from heptane to obtain 2-fluoro-1-(4-propylphenyl)-4-(4-silylethylphenyl)benzene (22 mmole). MS: m/e=348 (M+).

The following compounds were produced according to the methods of Examples 1 to 4.

| | $Y^1$ | $A^1$ | $Z^1$ | $A^2$ |
|---|---|---|---|---|
| 1 | —C$_2$H$_4$— | phenylene | — | phenylene |
| 2 | —CH$_2$O— | phenylene | — | phenylene |
| 3 | —C$_3$H$_6$— | phenylene | — | phenylene |
| 4 | —C$_4$H$_8$— | phenylene | — | phenylene |
| 5 | —C$_3$H$_6$O— | phenylene | — | phenylene |

-continued
| | Y¹ | A¹ | Z¹ | A² |
|---|---|---|---|---|
| 6 | —C₃H₆ | 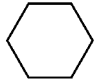 | — | 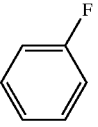 |
| 7 | —C₄H₈ | 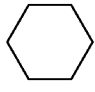 | — | 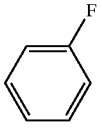 |
| 8 | —C₂H₄ | 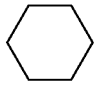 | — |  |
| 9 | —C₂H₄ | 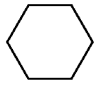 | — |  |
| 10 | 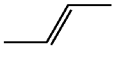 |  | — | 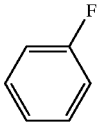 |
| 11 | 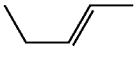 | 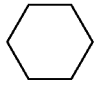 | — | 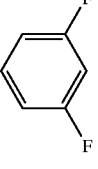 |
| 12 | —C₂H₄ | 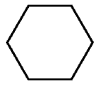 | — | 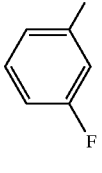 |
| 13 | —C₄H₈ | 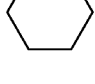 | — | 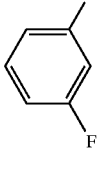 |
| 14 | 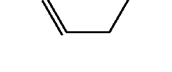 | 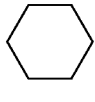 | — | 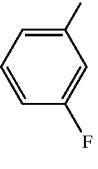 |

-continued
| | Y¹ | A¹ | Z¹ | A² |
|---|---|---|---|---|
| 15 | —CH₂O— | 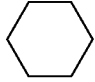 | — | 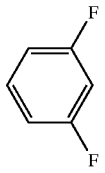 |
| 16 | —C₂H₄— | 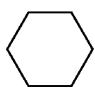 | 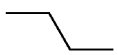 | 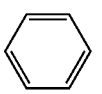 |
| 17 | —CH₂O— |  | 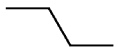 |  |
| 18 | —C₃H₆O— | 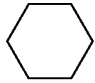 |  | 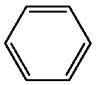 |
| 19 | —C₃H₆— |  | 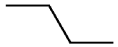 |  |
| 20 | —C₃H₆— | 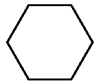 |  | 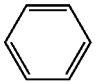 |
| 21 | —C₂H₄— |  | 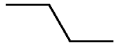 | 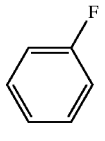 |
| 22 | —C₄H₈— | 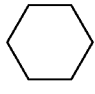 | 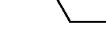 | 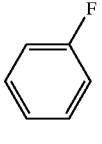 |
| 23 | —C₄H₈— |  | 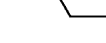 | 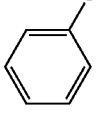 |
| 24 | 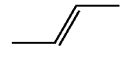 |  | 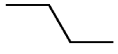 | 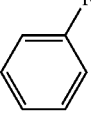 |
| 25 | —C₂H₄— |  | 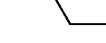 | 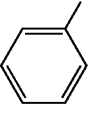 |

-continued
| | Y¹ | A¹ | Z¹ | A² |
|---|---|---|---|---|
| 26 | —C₂H₄O— | 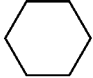 | 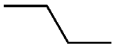 | 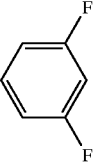 |
| 27 | —C₂H₄— | 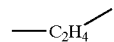 | 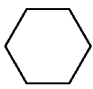 | 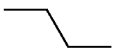 |
| 28 | —C₄H₈— | 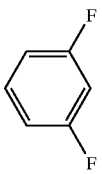 |  | 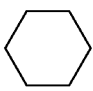 |
| 29 | —CH₂— | 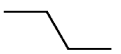 | 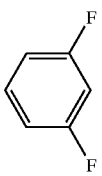 | 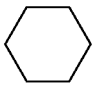 |
| 30 | 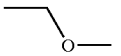 | 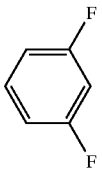 | 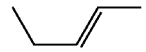 | 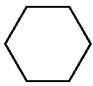 |
| 31 | —C₃H₆— | 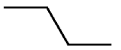 | — | 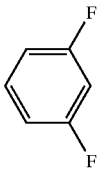 |
| 32 | —CH₂O— | 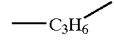 | — | 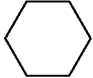 |
| 33 | 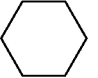 | 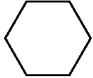 | — |  |
| 34 | —C₂H₄— | 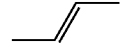 | — |  |
| 35 | —C₂H₄— |  | — | 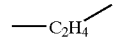 |
| 36 | —C₂H₄— |  | — |  |

-continued
| | Y¹ | A¹ | Z¹ | A² |
|---|---|---|---|---|
| 37 | —C₂H₄O— | 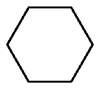 | — | 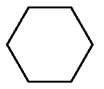 |
| 38 | —C₄H₈ | 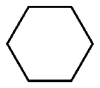 | — | 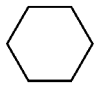 |
| 39 | —C₃H₆— | 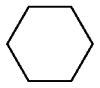 | — | 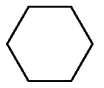 |
| 40 | —C₂H₄ |  | — |  |
| 41 | —C₂H₄— |  | — |  |
| 42 | —C₄H₈ | 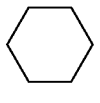 | — | 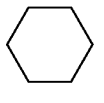 |
| 43 | —C₂H₄ | 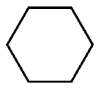 | — | 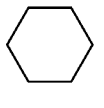 |
| 44 | —C₃H₆— |  | — |  |
| 45 | —C₄H₈ |  | — |  |
| 46 | —C₂H₄ |  | — |  |
| 47 | 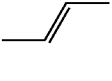 |  | — |  |
| 48 | —CH₂O— |  | — |  |
| 49 | —C₂H₄ |  | — |  |
| 50 | —C₃H₆ |  | — |  |
| 51 | —C₂H₄ |  | — |  |

-continued
| | Y¹ | A¹ | Z¹ | A² |
|---|---|---|---|---|
| 52 | —C₃H₆— | 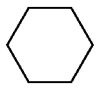 | — | 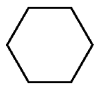 |
| 53 | —C₄H₈— | 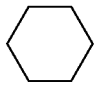 | — | 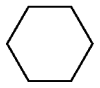 |
| 54 | —C₃H₆O— |  | — |  |
| 55 |  | 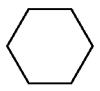 | — | 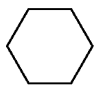 |
| 56 | —C₂H₄— | 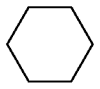 | — |  |
| 57 | —C₄H₈— |  | — |  |
| 58 | —C₂H₄— |  | — |  |
| 59 | —CH₂— |  | — |  |
| 60 | —C₂H₄O— |  | — |  |
| 61 | —C₂H₄— |  | 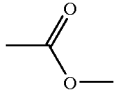 |  |
| 62 | —CH₂OCH₂— |  | 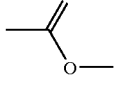 |  |
| 63 | —C₄H₈— |  | 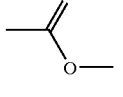 | 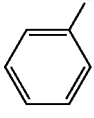 |
| 64 | —C₂H₄— |  | 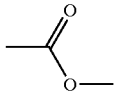 |  |

-continued

| | Y¹ | A¹ | Z¹ | A² |
|---|---|---|---|---|
| 65 | —C₃H₆— | ⬡ | —C(=O)O— | 2,4-difluorophenyl |
| 66 | —C₂H₄— | ⬡ | — | ⬡ |
| 67 | —C₃H₆— | ⬡ | — | ⬡ |
| 68 | —C₄H₈— | ⬡ | — | ⬡ |
| 69 | —C₃H₆O— | ⬡ | — | ⬡ |
| 70 | —CH=CH— | ⬡ | — | ⬡ |
| 71 | —C₂H₄— | ⬡ | — | ⬡ |
| 72 | —C₄H₈— | ⬡ | — | ⬡ |
| 73 | —C₂H₄— | ⬡ | — | ⬡ |
| 74 | —CH₂— | ⬡ | — | ⬡ |
| 75 | —C₂H₄O— | ⬡ | — | ⬡ |
| 76 | —C₂H₄— | ⬡ | —CH₂CH₂— | ⬡ |
| 77 | —CH₂CH=CH— | ⬡ | —CH₂CH₂— | ⬡ |
| 78 | —C₂H₄— | ⬡ | —CH₂CH₂— | ⬡ |

-continued

| | Y¹ | A¹ | Z¹ | A² |
|---|---|---|---|---|
| 79 | —CH₂O— | ⬡ | ⌐ | ⬡ |
| 80 | —C₃H₆— | ⬡ | ⌐ | ⬡ |
| 81 | —C₂H₄— | ⬡ | ⌐ | ⬡ |
| 82 | —C₃H₆O— | ⬡ | ⌐ | ⬡ |
| 83 | —C₄H₈— | ⬡ | ⌐ | ⬡ |
| 84 | —CH=CH— | ⬡ | ⌐ | ⬡ |
| 85 | —C₃H₆— | ⬡ | ⌐ | ⬡ |
| 86 | —C₂H₄— | ⬡ | ⌐ | ⬡ |
| 87 | —C₄H₈— | ⬡ | ⌐ | ⬡ |
| 88 | —C₂H₄— | ⬡ | ⌐ | ⬡ |
| 89 | —CH₂— | ⬡ | ⌐ | ⬡ |
| 90 | —C₂H₄O— | ⬡ | ⌐ | ⬡ |
| 91 | —C₂H₄— | ⬡ | =/ | ⬡ |
| 92 | —CH₂—CH=CH— | ⬡ | =/ | ⬡ |
| 93 | —CH₂O— | ⬡ | =/ | ⬡ |

-continued
| | Y¹ | A¹ | Z¹ | A² |
|---|---|---|---|---|
| 94 | —C₂H₄— |  | 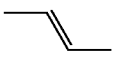 |  |
| 95 | —C₃H₆— | 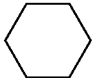 |  |  |
| 96 | —C₂H₄— |  | 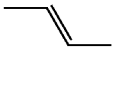 |  |
| 97 | —C₃H₆O— | 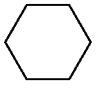 |  |  |
| 98 | —C₄H₈— |  | 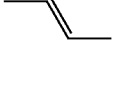 |  |
| 99 | —C₃H₆— | 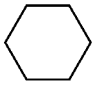 |  | 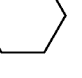 |
| 100 | —C₂H₄— |  | 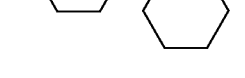 |  |
| 101 | —C₄H₈— |  | 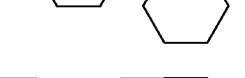 |  |
| 102 | 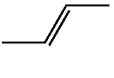 |  | 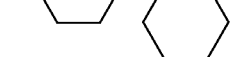 |  |
| 103 | —C₂H₄— |  | 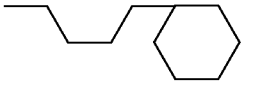 |  |
| 104 | —CH₂— |  | 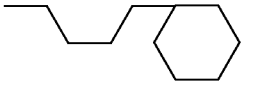 |  |
| 105 | —C₂H₄— |  | 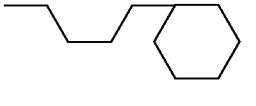 |  |
| 106 | —C₂H₄— |  | — |  |
| 107 | —CH₂OC₂H₄— |  | — |  |
| 108 | 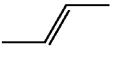 |  | — |  |

-continued
| | Y¹ | A¹ | Z¹ | A² |
|---|---|---|---|---|
| 109 | —C₄H₈ |  | — |  |
| 110 | —C₃H₆ |  | — |  |
| 111 | —C₂H₄ |  | — |  |
| 112 | —C₂H₄ |  | — |  |
| 113 | —C₃H₆ |  | — |  |
| 114 | —CH₂O— |  | — |  |
| 115 | —C₂H₄ |  | — |  |
| 116 | —C₂H₄O— |  | — |  |
| 117 | —CH₂— |  | — |  |
| 118 | —C₂H₄ |  | — |  |
| 119 | 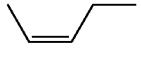 |  | — |  |
| 120 | —C₃H₆O— |  | — |  |
| 121 | —C₂H₄ |  | 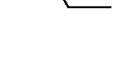 |  |
| 122 | —CH₂OC₂H₄ |  |  |  |
| 123 | 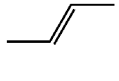 |  | 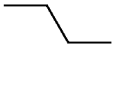 |  |

-continued
| | Y¹ | A¹ | Z¹ | A² |
|---|---|---|---|---|
| 124 | —C₄H₈ |  | 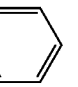 | 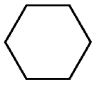 |
| 125 | —C₂H₄ | 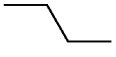 |  | 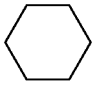 |
| 126 | —C₂H₄ | 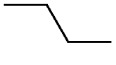 | 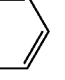 | 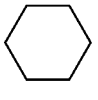 |
| 127 | —C₃H₆ | 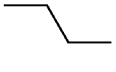 | 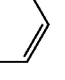 | 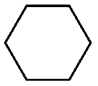 |
| 128 | —C₄H₈ |  | 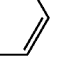 | 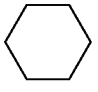 |
| 129 | —CH₂O— | 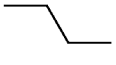 |  |  |
| 130 | —C₂H₄ |  |  |  |
| 131 | —C₂H₄O— |  |  |  |
| 132 | —C₂H₄— |  |  |  |
| 133 | —C₂H₄ |  |  | 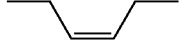 |
| 134 | 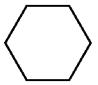 |  |  |  |
| 135 | —C₃H₆O— |  |  |  |
| 136 | —C₂H₄ |  |  |  |
| 137 | —C₂H₄ |  |  |  |
| 138 | —C₄H₈ |  |  |  |

|     | Y¹ | A¹ | Z¹ | A² |
| --- | --- | --- | --- | --- |
| 139 | —CH=CH—CH₂— | cyclohexyl | —(CH₂)₃— | phenyl |
| 140 | —C₂H₄— | cyclohexyl | —(CH₂)₃— | phenyl |
| 141 | —C₂H₄— | cyclohexyl | — | phenyl |
| 142 | —C₃H₆— | cyclohexyl | — | phenyl |
| 143 | —C₂H₄— | cyclohexyl | — | phenyl |
| 144 | —CH₂O— | cyclohexyl | — | phenyl |
| 145 | —C₂H₄— | cyclohexyl | — | phenyl |
| 146 | —C₂H₄O— | cyclohexyl | —C(=O)O— | phenyl |
| 147 | —C₄H₈— | cyclohexyl | —C(=O)O— | phenyl |
| 148 | —C₂H₄— | cyclohexyl | —C(=O)O— | phenyl |
| 149 | —CH₂—CH=CH—CH₂— | cyclohexyl | —C(=O)O— | phenyl |
| 150 | —C₂H₄— | cyclohexyl | —C(=O)O— | phenyl |
| 151 | —C₃H₆— | cyclohexyl | — | phenyl |
| 152 | —C₄H₈— | cyclohexyl | — | phenyl |

|     | Y¹ | A¹ | Z¹ | A² |
|-----|----|----|----|----|
| 153 | —CH₂O— | 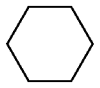 | — | 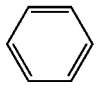 |
| 154 | —C₂H₄ |  | — |  |
| 155 | —C₂H₄ | 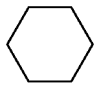 | — | 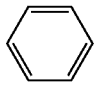 |
| 156 | —C₂H₄ | 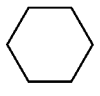 | — | 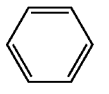 |
| 157 | —C₃H₆ | 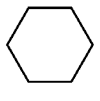 | — | 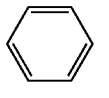 |
| 158 | —C₄H₈ | 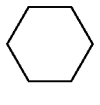 | — | 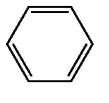 |
| 159 | —CH₂O— | 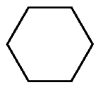 | — | 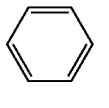 |
| 160 | —C₂H₄ | 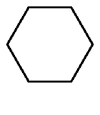 | — | 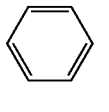 |
| 161 | —C₂H₄ | 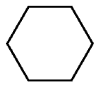 | — | 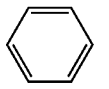 |
| 162 |  |  | — |  |
| 163 | —C₂H₄ |  | — |  |
| 164 | —CH₂— |  | — |  |
| 165 | —C₂H₄O— |  | — |  |
| 166 | —C₂H₄ |  | — |  |
| 167 | —CH₂O— |  | — |  |

-continued
| | Y¹ | A¹ | Z¹ | A² |
|---|---|---|---|---|
| 168 | —C₂H₄— | 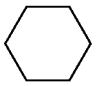 | — | 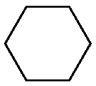 |
| 169 | —C₂H₄— | 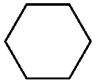 | — | 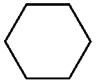 |
| 170 | —C₄H₈— | 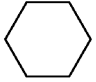 | — | 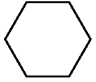 |
| 171 | —C₂H₄— | 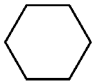 | — | 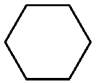 |
| 172 | 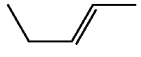 | 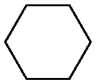 | — | 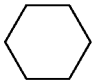 |
| 173 | —C₄H₈— | 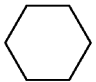 | — | 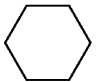 |
| 174 | —C₃H₆— | 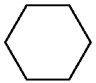 | — | 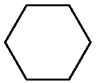 |
| 175 | —C₃H₆O— | 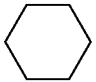 | — | 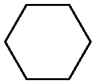 |
| 176 | —C₂H₄— | 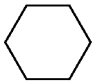 | — |  |
| 177 | —C₄H₈— |  | — |  |
| 178 | —C₂H₄— |  | — |  |
| 179 | —C₂H₄O— |  | — |  |
| 180 | —C₄H₈— |  | — |  |
| 181 | —C₂H₄— |  | — | 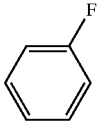 |

-continued
| | Y¹ | A¹ | Z¹ | A² |
|---|---|---|---|---|
| 182 | —C₄H₈— | 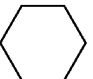 | — | 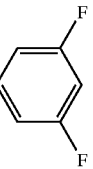 |
| 183 | 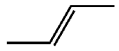 | 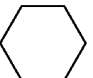 | — | 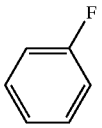 |
| 184 | —C₂H₄— | 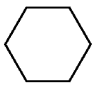 | — | 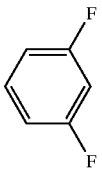 |
| 185 | —C₂H₄— | 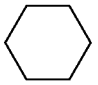 | — | 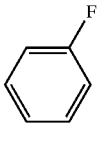 |
| 186 | —C₂H₄— | 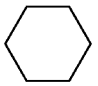 | — | 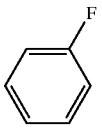 |
| 187 | 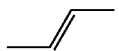 | 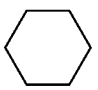 | — | 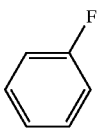 |
| 188 | —C₂H₄— | 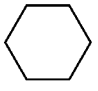 | — | 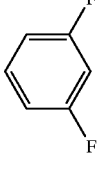 |
| 189 | —C₃H₆— | 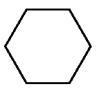 | — | 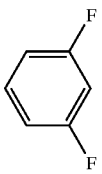 |
| 190 | —CH₂O— | 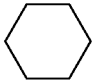 | — | 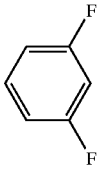 |

-continued
| | Y¹ | A¹ | Z¹ | A² |
|---|---|---|---|---|
| 191 | —C₄H₈ |  | — |  |
| 192 | —CH₂— | 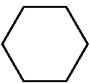 | — |  |
| 193 | —C₂H₄ |  | — | 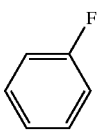 |
| 194 | —C₃H₆ |  | — |  |
| 195 | —C₄H₈ | 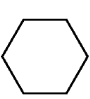 | — |  |
| 196 | —C₄H₈ |  | 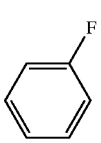 |  |
| 197 | —C₂H₄ |  | 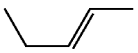 | 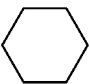 |
| 198 |  | 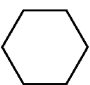 | 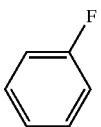 |  |
| 199 | —C₂H₄ | 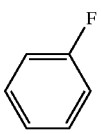 | | |
| 200 | —C₂H₄ | | | |

-continued
| | Y¹ | A¹ | Z¹ | A² |
|---|---|---|---|---|
| 201 | —C₂H₄— | 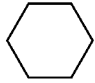 |  | 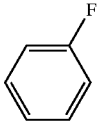 |
| 202 | —CH₂— |  | 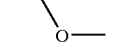 |  |
| 203 | —C₂H₄— | 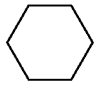 |  | 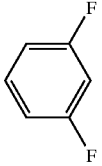 |
| 204 | —C₄H₈— |  | 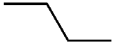 |  |
| 205 | —CH₂O— | 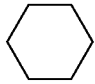 |  | 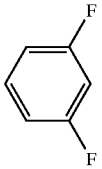 |
| 206 | —C₂H₄— |  | 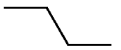 |  |
| 207 | —CH₂— |  | 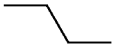 | 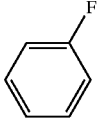 |
| 208 | —C₂H₄— |  | 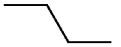 | 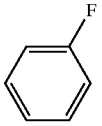 |
| 209 | —C₄H₈— |  | 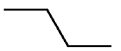 | 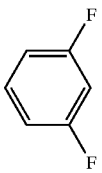 |

| | Y¹ | A¹ | Z¹ | A² |
|---|---|---|---|---|
| 210 | —CH=CH—CH₂— | cyclohexyl | —CH₂CH₂— | 3,4-difluorophenyl |
| 211 | —C₂H₄— | cyclohexyl | — | 2-fluorophenyl |
| 212 | —C₄H₈— | cyclohexyl | — | 2-fluorophenyl |
| 213 | —CH₂O— | cyclohexyl | — | 3,4-difluorophenyl |
| 214 | —C₂H₄— | cyclohexyl | — | 3,4-difluorophenyl |
| 215 | —C₂H₄— | cyclohexyl | — | 4-fluorophenyl |
| 216 | —C₂H₄— | cyclohexyl | — | 4-fluorophenyl |
| 217 | —C₃H₆— | cyclohexyl | — | 4-fluorophenyl |
| 218 | —C₂H₄— | cyclohexyl | — | 3,4-difluorophenyl |
| 219 | —C₄H₈— | cyclohexyl | — | 4-fluorophenyl |

-continued
| | Y¹ | A¹ | Z¹ | A² |
|---|---|---|---|---|
| 220 | —CH₂— | 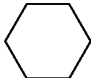 | — | 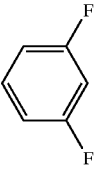 |
| 221 | —C₂H₄— | 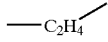 | — |  |
| 222 | 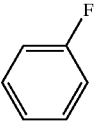 | 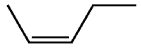 | — |  |
| 223 | —C₂H₄— | 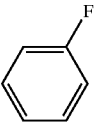 | — | 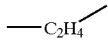 |
| 224 | —C₃H₆— |  | — | 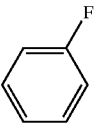 |
| 225 |  | 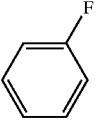 | — | 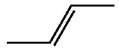 |
| 226 | —C₂H₄— |  | — | 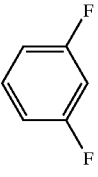 |
| 227 | 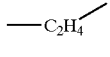 |  | — |  |
| 228 | —C₄H₈— | 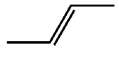 | — |  |
| 229 | —C₂H₄— |  | — | 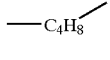 |
| 230 | —C₂H₄— |  | — |  |
| 231 | —C₄H₈— | 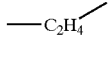 | — |  |

-continued
| | Y¹ | A¹ | Z¹ | A² |
|---|---|---|---|---|
| 232 | —C₃H₆— |  | — |  |
| 233 | —C₂H₄— |  | — | 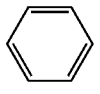 |
| 234 | —C₄H₈— | 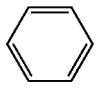 | — | 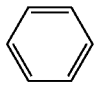 |
| 235 | —CH₂O— | 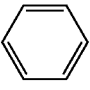 | — | 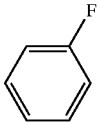 |
| 236 | —C₂H₄— | 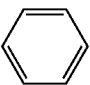 | — |  |
| 237 | —C₄H₈— |  | — | 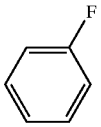 |
| 238 | —C₂H₄— |  | — | 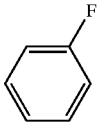 |
| 239 | —C₂H₄— |  | — | 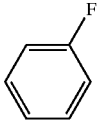 |
| 240 | —C₄H₈— |  | — | 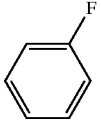 |
| 241 | —C₄H₈— |  | — | 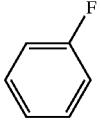 |
| 242 | 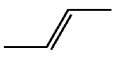 |  | — | 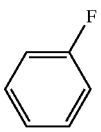 |

-continued
| | Y¹ | A¹ | Z¹ | A² |
|---|---|---|---|---|
| 243 | —C₂H₄ |  | — |  |
| 244 | —C₂H₄ | 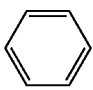 | — | 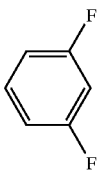 |
| 245 | —C₂H₄ | 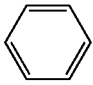 | — | 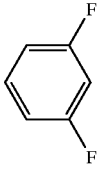 |
| 246 | —C₄H₈ | 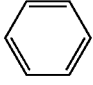 | — | 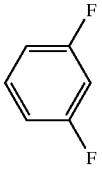 |
| 247 | —C₃H₆ |  | — |  |
| 248 | —C₂H₄ |  | — | 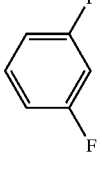 |
| 249 | —C₄H₈ |  | — | 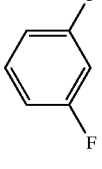 |
| 250 | —C₃H₆O— |  | 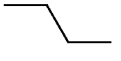 | 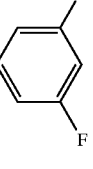 |

| | Y¹ | A¹ | Z¹ | A² |
|---|---|---|---|---|
| 251 | —C$_2$H$_4$ |  |  |  |
| 252 | —C$_4$H$_8$ |  |  | 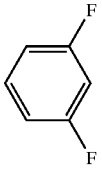 |
| 253 | —C$_2$H$_4$ |  |  |  |
| 254 | —C$_2$H$_4$ |  | 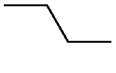 |  |
| 255 | —C$_4$H$_8$ | 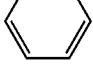 |  | 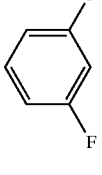 |
| 256 | —C$_4$H$_8$ |  | — | 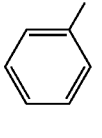 |
| 257 | —C$_2$H$_4$ |  | — | 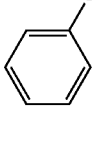 |
| 258 | —C$_5$H$_{10}$ |  | — | 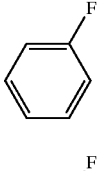 |
| 259 | —C$_2$H$_4$ |  | — | 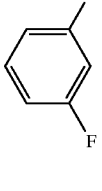 |

-continued
| | Y¹ | A¹ | Z¹ | A² |
|---|---|---|---|---|
| 260 | —C₄H₈ |  | — | 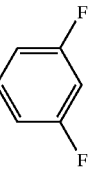 |
| 261 | —C₃H₆O— |  | — |  |
| 262 | —C₃H₆ |  | — | 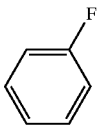 |
| 263 | —C₄H₈ | 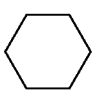 | — | 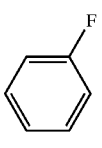 |
| 264 | —C₂H₄— | 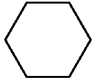 | — | 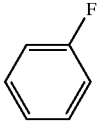 |
| 265 | —C₂H₄ | 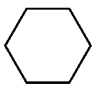 | — | 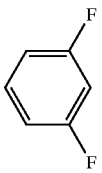 |
| 266 | —C₄H₈ |  | — | 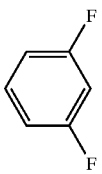 |
| 267 | 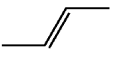 |  | — | 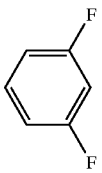 |
| 268 | —C₂H₄ |  | — | 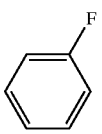 |

-continued
| | Y¹ | A¹ | Z¹ | A² |
|---|---|---|---|---|
| 269 | —CH₂— |  | — |  |
| 270 | 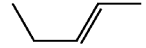 | 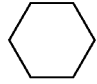 | — | 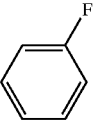 |
| 271 | —C₃H₆ | 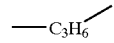 | — | 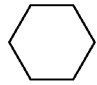 |
| 272 | —C₂H₄ | 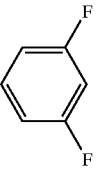 | — | 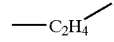 |
| 273 | —C₄H₈ |  | — | 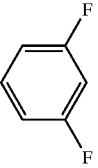 |
| 274 | —C₂H₄ |  | — | 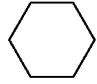 |
| 275 | —C₄H₈ |  | — | 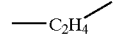 |
| 276 | —C₃H₆O— |  | — |  |
| 277 | —C₆H₁₂ | 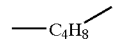 | — |  |
| 278 | —C₂H₄— |  | — |  |
| 279 | —C₄H₈ |  | — | 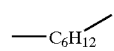 |
| 280 | —C₂H₄ |  | — |  |

-continued
| | Y¹ | A¹ | Z¹ | A² |
|---|---|---|---|---|
| 281 | —C₄H₈⟋ |  | — |  |
| 282 | 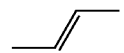 |  | — |  |
| 283 | —C₂H₄⟋ |  | — | 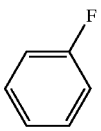 F |
| 284 | —CH₂O— |  | — | 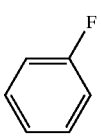 F |
| 285 | —C₄H₈⟋ |  | — | 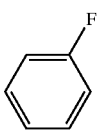 F |
| 286 | —C₄H₈⟋ |  | — | 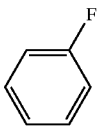 F |
| 287 | —C₂H₄⟋ |  | — | 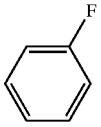 F |
| 288 | —C₃H₆⟋ |  | — | 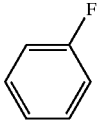 F |
| 289 | —C₂H₄⟋ |  | — | 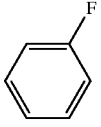 F |
| 290 | —C₄H₈⟋ |  | — | 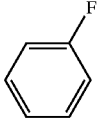 F |
| 291 | 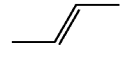 |  | — | 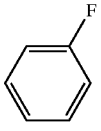 F |

-continued
| | Y¹ | A¹ | Z¹ | A² |
|---|---|---|---|---|
| 292 | —CH₂— |  | — | 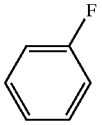 |
| 293 | —C₂H₄— |  | — | 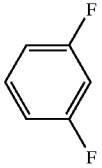 |
| 294 | —C₂H₄— |  | — | 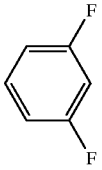 |
| 295 | —C₂H₄— |  | — | 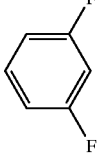 |
| 296 | —C₄H₈— |  | — | 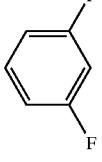 |
| 297 | —C₃H₆O— |  | — | 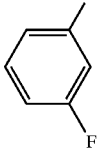 |
| 298 | —C₂H₄— |  | — | 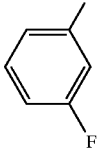 |
| 299 | —CH₂O— |  | — | 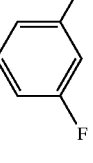 |

-continued
| | Y¹ | A¹ | Z¹ | A² |
|---|---|---|---|---|
| 300 | —C₄H₈ |  | — | 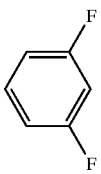 (3,5-difluorophenyl) |
| 301 | —C₅H₁₀ |  | — | 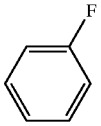 (fluorophenyl) |
| 302 | —C₂H₄ |  | — | 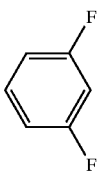 (3,5-difluorophenyl) |
| 303 | —C₄H₈ |  | — |  (3,5-difluorophenyl) |
| 304 | —C₂H₄ |  | — |  |
| 305 | —C₄H₈ |  | — |  |
| 306 | —C₃H₆O— |  | — |  |
| 307 | —C₃H₆ |  | — |  |
| 308 | —C₄H₈ |  | — |  |
| 309 | —C₂H₄— |  | — |  |
| 310 | —C₂H₄ |  | — |  |
| 311 | —C₄H₈ |  | — |  |

-continued
| | Y¹ | A¹ | Z¹ | A² |
|---|---|---|---|---|
| 312 | 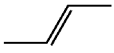 | 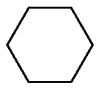 | — | 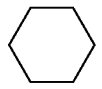 |
| 313 | —C₂H₄— | 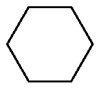 | — | 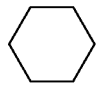 |
| 314 | —C₃H₆ | 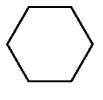 | — | 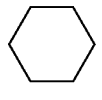 |
| 315 | —CH₂— | 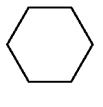 | — | 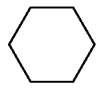 |
| 316 | —C₂H₄— | 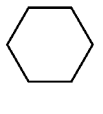 | — | 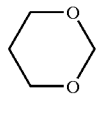 |
| 317 | —CH₂O— | 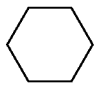 | — | 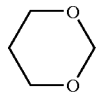 |
| 318 | —C₂H₄ | 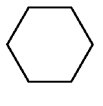 | — | 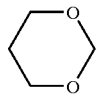 |
| 319 | —C₄H₈— | 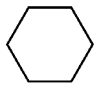 | — | 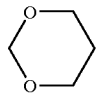 |
| 320 | —C₂H₄ | 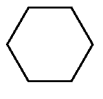 | — |  |
| 321 | —C₄H₈ |  | — |  |
| 322 | —C₂H₄ |  | — |  |
| 323 | —C₄H₈ |  | — |  |
| 324 | —C₂H₄— |  | — |  |
| 325 | —C₂H₄ |  | — |  |

-continued
| | $Y^1$ | $A^1$ | $Z^1$ | $A^2$ |
|---|---|---|---|---|
| 326 | —C$_2$H$_4$O— | 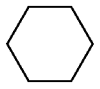 | — | 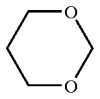 |
| 327 | 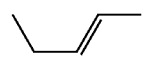 | 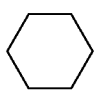 | — | 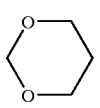 |
| 328 | —C$_2$H$_4$ | 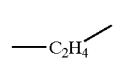 | 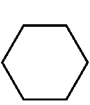 | 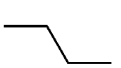 |
| 329 | —CH$_2$— |  |  |  |
| 330 | —C$_4$H$_8$ | 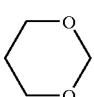 |  | 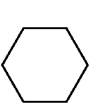 |
| 331 | —C$_4$H$_8$— | 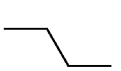 | 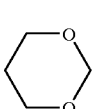 | 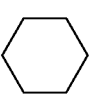 |
| 332 | —C$_2$H$_4$— | 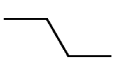 |  |  |
| 333 | —C$_3$H$_6$O— | 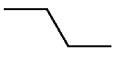 | 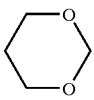 | 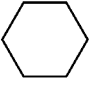 |
| 334 | —C$_3$H$_6$ | 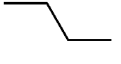 | 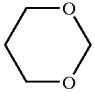 | 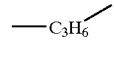 |
| 335 | —C$_2$H$_4$ |  | 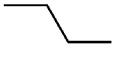 |  |
| 336 | —C$_2$H$_4$— | 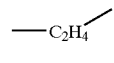 |  | 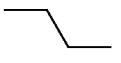 |
| 337 | —C$_2$H$_4$ |  | — |  |
| 338 | —C$_4$H$_8$ | 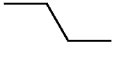 | — |  |
| 339 | —C$_2$H$_4$ | 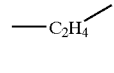 | — |  |

-continued
| | Y¹ | A¹ | Z¹ | A² |
|---|---|---|---|---|
| 340 | —C₂H₄— 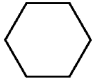 |  | — | 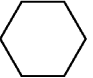 |
| 341 | —C₄H₈— |  | — | 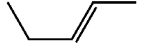 |
| 342 |  | 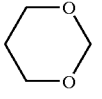 | — | 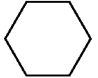 |
| 343 | —C₂H₄— | 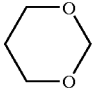 | — | 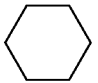 |
| 344 | —CH₂— | 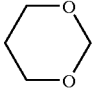 | — | 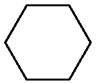 |
| 345 | —C₄H₈— | 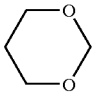 | — |  |
| 346 | —C₂H₄— | 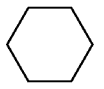 | — | 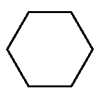 |
| 347 | —C₃H₆— | 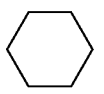 | — | 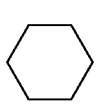 |
| 348 | —C₄H₈— |  | — |  |
| 349 | —C₃H₆— |  | — |  |
| 350 | —C₂H₄— |  | — |  |
| 351 | —C₂H₄— |  | — |  |
| 352 | —C₂H₄— |  | — |  |
| 353 | —C₄H₈— |  | — | |

-continued
| | Y¹ | A¹ | Z¹ | A² |
|---|---|---|---|---|
| 354 | —CH₂O— |  | — | 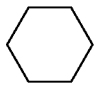 |
| 355 | —C₂H₄⟨ | 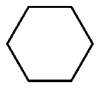 | — |  |
| 356 | —C₂H₄O— | 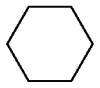 | — |  |
| 357 | 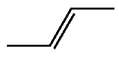 | 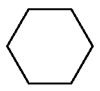 | — | 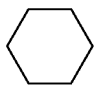 |
| 358 | —C₂H₄⟨ |  | — | 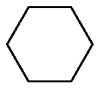 |
| 359 | —CH₂— | 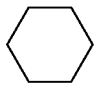 | — | 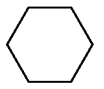 |
| 360 | —C₄H₈⟨ | 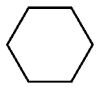 | — |  |
| 361 | —C₂H₄— | 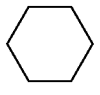 | — | 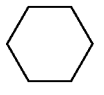 |
| 362 | —C₃H₆— |  | — | 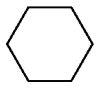 |
| 363 | —C₄H₈⟨ | 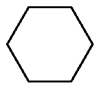 | — | 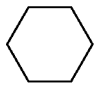 |
| 364 | —C₃H₆⟨ | 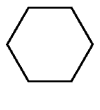 | — | 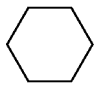 |
| 365 | —CH₂O— | 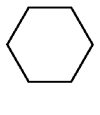 | — | 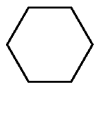 |
| 366 | —C₂H₄⟨ | 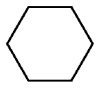 | — |  |
| 367 | —C₂H₄⟨ |  | — |  |
| 368 | —C₂H₄O— |  | — |  |

-continued
| | Y¹ | A¹ | Z¹ | A² |
|---|---|---|---|---|
| 369 | —C₄H₈⟋ |  | — |  |
| 370 | —C₂H₄⟋ |  | — |  |
| 371 | —C₃H₆⟋ | 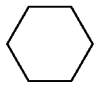 | — | 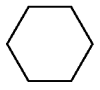 |
| 372 | —C₂H₄⟋ | 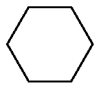 | — | 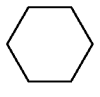 |
| 373 | 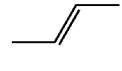 | 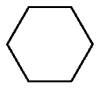 | — |  |
| 374 | —CH₂— |  | — |  |
| 375 | —C₂H₄⟋ |  | — |  |
| 376 | —C₂H₄— |  | — |  |
| 377 | —C₃H₆— |  | — |  |
| 378 | —CH₂O— |  | — |  |
| 379 | —C₃H₆⟋ |  | — |  |
| 380 | —C₄H₈⟋ |  | — |  |
| 381 | —C₂H₄⟋ |  | — |  |
| 382 | —C₂H₄⟋ |  | — |  |
| 383 | —C₅H₁₀O— |  | — |  |

-continued
| | Y¹ | A¹ | Z¹ | A² |
|---|---|---|---|---|
| 384 | —C₄H₈⟨ |  | — |  |
| 385 | —C₂H₄⟨ |  | — |  |
| 386 | —C₅H₁₀⟨ |  | — |  |
| 387 | —C₂H₄⟨ |  | — |  |
| 388 | —C₂H₄⟨ |  | — |  |
| 389 | —CH₂— |  | — |  |
| 390 | 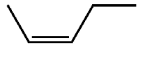 |  | — |  |
| 391 | —C₄H₈⟨ |  | — |  |
| 392 | —C₃H₆— |  | — |  |
| 393 | —C₂H₄— |  | — |  |
| 394 | —C₃H₆⟨ |  | — |  |
| 395 | —C₂H₄— |  | — |  |
| 396 | —CH₂O— |  | — |  |
| 397 | —C₂H₄O— |  | — |  |
| 398 | —C₂H₄⟨ |  | — |  |

| | Y¹ | A¹ | Z¹ | A² |
|---|---|---|---|---|
| 399 | ⟋═⟍ | ⬡ | — | ⬡ |
| 400 | —C₂H₄⟋ | ⬡ | — | ⬡ |
| 401 | —C₃H₆⟋ | ⬡ | — | ⬡ |
| 402 | —C₂H₄⟋ | ⬡ | — | ⬡ |
| 403 | —C₄H₈⟋ | ⬡ | — | ⬡ |
| 404 | —CH₂— | ⬡ | — | ⬡ |
| 405 | —C₂H₄⟋ | ⬡ | — | ⬡ |
| 406 | —C₂H₄— | ⬡ | — | ⬡ |
| 407 | —CH₂O— | ⬡ | — | ⬡ |
| 408 | —C₄H₈⟋ | ⬡ | — | ⬡ |
| 409 | —C₂H₄— | ⬡ | — | ⬡ |
| 410 | —C₂H₄— | ⬡ | — | ⬡ |
| 411 | —C₃H₆O— | ⬡ | — | ⬡ |
| 412 | —C₃H₆⟋ | ⬡ | — | ⬡ |
| 413 | —C₂H₄⟋ | ⬡ | — | ⬡ |

-continued
| | Y¹ | A¹ | Z¹ | A² |
|---|---|---|---|---|
| 414 | —C₂H₄— |  | — |  |
| 415 | —C₂H₄— |  | — |  |
| 416 | —C₃H₆— |  | — |  |
| 417 | 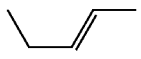 |  | — |  |
| 418 | —C₂H₄— |  | — |  |
| 419 | —CH₂— |  | — |  |
| 420 | —C₄H₈— |  | — |  |
| 421 | —C₄H₈— |  | — |  |
| 422 | —C₂H₄— |  | — |  |
| 423 | —CH₂O— |  | — |  |
| 424 | 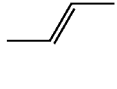 |  | — |  |
| 425 | —C₂H₄— |  | — |  |
| 426 | —C₂H₄O— |  | — |  |
| 427 | —C₃H₆— |  | — |  |
| 428 | —C₂H₄— |  | — |  |

-continued
| | Y¹ | A¹ | Z¹ | A² |
|---|---|---|---|---|
| 429 | —C₂H₄⟨ |  | — | 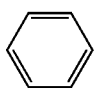 |
| 430 | —C₃H₆⟨ | 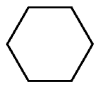 | — | 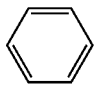 |
| 431 | —CH₂— | 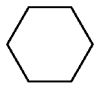 | — | 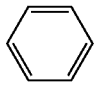 |
| 432 | —C₂H₄⟨ | 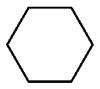 | — | 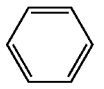 |
| 433 | —C₄H₈⟨ | 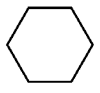 | — | 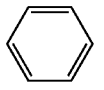 |
| 434 | —C₃H₆— |  | — | 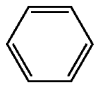 |
| 435 | —C₂H₄— | 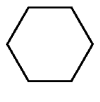 | — | 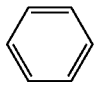 |
| 436 | —C₂H₄⟨ | 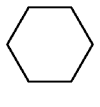 | — | 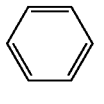 |
| 437 | —C₄H₈⟨ |  | — |  |
| 438 | 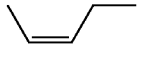 |  | — |  |
| 439 | —C₂H₄O— |  | — |  |
| 440 | —C₂H₄⟨ |  | — |  |
| 441 | —CH₂— |  | — |  |
| 442 | —C₂H₄⟨ |  | — |  |
| 443 | —C₃H₆⟨ |  | — |  |

-continued

| | Y¹ | A¹ | Z¹ | A² |
|---|---|---|---|---|
| 444 | —C₂H₄⟨ | ⬡ | — | ⬡ |
| 445 | —C₃H₆⟨ | ⬡ | — | ⬡ |
| 446 | —C₄H₈⟨ | ⬡ | — | ⬡ |
| 447 | —C₂H₄⟨ | ⬡ | — | ⬡ |
| 448 | —CH₂O— | ⬡ | — | ⬡ |
| 449 | —C₃H₆— | ⬡ | — | ⬡ |
| 450 | —C₂H₄— | ⬡ | — | ⬡ |
| 451 | —C₄H₈— | ⬡ | — | ⬡ |
| 452 | —C₃H₆O— | ⬡ | — | ⬡ |
| 453 | (CH=CH) | ⬡ | — | ⬡ |
| 454 | —C₄H₈— | ⬡ | — | ⬡ |
| 455 | —C₅H₁₀O— | ⬡ | — | ⬡ |
| 456 | (CH₂CH=CH) | ⬡ | — | ⬡-F |
| 457 | —C₄H₈— | ⬡ | — | ⬡-F |

-continued
| | Y¹ | A¹ | Z¹ | A² |
|---|---|---|---|---|
| 458 | —C₄H₈ |  | — | 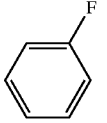 |
| 459 | —C₂H₄ |  | — | 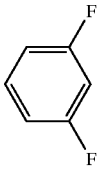 |
| 460 | 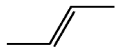 |  | — | 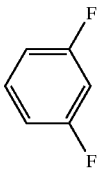 |
| 461 | —C₂H₄O— |  | — | 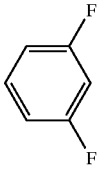 |
| 462 | —C₂H₄ |  | 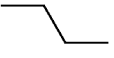 |  |
| 463 | —CH₂O— |  | 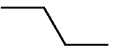 |  |
| 464 | 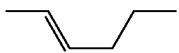 |  | 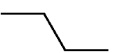 |  |
| 465 | —C₄H₈ |  | 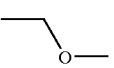 |  |
| 466 | —C₄H₈— |  | — |  |
| 467 | —C₃H₆O— |  | — |  |
| 468 | 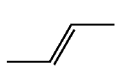 |  | — |  |
| 469 | —C₄H₈— |  | — |  |

-continued
| | Y¹ | A¹ | Z¹ | A² |
|---|---|---|---|---|
| 470 | —C₄H₈— |  | — | 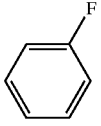 |
| 471 | —C₂H₄O— |  | — |  |
| 472 |  | 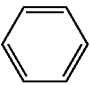 | — |  |
| 473 | —C₂H₄— |  | — |  |
| 474 | —C₂H₄— |  | — |  |
| 475 | —CH₂O— |  | — |  |
| 476 |  |  | — |  |
| 477 | —C₄H₈— |  | — | 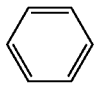 |
| 478 | —C₄H₈— |  | — | 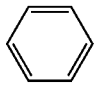 |
| 479 | —C₅H₁₀O— | 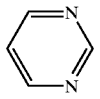 | — |  |
| 480 | —C₂H₄— |  | — |  |
| 481 | —C₂H₄— | 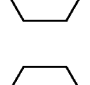 |  | 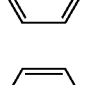 |
| 482 | —C₃H₆O— |  |  |  |

|     | Y¹ | A¹ | Z¹ | A² |
| --- | --- | --- | --- | --- |
| 483 | —CH=CH—CH₂— | cyclohexyl | —COO— | phenyl |
| 484 | —C₂H₄— | cyclohexyl | —COO— | phenyl |
| 485 | —C₄H₈— | cyclohexyl | —COO— | 4-F-phenyl |
| 486 | —C₂H₄O— | cyclohexyl | —COO— | 4-F-phenyl |
| 487 | —CH=CH—C₂H₄— | cyclohexyl | —COO— | 4-F-phenyl |
| 488 | —C₂H₄— | cyclohexyl | —COO— | 4-F-phenyl |
| 489 | —C₃H₆— | cyclohexyl | —COO— | 3,4-diF-phenyl |
| 490 | —C₃H₆O— | cyclohexyl | —COO— | 3,4-diF-phenyl |
| 491 | —CH=CH— | cyclohexyl | —COO— | 3,4-diF-phenyl |
| 492 | —C₂H₄— | phenyl | —COO— | phenyl |
| 493 | —CH₂O— | phenyl | —COO— | phenyl |

| | Y¹ | A¹ | Z¹ | A² |
|---|---|---|---|---|
| | -continued | | | |
| 494 | (cis-CH₂-CH=CH-CH₂) | phenyl | -C(=O)O- | phenyl |
| 495 | —C₄H₈⟨ | phenyl | -C(=O)O- | phenyl |
| 496 | —C₂H₄— | phenyl | -C(=O)O- | 4-F-phenyl |
| 497 | —C₃H₆O— | phenyl | -C(=O)O- | 4-F-phenyl |
| 498 | —C₄H₈⟨ | phenyl | -C(=O)O- | 4-F-phenyl |
| 499 | —C₄H₈⟨ | phenyl | -C(=O)O- | 3,4-diF-phenyl |
| 500 | —C₂H₄O— | phenyl | -C(=O)O- | 3,4-diF-phenyl |
| 501 | (trans-CH₂-CH=CH-) | phenyl | -C(=O)O- | 3,4-diF-phenyl |
| 502 | —C₂H₄⟨ | phenyl | -CF₂O- | phenyl |
| 503 | —C₃H₆O— | phenyl | -CF₂O- | phenyl |
| 504 | —C₃H₆— | phenyl | -CF₂O- | phenyl |

-continued
| | Y¹ | A¹ | Z¹ | A² |
|---|---|---|---|---|
| 505 | —C₂H₄⟋ |  |  |  |
| 506 | —C₄H₈⟋ |  |  |  |
| 507 | —C₂H₄⟋ |  |  |  |
| 508 | —CH₂O— |  |  | 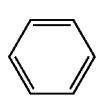 |
| 509 | —C₄H₈⟋ |  |  |  |
| 510 |  | 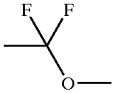 |  | 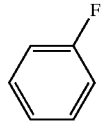 |
| 511 | —C₂H₄— |  | 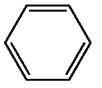 |  |
| 512 | —C₃H₆O— | 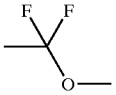 |  |  |
| 513 | —C₄H₈⟋ | 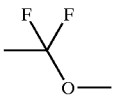 |  | 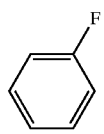 |
| 514 | —C₂H₄O— |  | 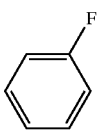 |  |

-continued
| | Y¹ | A¹ | Z¹ | A² |
|---|---|---|---|---|
| 515 | —C₄H₈ |  |  |  |
| 516 |  |  |  | 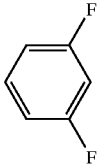 |
| 517 | —C₂H₄ |  |  |  |
| 518 | —C₃H₆O— |  |  |  |
| 519 | —C₃H₆— |  |  |  |
| 520 | —C₄H₈ |  |  | 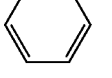 |
| 521 | —C₂H₄ |  |  |  |
| 522 | —CH₂O— |  |  | 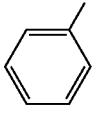 |

-continued

| | Y¹ | A¹ | Z¹ | A² |
|---|---|---|---|---|
| 523 | —C₂H₄— | 2,4-difluorophenyl | —OCF₂— | 4-fluorophenyl |
| 524 | —C₄H₈— | 2,4-difluorophenyl | —OCF₂— | 2,4-difluorophenyl |
| 525 | —C₃H₆O— | 2,4-difluorophenyl | —OCF₂— | 2,4-difluorophenyl |
| 526 | —C₃H₆— | cyclohexyl | — | cyclohexyl |
| 527 | —CH₂O— | cyclohexyl | — | cyclohexyl |
| 528 | —C₂H₄— | cyclohexyl | — | cyclohexyl |
| 529 | —C₃H₆— | cyclohexyl | — | cyclohexyl |
| 530 | —C₂H₄O— | cyclohexyl | — | cyclohexyl |
| 531 | —C₂H₄— | cyclohexyl | — | cyclohexyl |
| 532 | —C₂H₄— | cyclohexyl | — | cyclohexyl |
| 533 | —C₃H₆O— | cyclohexyl | — | cyclohexyl |
| 534 | —CH₂CH=CHCH₂— | cyclohexyl | — | cyclohexyl |
| 535 | —C₂H₄— | cyclohexyl | — | phenyl |

-continued
| | Y¹ | A¹ | Z¹ | A² |
|---|---|---|---|---|
| 536 | —C₂H₄O— |  | — |  |
| 537 | —CH₂— |  | — |  |
| 538 | —C₂H₄ |  | — |  |
| 539 | —CH₂O— |  | — |  |
| 540 | —C₄H₈ | 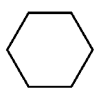 | — |  |
| 541 | —C₂H₄— |  | — |  |
| 542 | —C₃H₆O— |  | — |  |
| 543 | —C₂H₄ |  | — |  |
| 544 | —C₄H₈— |  | — |  |
| 545 | —C₂H₄O— |  | — |  |
| 546 | —C₃H₆— |  | — |  |
| 547 | —C₂H₄ |  | — |  |
| 548 | —C₃H₆O— |  | — |  |
| 549 | —C₄H₈ |  | — |  |
| 550 | —C₂H₄ |  | — |  |

-continued
| | Y¹ | A¹ | Z¹ | A² |
|---|---|---|---|---|
| 551 | —C₂H₄O— |  | — |  |
| 552 | —CH₂— |  | — |  |
| 553 | —C₂H₄ |  | — |  |
| 554 | —CH₂O— | 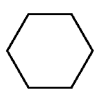 | — | 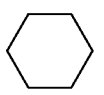 |
| 555 |  | 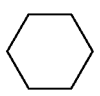 | — |  |
| 556 | —C₂H₄— | 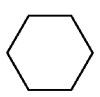 | — |  |
| 557 | —CH₂O— | 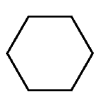 | — | 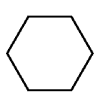 |
| 558 | —C₂H₄ |  | — |  |
| 559 | —C₇H₁₄— |  |  | 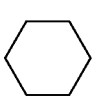 |
| 560 | —C₃H₆O— |  | 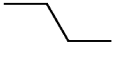 |  |
| 561 | —C₃H₆— |  | 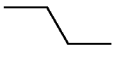 |  |
| 562 | —C₂H₄ |  | 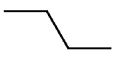 |  |
| 563 | —C₂H₄O— |  | 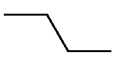 |  |
| 564 | —C₄H₈ |  | 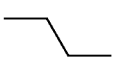 |  |
| 565 | —C₄H₈ |  | 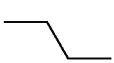 |  |

-continued
| | Y¹ | A¹ | Z¹ | A² |
|---|---|---|---|---|
| 566 | —C₂H₄O— |  | 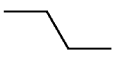 |  |
| 567 | —C₂H₄— |  | 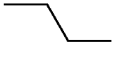 |  |
| 568 | —CH₂ |  | 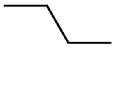 |  |
| 569 | 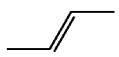 |  | 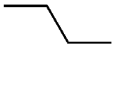 |  |
| 570 | —CH₂O— |  | 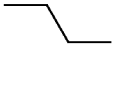 |  |
| 571 | —C₂H₄— |  | 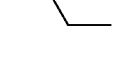 |  |
| 572 | —CH₂O— |  | 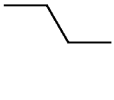 |  |
| 573 | —C₃H₆ |  | 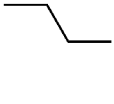 |  |
| 574 | —C₂H₄— |  | 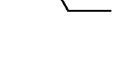 |  |
| 575 | —C₃H₆O— |  | 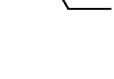 |  |
| 576 | —C₃H₆— |  | 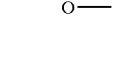 |  |
| 577 | —C₂H₄ |  | — |  |
| 578 | —C₃H₆O— |  | — |  |
| 579 | —C₂H₄ |  | — |  |
| 580 | —C₄H₈ |  | — |  |

-continued
| | $Y^1$ | $A^1$ | $Z^1$ | $A^2$ |
|---|---|---|---|---|
| 581 | —C$_2$H$_4$O— |  | — |  |
| 582 | —C$_2$H$_4$— |  | — |  |
| 583 | —CH$_2$— |  | — |  |
| 584 | 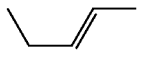 |  | — |  |
| 585 | —CH$_2$O— |  | — |  |
| 586 | —C$_2$H$_4$— |  | — |  |
| 587 | —C$_2$H$_4$O— |  | — |  |
| 588 | —C$_4$H$_8$— |  | — |  |
| 589 | —C$_4$H$_8$— |  | — |  |
| 590 | —C$_3$H$_6$O— |  | — |  |
| 591 | —C$_2$H$_4$— |  | — |  |
| 592 | —C$_2$H$_4$— |  | — |  |
| 593 | —C$_3$H$_6$O— |  | — |  |
| 594 | —C$_2$H$_4$— |  | — |  |

-continued
| | Y¹ | A¹ | Z¹ | A² |
|---|---|---|---|---|
| 595 | —C₄H₈⟨ |  | — | 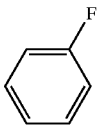 F |
| 596 | 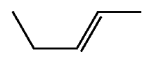 |  | — | 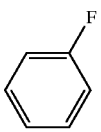 F |
| 597 | —CH₂O— |  | — | 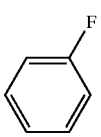 F |
| 598 | —C₂H₄⟨ |  | — |  |
| 599 | —C₂H₄O— |  | — |  |
| 600 | —C₃H₆— |  | — |  |
| 601 | —C₂H₄— |  | — |  |
| 602 | —C₃H₆O— |  | — |  |
| 603 | —C₄H₈⟨ |  | — |  |
| 604 | —C₄H₈— |  | — |  |
| 605 | —C₂H₄O— |  | — |  |
| 606 | —C₂H₄— |  | — |  |
| 607 | —C₈H₁₆— |  | — | 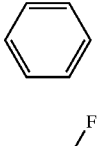 F |

|     | Y¹ | A¹ | Z¹ | A² |
|-----|-----|-----|-----|-----|
| 608 | —C₃H₆O— | 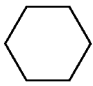 | — |  |
| 609 | —CH₂O— | 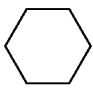 | — | 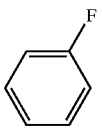 |
| 610 | —C₄H₈ |  | — |  |
| 611 | 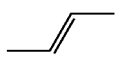 |  | — | 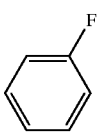 |
| 612 | —C₂H₄— | 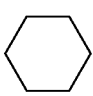 | — | 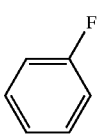 |
| 613 | —C₂H₄ |  | — | 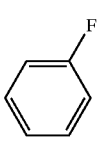 |
| 614 | —C₂H₄O— | 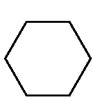 | — |  |
| 615 | —C₃H₆— |  | — | 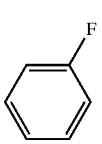 |
| 616 | —C₄H₈— |  | — | 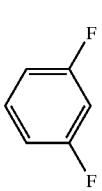 |
| 617 | —C₄H₈O— | 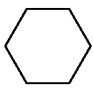 | — | 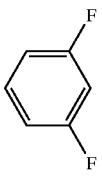 |

-continued

| | Y¹ | A¹ | Z¹ | A² |
|---|---|---|---|---|
| 618 | CH=CHCH₃ (propenyl) | cyclohexyl | — | 3,4-difluorophenyl |
| 619 | —C₂H₄— | cyclohexyl | — | 3,4-difluorophenyl |
| 620 | —C₂H₄O— | cyclohexyl | — | 3,4-difluorophenyl |
| 621 | —C₄H₈— | cyclohexyl | — | 3,4-difluorophenyl |
| 622 | —C₃H₆— | cyclohexyl | — | 4-fluorophenyl |
| 623 | —C₂H₄O— | cyclohexyl | — | 4-fluorophenyl |
| 624 | —CH₂O— | cyclohexyl | — | 4-fluorophenyl |
| 625 | —C₄H₈— | cyclohexyl | — | cyclohexyl |
| 626 | —CH₂O— | cyclohexyl | — | cyclohexyl |
| 627 | —C₂H₄— | cyclohexyl | — | cyclohexyl |
| 628 | —C₂H₄— | cyclohexyl | — | phenyl |

-continued
| | Y¹ | A¹ | Z¹ | A² |
|---|---|---|---|---|
| 629 | —C₂H₄O— |  | — |  |
| 630 | —C₃H₆— |  | — |  |
| 631 | —C₄H₈— |  | 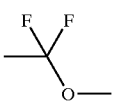 |  |
| 632 | —C₂H₄ |  | 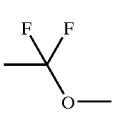 |  |
| 633 | —C₄H₈— |  | 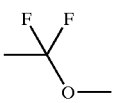 |  |
| 634 | —CH₂O— |  | 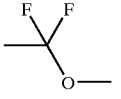 |  |
| 635 | —C₂H₄— |  | 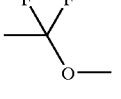 |  |
| 636 | —C₄H₈— |  | 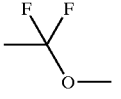 |  |
| 637 | —C₄H₈— |  | 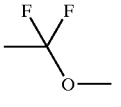 | 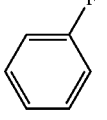 |
| 638 | —C₂H₄O— |  | 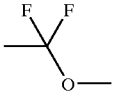 | 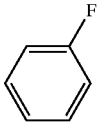 |
| 639 | —C₂H₄ |  | 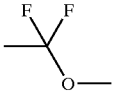 | 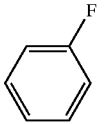 |
| 640 | —C₄H₈ |  | 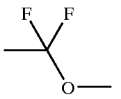 | 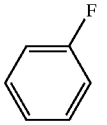 |

-continued
| | Y¹ | A¹ | Z¹ | A² |
|---|---|---|---|---|
| 641 | —C₂H₄— |  |  | 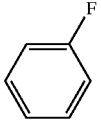 |
| 642 | —C₂H₄— |  |  | 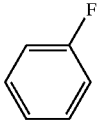 |
| 643 | —C₂H₄ |  |  | 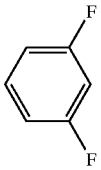 |
| 644 | —C₄H₈— |  |  | 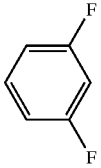 |
| 645 | 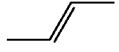 |  |  | 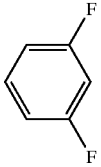 |
| 646 | —C₄H₈— |  |  | 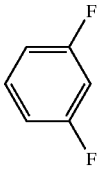 |
| 647 | —C₂H₄ |  |  | 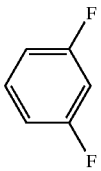 |
| 648 | —C₃H₆O— |  |  | 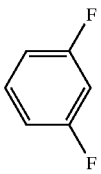 |
| 649 | —CH₂O— |  | — |  |
| 650 | —C₂H₄— |  | — |  |

| | Y¹ | A¹ | Z¹ | A² |
|---|---|---|---|---|
| 651 | —C₄H₈— |  | — |  |
| 652 | —C₂H₄— |  | — |  |
| 653 | —C₂H₄O— |  | — |  |
| 654 | —C₂H₄ |  | — |  |
| 655 | —C₂H₄ |  | — |  |
| 656 | —C₄H₈O— |  | — |  |
| 657 | —C₂H₄— |  | — |  |
| 658 | —C₂H₄ |  | — |  |
| 659 | —CH₂O— |  | — |  |
| 660 | —C₂H₄— |  | — |  |
| 661 | —C₄H₈— |  | — |  |
| 662 | 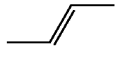 |  | — |  |
| 663 | —C₂H₄— |  | — |  |
| 664 | —CH₂O— |  | — |  |
| 665 | —C₄H₈— |  | — |  |

-continued
| | Y¹ | A¹ | Z¹ | A² |
|---|---|---|---|---|
| 666 | —C₂H₄— |  | — |  |
| 667 | —C₂H₄— |  | — |  |
| 668 | —C₆H₁₂O— |  | — |  |
| 669 | —C₂H₄OCH₂ |  | — | 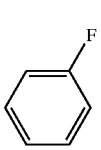 |
| 670 | —C₂H₄ |  | — | 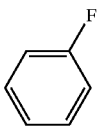 |
| 671 | —C₅H₁₀— |  | — | 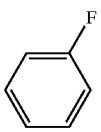 |
| 672 | —C₂H₄OC₂H₄ |  | — | 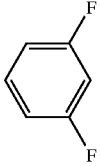 |
| 673 | —C₂H₄ |  | — |  |
| 674 | —C₄H₈O— |  | — |  |
| 675 | 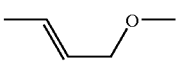 |  | — |  |
| 676 | —C₄H₈ |  | — |  |
| 677 | —C₃H₆— |  | — | 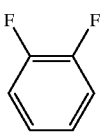 |

-continued
| | $Y^1$ | $A^1$ | $Z^1$ | $A^2$ |
|---|---|---|---|---|
| 678 | —C$_2$H$_4$— |  | — |  |
| 679 | —C$_4$H$_8$O— |  | — |  |
| 680 | 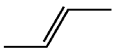 |  | — | 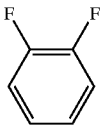 |
| 681 | —C$_4$H$_8$— |  | — | 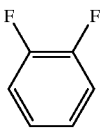 |
| 682 | —C$_3$H$_6$O— |  | — | 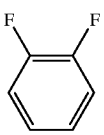 |
| 683 | —C$_7$H$_{14}$— |  | — | 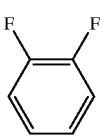 |
| 684 |  |  | — | 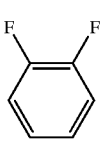 |
| 685 | 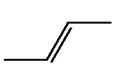 |  | — | 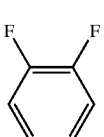 |
| 686 | —C$_2$H$_4$— |  | 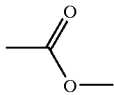 | 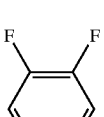 |
| 687 | —C$_4$H$_8$— |  | 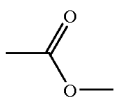 | 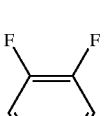 |
| 688 | —CH$_2$O— |  | 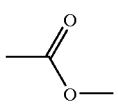 | 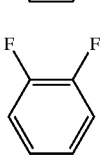 |

-continued

| | Y¹ | A¹ | Z¹ | A² |
|---|---|---|---|---|
| 689 | (CH=CH-CH₂-CH₃, trans pentenyl) | cyclohexyl | -C(=O)O- | 2,3-difluorophenyl |
| 690 | (cis pentenyl) | cyclohexyl | -C(=O)O- | 2,3-difluorophenyl |
| 691 | —C₂H₄— | cyclohexyl | — | cyclohexyl |
| 692 | —C₂H₄— | cyclohexyl | — | cyclohexyl |
| 693 | —C₄H₈— | cyclohexyl | — | cyclohexyl |
| 694 | —C₂H₄— | cyclohexyl | — | cyclohexyl |
| 695 | (CH=CH-CH₃) | cyclohexyl | — | cyclohexyl |
| 696 | —C₄H₈— | cyclohexyl | — | cyclohexyl |
| 697 | —C₃H₆O— | cyclohexyl | — | cyclohexyl |
| 698 | —C₇H₁₄— | cyclohexyl | — | cyclohexyl |
| 699 | —C₂H₄— | cyclohexyl | — | cyclohexyl |
| 700 | (CH=CH-CH₃) | cyclohexyl | — | cyclohexyl |
| 701 | —C₂H₄— | cyclohexyl | — | cyclohexyl |
| 702 | —C₄H₈— | cyclohexyl | — | cyclohexyl |

-continued
| | Y¹ | A¹ | Z¹ | A² |
|---|---|---|---|---|
| 703 | —CH₂O— |  | — |  |
| 704 | 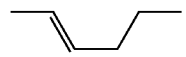 |  | — |  |
| 705 | 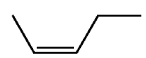 |  | — |  |
| 706 | —C₄H₈ |  | — |  |
| 707 | —C₂H₄— |  | — |  |
| 708 | —C₅H₁₀ |  | — |  |
| 709 | —C₃H₆O— | 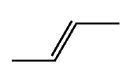 | — |  |
| 710 |  |  | — |  |
| 711 | —C₂H₄— |  | — |  |
| 712 | —CH₂O— |  | — |  |
| 713 | —C₄H₈— |  | — |  |
| 714 | —C₃H₆OCH₂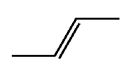 |  | — |  |
| 715 |  |  | — |  |
| 716 | —C₂H₄ | | — | |
| 717 | —C₄H₈ | | — | |

-continued
| | Y¹ | A¹ | Z¹ | A² |
|---|---|---|---|---|
| 718 | —C₂H₄— |  | — |  |
| 719 | —C₃H₆— |  | — | 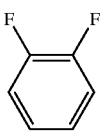 |
| 720 | 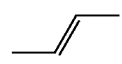 |  | — | 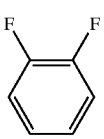 |
| 721 | —C₂H₄— |  | — |  |
| 722 | —C₄H₈— |  | — |  |
| 723 | —CH₂— |  | — |  |
| 724 | —C₃H₆O— |  | — |  |
| 725 | 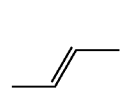 |  | — |  |
| 726 | —C₂H₄— |  | — | 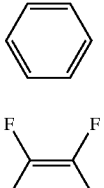 |
| 727 | —CH₂O— |  | — | 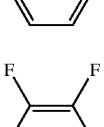 |
| 728 | —C₄H₈— |  | — | 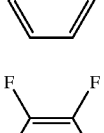 |
| 729 | —C₅H₁₀— |  | — | 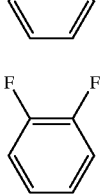 |

-continued

| | Y¹ | A¹ | Z¹ | A² |
|---|---|---|---|---|
| 730 | (CH=CH-CH₂-) | phenyl | — | 1,2-difluorophenyl |
| 731 | —C₂H₄— | phenyl | — | phenyl |
| 732 | —C₄H₈— | phenyl | — | phenyl |
| 733 | —C₇H₁₄— | phenyl | — | phenyl |
| 734 | —C₃H₆O— | phenyl | — | phenyl |
| 735 | (CH=CH-) | phenyl | — | phenyl |
| 736 | —C₂H₄— | cyclohexyl | — | cyclohexyl |
| 737 | —CH₂O— | cyclohexyl | — | cyclohexyl |
| 738 | —C₂H₄— | cyclohexyl | — | cyclohexyl |
| 739 | (CH=CH-) | cyclohexyl | — | cyclohexyl |
| 740 | (CH=CH-CH₂-) | cyclohexyl | — | cyclohexyl |
| 741 | —C₇H₁₄O— | cyclohexyl | — | cyclohexyl |
| 742 | —CH₂— | cyclohexyl | — | cyclohexyl |
| 743 | —C₂H₄— | cyclohexyl | — | cyclohexyl |
| 744 | —C₂H₄O— | cyclohexyl | — | cyclohexyl |

-continued

| | $Y^1$ | $A^1$ | $Z^1$ | $A^2$ |
|---|---|---|---|---|
| 745 | –CH=CH– | cyclohexyl | — | cyclohexyl |
| 746 | –C$_2$H$_4$– | cyclohexyl | –CH$_2$– | cyclohexyl |
| 747 | –C$_3$H$_6$– | cyclohexyl | –CH$_2$– | cyclohexyl |
| 748 | –C$_4$H$_8$– | cyclohexyl | –CH$_2$– | cyclohexyl |
| 749 | –CH=CH–CH$_2$– | cyclohexyl | –CH$_2$– | cyclohexyl |
| 750 | –CH$_2$–CH=CH– | cyclohexyl | –CH$_2$– | cyclohexyl |
| 751 | –C$_3$H$_6$– | cyclohexyl | –CH=CH– | cyclohexyl |
| 752 | –CH$_2$O– | cyclohexyl | –CH=CH– | cyclohexyl |
| 753 | –C$_2$H$_4$– | cyclohexyl | –CH=CH– | cyclohexyl |
| 754 | –CH=CH– | cyclohexyl | –CH=CH– | cyclohexyl |
| 755 | –CH$_2$–CH=CH– | cyclohexyl | –CH=CH– | cyclohexyl |
| 756 | –C$_4$H$_8$– | cyclohexyl | — | phenyl |
| 757 | –C$_2$H$_4$O– | cyclohexyl | — | phenyl |
| 758 | –C$_2$H$_4$– | cyclohexyl | — | phenyl |
| 759 | –C$_2$H$_4$– | cyclohexyl | — | phenyl |

|   | Y¹ | A¹ | Z¹ | A² |
|---|---|---|---|---|
| 760 | (CH=CH-CH2) | cyclohexane | — | benzene |
| 761 | (CH2-CH=CH-CH2) | cyclohexane | — | benzene |
| 762 | —C₆H₁₂— | cyclohexane | — | benzene |
| 763 | —C₄H₈— | cyclohexane | — | benzene |
| 764 | —C₃H₆— | cyclohexane | — | benzene |
| 765 | —C₂H₄— | cyclohexane | — | benzene |
| 766 | —CH₂OC₃H₆— | cyclohexane | — | benzene |
| 767 | —CH2-CH=CH-CH2-O— | cyclohexane | — | benzene |
| 768 | —C₂H₄— | cyclohexane | — | benzene |
| 769 | —C₂H₄— | cyclohexane | —C₂H₄— | benzene |
| 770 | —C₂H₄O— | cyclohexane | —C₂H₄— | benzene |
| 771 | (CH2-CH=CH-CH2-CH2) | cyclohexane | —C₂H₄— | benzene |
| 772 | —C₄H₈— | cyclohexane | —C₂H₄— | benzene |
| 773 | —C₂H₄— | cyclohexane | —C₂H₄— | benzene |
| 774 | —CH=CH— | cyclohexane | —C₂H₄— | benzene |

-continued
| | Y¹ | A¹ | Z¹ | A² |
|---|---|---|---|---|
| 775 | —C₂H₄— |  |  |  |
| 776 | —C₄H₈O— |  |  |  |
| 777 | 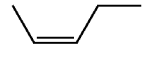 |  |  |  |
| 778 | —CH₂— |  |  |  |
| 779 | —C₃H₆— |  |  |  |
| 780 | 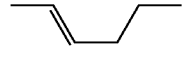 |  |  |  |
| 781 | —C₃H₆— |  |  |  |
| 782 | —C₂H₄O— |  |  |  |
| 783 | —C₂H₄— |  |  |  |
| 784 | 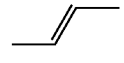 |  |  |  |
| 785 | 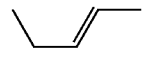 |  |  |  |
| 786 | —C₂H₄— |  |  |  |
| 787 | —CH₂— |  |  |  |
| 788 | —C₂H₄O— |  |  |  |

| | Y¹ | A¹ | Z¹ | A² |
|---|---|---|---|---|
| 789 | -CH=CH-CH₂- (cis) | phenyl | -O-C(=O)- | cyclohexyl |
| 790 | -C₄H₈- | phenyl | -O-C(=O)- | cyclohexyl |
| 791 | -C₄H₈- | phenyl | — | phenyl |
| 792 | -C₃H₆- | phenyl | — | phenyl |
| 793 | -C₄H₈O- | phenyl | — | phenyl |
| 794 | -C₂H₄- | phenyl | — | phenyl |
| 795 | -CH=CH-CH₂- | phenyl | — | phenyl |
| 796 | -C₂H₄- | phenyl | -C(=O)-O- | phenyl |
| 797 | -C₂H₄O- | phenyl | -C(=O)-O- | phenyl |
| 798 | -C₃H₆- | phenyl | -C(=O)-O- | phenyl |
| 799 | -CH=CH-CH₂-CH₂- | phenyl | -C(=O)-O- | phenyl |
| 800 | -C₂H₄OC₃H₆- | phenyl | -C(=O)-O- | phenyl |
| 801 | -C₂H₄- | phenyl | -O-C(=O)- | phenyl |
| 802 | -CH₂O- | phenyl | -O-C(=O)- | phenyl |

-continued
| | $Y^1$ | $A^1$ | $Z^1$ | $A^2$ |
|---|---|---|---|---|
| 803 | —C$_2$H$_4$— |  | —O—C(=O)— |  |
| 804 |  | 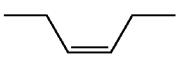 | —O—C(=O)— |  |
| 805 | —C$_3$H$_6$— | 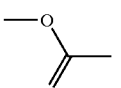 | —O—C(=O)— |  |
| 806 | —C$_3$H$_6$— |  | —C≡C— | 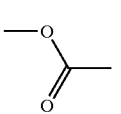 |
| 807 | —C$_3$H$_6$— |  | —C≡C— |  |
| 808 | —C$_4$H$_8$O— |  | —C≡C— |  |
| 809 | —C$_4$H$_8$— |  | —C≡C— |  |
| 810 |  |  | —C≡C— |  |
| 811 | —C$_2$H$_4$— |  | — |  |
| 812 | —CH$_2$O— |  | — |  |
| 813 | —C$_2$H$_4$— |  | — |  |
| 814 |  |  | — |  |
| 815 | 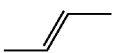 |  | — |  |
| 816 | —CH$_2$— | 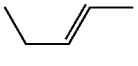 | — |  |
| 817 | —C$_4$H$_8$— |  | — |  |

-continued
| | Y¹ | A¹ | Z¹ | A² |
|---|---|---|---|---|
| 818 | —C₂H₄O— |  | — |  |
| 819 | 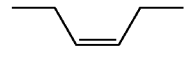 |  | — |  |
| 820 | |  | — |  |
| 821 | —C₂H₄— |  | 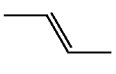 |  |
| 822 | —C₃H₆— | 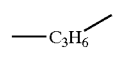 |  | 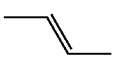 |
| 823 | —C₄H₈O— |  |  | 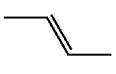 |
| 824 | —C₂H₄— |  | 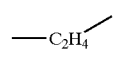 |  |
| 825 | 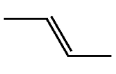 |  | 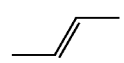 |  |
| 826 | —C₂H₄— | 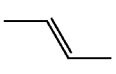 | — |  |
| 827 | —CH₂O— | 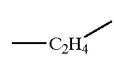 | — |  |
| 828 | —C₂H₄— |  | — |  |
| 829 |  |  | — |  |
| 830 | —CH₂— |  | — |  |
| 831 | —C₂H₄— |  | — |  |
| 832 | —C₃H₆— |  | — |  |

-continued
| | Y¹ | A¹ | Z¹ | A² |
|---|---|---|---|---|
| 833 | —C₃H₈O— |  | — |  |
| 834 | —C₂H₄  |  | — | 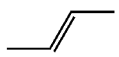 |
| 835 |  |  | — |  |
| 836 | —CH₂ 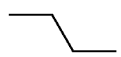 |  |  | 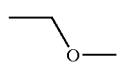 |
| 837 | —C₄H₈— |  |  | 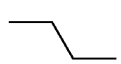 |
| 838 | —C₂H₄O— |  | 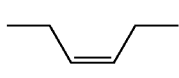 |  |
| 839 | 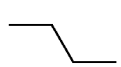 |  |  | 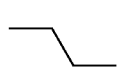 |
| 840 | —C₄H₈  |  |  |  |
| 841 | —CH₂— |  | — |  |
| 842 | —C₂H₄O— |  | — |  |
| 843 | —C₂H₄— |  | — |  |
| 844 | 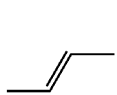 |  | — |  |
| 845 |  |  | — |  |
| 846 | —CH₂  | | — | |
| 847 | —C₄H₈— | | — | |

-continued
| | Y¹ | A¹ | Z¹ | A² |
|---|---|---|---|---|
| 848 | —C₂H₄O— |  | — |  |
| 849 | 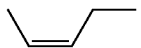 |  | — |  |
| 850 | —C₂H₄  |  | — |  |
| 851 | —C₂H₄— |  | — |  |
| 852 | —C₃H₆  |  | — |  |
| 853 | —C₄H₈O— |  | — |  |
| 854 | —C₂H₄ 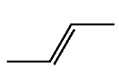 |  | — |  |
| 855 |  |  | — |  |
| 856 | —CH₂  | 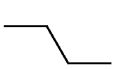 |  |  |
| 857 | —CH₂O— | 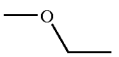 |  | 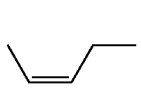 |
| 858 | —C₂H₄— |  | —O 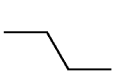 |  |
| 859 |  | 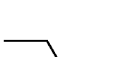 |  |  |
| 860 | —C₂H₄ 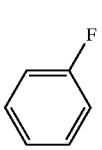 | | | |
| 861 | —C₂H₄— | | — | |

-continued
| | Y¹ | A¹ | Z¹ | A² |
|---|---|---|---|---|
| 862 | —C₃H₆⟨ |  | — |  |
| 863 | —C₄H₈O— |  | — |  |
| 864 | —C₂H₄⟨ |  | — |  |
| 865 | 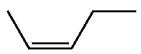 |  | — |  |
| 866 | —C₃H₆⟨ |  | — |  |
| 867 | —C₂H₄— |  | — |  |
| 868 | —C₂H₄O— |  | — |  |
| 869 | 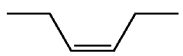 |  | — |  |
| 870 | —CH₂⟨ |  | — |  |
| 871 | —C₂H₄⟨ |  | — | 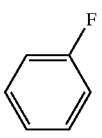 (F) |
| 872 | —CH₂O— |  | — | 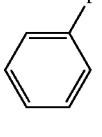 (F) |
| 873 | 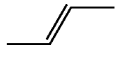 |  | — | 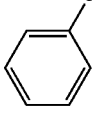 (F) |
| 874 | —C₄H₈— |  | — |  |
| 875 | —C₃H₈— |  | — |  |

|   | Y¹ | A¹ | Z¹ | A² |
|---|---|---|---|---|
| 876 | —CH₂— (branched) |  | — |  |
| 877 | —CH=CH— |  | — |  |
| 878 | —C₂H₄— |  | — |  |
| 879 | —C₄H₈— |  | — |  |
| 880 | —CH₂O— |  | — |  |
| 881 | —CH=CH— |  | — | 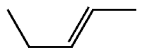 |
| 882 | —C₄H₈— |  | — |  |
| 883 | —C₃H₆— |  | — |  |
| 884 | —CH₂— |  | — |  |
| 885 | —CH=CH— |  | — |  F |
| 886 | —C₂H₄— |  | — |  |
| 887 | —CH₂— | 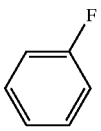 | — |  |
| 888 | —C₂H₄— |  | — |  |
| 889 | —CH=CH— |  | — |  |

-continued
| | Y¹ | A¹ | Z¹ | A² |
|---|---|---|---|---|
| 890 | —C₂H₄— |  | — |  |
| 891 | —CH₂— |  | — | 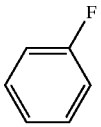 |
| 892 | —CH₂O— |  | — |  |
| 893 | 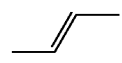 |  | — |  |
| 894 | —C₂H₄— |  | — |  |
| 895 | —CH₂O— |  | — |  |
| 896 | 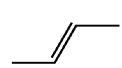 |  | — |  |
| 897 | —C₃H₆— |  | — |  |
| 898 | —C₄H₈— |  | — | 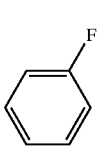 |
| 899 | —CH₂— |  | — |  |
| 900 |  |  | — |  |
| 901 | —C₄H₈— | 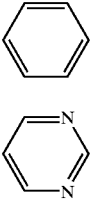 | — |  |
| 902 | —CH₂O— | 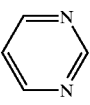 | — |  |
| 903 | —C₂H₄— |  | — |  |

-continued
| | Y¹ | A¹ | Z¹ | A² |
|---|---|---|---|---|
| 904 | —C₂H₄— |  | — |  |
| 905 | —C₃H₆O— |  | — |  |
| 906 | —CH₂— |  | — |  |
| 907 | —C₂H₄— |  | — |  |
| 908 | —C₂H₄O— |  | — |  |
| 909 | —C₂H₄— |  | — |  |
| 910 | —C₂H₄— |  | — |  |
| 911 | —C₃H₆O— |  | — |  |
| 912 | —C₆H₁₂— |  | — |  |
| 913 | —C₂H₄— |  | — |  |
| 914 | —C₄H₈O— |  | — |  |
| 915 |  |  | — |  |
| 916 | —C₄H₈— |  | — |  |
| 917 | —C₂H₄O— |  | — |  |

|  | Y¹ | A¹ | Z¹ | A² |
|---|---|---|---|---|
| 918 | —C₂H₄— |  | — |  |
| 919 | —C₂H₄— |  | — |  |
| 920 | —C₃H₆— |  | — |  |
| 921 | 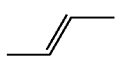 |  | — |  |
| 922 | —C₂H₄— |  | — |  |
| 923 | —C₂H₄— |  | — |  |
| 924 | 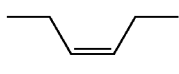 |  | — |  |
| 925 | —C₂H₄— |  | — |  |
| 926 | —C₃H₆— |  | — |  |
| 927 | 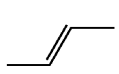 |  | — |  |
| 928 | —C₂H₄— |  | — |  |
| 929 | —C₃H₆— |  | — |  |
| 930 | —C₄H₈O— |  | — |  |
| 931 | —C₂H₄— |  | — |  |

-continued
| | Y¹ | A¹ | Z¹ | A² |
|---|---|---|---|---|
| 932 | —CH₂— |  | — |  |
| 933 | —C₃H₆ |  | — |  |
| 934 | 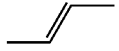 |  | — |  |
| 935 | —C₃H₆— |  |  |  |
| 936 | —CH₂— |  |  |  |
| 937 | —CH₂O— |  |  |  |
| 938 |  |  |  |  |
| 939 | —C₃H₆ | 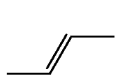 | — |  |
| 940 | —C₃H₆O— |  | — |  |
| 941 |  |  | — |  |
| 942 | —C₂H₄— |  |  |  |
| 943 | —C₄H₈— | | | |
| 944 | —CH₂ | | | |
| 945 |  | |  | |

-continued
| | Y¹ | A¹ | Z¹ | A² |
|---|---|---|---|---|
| 946 | —C₄H₈— |  | 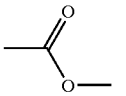 |  |
| 947 | —CH₂— |  | 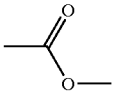 |  |
| 948 | —C₂H₄⟨ |  | 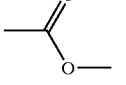 |  |
| 949 | 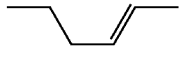 |  | 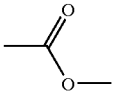 |  |
| 950 | —C₃H₆— |  | 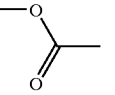 |  |
| 951 | —CH₂— |  | 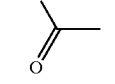 |  |
| 952 | —C₂H₄O— |  | 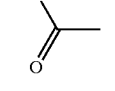 |  |
| 953 | 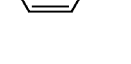 |  | 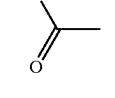 |  |
| 954 | —C₃H₆⟨ |  | — |  |
| 955 | —C₂H₄O— |  | — |  |
| 956 | 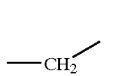 |  | — |  |
| 957 | —CH₂⟨ |  | 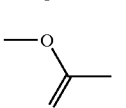 |  |
| 958 | —C₄H₈— |  | 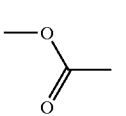 |  |
| 959 | —C₂H₄— |  |  |  |

|  | Y¹ | A¹ | Z¹ | A² |
|---|---|---|---|---|
| 960 | -CH=CH-CH₂- | cyclohexane | -O-C(=O)- | benzene |
| 961 | —C₄H₈— | cyclohexane | — | cyclohexane |
| 962 | —C₅H₁₀— | benzene | -C₃H₆- | cyclohexane |
| 963 | —C₂H₄— | cyclohexane | — | benzene |
| 964 | -CH₂-CH=CH-CH₂- | cyclohexane | -C(=O)-O- | benzene |
| 965 | —CH₂— | benzene | — | benzene |
| 966 | —C₃H₆— | benzene | -CH₂-O- | cyclohexane |
| 967 | —C₂H₄O— | benzene | — | benzene |
| 968 | —C₄H₈— | cyclohexane | -C₃H₆- | benzene |
| 969 | —C₃H₆O— | cyclohexane | -CH=CH- | cyclohexane |
| 970 | —C₂H₄— | benzene | -C≡C- | benzene |
| 971 | —C₃H₆— | benzene | — | benzene |
| 972 | —C₂H₄— | benzene | -C≡C- | benzene |
| 973 | —C₄H₈— | cyclohexane | -O-C(=O)- | benzene |
| 974 | —C₂H₄— | cyclohexane | -C≡C- | cyclohexane |

-continued
| | Y¹ | A¹ | Z¹ | A² |
|---|---|---|---|---|
| 975 | —CH₂— |  | 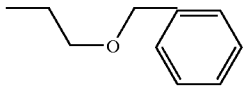 | |
| 976 | —CH₂— |  | — | 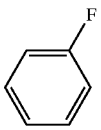 F |
| 977 | —C₃H₆— |  | — |  |
| 978 | —C₂H₄— |  | — |  |
| 979 | —CH₂O— |  | — | 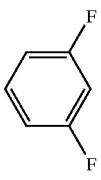 F, F |
| 980 | —C₂H₄— |  | — |  |
| 981 | —C₃H₆— |  | — |  |
| 982 | —C₂H₄— |  | — | 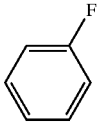 F |
| 983 | —C₃H₆— |  | — |  |
| 984 | —C₂H₄— |  | — | 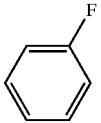 F |
| 985 | —C₃H₆— |  | — |  |
| 986 | —C₂H₄— |  | — |  |

-continued
| | Y¹ | A¹ | Z¹ | A² |
|---|---|---|---|---|
| 987 | —C₃H₆— |  | — | 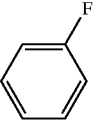 (F) |
| 988 | —C₂H₄— |  | — |  |
| 989 | —C₃H₆— |  | — | 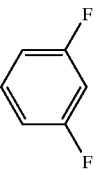 (F, F) |
| 990 | —C₂H₄— |  | — |  |
| 991 | —C₂H₄— |  | — |  |
| | Z² | A³ | Z³ | A⁴ | Y² |
|---|---|---|---|---|---|
| 1 | | | | | —F |
| 2 | | | | | —Cl |
| 3 | | | | | —OCF₂H |
| 4 | | | | | —OCF₃ |
| 5 | | | | | —F |
| 6 | | | | | —OCF₂H |
| 7 | | | | | —CF₃ |
| 8 | | | | | —F |
| 9 | | | | | —OCF₃ |
| 10 | | | | | —F |
| 11 | | | | | —CF₃ |
| 12 | | | | | —OCF₃ |
| 13 | | | | | —F |
| 14 | | | | | —OCF₂H |
| 15 | | | | | —F |
| 16 | | | | | —OCF₃ |
| 17 | | | | | —OCF₂CF₃ |
| 18 | | | | | —CF₃ |
| 19 | | | | | —OCF₃ |
| 20 | | | | | —F |
| 21 | | | | | —OCF₂H |
| 22 | | | | | —CF₃ |
| 23 | | | | | —F |
| 24 | | | | | —OCF₃ |
| 25 | | | | | —F |
| 26 | | | | | —CF₂H |
| 27 | | | | | —OCF₃ |
| 28 | | | | | —F |
| 29 | | | | | —OCF₂H |
| 30 | | | | | —F |
| 31 | — |  | | | —F |

-continued
| | $Z^2$ | $A^3$ | $Z^3$ | $A^4$ | $Y^2$ |
|---|---|---|---|---|---|
| 32 | — |  | | | —Cl |
| 33 | — |  | | | —OCF$_3$ |
| 34 | — |  | | | —OCF$_3$ |
| 35 | — |  | | | —F |
| 36 | — | 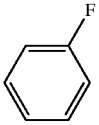 | | | —OCF$_3$ |
| 37 | — | 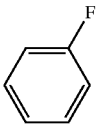 | | | —CF$_3$ |
| 38 | — | 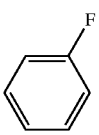 | | | —OCF$_3$ |
| 39 | — | 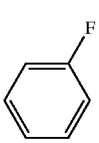 | | | —OCF$_3$ |
| 40 | — | 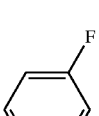 | | | —F |
| 41 | — | 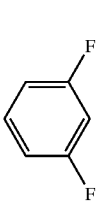 | | | —OCF$_2$H |
| 42 | — | 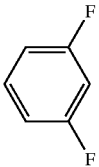 | | | —OCF$_3$ |

-continued

| | Z² | A³ | Z³ | A⁴ | Y² |
|---|---|---|---|---|---|
| 43 | — | 3,5-difluorophenyl | | | —F |
| 44 | — | 3,4-difluorophenyl | | | —OCF₂H |
| 45 | — | 3,4-difluorophenyl | | | —OCF₂H |
| 46 | —CH₂CH₂— | phenyl | | | —OCF₂H |
| 47 | —CH₂CH₂— | phenyl | | | —F |
| 48 | —CH₂O— | phenyl | | | —CF₃ |
| 49 | —CH₂CH₂— | phenyl | | | —OCF₃ |
| 50 | —CH₂CH₂— | phenyl | | | —F |
| 51 | —CH₂CH₂— | 3-fluorophenyl | | | —OCF₃ |
| 52 | —CH₂O— | 3-fluorophenyl | | | —CF₂H |
| 53 | —CH₂CH₂— | 3-fluorophenyl | | | —F |

-continued

| | Z² | A³ | Z³ | A⁴ | Y² |
|---|---|---|---|---|---|
| 54 | —CH₂CH₂— | 2-F-phenyl | | | —OCF₃ |
| 55 | —CH₂CH₂— | 2-F-phenyl | | | —F |
| 56 | —CH₂CH₂— | 2,4-diF-phenyl | | | —OCF₃ |
| 57 | —CH₂CH₂— | 2,4-diF-phenyl | | | —OCF₃ |
| 58 | —CH₂CH₂— | 2,4-diF-phenyl | | | —F |
| 59 | —CH₂CH₂— | 2,4-diF-phenyl | | | —OCF₂H |
| 60 | —CH₂CH₂— | 2,4-diF-phenyl | | | —F |
| 61 | | | | | —OCF₃ |
| 62 | | | | | —F |
| 63 | | | | | —OCF₃ |
| 64 | | | | | —F |
| 65 | | | | | —F |
| 66 | —CH₂CH₂CH₂CH₂— | phenyl | | | —OCF₃ |
| 67 | —CH₂CH₂CH₂CH₂— | phenyl | | | —Cl |

-continued

| | $Z^2$ | $A^3$ | $Z^3$ | $A^4$ | $Y^2$ |
|---|---|---|---|---|---|
| 68 | ~~~ | F-phenyl | | | —OCF$_3$ |
| 69 | ~O~ | F-phenyl | | | —F |
| 70 | ~~~ | 3,4-diF-phenyl | | | —F |
| 71 | —C(O)O— | phenyl | | | —F |
| 72 | —C(O)O— | phenyl | | | —OCF$_3$ |
| 73 | —C(O)O— | F-phenyl | | | —F |
| 74 | —C(O)O— | F-phenyl | | | —OCF$_2$H |
| 75 | —C(O)O— | 3,4-diF-phenyl | | | —F |
| 76 | — | phenyl | | | —Cl |
| 77 | — | phenyl | | | —OCF$_3$ |
| 78 | — | phenyl | | | —CF$_2$H |
| 79 | — | phenyl | | | —OCF$_3$ |

-continued
| | Z² | A³ | Z³ | A⁴ | Y² |
|---|---|---|---|---|---|
| 80 | — |  | | | —F |
| 81 | — | 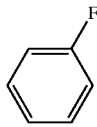 | | | —OCF₃ |
| 82 | — | 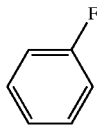 | | | —OCF₂H |
| 83 | — | 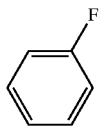 | | | —F |
| 84 | — | 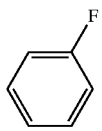 | | | —OCF₃ |
| 85 | — | 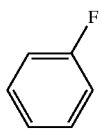 | | | —F |
| 86 | — | 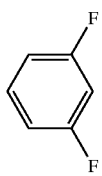 | | | —CF₃ |
| 87 | — | 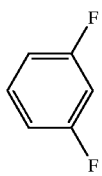 | | | —OCF₃ |
| 88 | — | 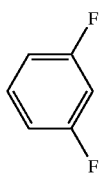 | | | —F |
| 89 | — | 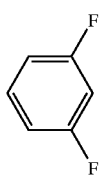 | | | —OCF₂H |

-continued
| | Z² | A³ | Z³ | A⁴ | Y² |
|---|---|---|---|---|---|
| 90 | — | 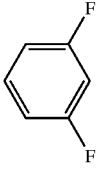 | | | —F |
| 91 | — |  | | | —F |
| 92 | — |  | | | —OCF₃ |
| 93 | — |  | | | —CF₂H |
| 94 | — | 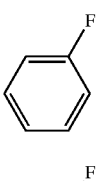 | | | —OCF₃ |
| 95 | — | 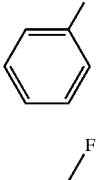 | | | —F |
| 96 | — | 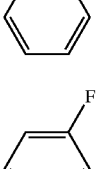 | | | —OCF₂H |
| 97 | — | 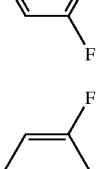 | | | —OCF₂H |
| 98 | — | 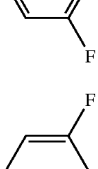 | | | —F |
| 99 | — | 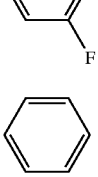 | | | —OCF₃ |
| 100 | — |  | | | —F |

-continued
| | $Z^2$ | $A^3$ | $Z^3$ | $A^4$ | $Y^2$ |
|---|---|---|---|---|---|
| 101 | — |  | | | —OCF$_2$H |
| 102 | — | 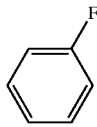 | | | —OCF$_3$ |
| 103 | — | 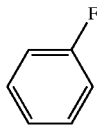 | | | —F |
| 104 | — | 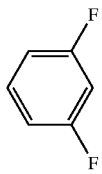 | | | —CF$_3$ |
| 105 | — | 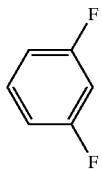 | | | —F |
| 106 | — |  | | | —F |
| 107 | — |  | | | —Cl |
| 108 | — |  | | | —OCF$_3$ |
| 109 | — |  | | | —OCF$_3$ |
| 110 | — |  | | | —F |
| 111 | — | 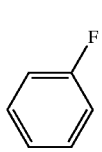 | | | —OCF$_3$ |
| 112 | — | 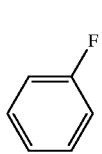 | | | —OCF$_2$H |

-continued

| | Z² | A³ | Z³ | A⁴ | Y² |
|---|---|---|---|---|---|
| 113 | — | phenyl-F | | | —F |
| 114 | — | phenyl-F | | | —OCF₃ |
| 115 | — | phenyl-F | | | —F |
| 116 | — | phenyl-diF | | | —CF₃ |
| 117 | — | phenyl-diF | | | —OCF₃ |
| 118 | — | phenyl-diF | | | —F |
| 119 | — | phenyl-diF | | | —OCF₂H |
| 120 | — | phenyl-diF | | | —F |
| 121 | — | phenyl | | | —OCF₃ |
| 122 | — | phenyl | | | —Cl |

-continued
| | $Z^2$ | $A^3$ | $Z^3$ | $A^4$ | $Y^2$ |
|---|---|---|---|---|---|
| 123 | — |  | | | —F |
| 124 | — |  | | | —OCF$_3$ |
| 125 | — |  | | | —F |
| 126 | — | 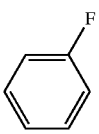 | | | —OCF$_3$ |
| 127 | — | 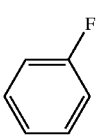 | | | —CF$_2$H |
| 128 | — | 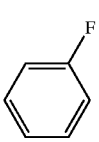 | | | —F |
| 129 | — | 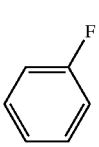 | | | —OCF$_3$ |
| 130 | — | 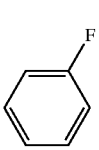 | | | —F |
| 131 | — | 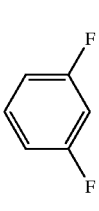 | | | —OCF$_3$ |
| 132 | — | 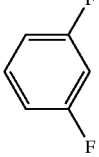 | | | —OCF$_3$ |
| 133 | — | 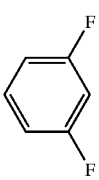 | | | —F |

-continued
| | $Z^2$ | $A^3$ | $Z^3$ | $A^4$ | $Y^2$ |
|---|---|---|---|---|---|
| 134 | — | 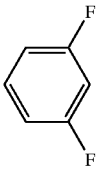 | | | —OCF$_2$H |
| 135 | — | 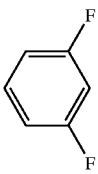 | | | —F |
| 136 | — |  | | | —OCF$_3$ |
| 137 | — | 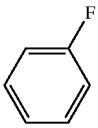 | | | —F |
| 138 | — | 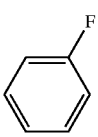 | | | —OCF$_3$ |
| 139 | — | 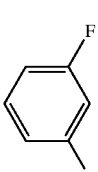 | | | —OCF$_3$ |
| 140 | — | 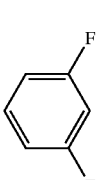 | | | —F |
| 141 | 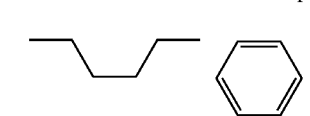 |  | | | —OCF$_3$ |
| 142 | 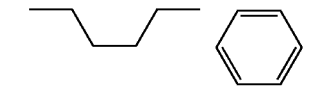 |  | | | —OCF$_2$H |
| 143 | 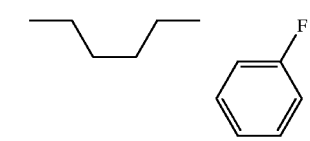 | 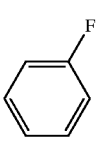 | | | —OCF$_3$ |

-continued

| | $Z^2$ | $A^3$ | $Z^3$ | $A^4$ | $Y^2$ |
|---|---|---|---|---|---|
| 144 | ⌇⌇⌇ (propylene) | | 2,3-difluorophenyl | | —F |
| 145 | ⌇⌇⌇ (butylene) | | 2,3-difluorophenyl | | —F |
| 146 | — | | phenyl | | —F |
| 147 | — | | phenyl | | —OCF$_3$ |
| 148 | — | | 3-fluorophenyl | | —F |
| 149 | — | | 3-fluorophenyl | | —OCF$_3$ |
| 150 | — | | 2,3-difluorophenyl | | —F |
| 151 | —CF$_2$O— | | phenyl | | —OCF$_3$ |
| 152 | —CF$_2$O— | | phenyl | | —F |
| 153 | —CF$_2$O— | | phenyl | | —CF$_3$ |
| 154 | —CF$_2$O— | | phenyl | | —OCF$_3$ |

-continued
| | $Z^2$ | $A^3$ | $Z^3$ | $A^4$ | $Y^2$ |
|---|---|---|---|---|---|
| 155 | 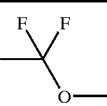 |  | | | —F |
| 156 | 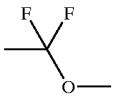 | 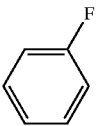 | | | —OCF$_3$ |
| 157 | 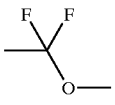 | 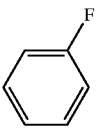 | | | —CF$_3$ |
| 158 | 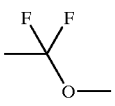 | 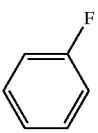 | | | —F |
| 159 | 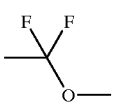 | 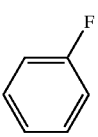 | | | —OCF$_3$ |
| 160 | 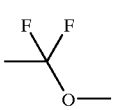 | 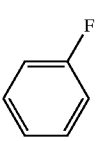 | | | —F |
| 161 | 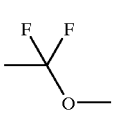 | 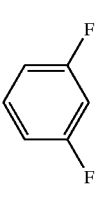 | | | —OCF$_3$ |
| 162 | 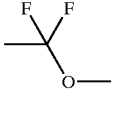 | 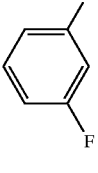 | | | —OCF$_3$ |
| 163 | 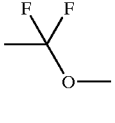 | 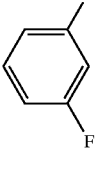 | | | —F |
| 164 | 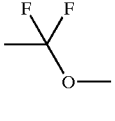 | 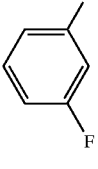 | | | —OCF$_2$H |

-continued
| | $Z^2$ | $A^3$ | $Z^3$ | $A^4$ | $Y^2$ |
|---|---|---|---|---|---|
| 165 | 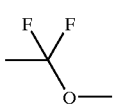 | 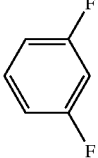 | | | —F |
| 166 |  |  | | | —OCF$_3$ |
| 167 |  |  | | | —F |
| 168 |  |  | | | —CF$_3$ |
| 169 |  |  | | | —OCF$_3$ |
| 170 |  |  | | | —F |
| 171 |  | 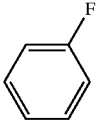 | | | —OCF$_3$ |
| 172 |  | 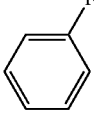 | | | —OCF$_2$H |
| 173 |  | 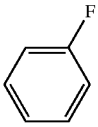 | | | —F |
| 174 |  | 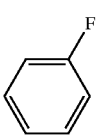 | | | —OCF$_3$ |
| 175 |  | 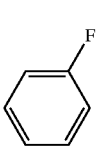 | | | —F |

-continued

| | $Z^2$ | $A^3$ | $Z^3$ | $A^4$ | $Y^2$ |
|---|---|---|---|---|---|
| 176 | —O—CF$_2$— | 3,4-difluorophenylene | | | —OCF$_3$ |
| 177 | —O—CF$_2$— | 3,5-difluorophenylene | | | —OCF$_3$ |
| 178 | —O—CF$_2$— | 3,5-difluorophenylene | | | —F |
| 179 | —O—CF$_2$— | 3,5-difluorophenylene | | | —OCF$_2$H |
| 180 | —O—CF$_2$— | 3,5-difluorophenylene | | | —F |
| 181 | — | phenylene | | | —OCF$_3$ |
| 182 | — | fluorophenylene | | | —F |
| 183 | — | phenylene | | | —CF$_3$ |
| 184 | — | phenylene | | | —OCF$_3$ |
| 185 | — | fluorophenylene | | | —F |

-continued
| | Z² | A³ | Z³ | A⁴ | Y² |
|---|---|---|---|---|---|
| 186 | — | 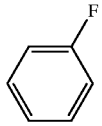 | | | —OCF₃ |
| 187 | — | 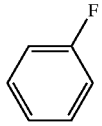 | | | —OCF₂H |
| 188 | — | 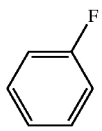 | | | —F |
| 189 | — | 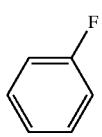 | | | —F |
| 190 | — | 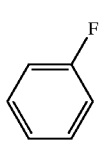 | | | —OCF₃ |
| 191 | — | 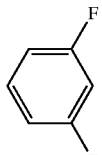 | | | —F |
| 192 | — | 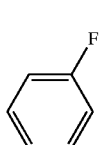 | | | —OCF₃ |
| 193 | — | 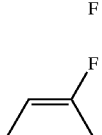 | | | —F |
| 194 | — | 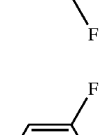 | | | —F |

-continued
| | $Z^2$ | $A^3$ | $Z^3$ | $A^4$ | $Y^2$ |
|---|---|---|---|---|---|
| 195 | — | 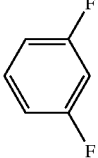 | | | —F |
| 196 | — |  | | | —OCF$_3$ |
| 197 | — |  | | | —F |
| 198 | — |  | | | —F |
| 199 | — |  | | | —OCF$_3$ |
| 200 | — | 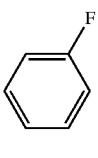 | | | —F |
| 201 | — | 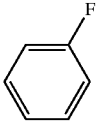 | | | —OCF$_3$ |
| 202 | — | 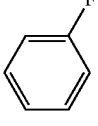 | | | —CF$_2$H |
| 203 | — | 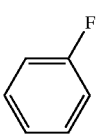 | | | —F |
| 204 | — | 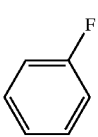 | | | —OCF$_3$ |
| 205 | — | 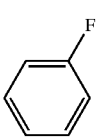 | | | —OCF$_3$ |

|     | Z² | A³ | Z³ | A⁴ | Y² |
|-----|----|----|----|----|----|
| 206 | — | 3,5-difluorophenyl | | | —F |
| 207 | — | 3,5-difluorophenyl | | | —OCF₃ |
| 208 | — | 2,6-difluorophenyl | | | —F |
| 209 | — | 2,5-difluorophenyl | | | —F |
| 210 | — | 2,3-difluorophenyl | | | —F |
| 211 | —COO— | phenyl | | | —OCF₃ |
| 212 | —COO— | phenyl | | | —F |
| 213 | —COO— | phenyl | | | —CF₃ |
| 214 | —COO— | phenyl | | | —OCF₃ |
| 215 | —COO— | fluorophenyl | | | —F |

-continued

| | Z² | A³ | Z³ | A⁴ | Y² |
|---|---|---|---|---|---|
| 216 | -C(=O)O- | | phenyl (F) | | —OCF₃ |
| 217 | -C(=O)O- | | phenyl (F) | | —OCF₂CFHCF₃ |
| 218 | -C(=O)O- | | phenyl (F) | | —F |
| 219 | -C(=O)O- | | phenyl | | —OCF₃ |
| 220 | -C(=O)O- | | phenyl (F) | | —OCF₃ |
| 221 | -C(=O)O- | | phenyl (F,F) | | —F |
| 222 | -C(=O)O- | | phenyl (F,F) | | —OCF₃ |
| 223 | -C(=O)O- | | phenyl (F,F) | | —F |
| 224 | -C(=O)O- | | phenyl | | —OCF₃ |
| 225 | -C(=O)O- | | phenyl (F,F) | | —F |

-continued
| | $Z^2$ | $A^3$ | $Z^3$ | $A^4$ | $Y^2$ |
|---|---|---|---|---|---|
| 226 | — |  | | | —F |
| 227 | — |  | | | —Cl |
| 228 | — |  | | | —OCF$_3$ |
| 229 | — | 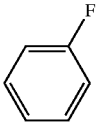 | | | —F |
| 230 | — | 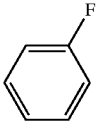 | | | —OCF$_3$ |
| 231 | — | 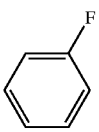 | | | —OCF$_2$H |
| 232 | — | 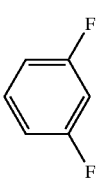 | | | —F |
| 233 | — | 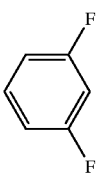 | | | —F |
| 234 | — | 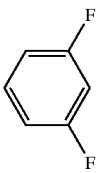 | | | —OCF$_3$ |
| 235 | — |  | | | —F |
| 236 | — |  | | | —OCF$_3$ |

-continued
| | $Z^2$ | $A^3$ | $Z^3$ | $A^4$ | $Y^2$ |
|---|---|---|---|---|---|
| 237 | — |  | | | —OCF$_3$ |
| 238 | — | 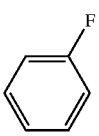 | | | —F |
| 239 | — | 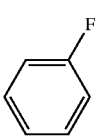 | | | —OCF$_3$ |
| 240 | — | 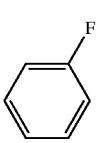 | | | —CF$_3$ |
| 241 | — | 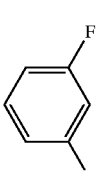 | | | —F |
| 242 | — | 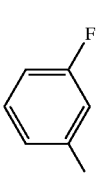 | | | —F |
| 243 | — | 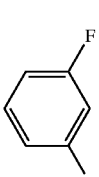 | | | —OCF$_3$ |
| 244 | — |  | | | —F |
| 245 | — |  | | | —OCF$_3$ |
| 246 | — |  | | | —OCF$_2$H |
| 247 | — | 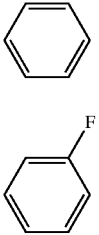 | | | —F |

-continued

| | $Z^2$ | $A^3$ | $Z^3$ | $A^4$ | $Y^2$ |
|---|---|---|---|---|---|
| 248 | — | 4-F-phenyl | | | —F |
| 249 | — | 4-F-phenyl | | | —OCF$_3$ |
| 250 | — | phenyl | | | —F |
| 251 | — | phenyl | | | —OCF$_3$ |
| 252 | — | phenyl | | | —OCF$_3$ |
| 253 | — | 3-F-phenyl | | | —F |
| 254 | — | 3-F-phenyl | | | —OCF$_3$ |
| 255 | — | 3-F-phenyl | | | —CF$_3$ |
| 256 | —OCF$_2$— | phenyl | | | —OCF$_3$ |
| 257 | —OCF$_2$— | phenyl | | | —F |
| 258 | —OCF$_2$— | phenyl | | | —CF$_3$ |
| 259 | —OCF$_2$— | phenyl | | | —OCF$_3$ |
| 260 | —OCF$_2$— | phenyl | | | —F |

-continued
| | $Z^2$ | $A^3$ | $Z^3$ | $A^4$ | $Y^2$ |
|---|---|---|---|---|---|
| 261 | 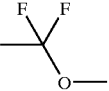 |  | | | —OCF$_3$ |
| 262 | 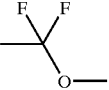 | 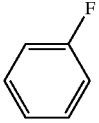 | | | —CF$_3$ |
| 263 | 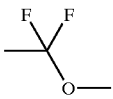 | 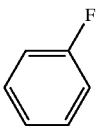 | | | —F |
| 264 | 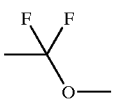 | 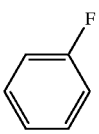 | | | —OCF$_3$ |
| 265 | 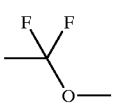 | 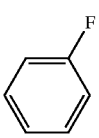 | | | —F |
| 266 | 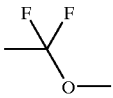 | 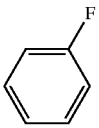 | | | —OCF$_3$ |
| 267 | 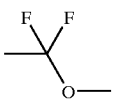 | 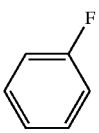 | | | —OCF$_3$ |
| 268 | 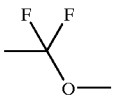 | 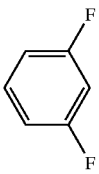 | | | —F |
| 269 | 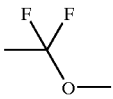 | 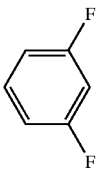 | | | —OCF$_2$H |
| 270 | 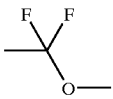 | 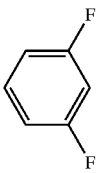 | | | —F |

-continued
| | $Z^2$ | $A^3$ | $Z^3$ | $A^4$ | $Y^2$ |
|---|---|---|---|---|---|
| 271 | 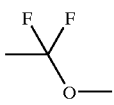 | 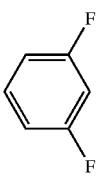 | | | —OCF$_3$ |
| 272 | 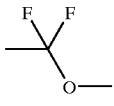 | 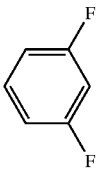 | | | —F |
| 273 | 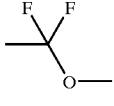 | 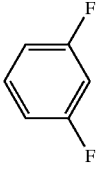 | | | —CF$_3$ |
| 274 | 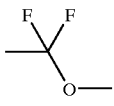 |  | | | —OCF$_3$ |
| 275 | 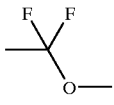 |  | | | —F |
| 276 | 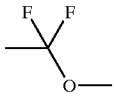 |  | | | —Cl |
| 277 | 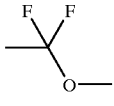 | 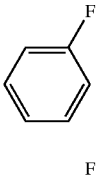 | | | —CF$_3$ |
| 278 | 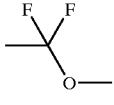 | 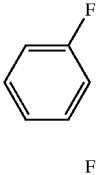 | | | —F |
| 279 | 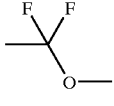 | 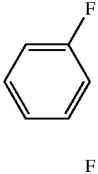 | | | —OCF$_3$ |
| 280 | 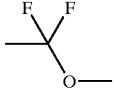 | 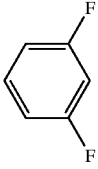 | | | —F |

-continued
| | $Z^2$ | $A^3$ | $Z^3$ | $A^4$ | $Y^2$ |
|---|---|---|---|---|---|
| 281 | 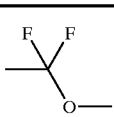 | 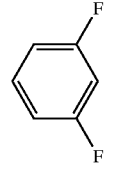 | | | —OCF$_3$ |
| 282 | 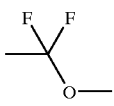 | 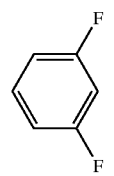 | | | —F |
| 283 | 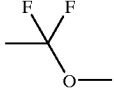 |  | | | —F |
| 284 | 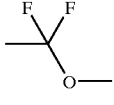 |  | | | —OCF$_2$H |
| 285 | 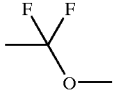 |  | | | —OCF$_3$ |
| 286 | 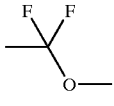 | 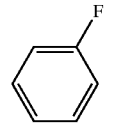 | | | —OCF$_3$ |
| 287 | 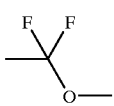 | 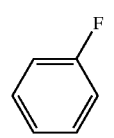 | | | —F |
| 288 | 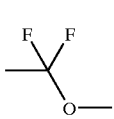 | 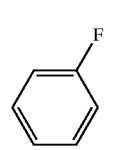 | | | —CF$_3$ |
| 289 | 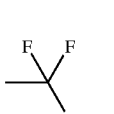 | 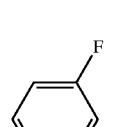 | | | —F |
| 290 | 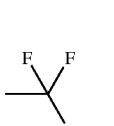 | 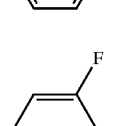 | | | —F |

-continued
| | $Z^2$ | $A^3$ | $Z^3$ | $A^4$ | $Y^2$ |
|---|---|---|---|---|---|
| 291 | 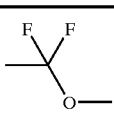 | 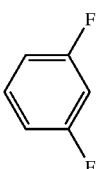 | | | —OCF$_3$ |
| 292 | 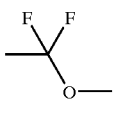 | 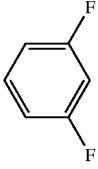 | | | —CF$_2$H |
| 293 | 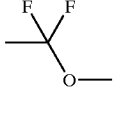 |  | | | —F |
| 294 | 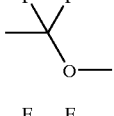 |  | | | —OCF$_3$ |
| 295 | 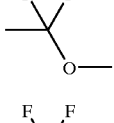 |  | | | —Cl |
| 296 | 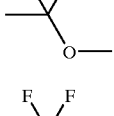 |  | | | —OCF$_3$ |
| 297 | 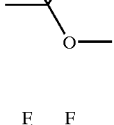 |  | | | —F |
| 298 | 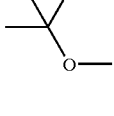 |  | | | —F |
| 299 | 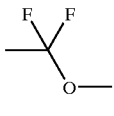 |  | | | —OCF$_2$H |
| 300 | 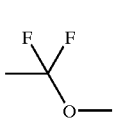 | 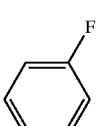 | | | —OCF$_3$ |
| 301 | 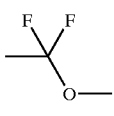 | 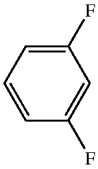 | | | —OCF$_3$ |

| | Z² | A³ | Z³ | A⁴ | Y² |
|---|---|---|---|---|---|
| 302 | 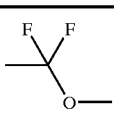 | 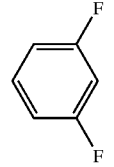 | | | —F |
| 303 | 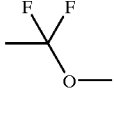 | 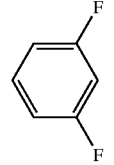 | | | —CF₃ |
| 304 | 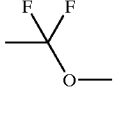 | 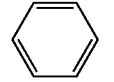 | | | —OCF₃ |
| 305 | 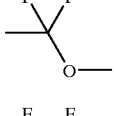 |  | | | —F |
| 306 | 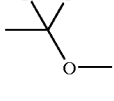 | 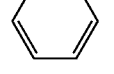 | | | —Cl |
| 307 | 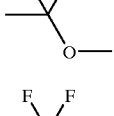 | 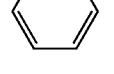 | | | —CF₂H |
| 308 | 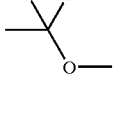 | 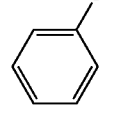 | | | —F |
| 309 | 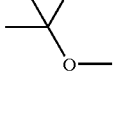 | 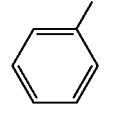 | | | —OCF₃ |
| 310 | 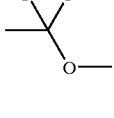 | 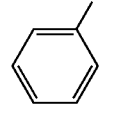 | | | —F |
| 311 | 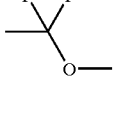 | 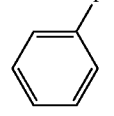 | | | —OCF₃ |
| 312 | 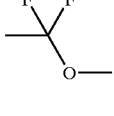 | 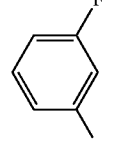 | | | —OCF₃ |

-continued
| | Z² | A³ | Z³ | A⁴ | Y² |
|---|---|---|---|---|---|
| 313 | 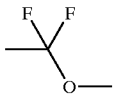 | 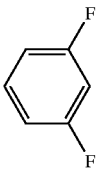 | | | —F |
| 314 | 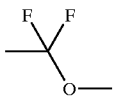 | 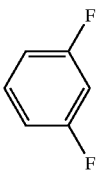 | | | —OCF₂H |
| 315 | 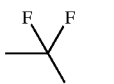 | 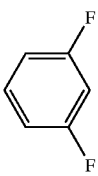 | | | —F |
| 316 | — |  | | | —F |
| 317 | — |  | | | —Cl |
| 318 | — |  | | | —OCF₃ |
| 319 | — |  | | | —OCF₃ |
| 320 | — | 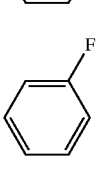 | | | —F |
| 321 | — | 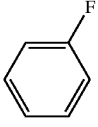 | | | —OCF₃ |
| 322 | — | 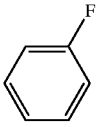 | | | —CF₃ |
| 323 | — | 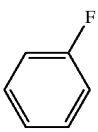 | | | —F |

-continued
| | Z² | A³ | Z³ | A⁴ | Y² |
|---|---|---|---|---|---|
| 324 | — | 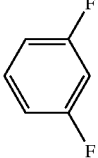 | | | —OCF₃ |
| 325 | — | 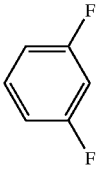 | | | —F |
| 326 | — | 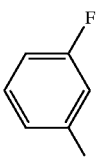 | | | —CFH₂ |
| 327 | — | 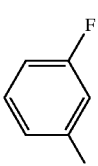 | | | —OCF₃ |
| 328 | — |  | | | —F |
| 329 | — |  | | | —OCF₂H |
| 330 | — |  | | | —OCF₃ |
| 331 | — | 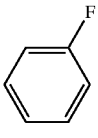 | | | —F |
| 332 | — | 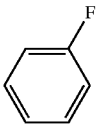 | | | —OCF₃ |
| 333 | — | 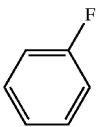 | | | —OCF₃ |

-continued
| | $Z^2$ | $A^3$ | $Z^3$ | $A^4$ | $Y^2$ |
|---|---|---|---|---|---|
| 334 | — | 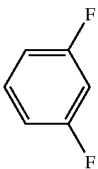 | | | —OCF$_3$ |
| 335 | — | 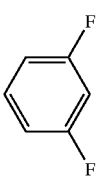 | | | —F |
| 336 | — | 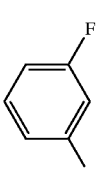 | | | —F |
| 337 | — |  | | | —CF$_3$ |
| 338 | — |  | | | —F |
| 339 | — |  | | | —OCF$_3$ |
| 340 | — | 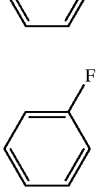 | | | —F |
| 341 | — | 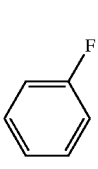 | | | —OCF$_3$ |
| 342 | — | 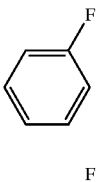 | | | —CF$_3$ |
| 343 | — | 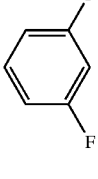 | | | —F |

-continued

| | Z² | A³ | Z³ | A⁴ | Y² |
|---|---|---|---|---|---|
| 344 | — | 3,5-difluorophenyl | | | —OCF₂H |
| 345 | — | 3,5-difluorophenyl | | | —F |
| 346 | — | cyclohexyl | — | phenyl | —F |
| 347 | — | cyclohexyl | — | phenyl | —Cl |
| 348 | — | cyclohexyl | — | phenyl | —OCF₃ |
| 349 | — | cyclohexyl | — | 3-fluorophenyl | —OCF₃ |
| 350 | — | cyclohexyl | — | 3-fluorophenyl | —F |
| 351 | — | cyclohexyl | — | 3-fluorophenyl | —OCF₃ |
| 352 | — | cyclohexyl | — | 3,5-difluorophenyl | —CF₃ |
| 353 | — | cyclohexyl | — | 3,5-difluorophenyl | —F |

-continued
| | Z² | A³ | Z³ | A⁴ | Y² |
|---|---|---|---|---|---|
| 354 | — |  | — | 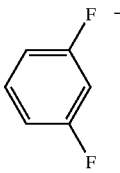 | —OCF₃ |
| 355 | — |  | — | 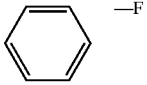 | —F |
| 356 | — |  | — |  | —CF₃ |
| 357 | — |  | — | 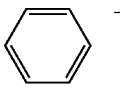 | —OCF₃ |
| 358 | — |  | — | 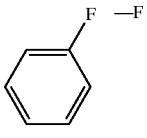 | —F |
| 359 | — |  | — | 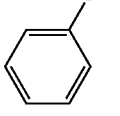 | —CF₂H |
| 360 | — |  | — | 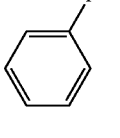 | —OCF₃ |
| 361 | — |  | — | 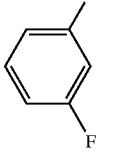 | —F |
| 362 | — |  | — | 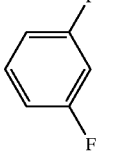 | —CFH₂ |
| 363 | — |  | — | 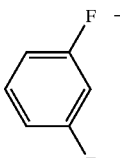 | —OCF₃ |

-continued

| | Z² | A³ | Z³ | A⁴ | Y² |
|---|---|---|---|---|---|
| 364 | — | 2-F-phenyl | — | phenyl | —OCF₃ |
| 365 | — | 2-F-phenyl | — | phenyl | —F |
| 366 | — | 2-F-phenyl | — | phenyl | —OCF₂H |
| 367 | — | 2,4-diF-phenyl | — | phenyl | —CF₃ |
| 368 | — | 2,4-diF-phenyl | — | phenyl | —F |
| 369 | — | 2,4-diF-phenyl | — | phenyl | —OCF₃ |
| 370 | — | 2,4-diF-phenyl | — | 2-F-phenyl | —F |
| 371 | — | 2,4-diF-phenyl | — | 2-F-phenyl | —CF₃ |
| 372 | — | 2,4-diF-phenyl | — | 2-F-phenyl | —OCF₃ |

|     | Z² | A³ | Z³ | A⁴ | Y² |
|-----|----|----|----|----|----|
| 373 | — | 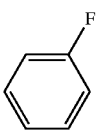 (F) | — |  | —F |
| 374 | — | 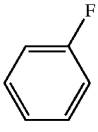 (F) | — | 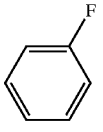 (F) | —CF₂H |
| 375 | — | 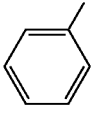 (F) | — |  | —OCF₃ |
| 376 | — | 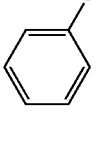 (F) | — | 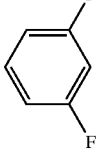 (F, F) | —F |
| 377 | — | 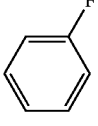 (F) | — | 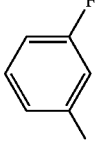 (F, F) | —CFH₂ |
| 378 | — | 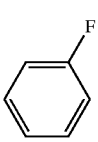 (F) | — | 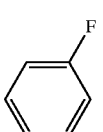 (F, F) | —OCF₃ |
| 379 | — | 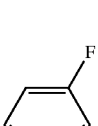 (F, F) | — | 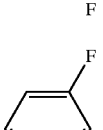 (F, F) | —OCF₃ |
| 380 | — | 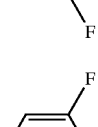 (F, F) | — | 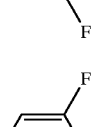 (F, F) | —F |
| 381 | — | 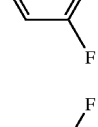 (F, F) | — | 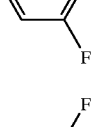 (F, F) | —CF₃ |

-continued
| | Z² | A³ | Z³ | A⁴ | Y² |
|---|---|---|---|---|---|
| 382 |  |  | — |  | —CF₃ |
| 383 |  |  | — |  | —F |
| 384 |  |  | — |  | —OCF₃ |
| 385 |  |  | — |  | —F |
| 386 |  |  | — |  | —CF₃ |
| 387 |  |  | — |  | —OCF₃ |
| 388 |  |  | — |  | —F |
| 389 |  |  | — |  | —CF₂H |
| 390 | — | | — | | —OCF₃ |
| 391 | — | | | | —F |
| 392 | — | | | | —CFH₂ |

-continued
| | Z² | A³ | Z³ | A⁴ | Y² |
|---|---|---|---|---|---|
| 393 | — | 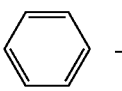 | 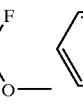 |  | —OCF₃ |
| 394 | — |  | 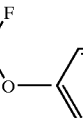 | 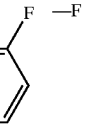 | —F |
| 395 | — | 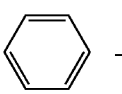 | 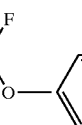 | 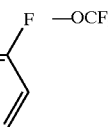 | —OCF₃ |
| 396 | — | 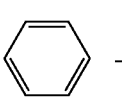 | 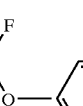 | 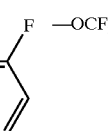 | —OCF₂H |
| 397 | — | 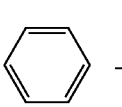 | 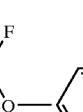 | 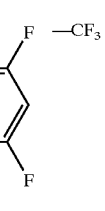 | —CF₃ |
| 398 | — | 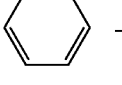 | 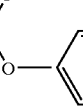 | 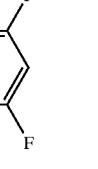 | —F |
| 399 | — |  | 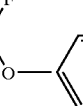 | 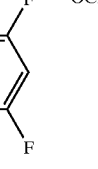 | —OCF₃ |
| 400 | — | 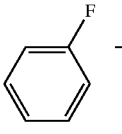 | 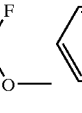 |  | —F |
| 401 | — | 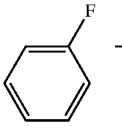 | 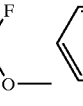 |  | —CF₃ |
| 402 | — | 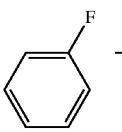 | 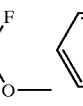 |  | —OCF₃ |

-continued
| | Z² | A³ | Z³ | A⁴ | Y² |
|---|---|---|---|---|---|
| 403 | — | 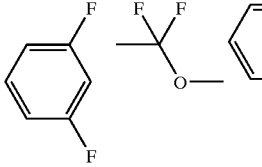 | 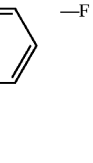 | | —F |
| 404 | — | 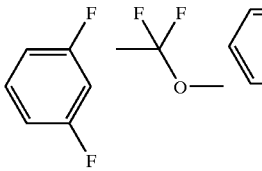 | 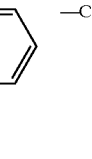 | | —CF₂H |
| 405 | — | 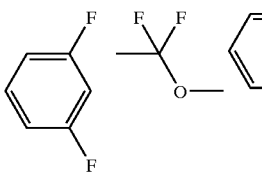 | 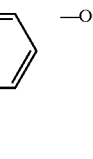 | | —OCF₃ |
| 406 | — | 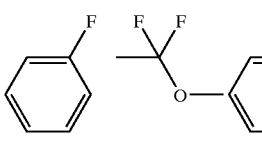 | 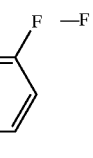 | | —F |
| 407 | — | 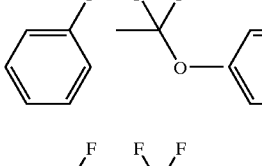 | 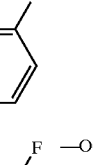 | | —CF₂H |
| 408 | — | 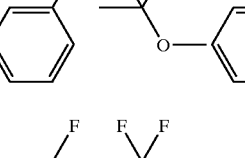 | 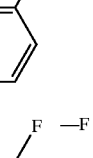 | | —OCF₃ |
| 409 | — | 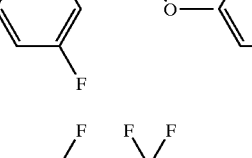 | 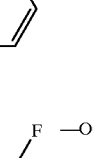 | | —F |
| 410 | — | 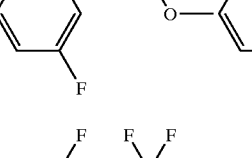 | 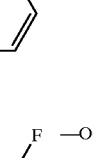 | | —OCF₃ |
| 411 | — | 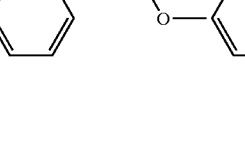 | 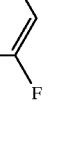 | | —OCFH₂ |

-continued
| | Z² | A³ | Z³ | A⁴ | Y² |
|---|---|---|---|---|---|
| 412 | — | 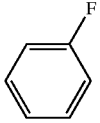 | 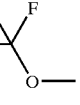 | 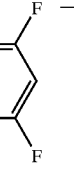 | —CF₃ |
| 413 | — | 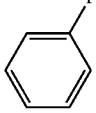 | 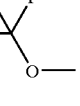 | 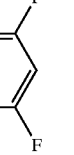 | —F |
| 414 | — | 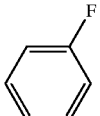 | 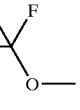 | 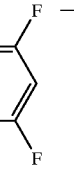 | —OCF₃ |
| 415 | — | 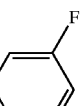 | 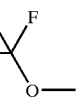 | 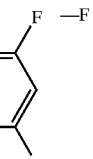 | —F |
| 416 | — | 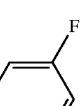 | 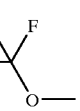 | 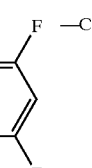 | —CF₃ |
| 417 | — | 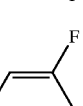 | 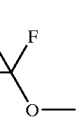 | 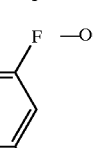 | —OCF₃ |
| 418 | — | 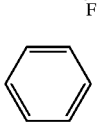 | 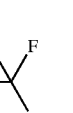 | 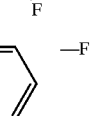 | —F |
| 419 | — |  | 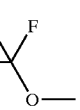 | 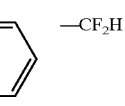 | —CF₂H |
| 420 | — | 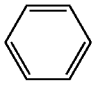 | 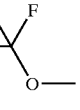 | 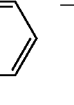 | —OCF₃ |
| 421 | — | 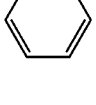 | 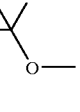 | 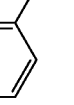 | —F |

-continued
| | Z² | A³ | Z³ | A⁴ | Y² |
|---|---|---|---|---|---|
| 422 | — |  |  | 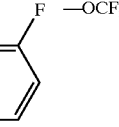 | —OCF₃ |
| 423 | — |  |  | 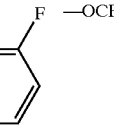 | —OCF₂H |
| 424 | — |  |  | 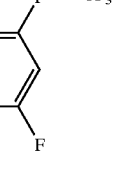 | —CF₃ |
| 425 | — |  |  | 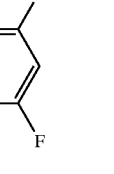 | —F |
| 426 | — |  |  | 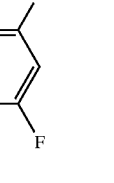 | —OCF₃ |
| 427 | — | 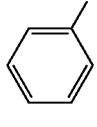 |  | 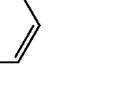 | —F |
| 428 | — | 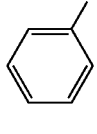 |  | 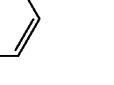 | —CF₃ |
| 429 | — |  |  | 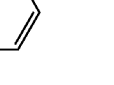 | —OCF₃ |
| 430 | — | 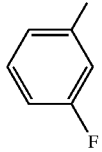 |  | 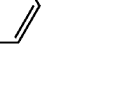 | —F |

-continued
| | $Z^2$ | $A^3$ | $Z^3$ | $A^4$ | $Y^2$ |
|---|---|---|---|---|---|
| 431 | — | 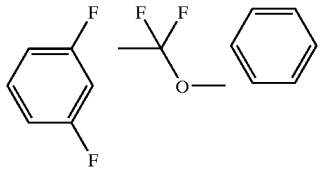 |  | | —CF$_2$H |
| 432 | — | 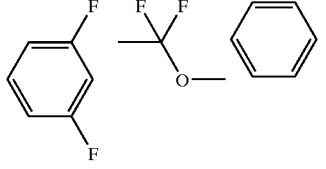 |  | | —OCF$_3$ |
| 433 | — | 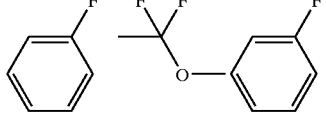 |  | | —F |
| 434 | — | 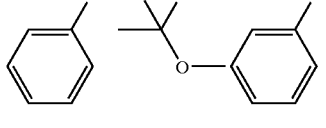 |  | | —CFH$_2$ |
| 435 | — | 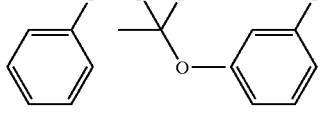 |  | | —OCF$_3$ |
| 436 | — | 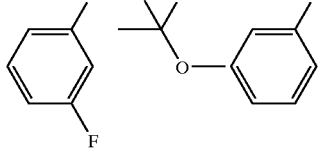 |  | | —F |
| 437 | — | 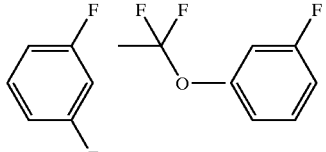 |  | | —OCF$_3$ |
| 438 | — | 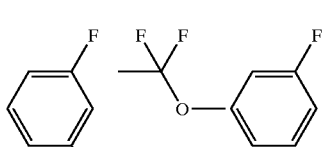 |  | | —CF$_2$H |
| 439 | — | 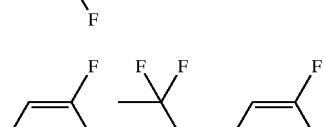 |  | | —CF$_3$ |

-continued
| | Z² | A³ | Z³ | A⁴ | Y² |
|---|---|---|---|---|---|
| 440 | — |  | |  | —F |
| 441 | — |  | |  | —OCF₃ |
| 442 | — |  | |  | —F |
| 443 | — |  | |  | —CF₃ |
| 444 | — |  | |  | —OCF₃ |
| 445 | — |  | |  | —F |
| 446 | — |  | |  | —OCF₂H |
| 447 | — |  | |  | —OCF₃ |
| 448 | — |  | |  | —F |
| 449 | — |  | |  | —OCFH₂ |

-continued
| | $Z^2$ | $A^3$ | $Z^3$ | $A^4$ | $Y^2$ |
|---|---|---|---|---|---|
| 450 | — | | | | —OCF$_3$ |
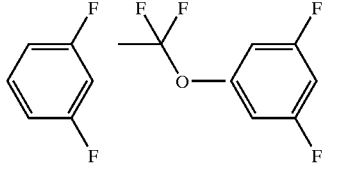
| | $Y^2$ |
|---|---|
| 451 | —CN |
| 452 | —CN |
| 453 | —CN |
| 454 | —CN |
| 455 | —CN |
| 456 | —CN |
| 457 | ≡—CN |
| 458 | —CN |
| 459 | —CN |
| 460 | —CN |
| 461 | ≡—CN |
| 462 | —CN |
| 463 | —CN |
| 464 | —CN |
| 465 | —CN |
| 466 | —CN |
| 467 | —CN |
| 468 | —CN |
| 469 | ≡—CN |
| 470 | —CN |
| 471 | —CN |
| 472 | —CN |
| 473 | ≡—CN |
| 474 | —CN |
| 475 | —CN |
| 476 | —CN |
| 477 | ≡—CN |
| 478 | —CN |
| 479 | —CN |
| 480 | ≡—CN |
| 481 | —CN |
| 482 | —CN |
| 483 | —CN |
| 484 | ≡—CN |
| 485 | —CN |
| 486 | —CN |
| 487 | —CN |
| 488 | ≡—CN |
| 489 | —CN |
| 490 | —CN |
| 491 | —CN |
| 492 | —CN |
| 493 | —CN |
| 494 | —CN |
| 495 | ≡—CN |
| 496 | —CN |
| 497 | —CN |
| 498 | ≡—CN |
| 499 | —CN |
| 500 | —CN |
| 501 | —CN |
| 502 | —CN |
| 503 | —CN |
| 504 | ≡—CN |
| 505 | —CN |
| 506 | —CN |
| 507 | ≡—CN |
| 508 | —CN |
| 509 | —CN |
| 510 | —CN |
| 511 | —CN |
| 512 | —CN |
| 513 | —CN |
| 514 | —CN |
| 515 | ≡—CN |
| 516 | —CN |
| 517 | —CN |
| 518 | —CN |

-continued
| | $Z^2$ | $A^3$ | $Z^3$ | $A^4$ | $Y^2$ |
|---|---|---|---|---|---|
| 519 | | | | | —CN |
| 520 | | | | | —≡—CN |
| 521 | | | | | —CN |
| 522 | | | | | —CN |
| 523 | | | | | —≡—CN |
| 524 | | | | | —CN |
| 525 | | | | | —CN |
| 526 | — |  | | | —CN |
| 527 | — |  | | | —CN |
| 528 | — |  | | | —≡—CN |
| 529 | — | 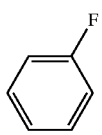 | | | —CN |
| 530 | — | 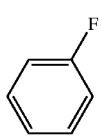 | | | —CN |
| 531 | — | 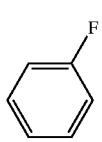 | | | —≡—CN |
| 532 | — | 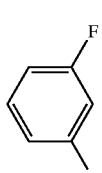 | | | —CN |
| 533 | — | 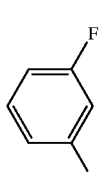 | | | —CN |
| 534 | — | 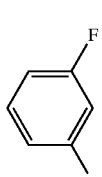 | | | —CN |
| 535 | — |  | | | —CN |

-continued
| | $Z^2$ | $A^3$ | $Z^3$ | $A^4$ | $Y^2$ |
|---|---|---|---|---|---|
| 536 | — |  | | | —CN |
| 537 | — |  | | | —≡—CN |
| 538 | — | 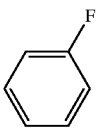 | | | —CN |
| 539 | — | 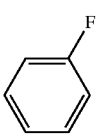 | | | —CN |
| 540 | — | 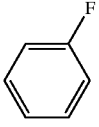 | | | —≡—CN |
| 541 | — | 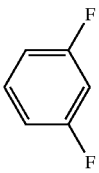 | | | —CN |
| 542 | — | 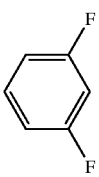 | | | —CN |
| 543 | — | 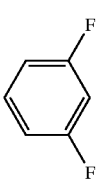 | | | —≡—CN |
| 544 | — |  | | | —CN |
| 545 | — |  | | | —CN |
| 546 | — |  | | | —≡—CN |

-continued
| | $Z^2$ | $A^3$ | $Z^3$ | $A^4$ | $Y^2$ |
|---|---|---|---|---|---|
| 547 | — |  | | | —CN |
| 548 | — |  | | | —CN |
| 549 | — |  | | | ≡—CN |
| 550 |  |  | | | —CN |
| 551 | 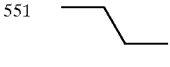 |  | | | —CN |
| 552 |  |  | | | ≡—CN |
| 553 |  | 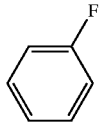 | | | —CN |
| 554 |  | 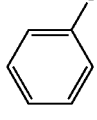 | | | —CN |
| 555 |  | 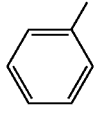 | | | ≡—CN |
| 556 |  | 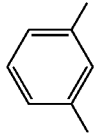 | | | —CN |
| 557 |  | 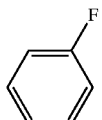 | | | —CN |

-continued
| | $Z^2$ | $A^3$ | $Z^3$ | $A^4$ | $Y^2$ |
|---|---|---|---|---|---|
| 558 |  | 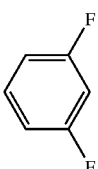 | | | —≡—CN |
| 559 | — |  | | | —CN |
| 560 | — |  | | | —CN |
| 561 | — |  | | | —≡—CN |
| 562 | — | 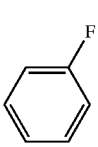 | | | —CN |
| 563 | — | 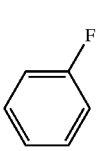 | | | —CN |
| 564 | — | 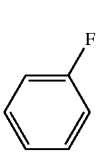 | | | —≡—CN |
| 565 | — | 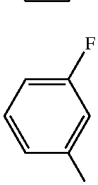 | | | —CN |
| 566 | — | 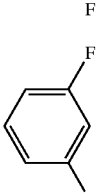 | | | —CN |
| 567 | — | 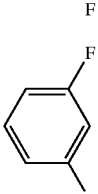 | | | —≡—CN |
| 568 | — | 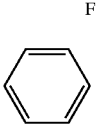 | | | —CN |

-continued
| | $Z^2$ | $A^3$ | $Z^3$ | $A^4$ | $Y^2$ |
|---|---|---|---|---|---|
| 569 | — |  | | | —CN |
| 570 | — |  | | | ≡—CN |
| 571 | — | 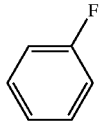 | | | —CN |
| 572 | — | 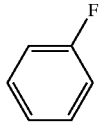 | | | —CN |
| 573 | — | 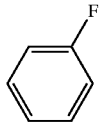 | | | ≡—CN |
| 574 | — | 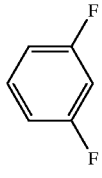 | | | —CN |
| 575 | — | 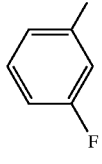 | | | —CN |
| 576 | — | 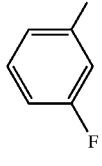 | | | —CN |
| 577 | 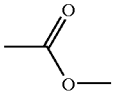 |  | | | —CN |
| 578 | 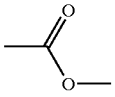 |  | | | —CN |
| 579 | 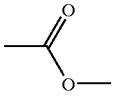 |  | | | ≡—CN |

-continued

| | Z² | A³ | Z³ | A⁴ | Y² |
|---|---|---|---|---|---|
| 580 | (methyl ester -C(=O)-O-) | (fluorophenyl) | | | —CN |
| 581 | (methyl ester -C(=O)-O-) | (fluorophenyl) | | | —CN |
| 582 | (methyl ester -C(=O)-O-) | (fluorophenyl) | | | —≡—CN |
| 583 | (methyl ester -C(=O)-O-) | (difluorophenyl) | | | —CN |
| 584 | (methyl ester -C(=O)-O-) | (difluorophenyl) | | | —CN |
| 585 | (methyl ester -C(=O)-O-) | (difluorophenyl) | | | —≡—CN |
| 586 | (methyl ester -C(=O)-O-) | (phenyl) | | | —CN |
| 587 | (methyl ester -C(=O)-O-) | (phenyl) | | | —CN |
| 588 | (methyl ester -C(=O)-O-) | (phenyl) | | | —≡—CN |
| 589 | (methyl ester -C(=O)-O-) | (fluorophenyl) | | | —CN |

-continued

| | $Z^2$ | $A^3$ | $Z^3$ | $A^4$ | $Y^2$ |
|---|---|---|---|---|---|
| 590 | —C(=O)O— | phenyl-F | | | —CN |
| 591 | —C(=O)O— | phenyl-F | | | —C≡C—CN |
| 592 | —C(=O)O— | phenyl-2F | | | —CN |
| 593 | —C(=O)O— | phenyl-2F | | | —CN |
| 594 | —C(=O)O— | phenyl-2F | | | —CN |
| 595 | —C(=O)O— | phenyl-F | | | —CN |
| 596 | —C(=O)O— | phenyl-F | | | —CN |
| 597 | —C(=O)O— | phenyl-F | | | —C≡C—CN |
| 598 | —C(=O)O— | phenyl | | | —CN |
| 599 | —C(=O)O— | phenyl | | | —CN |

-continued

| | Z² | A³ | Z³ | A⁴ | Y² |
|---|---|---|---|---|---|
| 600 | CH₃-C(=O)-O- | phenyl | | | -C≡C-CN |
| 601 | CF₂H-O- | 2-fluorophenyl | | | -CN |
| 602 | CF₂H-O- | 3-fluorophenyl | | | -CN |
| 603 | CF₂H-O- | 3-fluorophenyl | | | -C≡C-CN |
| 604 | CF₂H-O- | 3,5-difluorophenyl | | | -CN |
| 605 | CF₂H-O- | 3,5-difluorophenyl | | | -CN |
| 606 | CF₂H-O- | 3,5-difluorophenyl | | | -C≡C-CN |
| 607 | CF₂H-O- | phenyl | | | -CN |
| 608 | CF₂H-O- | phenyl | | | -CN |
| 609 | CF₂H-O- | phenyl | | | -C≡C-CN |
| 610 | CF₂H-O- | 2-fluorophenyl | | | -CN |

-continued
| | Z² | A³ | Z³ | A⁴ | Y² |
|---|---|---|---|---|---|
| 611 | 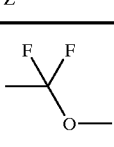 | 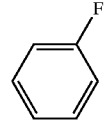 | | | —CN |
| 612 | 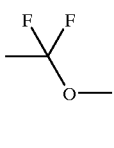 | 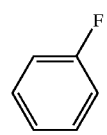 | | | —≡—CN |
| 613 | 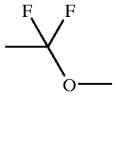 | 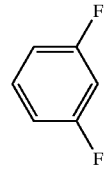 | | | —CN |
| 614 | 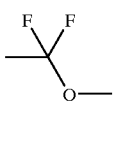 | 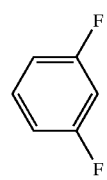 | | | —CN |
| 615 | 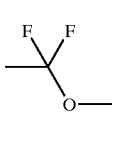 | 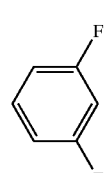 | | | —≡—CN |
| 616 | 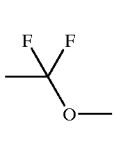 | 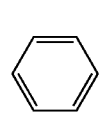 | | | —CN |
| 617 | 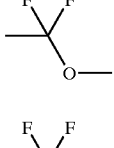 | 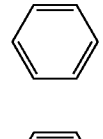 | | | —CN |
| 618 | 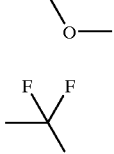 | 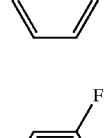 | | | —≡—CN |
| 619 | 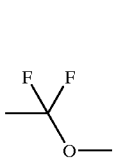 | 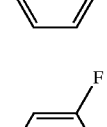 | | | —CN |
| 620 |  |  | | | —CN |

-continued
| | Z² | A³ | Z³ | A⁴ | Y² |
|---|---|---|---|---|---|
| 621 | 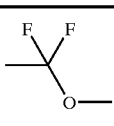 | 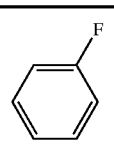 | | | —≡—CN |
| 622 | 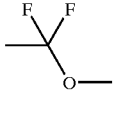 | 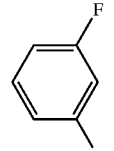 | | | —CN |
| 623 | 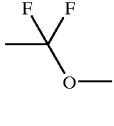 | 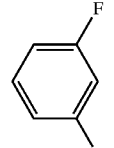 | | | —CN |
| 624 | 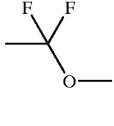 | 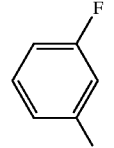 | | | —≡—CN |
| 625 | 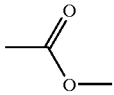 |  | — |  | —CN |
| 626 | 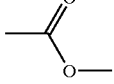 |  | — | 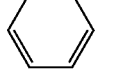 | —CN |
| 627 | 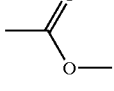 | 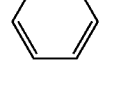 | — | 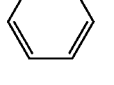 | —≡—CN |
| 628 | 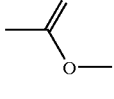 | 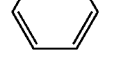 | — | 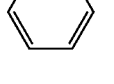 | —CN |
| 629 | 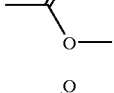 | 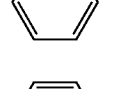 | — | 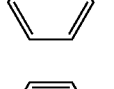 | —CN |
| 630 | 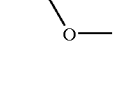 | 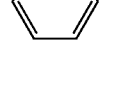 | — | 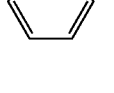 | —≡—CN |
| 631 | | | | | —F |
| 632 | | | | | —OCF₃ |
| 633 | | | | | —CF₃ |
| 634 | | | | | —OCF₂H |
| 635 | | | | | —CN |
| 636 | | | | | —≡—CN |
| 637 | | | | | —F |
| 638 | | | | | —F |
| 639 | | | | | —OCF₃ |
| 640 | | | | | —CF₂H |

-continued
| | $Z^2$ | $A^3$ | $Z^3$ | $A^4$ | $Y^2$ |
|---|---|---|---|---|---|
| 641 | | | | | —CN |
| 642 | | | | | ≡—CN |
| 643 | | | | | —F |
| 644 | | | | | —OCF$_3$ |
| 645 | | | | | —OCF$_3$ |
| 646 | | | | | —CF$_3$ |
| 647 | | | | | —CN |
| 648 | | | | | ≡—CN |
| 649 | 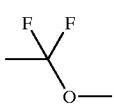 |  | | | —CN |
| 650 | 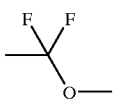 |  | | | —CN |
| 651 | 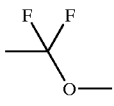 |  | | | ≡—CN |
| 652 | 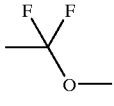 | 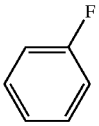 | | | —CN |
| 653 | 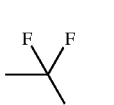 | 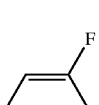 | | | —CN |
| 654 | 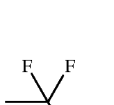 | 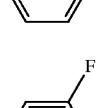 | | | ≡—CN |
| 655 | 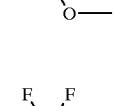 | 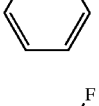 | | | —CN |
| 656 | 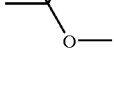 | 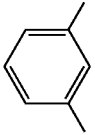 | | | —CN |
| 657 | 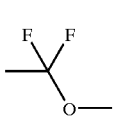 | 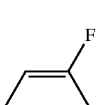 | | | ≡—CN |

-continued
| | Z² | A³ | Z³ | A⁴ | Y² |
|---|---|---|---|---|---|
| 658 | — |  | 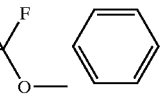 | 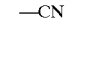 | —CN |
| 659 | — |  | 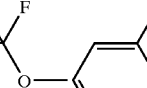 |  | —CN |
| 660 | — | 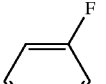 | 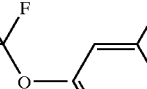 | 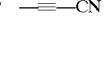 | —≡—CN |
| 661 | — |  | 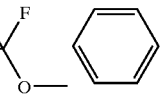 | 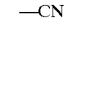 | —CN |
| 662 | — | 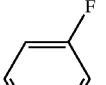 | 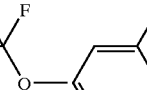 |  | —CN |
| 663 | — | 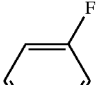 | 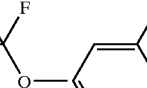 |  | —CN |
| 664 | — | 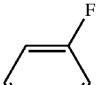 | 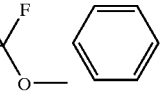 | 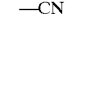 | —CN |
| 665 | — | 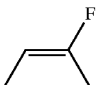 | 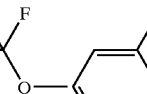 | 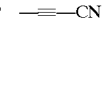 | —≡—CN |
| 666 | — | 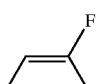 | 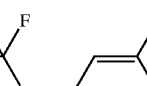 | 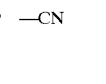 | —CN |
| 667 | | | | | —F |
| 668 | | | | | —F |
| 669 | | | | | —F |
| 670 | | | | | —F |
| 671 | | | | | —F |
| 672 | | | | | —F |

-continued
| | $Z^2$ | $A^3$ | $Z^3$ | $A^4$ | $Y^2$ |
|---|---|---|---|---|---|
| 673 | — |  | | | —F |
| 674 | — |  | | | —F |
| 675 | — |  | | | —F |
| 676 | | | | | —OC$_2$H$_5$ |
| 677 | | | | | —CH$_3$ |
| 678 | | | | | —OC$_2$H$_5$ |
| 679 | | | | | —C$_3$H$_7$ |
| 680 | | | | | —OC$_3$H$_7$ |
| 681 | | | | | —OC$_2$H$_5$ |
| 682 | | | | | —C$_2$H$_5$ |
| 683 | | | | | —SCH$_3$ |
| 684 | | | | | —OC$_2$H$_5$ |
| 685 | | | | | —C$_4$H$_9$ |
| 686 | | | | | —OC$_2$H$_5$ |
| 687 | | | | | —C$_3$H$_7$ |
| 688 | | | | | —OC$_3$H$_7$ |
| 689 | | | | | —OCH$_3$ |
| 690 | | | | | —C$_5$H$_{11}$ |
| 691 | — |  | | | —OC$_2$H$_5$ |
| 692 | — | 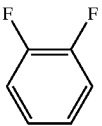 | | | —CH$_3$ |
| 693 | — | 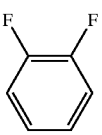 | | | —OC$_2$H$_5$ |
| 694 | — | 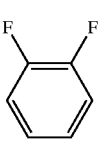 | | | —C$_2$H$_5$ |
| 695 | — | 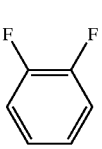 | | | —OC$_3$H$_7$ |
| 696 | 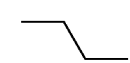 | 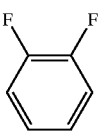 | | | —OC$_2$H$_5$ |

-continued

| | Z² | A³ | Z³ | A⁴ | Y² |
|---|---|---|---|---|---|
| 697 | propyl | 1,2-difluorophenyl | | | —C₂H₅ |
| 698 | propyl | 1,2-difluorophenyl | | | —OCH₃ |
| 699 | —CH₂O— | 1,2-difluorophenyl | | | —OC₂H₅ |
| 700 | propyl | 1,2-difluorophenyl | | | —C₄H₉ |
| 701 | —C(O)O— | 1,2-difluorophenyl | | | —OC₂H₅ |
| 702 | —C(O)O— | 1,2-difluorophenyl | | | —C₃H₇ |
| 703 | —C(O)O— | 1,2-difluorophenyl | | | —OC₃H₇ |
| 704 | —C(O)O— | 1,2-difluorophenyl | | | —OCH₃ |
| 705 | —C(O)O— | 1,2-difluorophenyl | | | —C₅H₁₁ |
| 706 | — | 1,2-difluorophenyl | | | —OC₂H₅ |
| 707 | — | 1,2-difluorophenyl | | | —C₃H₇ |

-continued

| | $Z^2$ | $A^3$ | $Z^3$ | $A^4$ | $Y^2$ |
|---|---|---|---|---|---|
| 708 | — | 2,3-difluorophenyl | | | —OCH$_3$ |
| 709 | — | 2,3-difluorophenyl | | | —C$_6$H$_{13}$ |
| 710 | — | 2,3-difluorophenyl | | | —OC$_2$H$_5$ |
| 711 | —CH$_2$CH$_2$— | 2,3-difluorophenyl | | | —OC$_2$H$_5$ |
| 712 | —CH$_2$CH$_2$— | 2,3-difluorophenyl | | | —CH$_3$ |
| 713 | —CH$_2$CH$_2$— | 2,3-difluorophenyl | | | —OCH$_3$ |
| 714 | —CH$_2$CH$_2$— | 2,3-difluorophenyl | | | —SC$_2$H$_5$ |
| 715 | —CH$_2$CH$_2$— | 2,3-difluorophenyl | | | —C$_4$H$_9$ |
| 716 | —CH$_2$O— | 2,3-difluorophenyl | | | —OC$_2$H$_5$ |
| 717 | —CH$_2$O— | 2,3-difluorophenyl | | | —C$_3$H$_7$ |

-continued

| | $Z^2$ | $A^3$ | $Z^3$ | $A^4$ | $Y^2$ |
|---|---|---|---|---|---|
| 718 | — | 2,3-difluorophenylene | | | $-OC_2H_5$ |
| 719 | — | 2,3-difluorophenylene | | | $-C_3H_7$ |
| 720 | — | 2,3-difluorophenylene | | | $-OC_2H_5$ |
| 721 | — | 2,3-difluorophenylene | | | $-OC_2H_5$ |
| 722 | — | 2,3-difluorophenylene | | | $-CH_3$ |
| 723 | — | 2,3-difluorophenylene | | | $-OC_3H_7$ |
| 724 | — | 2,3-difluorophenylene | | | $-C_6H_{13}$ |
| 725 | — | 2,3-difluorophenylene | | | $-OC_2H_5$ |
| 726 | — | phenylene | | | $-OC_2H_5$ |
| 727 | — | phenylene | | | $-SCH_3$ |
| 728 | — | phenylene | | | $-C_2H_5$ |
| 729 | — | phenylene | | | $-OC_2H_5$ |

-continued
| | Z² | A³ | Z³ | A⁴ | Y² |
|---|---|---|---|---|---|
| 730 | — |  | | | —CH₃ |
| 731 | 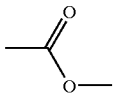 | 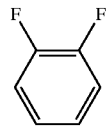 | | | —OC₂H₅ |
| 732 | 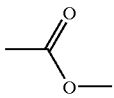 | 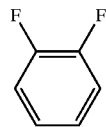 | | | —CH₃ |
| 733 | 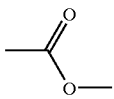 | 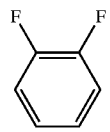 | | | —OC₂H₅ |
| 734 | 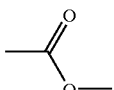 | 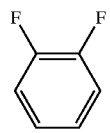 | | | —C₃H₇ |
| 735 | 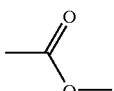 |  | | | —OC₂H₅ |
| 736 | | | | | —C₄H₉ |
| 737 | | | | | —C₇H₁₅ |
| 738 | | | | | 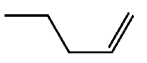 |
| 739 | | | | | 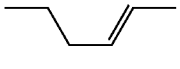 |
| 740 | | | | | —C₅H₁₁ |
| 741 | | | | | —OC₈H₁₇ |
| 742 | | | | | —C₅H₁₁ |
| 743 | | | | | —COOCH₃ |
| 744 | | | | | —COOC₂H₅ |
| 745 | | | | | —COOC₃H₇ |
| 746 | | | | | —C₅H₁₁ |
| 747 | | | | | —OC₄H₉ |
| 748 | | | | | 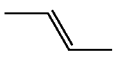 |
| 749 | | | | | —C₂H₅ |
| 750 | | | | | 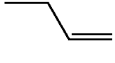 |
| 751 | | | | | —C₂H₅ |
| 752 | | | | | —C₈H₁₇ |
| 753 | | | | | 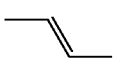 |
| 754 | | | | |  |

-continued

| | Z² | A³ | Z³ | A⁴ | Y² |
|---|---|---|---|---|---|
| 755 | | | | | —C$_3$H$_7$ |
| 756 | | | | | —C$_3$H$_7$ |
| 757 | | | | | —C$_4$H$_9$ |
| 758 | | | | | (but-3-enyl chain) |
| 759 | | | | | —OC$_5$H$_{11}$ |
| 760 | | | | | (pent-4-enyl chain) |
| 761 | | | | | —C$_5$H$_{11}$ |
| 762 | | | | | —CH$_2$OCH$_3$ |
| 763 | | | | | —C$_2$H$_5$ |
| 764 | | | | | (allyl chain) |
| 765 | | | | | —OC$_2$H$_5$ |
| 766 | | | | | —OC$_6$H$_{13}$ |
| 767 | | | | | —C$_8$H$_{17}$ |
| 768 | | | | | (cis-alkenyl chain) |
| 769 | | | | | —C$_3$H$_7$ |
| 770 | | | | | —C$_4$H$_9$ |
| 771 | | | | | —C$_5$H$_{11}$ |
| 772 | | | | | —OC$_7$H$_{15}$ |
| 773 | | | | | (cis-alkenyl chain) |
| 774 | | | | | (alkenyl chain) |
| 775 | | | | | —C$_5$H$_{11}$ |
| 776 | | | | | —C$_2$H$_5$ |
| 777 | | | | | —C$_4$H$_9$ |
| 778 | | | | | —C$_2$H$_4$OCH$_3$ |
| 779 | | | | | (alkenyl chain) |
| 780 | | | | | (allyloxy chain) |
| 781 | | | | | —C$_3$H$_7$ |
| 782 | | | | | —C$_6$H$_{13}$ |
| 783 | | | | | —OC$_7$H$_{15}$ |
| 784 | | | | | (alkenyl chain) |
| 785 | | | | | —C$_3$H$_7$ |
| 786 | | | | | —C$_3$H$_7$ |
| 787 | | | | | —OC$_5$H$_{11}$ |
| 788 | | | | | —C$_6$H$_{13}$ |
| 789 | | | | | (vinyl chain) |
| 790 | | | | | (alkenyloxy chain) |
| 791 | | | | | —C$_3$H$_7$ |
| 792 | | | | | —OC$_4$H$_9$ |

-continued

| | Z² | A³ | Z³ | A⁴ | Y² |
|---|---|---|---|---|---|
| 793 | | | | | (CH=CH-CH₂ structure) |
| 794 | | | | | —C₃H₆OC₃H₇ |
| 795 | | | | | —CH₂OC₂H₅ |
| 796 | | | | | —C₃H₇ |
| 797 | | | | | —C₅H₁₁ |
| 798 | | | | | —OC₇H₁₅ |
| 799 | | | | | (CH₂-CH=CH-CH₂-CH₃ structure) |
| 800 | | | | | —C₃H₇ |
| 801 | | | | | —C₅H₁₁ |
| 802 | | | | | —OC₆H₁₁ |
| 803 | | | | | —C₄H₉ |
| 804 | | | | | —C₂H₄OC₃H₇ |
| 805 | | | | | —O—CH₂—CH=CH—CH₂—CH₃ |
| 806 | | | | | —C₃H₇ |
| 807 | | | | | —OC₂H₅ |
| 808 | | | | | (CH=CH-CH₃ structure) |
| 809 | | | | | —CH₂OC₄H₉ |
| 810 | | | | | —CH₂OC₂H₅ |
| 811 | — | | phenyl | | —C₉H₁₉ |
| 812 | — | | phenyl | | —C₅H₁₁ |
| 813 | — | | phenyl | | —OCH₃ |
| 814 | — | | phenyl | | (CH₂-CH₂-CH=CH₂ structure) |
| 815 | — | | phenyl | | —C₂H₅ |
| 816 | — | | cyclohexyl | | —C₃H₇ |
| 817 | — | | cyclohexyl | | —OC₅H₁₁ |
| 818 | — | | cyclohexyl | | —C₄H₉ |
| 819 | — | | cyclohexyl | | (CH=CH-CH₃ structure) |

-continued
| | $Z^2$ | $A^3$ | $Z^3$ | $A^4$ | $Y^2$ |
|---|---|---|---|---|---|
| 820 | — |  | | | 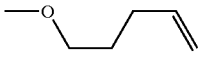 |
| 821 | — |  | | | —$C_3H_7$ |
| 822 | — |  | | | —$OC_3H_7$ |
| 823 | — |  | | | 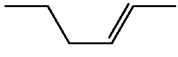 |
| 824 | — |  | | | —$CH_2OC_3H_7$ |
| 825 | — |  | | | —$CH_3$ |
| 826 |  |  | | | —$C_3H_7$ |
| 827 |  |  | | | —$C_2H_5$ |
| 828 |  |  | | | —$OCH_3$ |
| 829 |  |  | | |  |
| 830 | 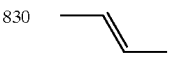 |  | | | 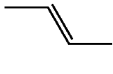 |
| 831 | 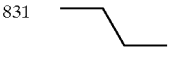 |  | | | —$C_3H_7$ |
| 832 |  |  | | | —$OC_3H_7$ |
| 833 | 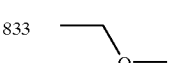 |  | | | 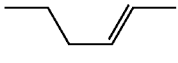 |
| 834 |  |  | | | —$C_3H_6OC_2H_5$ |

| | Z² | A³ | Z³ | A⁴ | Y² |
|---|---|---|---|---|---|
| 835 | ⟋⟍⟋ | ⌬ | | | —CH₃ |
| 836 | — | ⬡ | | | —C₃H₇ |
| 837 | — | ⬡ | | | —OC₃H₇ |
| 838 | — | ⬡ | | | —C₂H₅ |
| 839 | — | ⬡ | | | ⟋\O⟋⟍⟍ |
| 840 | — | ⬡ | | | ⟋═⟍⟋O⟍ |
| 841 | — | ⌬ | | | —C₁₀H₂₁ |
| 842 | — | ⌬ | | | —C₄H₉ |
| 843 | — | ⌬ | | | —OC₂H₅ |
| 844 | — | ⌬ | | | ⟋⟍⟋═ |
| 845 | — | ⌬ | | | —C₂H₅ |
| 846 | — | ⬡ | | | —C₃H₇ |
| 847 | — | ⬡ | | | —OC₆H₁₃ |
| 848 | — | ⬡ | | | —C₂H₅ |
| 849 | — | ⬡ | | | ⟋═⟍⟋ |

-continued
| | $Z^2$ | $A^3$ | $Z^3$ | $A^4$ | $Y^2$ |
|---|---|---|---|---|---|
| 850 | — |  | | | 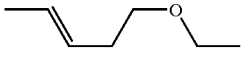 |
| 851 |  |  | | | —$C_3H_7$ |
| 852 |  |  | | | —$OC_4H_9$ |
| 853 |  |  | | | 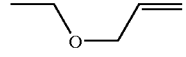 |
| 854 | 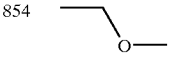 |  | | | —$C_3H_6OCH_3$ |
| 855 |  |  | | | 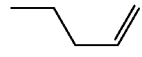 |
| 856 | — |  | | | —$C_3H_7$ |
| 857 | — |  | | | —$C_2H_5$ |
| 858 | — |  | | | —$OC_3H_7$ |
| 859 | — |  | | |  |
| 860 | — |  | | |  |
| 861 | — |  | | | —$C_3H_7$ |
| 862 | — |  | | | —$OC_7H_{15}$ |
| 863 | — |  | | | 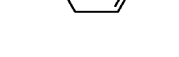 |
| 864 | — |  | | | —$C_2H_4OC_2H_5$ |

-continued
| | $Z^2$ | $A^3$ | $Z^3$ | $A^4$ | $Y^2$ |
|---|---|---|---|---|---|
| 865 | — |  | | | —CH$_3$ |
| 866 | — |  | — |  | —C$_3$H$_7$ |
| 867 | — |  | — |  | —OC$_3$H$_7$ |
| 868 | — |  | — |  | —C$_2$H$_5$ |
| 869 | — |  | — |  |  |
| 870 | — |  | — |  | 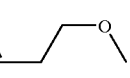 |
| 871 | — |  | — |  | —C$_3$H$_7$ |
| 872 | — |  | — |  | —C$_5$H$_{11}$ |
| 873 | — | 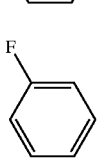 | — |  | —OC$_2$H$_5$ |
| 874 | — | 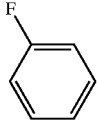 | — |  | —C$_3$H$_7$ |
| 875 | — | 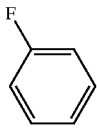 | — |  | —OC$_2$H$_5$ |
| 876 | — | 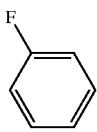 | — |  |  |
| 877 | — | 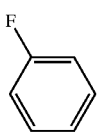 | — |  | —C$_2$H$_5$ |

-continued
| | Z² | A³ | Z³ | A⁴ | Y² |
|---|---|---|---|---|---|
| 878 | — |  | — |  | —C₃H₇ |
| 879 | — |  | — |  | —OCH₃ |
| 880 | — |  | — |  | 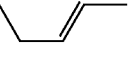 |
| 881 | — |  | — |  | —CH₃ |
| 882 | — |  | — |  | —C₃H₇ |
| 883 | — |  | — |  | —C₂H₄OC₂H₅ |
| 884 | — |  | — |  |  |
| 885 | — |  | — |  | —C₆H₁₃ |
| 886 | — | 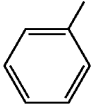 | — |  | —CH₃ |
| 887 | — |  | — |  | —OCH₃ |
| 888 | — |  | — |  | 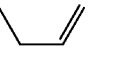 |
| 889 | — |  | — |  | —C₃H₇ |
| 890 | — |  | — |  | —C₂H₅ |
| 891 | — |  | — |  | —OC₂H₅ |

-continued
| | $Z^2$ | $A^3$ | $Z^3$ | $A^4$ | $Y^2$ |
|---|---|---|---|---|---|
| 892 | — |  | — |  |  |
| 893 | — |  | — |  | —$C_3H_7$ |
| 894 | — |  | — |  | —$C_3H_7$ |
| 895 | — |  | — |  | —$CH_3$ |
| 896 | — |  | — |  | —$OC_2H_5$ |
| 897 | — |  | — |  | —$C_3H_7$ |
| 898 | — |  | — |  | —$OCH_3$ |
| 899 | — |  | — |  | 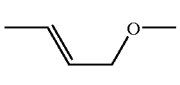 |
| 900 | — |  | — |  | —$C_8H_{17}$ |
| 901 | | | | | —$C_3H_7$ |
| 902 | | | | | —$C_5H_{11}$ |
| 903 | | | | | —$OC_4H_9$ |
| 904 | — | | |  | —$C_5H_{11}$ |
| 905 | — | | |  | —$C_3H_7$ |
| 906 | — | | |  | 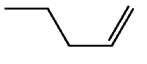 |
| 907 | — | | |  | —$C_3H_7$ |
| 908 | — | | |  | —$C_5H_{11}$ |

-continued
| | $Z^2$ | $A^3$ | $Z^3$ | $A^4$ | $Y^2$ |
|---|---|---|---|---|---|
| 909 | — |  | | |  |
| 910 | — |  | | | —C$_2$H$_5$ |
| 911 | — |  | | | —C$_3$H$_7$ |
| 912 | — |  | | | —OC$_5$H$_{11}$ |
| 913 | — |  | | | —C$_3$H$_7$ |
| 914 | — |  | | | —C$_5$H$_{11}$ |
| 915 | — |  | | | —OCH$_3$ |
| 916 | | | | | —C$_3$H$_7$ |
| 917 | | | | | —C$_4$H$_9$ |
| 918 | | | | | —OC$_6$H$_{13}$ |
| 919 | — | 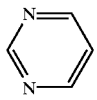 | | | —C$_5$H$_{11}$ |
| 920 | — |  | | | —OC$_3$H$_7$ |
| 921 | — |  | | | —CH$_3$ |
| 922 | — |  | | | —C$_3$H$_7$ |
| 923 | — |  | | | —OC$_3$H$_7$ |
| 924 | — |  | | | —CH$_3$ |

-continued
| | Z² | A³ | Z³ | A⁴ | Y² |
|---|---|---|---|---|---|
| 925 | — |  | | | —C₂H₅ |
| 926 | — |  | | | —OC₃H₇ |
| 927 | — |  | | | —C₆H₁₃ |
| 928 | — |  | | | —C₃H₇ |
| 929 | — |  | | | —OC₅H₁₁ |
| 930 | — |  | | | 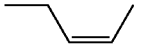 |
| 931 | 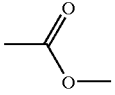 |  | | | —CH₃ |
| 932 | 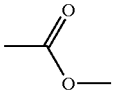 |  | | | —OC₂H₅ |
| 933 | 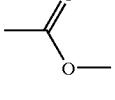 |  | | | 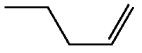 |
| 934 | 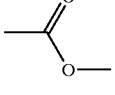 |  | | | —C₃H₇ |
| 935 | — |  | | | —C₃H₇ |
| 936 | — |  | | | —OC₄H₉ |
| 937 | — |  | | | 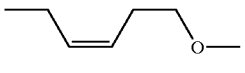 |
| 938 | — |  | | | —C₃H₇ |

-continued

| | $Z^2$ | $A^3$ | $Z^3$ | $A^4$ | $Y^2$ |
|---|---|---|---|---|---|
| 939 | —C(=O)O— | phenyl | | | —C$_2$H$_5$ |
| 940 | —C(=O)O— | phenyl | | | —CH$_3$ |
| 941 | —C(=O)O— | phenyl | | | —OC$_3$H$_7$ |
| 942 | — | cyclohexyl | | | —C$_3$H$_7$ |
| 943 | — | cyclohexyl | | | —OC$_2$H$_5$ |
| 944 | — | cyclohexyl | | | —CH$_2$CH=CHCH$_2$OCH$_3$ |
| 945 | — | cyclohexyl | | | —C$_8$H$_{17}$ |
| 946 | —C(=O)O— | phenyl | | | —CH$_3$ |
| 947 | —C(=O)O— | phenyl | | | —OC$_2$H$_5$ |
| 948 | —C(=O)O— | phenyl | | | —CH$_2$CH$_2$CH=CH$_2$ |
| 949 | —C(=O)O— | phenyl | | | —C$_3$H$_7$ |
| 950 | —OC(=O)— | cyclohexyl | | | —C$_4$H$_9$ |
| 951 | —OC(=O)— | cyclohexyl | | | —OC$_2$H$_5$ |
| 952 | —OC(=O)— | cyclohexyl | | | —CH$_2$CH$_2$CH=CHCH$_3$ |

-continued

| | Z² | A³ | Z³ | A⁴ | Y² |
|---|---|---|---|---|---|
| 953 | —O-C(=O)— | ⬡ | | | —C₃H₇ |
| 954 | —C(=O)O— | ⬡ | — | ⬡ | —C₂H₅ |
| 955 | —C(=O)O— | ⬡ | — | ⬡ | —C₂H₅ |
| 956 | —C(=O)O— | ⬡ | — | ⬡ | —OC₄H₉ |
| 957 | — | ⬡ | — | ⬡ | —C₃H₇ |
| 958 | — | ⬡ | — | ⬡ | —OC₂H₅ |
| 959 | — | ⬡ | — | ⬡ | —CH₂CH₂OCH₂CH=CH₂ |
| 960 | — | ⬡ | — | ⬡ | —C₆H₁₁ |
| 961 | | | | | —C≡CH |
| 962 | | | | | —C≡C— |
| 963 | — | ⬡ | | | —C≡C— |
| 964 | | | | | —CH₂C≡CH |
| 965 | — | ⬡ | | | —CH₂C≡C— |
| 966 | | | | | —CH₂C≡CH |
| 967 | — | ⬡(F) | — | ⬡ | —C≡C—CH₂— |
| 968 | — | ⬡ | | | —C≡C—CH₂— |

-continued

| | $Z^2$ | $A^3$ | $Z^3$ | $A^4$ | $Y^2$ |
|---|---|---|---|---|---|
| 969 | | | | | propynyl chain |
| 970 | | | | | propynyl chain |
| 971 | — | fluorophenyl | —≡— | phenyl | propynyl chain |
| 972 | —≡— | phenyl | | | propynyl chain |
| 973 | | | | | propynyl chain |
| 974 | —≡— | phenyl | —≡— | phenyl | propynyl chain |
| 975 | | | | | pentynyl chain |
| 976 | — | phenyl | — | phenyl | —F |
| 977 | — | fluorophenyl | — | phenyl | —Cl |
| 978 | — | phenyl | — | fluorophenyl | —OCF$_3$ |
| 979 | — | phenyl | — | phenyl | —CF$_3$ |
| 980 | — | difluorophenyl | — | phenyl | —OCHF$_2$ |
| 981 | — | phenyl | — | difluorophenyl | —OCH$_2$CF$_3$ |

-continued
| | Z² | A³ | Z³ | A⁴ | Y² |
|---|---|---|---|---|---|
| 982 | — | 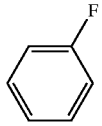 | — |  | —F |
| 983 | — | 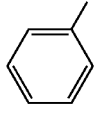 | — | 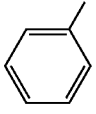 | —OCHF₂ |
| 984 | — |  | — |  | —F |
| 985 | — | 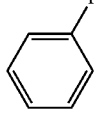 | — |  | —OCF₃ |
| 986 | — | 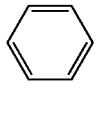 | — | 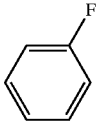 | —F |
| 987 | — | 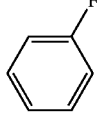 | — |  | —Cl |
| 988 | — | 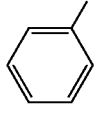 | — | 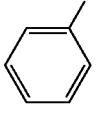 | —F |
| 989 | — |  | — |  | —OCHF₂ |
| 990 | — | 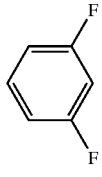 | — |  | —OCF₃ |
| 991 | — | 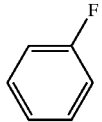 | — | 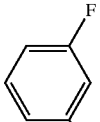 | —F |

Examples in which the compounds of the present invention were used as the components for the compositions shall be shown below. The compounds used in the composition examples and the examples described later were represented by codes exhibited by definitions which were shown in the following Table 1.

TABLE 1

Method for Description of Compounds Using Symbols
R—(SiH$_3$—Y1—)A1—Z1— · · · · · · —Zn—An—X(—Y2)

| 1) Left Terminal Group R—, SiH$_3$—Y1— | Symbol |
|---|---|
| C$_n$H$_{2n+1}$— | n— |
| C$_n$H$_{2n+1}$O— | nO— |
| C$_n$H$_{2n+1}$OC$_m$H$_{2m+1}$— | nOm— |
| CH$_2$=CH— | V— |
| CH$_2$=CHC$_n$H$_{2n}$— | Vn— |
| C$_n$H$_{2n+1}$CH=CHC$_m$H$_{2m}$— | nVm— |
| C$_n$H$_{2n+1}$CH=CHC$_m$H$_{2m}$CH=CHC$_k$H$_{2k}$— | nVmVk— |
| CF$_2$=CH— | VFF— |
| CF$_2$=CHC$_n$H$_{2n}$— | VFFn— |
| SiH$_3$C$_n$H$_{2n}$— | Sin— |

| 2) Ring Structure —An— | Symbol |
|---|---|
| 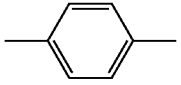 | B |
| 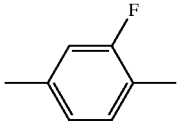 | B(F) |
| 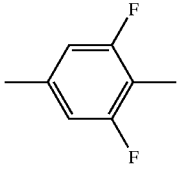 | B(F, F) |
|  | H |
| 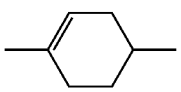 | Ch |
| 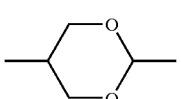 | G |
| 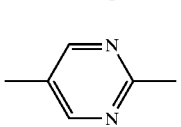 | Py |
|  | B(2F, 3F) |

TABLE 1-continued

Method for Description of Compounds Using Symbols
R—(SiH$_3$—Y1—)A1—Z1— · · · · · · —Zn—An—X(—Y2)

| | |
|---|---|
| 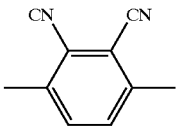 | B(2CN, 3CN) |

| 3) Bonding Group —Zn— | Symbol |
|---|---|
| —C$_2$H$_4$— | 2 |
| —C$_4$H$_8$— | 4 |
| —COO— | E |
| —C≡C— | T |
| —CH=CH— | V |
| —CF$_2$O— | CF2O |
| —OCF$_2$— | OCF2 |

| 4) Right Terminal Group —X, —Y2 | Symbol |
|---|---|
| —F | —F |
| —Cl | —CL |
| —CN | —C |
| —CF$_3$ | —CF3 |
| —OCF$_3$ | —OCF3 |
| —OCF$_2$H | —OCF2H |
| —C$_n$H$_{2n+1}$ | —n |
| —OC$_n$H$_{2n+1}$ | —On |
| —COOCH$_3$ | —EMe |
| —C$_n$H$_{2n}$CH=CH$_2$ | —nV |
| —C$_m$H$_{2m}$CH=CHC$_n$H$_{2n+1}$ | —mVn |
| —CH=CF$_2$ | —VFF |
| —C$_n$H$_{2n}$CH=CF$_2$ | —nVFF |
| —C≡C—CN | —TC |

5) Examples of Description

Example 1  3-H2B(F, F)B(F)—F

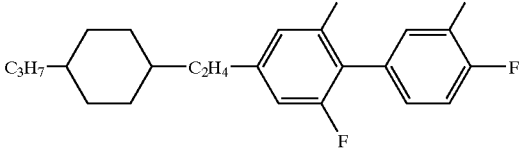

Example 2  Si1-HH-5

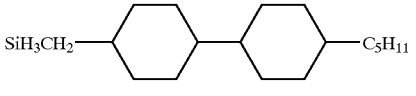

Example 3  Si2-HB(F, F)—C

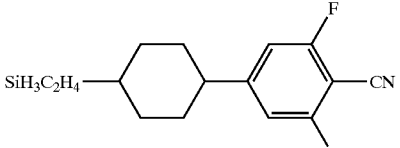

In the examples, "%" represents "weight %", and "part" represents "part by weight" unless otherwise described. When a cis-trans isomer is present in the compound, it means a trans type. When a left terminal group is not described, the group represents a hydrogen atom.

Example 5

| | |
|---|---|
| Si2-HB (F, F)-C (No. 459) | 15.0% |
| Si1-HH-5 (No. 742) | 8.0% |
| 1V2-BEB (F, F)-C | 5.0% |
| 3-HB-C | 10.0% |
| 1-BTB-3 | 5.0% |
| 2-BTB-1 | 10.0% |
| 3-HH-4 | 3.0% |
| 3-HHB-1 | 11.0% |
| 3-HHB-3 | 9.0% |
| 3-H2BTB-2 | 4.0% |
| 3-H2BTB-3 | 4.0% |
| 3-H2BTB-4 | 4.0% |
| 3-HB (F) TB-2 | 6.0% |
| 3-HB (F) TB-3 | 6.0% |
| NI = 74.1 (° C.) | |
| η = 15.5 (mPa · s) | |
| Δn = 0.150 | |
| Δε = 9.6 | |
| Vth = 1.81 (V) | |

When adding 0.8 part of CM33 to 100 parts of the composition described above, the pitch was 11.3 μm.

Example 6

| | |
|---|---|
| Si2-HB (F, F)-C (No. 459) | 13.0% |
| 2O1-BEB (F)-C | 5.0% |
| 3O1-BEB (F)-C | 15.0% |
| 4O1-BEB (F)-C | 13.0% |
| 2-HHB (F)-C | 15.0% |
| 3-HHB (F)-C | 15.0% |
| 3-HB (F) TB-2 | 4.0% |
| 3-HB (F) TB-3 | 4.0% |
| 3-HB (F) TB-4 | 4.0% |
| 3-HHB-1 | 8.0% |
| 3-HHB-O1 | 4.0% |
| NI = 85.4 (° C.) | |
| η = 80.2 (mPa · s) | |
| Δn = 0.143 | |
| Δε = 31.1 | |
| Vth = 0.86 (V) | |

Example 7

| | |
|---|---|
| Si3-HB (F, F) B (F)-F (No. 189) | 4.0% |
| 5-PyB-F | 4.0% |
| 3-PyB (F)-F | 4.0% |
| 2-BB-C | 5.0% |
| 5-BB-C | 5.0% |
| 2-PyB-2 | 2.0% |
| 3-PyB-2 | 2.0% |
| 4-PyB-2 | 2.0% |
| 6-PyB-O5 | 3.0% |
| 6-PyB-O6 | 3.0% |
| 6-PyB-O7 | 3.0% |
| 6-PyB-O8 | 3.0% |
| 3-PyBB-F | 6.0% |
| 4-PyBB-F | 6.0% |
| 5-PyBB-F | 6.0% |
| 3-HHB-1 | 6.0% |
| 3-HHB-3 | 8.0% |
| 2-H2BTB-2 | 4.0% |
| 2-H2BTB-3 | 4.0% |
| 2-H2BTB-4 | 5.0% |
| 3-H2BTB-2 | 5.0% |
| 3-H2BTB-3 | 5.0% |
| 3-H2BTB-4 | 5.0% |
| NI = 93.2 (° C.) | |
| η = 33.4 (mPa · s) | |
| Δn = 0.198 | |
| Δε = 6.5 | |
| Vth = 2.26 (V) | |

Example 8

| | |
|---|---|
| Si2-HHB (F)-OCF3 (No. 36) | 5.0% |
| Si3-HHB (F)-OCF3 (No. 39) | 5.0% |
| 3-GB-C | 10.0% |
| 2-BEB-C | 12.0% |
| 3-BEB-C | 4.0% |
| 3-PyB (F)-F | 6.0% |
| 3-HEB-O4 | 8.0% |
| 4-HEB-O2 | 6.0% |
| 5-HEB-O1 | 6.0% |
| 3-HEB-O2 | 5.0% |
| 5-HEB-O2 | 4.0% |
| 5-HEB-5 | 5.0% |
| 4-HEB-5 | 5.0% |
| 1O-BEB-2 | 4.0% |
| 3-HHB-1 | 6.0% |
| 3-HHEBB-C | 3.0% |
| 3-HBEBB-C | 3.0% |
| 5-HBEBB-C | 3.0% |
| NI = 74.0 (° C.) | |
| η = 39.5 (mPa · s) | |
| Δn = 0.117 | |
| Δε = 10.7 | |
| Vth = 1.36 (V) | |

Example 9

| | |
|---|---|
| Si4-HB (F) EB-OCF3 (No. 219) | 3.0% |
| 3-HR-C | 18.0% |
| 1O1-HB-C | 10.0% |
| 3-HB (F)-C | 10.0% |
| 2-PyB-2 | 2.0% |
| 3-PyB-2 | 2.0% |
| 4-PyB-2 | 2.0% |
| 1O1-HH-3 | 7.0% |
| 2-BTB-O1 | 7.0% |
| 3-HHB-1 | 7.0% |
| 3-HHB-F | 4.0% |
| 3-HHB-O1 | 4.0% |
| 3-HHB-3 | 8.0% |
| 3-H2BTB-2 | 3.0% |
| 3-H2BTB-3 | 3.0% |
| 2-PyBH-3 | 4.0% |
| 3-PyBH-3 | 3.0% |
| 3-PyBB-2 | 3.0% |
| NI = 80.2 (° C.) | |
| η = 18.3 (mPa · s) | |
| Δn = 0.140 | |
| Δε = 8.3 | |
| Vth = 1.73 (V) | |

Example 10

| | |
|---|---|
| Si2-HB (F, F)-C (No. 459) | 12.0% |
| 2-BEB (F)-C | 6.0% |
| 3-BEB (F)-C | 4.0% |
| 1V2-BEB (F, F)-C | 10.0% |
| 3-HH-EMe | 10.0% |
| 3-HB-O2 | 18.0% |

-continued

| | |
|---|---|
| 7-HEB-F | 2.0% |
| 3-HHEB-F | 2.0% |
| 5-HHEB-F | 2.0% |
| 3-HBEB-F | 4.0% |
| 2O1-HBEB (F)-C | 2.0% |
| 3-HB (F) EB (F)-C | 2.0% |
| 3-HBEB (F, F)-C | 2.0% |
| 3-HHB-F | 4.0% |
| 3-HHB-O1 | 4.0% |
| 3-HHB-3 | 13.0% |
| 3-HEBEB-F | 2.0% |
| 3-HEBEB-1 | 2.0% |
| NI = 69.6 (° C.) | |
| η = 31.6 (mPa · s) | |
| Δn = 0.109 | |
| Δε = 24.1 | |
| Vth = 0.90 (V) | |

Example 11

| | |
|---|---|
| Si2-HB (F, F)-C (No. 459) | 10.0% |
| 2-BEB (F)-C | 5.0% |
| 3-BEB (F)-C | 4.0% |
| 4-BEB (F)-C | 12.0% |
| 1V2-BEB (F, F)-C | 6.0% |
| 3-HB-O2 | 10.0% |
| 3-HH-4 | 3.0% |
| 3-HHB-F | 3.0% |
| 3-HHB-1 | 8.0% |
| 3-HHB-O1 | 4.0% |
| 3-HBEB-F | 4.0% |
| 3-HHEB-F | 7.0% |
| 5-HHEB-F | 7.0% |
| 3-H2BTB-2 | 4.0% |
| 3-H2BTB-3 | 4.0% |
| 3-H2BTB-4 | 4.0% |
| 3-HB (F) TB-2 | 5.0% |
| NI = 81.3 (° C.) | |
| η = 36.2 (mPa · s) | |
| Δn = 0.133 | |
| Δε = 24. 5 | |
| Vth = 1.12 (V) | |

Example 12

| | |
|---|---|
| Si2-HB (2F3F)-O2 (No. 678) | 6.0% |
| Si4-HB (2F3F)-O2 (No. 676) | 6.0% |
| 2-BEB-C | 12.0% |
| 3-BEB-C | 4.0% |
| 4-BEB-C | 6.0% |
| 3-HB-C | 28.0% |
| 4-HEB-O2 | 8.0% |
| 5-HEB-O1 | 8.0% |
| 3-HEB-O2 | 6.0% |
| 5-HEB-O2 | 5.0% |
| 3-HHB-1 | 7.0% |
| 3-HHB-O1 | 4.0% |
| NI = 55.4 (° C.) | |
| η = 27.6 (mPa · s) | |
| Δn = 0.114 | |
| Δε = 9.3 | |
| Vth = 1.41 (V) | |

Example 13

| | |
|---|---|
| Si2-HB (F) B (F, F)-F (No. 193) | 7.0% |
| 2-BEB-C | 10.0% |
| 5-BB-C | 12.0% |
| 1-BTB-3 | 7.0% |
| 2-BTB-1 | 10.0% |
| 1O-BEB-2 | 10.0% |
| 1O-BEB-5 | 12.0% |
| 2-HHB-1 | 4.0% |
| 3-HHB-F | 4.0% |
| 3-HHB-1 | 7.0% |
| 3-HHB-O1 | 4.0% |
| 3-HHB-3 | 13.0% |
| NI = 65.2 (° C.) | |
| η = 20.6 (mPa · s) | |
| Δn = 0.155 | |
| Δε = 6.9 | |
| Vth = 1.71 (V) | |

Example 14

| | |
|---|---|
| Si2-HB (F, F)-C (No. 459) | 12.0% |
| Si2-HHB (F, F)-OCF2H (No. 41) | 7.0% |
| Si3-HHB (F, F)-OCF2H (No. 44) | 7.0% |
| Si4-HHB (F, F)-OCF2H (No. 45) | 7.0% |
| 2-HB-C | 5.0% |
| 3-HB-O2 | 15.0% |
| 2-BTB-1 | 3.0% |
| 3-HHB-1 | 8.0% |
| 3-HHB-F | 4.0% |
| 3-HHB-O1 | 5.0% |
| 3-HHB-3 | 14.0% |
| 3-HHEB-F | 4.0% |
| 5-HHEB-F | 4.0% |
| 3-HHB (F, F)-F | 5.0% |
| NI = 81.4 (° C.) | |
| η = 24.9 (mPa · s) | |
| Δn = 0.091 | |
| Δε = 7.3 | |
| Vth = 2.00 (V) | |

Example 15

| | |
|---|---|
| Si2-HB (F) EB-OCF3 (No. 211) | 4.0% |
| Si3-HB (F) EB-OCF3 (No. 224) | 4.0% |
| Si2-HH-2V (No.738) | 7.0% |
| 3-BEB (F)-C | 8.0% |
| 3-HB-C | 8.0% |
| V-HB-C | 8.0% |
| 3-HB-O2 | 3.0% |
| 3-HH-2V | 14.0% |
| V2-HHB-1 | 15.0% |
| 3-HHB-1 | 5.0% |
| 3-HHEB-F | 7.0% |
| 3-H2BTB-2 | 6.0% |
| 3-H2BTB-3 | 6.0% |
| 3-H2BTB-4 | 5.0% |
| NI = 101.0 (° C.) | |
| η = 17.1 (mPa · s) | |
| Δn = 0.130 | |
| Δε = 8.6 | |
| Vth = 2.18 (V) | |

Example 16

| | |
|---|---|
| Si2-HB (F, F)-C (No. 459) | 24.0% |
| V2-HB-C | 12.0% |
| 1V2-HB-C | 12.0% |
| 3-HB (F)-C | 5.0% |
| 2-BTB-1 | 2.0% |
| 3-HH-4 | 8.0% |
| 3-HH-VFF | 6.0% |
| 2-HHB-C | 3.0% |
| 3-HHB-C | 6.0% |
| 3-HB (F) TB-2 | 8.0% |
| 3-H2BTB-2 | 5.0% |
| 3-H2BTB-3 | 5.0% |
| 3-H2BTB-4 | 4.0% |
| NI = 60.6 (° C.) | |
| η = 19.3 (mPa · s) | |
| Δn = 0.135 | |
| Δε = 12.8 | |
| Vth = 1.67 (V) | |

Example 17

| | |
|---|---|
| Si2-HHB (2F, 3F)-O2 (No. 691) | 7.0% |
| 5-BEB (F)-C | 5.0% |
| V-HB-C | 11.0% |
| 5-PyB-C | 6.0% |
| 4-BB-3 | 11.0% |
| 3-HH-2V | 10.0% |
| 5-HH-V | 11.0% |
| V2-HHB-1 | 15.0% |
| 3-HHB-1 | 9.0% |
| 1V2-HBB-2 | 10.0% |
| 3-HHEBH-3 | 5.0% |
| NI = 91.1 (° C.) | |
| η = 17.8 (mPa · s) | |
| Δn = 0.116 | |
| Δε = 4.2 | |
| Vth = 2.53 (V) | |

Example 18

| | |
|---|---|
| Si2-HB (F, F)-C (No. 459) | 10.0% |
| 1V2-BEB (F, F)-C | 8.0% |
| 3-HB-C | 10.0% |
| V2V-HB-C | 4.0% |
| V2V-HH-3 | 19.0% |
| 3-HB-O2 | 4.0% |
| 3-HHB-1 | 10.0% |
| 3-HHB-3 | 15.0% |
| 3-HB (F) TB-2 | 4.0% |
| 3-HB (F) TB-3 | 4.0% |
| 3-H2BTB-2 | 4.0% |
| 3-H2BTB-3 | 4.0% |
| 3-H2BTB-4 | 4.0% |
| NI = 87.6 (° C.) | |
| η = 17.6 (mPa · s) | |
| Δn = 0.121 | |
| Δε = 9.7 | |
| Vth = 1.91 (V) | |

Example 19

| | |
|---|---|
| Si2-HB (F, F)-C (No. 459) | 10.0% |
| V2-HB-TC | 10.0% |

-continued

| | |
|---|---|
| 3-HB-TC | 10.0% |
| 5-HB-C | 7.0% |
| 5-BB-C | 3.0% |
| 2-BTB-1 | 10.0% |
| 2-BTB-O1 | 5.0% |
| 3-HH-4 | 5.0% |
| 3-HHB-1 | 10.0% |
| 3-HHB-3 | 11.0% |
| 3-H2BTB-2 | 3.0% |
| 3-H2BTB-3 | 3.0% |
| 3-HB (F) TB-2 | 3.0% |
| 5-BTB (F) TB-3 | 10.0% |
| NI = 89.6 (° C.) | |
| η = 14.5 (mPa · s) | |
| Δn = 0.197 | |
| Δε = 8.5 | |
| Vth = 1.87 (V) | |

Example 20

| | | |
|---|---|---|
| Si2-HB (F, F)-C | (No. 459) | 12.0% |
| Si1-HH-5 | (No. 742) | 10.0% |
| Si2-HH-2V | (No. 738) | 10.0% |
| 1V2-BEB (F, F)-C | | 6.0% |
| 3-HB-C | | 6.0% |
| 2-BTB-1 | | 10.0% |
| 5-HH-VFF | | 10.0% |
| 1-BHH-VFF | | 8.0% |
| 1-BHH-2VFF | | 11.0% |
| 3-H2BTB-2 | | 5.0% |
| 3-H2BTB-3 | | 4.0% |
| 3-H2BTB-4 | | 4.0% |
| 3-HHB-1 | | 4.0% |
| NI = 67.8 (° C.) | | |
| η = 12.7 (mPa.s) | | |
| Δn = 0.121 | | |
| Δε = 8.5 | | |
| Vth = 1.79 (V) | | |

Example 21

| | | |
|---|---|---|
| Si2-HB (F, F)-C | (No. 459) | 15.0% |
| 5-HBCF2OB (F, F)-C | | 3.0% |
| 3-HB (F, F) CF2OB (F, F)-C | | 3.0% |
| 3-HB-C | | 3.0% |
| 2-BTB-1 | | 10.0% |
| 5-HH-VFF | | 30.0% |
| 1-BHH-VFF | | 8.0% |
| 1-BHH-2VFF | | 11.0% |
| 3-H2BTB-2 | | 5.0% |
| 3-H2BTB-3 | | 4.0% |
| 3-H2BTB-4 | | 4.0% |
| 3-HHB-1 | | 4.0% |
| NI = 66.8 (° C.) | | |
| η = 13.0 (mPa.s) | | |
| Δn = 0.116 | | |
| Δε = 7.0 | | |
| Vth = 2.03 (V) | | |

Example 22

| | | |
|---|---|---|
| Si3-HHB (F)-OCF3 | (No. 39) | 8.0% |
| Si4-HHB (F)-OCF3 | (No. 38) | 8.0% |
| Si2-HB (F, F) B (F)-F | (No. 188) | 6.0% |
| Si3-HB (F, F) B (F)-F | (No. 189) | 6.0% |

-continued

| | |
|---|---|
| 2-HHB (F) -F | 17.0% |
| 3-HHB (F) -F | 17.0% |
| 2-H2HB (F) -F | 10.0% |
| 3-H2HB (F) -F | 5.0% |
| 5-H2HB (F) -F | 10.0% |
| 5-HBB (F) -F | 13.0% |

NI = 86.7 (° C.)
η = 29.8 (mPa.s)
Δn = 0.089
Δε = 6.6
Vth = 1.90 (V)

When adding 0.3 part of CN to 100 parts of the composition described above, the pitch was 78.7 μm.

Example 23

| | | |
|---|---|---|
| Si2-HHB (F, F) -OCF2H | (No. 41) | 10.0% |
| Si3-HHB (F, F) -OCF2H | (No. 44) | 10.0% |
| Si2-HB (F) B (F, F) -F | (No. 193) | 9.0% |
| Si3-HB (F) B (F, F) -F | (No. 194) | 9.0% |
| 7-HB (F, F) -F | | 3.0% |
| 3-HB-O2 | | 7.0% |
| 5-HHB (F) -F | | 10.0% |
| 5-HBB (F) -F | | 16.0% |
| 2-HBB-F | | 4.0% |
| 3-HBB-F | | 4.0% |
| 5-HBB-F | | 3.0% |
| 3-HBB (F, F) -F | | 5.0% |
| 5-HBB (F, F) -F | | 10.0% |

NI = 71.1 (° C.)
η = 31.5 (mPa.s)
Δn = 0.111
Δε = 7.7
Vth = 1.69 (V)

Example 24

| | | |
|---|---|---|
| Si2-HB (F, F) -C | (No. 459) | 8.0% |
| Si1-HH-5 | (No. 742) | 6.0% |
| 5-HB-CL | | 16.0% |
| 3-HH-4 | | 6.0% |
| 3-HH-5 | | 4.0% |
| 3-HHB-F | | 4.0% |
| 3-HHB-CL | | 3.0% |
| 4-HHB-CL | | 4.0% |
| 3-HHB (F) -F | | 10.0% |
| 4-HHB (F) -F | | 9.0% |
| 5-HHB (F) -F | | 9.0% |
| 5-HBB (F) -F | | 4.0% |
| 5-HBBH-101 | | 3.0% |
| 3-HHBB (F, F) -F | | 2.0% |
| 4-HHBB (F, F) -F | | 3.0% |
| 5-HHBB (F, F) -F | | 3.0% |
| 3-HH2BB (F, F) -F | | 3.0% |
| 4-HH2BB (F, F) -F | | 3.0% |

NI = 100.8 (° C.)
η = 18.7 (mPa.s)
Δn = 0.089
Δε = 5.7
Vth = 2.25 (V)

Example 25

| | | |
|---|---|---|
| Si2-HHB (F) -OCF3 | (No. 36) | 8.0% |
| Si3-HHB (F) -OCF3 | (No. 39) | 8.0% |
| Si2-HB (F) EB-OCF3 | (No. 211) | 10.0% |
| Si4-HB (F, F) B (F) -F | (No. 182) | 10.0% |
| Si4-HB (F) B (F, F) -F | (No. 191) | 10.0% |
| 3-HHB (F, F) -F | | 9.0% |
| 5-H2HB (F, F) -F | | 8.0% |
| 3-HBB (F, F) -F | | 11.0% |
| 3-H2BB (F, F) -F | | 10.0% |
| 5-HHBB (F, F) -F | | 3.0% |
| 5-HHEBB-F | | 2.0% |
| 3-HH2BB (F, F) -F | | 3.0% |
| 4-HBBH-1O1 | | 4.0% |
| 5-HBBH-1O1 | | 4.0% |

NI = 83.7 (° C.)
η = 38.0 (mPa.s)
Δn = 0.118
Δε = 11.1
Vth = 1.58 (V)

When adding 0.25 part of CM-43L to 100 parts of the composition described above, the pitch was 63.7 μm.

Example 26

| | | |
|---|---|---|
| Si2-HB (F, F) -C | (No. 459) | 12.0% |
| Si4-HHB (F) -OCF3 | (No. 38) | 5.0% |
| Si4-HB (F) EB-OCF3 | (No. 219) | 10.0% |
| 6-HB-F | | 9.0% |
| 7-HB-F | | 7.0% |
| 2-HHB-OCF3 | | 7.0% |
| 3-HHB-OCF3 | | 7.0% |
| 4-HHB-OCF3 | | 7.0% |
| 3-HH2B-OCF3 | | 4.0% |
| 5-HH2B-OCF3 | | 4.0% |
| 3-HHB (F, F) -OCF3 | | 5.0% |
| 3-HBB (F) -F | | 10.0% |
| 3-HH2B (F) -F | | 3.0% |
| 3-HB (F) BH-3 | | 3.0% |
| 5-HBBH-3 | | 3.0% |
| 3-HHB (F, F) -OCF2H | | 4.0% |

NI = 79.4 (° C.)
η = 22.0 (mPa.s)
Δn = 0.094
Δε = 8.8
Vth = 1.65 (V)

Example 27

| | | |
|---|---|---|
| Si2-HB (F, F) B (F) -F | (No. 188) | 7.0% |
| Si3-HB (F, F) B (F) -F | (No. 189) | 7.0% |
| Si4-HB (F, F) B (F) -F | (No. 182) | 15.0% |
| Si2-HB (F) B (F, F) -F | (No. 193) | 10.0% |
| Si3-HB (F) B (F, F) -F | (No. 194) | 11.0% |
| Si4-HB (F) B (F, F) -F | (No. 191) | 11.0% |
| 2-HHB (F) -F | | 3.0% |
| 4-HBB (F) -F | | 2.0% |
| 3-H2BB (F) -F | | 10.0% |
| 5-HBB (F, F) -F | | 6.0% |
| 2-HHB (F, F) -F | | 5.0% |
| 3-HHB (F, F) -F | | 5.0% |

-continued

| | | |
|---|---|---|
| 4-HHB (F, F) -F | | 5.0% |
| 3-HHB-F | | 3.0% |

NI = 64.0 (° C.)
η = 41.6 (mPa.s)
Δn = 0.125
Δε = 11.1
Vth = 1.53 (V)

Example 28

| | | |
|---|---|---|
| Si2-HHB (F, F) -OCF2H | (No. 41) | 10.0% |
| Si4-HHB (F, F) -OCF2H | (No. 45) | 10.0% |
| Si2-HB (F) EB-OCF3 | (No. 211) | 3.0% |
| Si3-HB (F) EB-OCF3 | (No. 224) | 3.0% |
| Si4-HB (F) EB-OCF3 | (No. 219) | 3.0% |
| 5-HB-CL | | 11.0% |
| 3-HH-4 | | 8.0% |
| 5-HBB (F, F) -F | | 15.0% |
| 3-HHB (F, F) -F | | 8.0% |
| 3-HHEB (F, F) -F | | 10.0% |
| 3-HBEB (F, F) -F | | 5.0% |
| 5-HBEB (F, F) -F | | 3.0% |
| 3-HHBB (F, F) -F | | 6.0% |
| 3-HHB-1 | | 5.0% |

NI = 85.7 (° C.)
η = 25.5 (mPa.s)
Δn = 0.100
Δε = 8.6
Vth = 1.70 (V)

Example 29

| | | |
|---|---|---|
| Si4-HB (F) B (F, F) -F | (No. 191) | 4.0% |
| Si2-HH-2V | (No. 738) | 6.0% |
| 7-HB (F) -F | | 6.0% |
| 5-H2B (F) -F | | 6.0% |
| 3-HB-O2 | | 4.0% |
| 3-HH-4 | | 6.0% |
| 2-HHB (F) -F | | 11.0% |
| 3-HHB (F) -F | | 11.0% |
| 5-HHB (F) -F | | 11.0% |
| 2-HBB (F) -F | | 2.0% |
| 3-HBB (F) -F | | 2.0% |
| 3-HBB (F, F) -F | | 3.0% |
| 2-HHBB (F, F) -F | | 4.0% |
| 3-HHBB (F, F) -F | | 5.0% |
| 3-HHEB-F | | 4.0% |
| 5-HHEB-F | | 4.0% |
| 3-HHB-1 | | 7.0% |
| 3-HHB-F | | 4.0% |

NI = 97.3 (° C.)
η = 20.4 (mPa.s)
Δn = 0.086
Δε = 4.8
Vth = 2.34 (V)

Example 30

| | | |
|---|---|---|
| Si2-HHB (F) -OCF3 | (No. 36) | 10.0% |
| Si3-HHB (F) -OCF3 | (No. 39) | 10.0% |
| Si2-HB (F, F) B (F) -F | (No. 188) | 15.0% |
| Si4-HB (F, F) B (F) -F | (No. 182) | 15.0% |
| Si2-HB (F) B (F, F) -F | (No. 193) | 16.0% |
| Si4-HB (F) B (F, F) -F | (No. 191) | 16.0% |
| 3-HH-4 | | 4.0% |

-continued

| | | |
|---|---|---|
| 5-H2HB (F, F) -F | | 8.0% |
| 3-HBB (F, F) -F | | 3.0% |
| 3-HHBB (F, F) -F | | 3.0% |

NI = 41.8 (° C.)
η = 34.8 (mPa.s)
Δn = 0.102
Δε = 12.2
Vth = 1.18 (V)

Example 31

| | | |
|---|---|---|
| Si2-HHB (F, F) -OCF2H | (No. 41) | 10.0% |
| Si4-HHB (F, F) -OCF2H | (No. 45) | 10.0% |
| Si2-HHB (F) -OCF3 | (No. 36) | 10.0% |
| SI2-HB (F) EB -OCF3 | (No. 211) | 10.0% |
| 7-HB (F, F) -F | | 5.0% |
| 3-H2HB (F, F) -F | | 2.0% |
| 4-HHB (F, F) -F | | 5.0% |
| 3-HBB (F, F) -F | | 10.0% |
| 4-HHEB (F, F) -F | | 3.0% |
| 5-HHEB (F, F) -F | | 3.0% |
| 2-HBEB (F, F) -F | | 3.0% |
| 3-HBEB (F, F) -F | | 5.0% |
| 5-HBEB (F, F) -F | | 3.0% |
| 3-HGB (F, F) -F | | 15.0% |
| 3-HHBB (F, F) -F | | 6.0% |

NI = 76.9 (° C.)
η = 39.0 (mPa.s)
Δn = 0.094
Δε = 14.5
Vth = 1.32 (V)

Example 32

| | | |
|---|---|---|
| Si2-HB (F, F) B (F) -F | (No. 188) | 5.0% |
| Si3-HB (F, F) B (F) -F | (No. 189) | 5.0% |
| Si4-HHB (F) -OCF3 | (No. 38) | 5.0% |
| 5-H4HB (F, F) -F | | 7.0% |
| 5-H4HB-OCF3 | | 15.0% |
| 3-H4HB (F, F) -CF3 | | 8.0% |
| 5-H4HB (F, F) -CF3 | | 10.0% |
| 3-HB-CL | | 6.0% |
| 5-HB-CL | | 4.0% |
| 2-H2BB (F) -F | | 5.0% |
| 5-H2HB (F, F) -F | | 5.0% |
| 3-HHB-OCF3 | | 5.0% |
| 3-H2HB-OCF3 | | 5.0% |
| V-HHB (F) -F | | 5.0% |
| 3-HHB (F) -F | | 5.0% |
| 3-HBEB (F, F) -F | | 5.0% |

NI = 60.5 (° C.)
η = 28.6 (mPa.s)
Δn = 0.093
Δε = 9.3
Vth = 1.64 (V)

Example 33

| | | |
|---|---|---|
| Si4-HHB (2F, 3F) -O2 | (No. 693) | 3.0% |
| Si1-HH-5 | (No. 742) | 5.0% |
| Si2-HH-2V | (No. 738) | 5.0% |
| S-HB-CL | | 17.0% |
| 7-HB (F, F)-F | | 3.0% |
| 3-HH-5 | | 5.0% |
| 3-HB-O2 | | 15.0% |

-continued

| | | |
|---|---|---|
| 3-H2HB (F, F) -F | | 5.0% |
| 4-H2HB (F, F) -F | | 5.0% |
| 3-HHB (F, F) -F | | 6.0% |
| 2-HHB (F) -F | | 7.0% |
| 3-HHB (F) -F | | 7.0% |
| 5-HHB (F) -F | | 7.0% |
| 3-HHB-1 | | 5.0% |
| 3-HHB-O1 | | 5.0% |

NI = 70.6 (° C.)  
$\eta$ = 14.0 (mPa.s)  
$\Delta n$ = 0.074  
$\Delta\epsilon$ = 2.5  
Vth = 2.45 (V)

Example 34

| | | |
|---|---|---|
| Si3-HHB (F) -OCF3 | (No. 39) | 10.0% |
| Si4-HHB (F) -OCF3 | (No. 38) | 9.0% |
| Si2-HHB (F, F) -OCF2H | (No. 41) | 8.0% |
| Si2-HB (F, F) B (F) -F | (No. 188) | 10.0% |
| Si4-HB (F) B (F, F) -F | (No. 191) | 10.0% |
| 5-HB-CL | | 4.0% |
| 7-HHB (F) -F | | 9.0% |
| 4-HHB (F, F) -F | | 3.0% |
| 3-H2HB (F, F) -F | | 12.0% |
| 3-HBB (F, F) -F | | 2.0% |
| 2-HHBB (F, F) -F | | 6.0% |
| 3-GHB (F, F) -F | | 3.0% |
| 4-GHB (F, F) -F | | 8.0% |
| 5-GHB (F, F) -F | | 6.0% |

NI = 66.8 (° C.)  
$\eta$ = 39.4 (mPa.s)  
$\Delta n$ = 0.089  
$\Delta\epsilon$ = 10.6  
Vth = 1.18 (V)

Example 35

| | | |
|---|---|---|
| S i 2-HHB (F) -OCF3 | (No. 36) | 7.0% |
| S i 4-HHB (F) -OCF3 | (No. 38) | 7.0% |
| S i 3-HB (F) EB-OCF3 | (No. 224) | 10.0% |
| S i 3-HB (F, F) B (F) -F | (No. 189) | 7.0% |
| S i 3-HB (F) B (F, F) -F | (No. 194) | 7.0% |
| 3-HHB (F) -F | | 8.0% |
| 3-HHB (F, F) -F | | 8.0% |
| 3-HBB (F, F) -F | | 7.0% |
| 3-H2HB (F, F) -F | | 10.0% |
| 4-HHEB (F, F) -F | | 3.0% |
| 2-HBEB (F, F) -F | | 2.0% |
| 3-HBEB (F, F) -F | | 3.0% |
| 3-GHB (F, F) -F | | 3.0% |
| 4-GHB (F, F) -F | | 7.0% |
| 5-GHB (F, F) -F | | 7.0% |
| 3-HHBB (F, F) -F | | 4.0% |

NI = 70.5 (° C.)  
$\eta$ = 41.0 (mPa · s)  
$\Delta_n$ = 0.092  
$\Delta_\epsilon$ = 12.3  
Vth = 1.16 (V)

Example 36

| | | |
|---|---|---|
| S i 2-HB (F, F) -C | (No. 459) | 4.0% |
| S i 3-HB (F) EB-OCF3 | (No. 224) | 5.0% |
| S i 4-HHB (F, F) -OCF2H | (No. 45) | 6.0% |

-continued

| | | |
|---|---|---|
| S i 2-HHB (F) -OCF3 | (No. 36) | 4.0% |
| 7-HB (F) -F | | 3.0% |
| 5-HB-CL | | 3.0% |
| 3-HH-4 | | 9.0% |
| 3-HH-EMe | | 23.0% |
| 3-HHEB (F, F) -F | | 10.0% |
| 3-HHEB-F | | 8.0% |
| 5-HHEB-F | | 8.0% |
| 4-HGB (F, F) -F | | 5.0% |
| 3-H2GB (F, F) -F | | 5.0% |
| 5-GHB (F, F) -F | | 7.0% |

NI = 81.0 (° C.)  
$\eta$ = 22.5 (mPa · s)  
$\Delta_n$ = 0.069  
$\Delta_\epsilon$ = 6.7  
Vth = 1.41 (V)

Example 37

| | | |
|---|---|---|
| S i 2-HB (F) B (F, F) -F | (No. 193) | 10.0% |
| S i 3-HB (F) B (F, F) -F | (No. 194) | 10.0% |
| S i 4-HB (F) B (F, F) -F | (No. 191) | 10.0% |
| 3-H2HB (F, F) -F | | 5.0% |
| 5-H2HB (F, F) -F | | 5.0% |
| 5-HBB (F, F) -F | | 30.0% |
| 5-HBB (F) B-2 | | 10.0% |
| 5-HBB (F) B-3 | | 10.0% |
| 3-BB (F) B (F, F) -F | | 5.0% |
| 5-B2B (F, F) B (F) -F | | 5.0% |

NI = 94.0 (° C.)  
$\eta$ = 52.1 (mPa · s)  
$\Delta_n$ = 0.148  
$\Delta_\epsilon$ = 11.3  
Vth = 1.66 (V)

Example 38

| | | |
|---|---|---|
| S i 2-HHB (F, F) -OCF2H | (No. 41) | 6.0% |
| S i 2-HB (F) EB-OCF3 | (No. 211) | 8.0% |
| S i 2-HH-2V | (No. 738) | 10.0% |
| 3-HB (F, F) CF2OB (F, F) -F | | 11.0% |
| 5-HB (F, F) CF2OB (F, F) -F | | 11.0% |
| 5-HB-CL | | 7.0% |
| 3-HH-4 | | 4.0% |
| 2-HH-5 | | 4.0% |
| 3-HHB-1 | | 4.0% |
| 3-HHEB-F | | 6.0% |
| 5-HHEB-F | | 6.0% |
| 4-HHB (F, F) -F | | 3.0% |
| 4-HHEB (F, F) -F | | 3.0% |
| 5-HHEB (F, F) -F | | 2.0% |
| 2-HBEB (F, F) -F | | 3.0% |
| 3-HBEB (F, F) -F | | 3.0% |
| 5-HBEB (F, F) -F | | 3.0% |
| 2-HHBB (F, F) -F | | 3.0% |
| 3-HHBB (F, F) -F | | 3.0% |

NI = 81.0 (° C.)  
$\eta$ = 22.1 (mPa · s)  
$\Delta_n$ = 0.083  
$\Delta_\epsilon$ = 9.0  
Vth = 1.38 (V)

Example 39

| | | |
|---|---|---|
| S i 2-HHB (F) -OCF3 | (No. 36) | 5.0% |
| S i 2-HB (F, F) B (F) -F | (No. 188) | 5.0% |
| S i 2-HB (F) B (F, F) -F | (No. 193) | 5.0% |
| 3-BB (F, F) CF2OB (F, F) -F | | 35.0% |
| 3-HH-4 | | 8.0% |
| 3-HHB (F, F) -F | | 5.0% |
| 3-H2HB (F, F) -F | | 9.0% |
| 3-HBB (F, F) -F | | 5.0% |
| 2-HHBB (F, F) -F | | 3.0% |
| 3-HHBB (F, F) -F | | 3.0% |
| 3-HH2BB (F, F) -F | | 4.0% |
| 3-HHB-1 | | 6.0% |
| 5-HBBH-101 | | 7.0% |

NI = 76.7 (° C.)
$\eta$ = 29.8 (mPa · s)
$\Delta_n$ = 0.114
$\Delta_\epsilon$ = 12.8
Vth = 1.36 (V)

Example 40

| | | |
|---|---|---|
| S i 2-HB (2F, 3F) -O2 | (No. 678) | 7.0% |
| S i 4-HB (2F, 3F) -O2 | (No. 676) | 7.0% |
| 3-HEB-O4 | | 28.0% |
| 4-HEB-O2 | | 20.0% |
| 5-HEB-O1 | | 20.0% |
| 3-HEB-O2 | | 18.0% |

NI = 64.7 (° C.)
$\eta$ = 19.8 (mPa · s)
$\Delta_n$ = 0.089

Example 41

| | | |
|---|---|---|
| S i 2-HB (2F, 3F) -O2 | (No. 678) | 12.0% |
| S i 4-HB (2F, 3F) -O2 | (No. 676) | 11.0% |
| S i 2-HHB (2F, 3F) -O2 | (No. 691) | 14.0% |
| S i 4-HHB (2F, 3F) -O2 | (No. 693) | 15.0% |
| S i 2-HHB (2F, 3F) -2 | (No. 694) | 14.0% |
| 3-HH-2 | | 5.0% |
| 3-HH-4 | | 6.0% |
| 3-HH-O1 | | 4.0% |
| 3-HH-O3 | | 5.0% |
| 5-HH-O1 | | 4.0% |
| 3-HHB (2F, 3F) -2 | | 10.0% |

NI = 74.0 (° C.)
$\Delta_n$ = 0.080
$\Delta_\epsilon$ = −4.0

Example 42

| | | |
|---|---|---|
| S i 2-HB (2F, 3F) -O2 | (No. 678) | 10.0% |
| S i 4-HB (2F, 3F) -O2 | (No. 676) | 10.0% |
| S i 2-HHB (2F, 3F) -O2 | (No. 691) | 12.0% |
| S i 4-HHB (2F, 3F) -O2 | (No. 693) | 13.0% |
| S i 2-HHB (2F, 3F) -2 | (No. 694) | 4.0% |
| 3-HH-5 | | 5.0% |
| 3-HH-4 | | 5.0% |
| 3-HH-O1 | | 6.0% |
| 3-HH-O3 | | 6.0% |
| 3-HB-O1 | | 5.0% |
| 3-HB-O2 | | 5.0% |
| 2-HHB (2F, 3F) -1 | | 4.0% |
| 3-HHEH-3 | | 5.0% |
| 3-HHEH-5 | | 5.0% |
| 4-HHEH-3 | | 5.0% |

NI = 78.5 (° C.)
$\Delta_n$ = 0.077
$\Delta_\epsilon$ = −3.3

Example 43

| | | |
|---|---|---|
| S i 2-HB (F, F) -C | (No. 459) | 5.0% |
| 3-BB (2F, 3F) -O2 | | 12.0% |
| 3-BB (2F, 3F) -O4 | | 10.0% |
| 5-BB (2F, 3F) -O4 | | 10.0% |
| 2-BB (2F, 3F) B-3 | | 20.0% |
| 3-BB (2F, 3F) B-5 | | 13.0% |
| 5-BB (2F, 3F) B-5 | | 14.0% |
| 5-BB (2F, 3F) B-7 | | 16.0% |

NI = 66.4 (° C.)
$\Delta_n$ = 0.190
$\Delta_\epsilon$ = −1.9

Example 44

| | | |
|---|---|---|
| S i 2-HB (F, F) B (F) -F | (No. 188) | 3.0% |
| S i 2-HB (F) B (F, F) -F | (No. 193) | 3.0% |
| 3-HB-O1 | | 15.0% |
| 3-HB-O2 | | 6.0% |
| 3-HEB (2F, 3F) -O2 | | 9.0% |
| 4-HEB (2F, 3F) -O2 | | 9.0% |
| 5-HEB (2F, 3F) -O2 | | 9.0% |
| 2-BB2B-O2 | | 6.0% |
| 3-BB2B-O2 | | 6.0% |
| 5-BB2B-O1 | | 6.0% |
| 1-B2BB (2F) -5 | | 7.0% |
| 3-B2BB (2F) -5 | | 7.0% |
| 5-B (F) BB-O2 | | 7.0% |
| 3-BB (2F, 3F) B-3 | | 7.0% |

NI = 75.4 (° C.)
$\eta$ = 24.2 (mPa · s)
$\Delta_n$ = 0.155

Example 45

| | | |
|---|---|---|
| S i 4-HHB (F) -OCF3 | (No. 38) | 5.0% |
| 3-HH-O1 | | 8.0% |
| 5-HH-O1 | | 4.0% |
| 3-HH-4 | | 5.0% |
| 3-HB (2F, 3F) -O2 | | 16.0% |
| 5-HB (2F, 3F) -O2 | | 21.0% |
| 3-HHB (2F, 3F) -1 | | 7.0% |
| 3-HHB (2F, 3F) -O2 | | 14.0% |
| 5-HHB (2F, 3F) -O2 | | 20.0% |

NI = 61.0 (° C.)
$\eta$ = 23.8 (mPa · s)
$\Delta_n$ = 0.076
$\Delta_\epsilon$ = −3.5

Example 46

| | | |
|---|---|---|
| S i 2-HB (2F, 3F) -O2 | (No. 678) | 12.0% |
| S i 4-HB (2F, 3F) -O2 | (No. 676) | 12.0% |
| S i 2-HHB (2F, 3F) -1 | (No. 692) | 12.0% |
| S i 2-HHB (2F, 3F) -2 | (No. 694) | 12.0%. |
| S i 2-HHB (2F, 3F) -O2 | (No. 691) | 13.0% |
| S i 4-HHB (2F, 3F) -O2 | (No. 693) | 13.0% |
| 3-HB-O1 | | 15.0% |
| 3-HH-4 | | 5.0% |
| 3-HHB-1 | | 6.0% |
| NI = 74.5 (° C.) | | |
| η = 38.3 (mPa · s) | | |
| $\Delta_n$ = 0.090 | | |
| $\Delta_\epsilon$ = −3.4 | | |

Example 47

| | | |
|---|---|---|
| S i 2-HB (2F, 3F) -O2 | (No. 678) | 12.0% |
| S i 4-HB (2F, 3F) -O2 | (No. 676) | 12.0% |
| S i 2-HHB (2F, 3F) -1 | (No. 692) | 12.0% |
| S i 2-HHB (2F, 3F) -2 | (No. 694) | 12.0% |
| 3-HB-O1 | | 15.0% |
| 3-HH-4 | | 5.0% |
| 3-HHB (2F, 3F) -O2 | | 13.0% |
| 5-HHB (2F, 3F) -O2 | | 13.0% |
| 6-HEB (2F, 3F) -O2 | | 6.0% |
| NI = 74.2 (° C.) | | |
| η = 36.2 (mPa · s) | | |
| $\Delta_n$ = 0.087 | | |
| $\Delta_\epsilon$ = −3.7 | | |

Example 48

| | | |
|---|---|---|
| S i 2-HB (2F, 3F) -O2 | (No. 678) | 3.0% |
| S i 4-HHB (2F, 3F) -O2 | (No. 693) | 3.0% |
| 3-HB-O2 | | 20.0% |
| 1O1-HH-3 | | 6.0% |
| 1O1-HH-5 | | 5.0% |
| 3-HH-EMe | | 12.0% |
| 4-HEB-O1 | | 9.0% |
| 4-HEB-O2 | | 7.0% |
| 5-HEB-O1 | | 8.0% |
| 3-HHB-1 | | 6.0% |
| 3-HHB-3 | | 6.0% |
| 3-HEB (2CN, 3CN) -O5 | | 4.0% |
| 4-HEB (2CN, 3CN) -O5 | | 3.0% |
| 5-HEB (2CN, 3CN) -O5 | | 2.0% |
| 2-HBEB (2CN, 3CN) -O2 | | 2.0% |
| 4-HBEB (2CN, 3CN) -O4 | | 4.0% |
| NI = 70.4 (° C.) | | |
| η = 30.7 (mPa · s) | | |
| $\Delta_n$ = 0.080 | | |
| $\Delta_\epsilon$ = −5.4 | | |
| Vth = 1.60 (V) | | |

EFFECTS OF THE INVENTION

The compounds of the present invention, that is, the di- to tetracyclic compounds having $SiH_3$ at a terminal are sufficiently stable physically and chemically under the condition where the a liquid crystal display device is usually used. It is characterized by having a good mutual solubility, a low viscosity and a low threshold voltage. Further, addition of the compound of the present invention makes it possible, as shown in the examples, to provide a liquid crystal composition and a liquid crystal display which have good characteristics and are novel.

What is claimed is:

1. A silicon compound represented by formula (1):

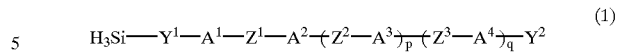

(1)

wherein $Y^1$ is alkylene having 1 to 10 carbon, in which any —$CH_2$— in the alkylene may be replaced by —O—, —S—, —CO—, —CH=CH—, or —C≡C—, but —O— and —O—, —S— and —S—, —O— and —S—, —O— and $SiH_3$, or —S— and $SiH_3$ are not adjacent, and at least one hydrogen in the alkylene may be replaced by halogen or —CN; $Y^2$ is hydrogen, halogen, —CN, —C≡C—CN, or alkyl having 1 to 10 carbon, in which any —$CH_2$— in the alkyl may be replaced by —O—, —S—, —CO—, —CH=CH—, or —C≡C—, but —O— and —O—, —S— and —S—, or —O— and —S— are not adjacent, and any hydrogen in the alkyl may be replaced by halogen or —CN; $A^1$, $A^2$, $A^3$, and $A^4$ each are independently 1,4-cyclohexylene, 1,4-cyclohexenylene, 1,4-phenylene, or 1,4-phenylene in which any hydrogen is replaced by halogen, in which any hydrogen in 1,4-cyclohexylene or 1,4-cyclohexenylene may be replaced by halogen, any —$CH_2$— in these rings may be replaced by —O—, but —O— and —O— are not adjacent, and any —CH= in 1,4-phenylene may be replaced by —N=; $Z^1$, $Z^2$ and $Z^3$ each are independently a single bond, —$(CH_2)_2$—, —$OCH_2$—, —$CH_2O$—, —CH=CH—, —C≡C—, —$(CH_2)_4$—, —$O(CH_2)_3$—, —$(CH_2)_3O$—, —COO—, —OCO—, —$OCF_2$—, or —$CF_2O$—; and p and q each are independently 0 or 1.

2. The silicon compound defined in claim 1, wherein in formula (1) described in claim 1, p and q are 0; $A^1$ and $A^2$ each are independently 1,4-cyclohexylene, 1,4-cyclohexylene in which one or more non-adjacent —$CH_2$— are replaced by —O—, 1,4-phenylene, 1,4-phenylene in which any hydrogen is replaced by halogen, or pirimidine-2,5-diyl; and $Z^1$ is a single bond, —$(CH_2)_2$—, —CH=CH—, —C≡C—, —$(CH_2)_4$—, —COO—, —OCO—, —$OCF_2$—, or —$CF_2O$—.

3. The silicon compound defined in claim 1, wherein in formula (1) described in claim 1, p is 1; q is 0; $A^1$, $A^2$ and $A^3$ each are independently 1,4-cyclohexylene, 1,4-cyclohexylene in which one or more non-adjacent —$CH_2$— are replaced by —O—, 1,4-phenylene, 1,4-phenylene in which any hydrogen is replaced by halogen, or pirimidine-2,5-diyl; and $Z^1$ and $Z^2$ each are independently a single bond, —$(CH_2)_2$—, —CH=CH—, —C≡C—, —COO—, —OCO—, —$(CH_2)_4$—, —$OCF_2$—, or —$CF_2O$—.

4. The silicon compound defined in claim 1, wherein in formula (1) described in claim 1, p and q are 1; $A^1$, $A^2$, $A^3$, and $A^4$ each are independently 1,4-cyclohexylene, 1,4-cyclohexylene in which one or more non-adjacent —$CH_2$— are replaced by —O—, 1,4-phenylene, 1,4-phenylene in which any hydrogen is replaced by halogen, or pirimidine-2,5-diyl; and $Z^1$, $Z^2$ and $Z^3$ each are independently a single bond, —$(CH_2)_2$—, —CH=CH—, —C≡C—, —COO—, —OCO—, —$(CH_2)_4$—, —$OCF_2$—, or —$CF_2O$—.

5. The silicon compound defined in claim 1, wherein in formula (1) described in claim 1, $Y^1$ is alkylene having 1 to 10 carbon, in which any —$CH_2$— in the alkylene may be replaced by —O— or —CH=CH—, but —O— and —O— or —O— and $SiH_3$ are not adjacent; $Y^2$ is alkyl having 1 to 10 carbon, in which any —$CH_2$— in the alkyl may be replaced by —O—, —CH=CH— or —C≡C—, but —O— and —O— are not adjacent; and $A^1$, $A^2$, $A^3$, and $A^4$ each are independently 1,4-cyclohexylene, 1,4-cyclohexylene in which one or more non-adjacent —CH$_2$— are replaced by —O—, 1,4-phenylene, or pirimidine-2,5-diyl.

6. The silicon compound defined in claim 1, wherein in formula (1) described in claim 1, Y$^1$ is alkylene having 1 to 10 carbon, in which any —CH$_2$— in the alkylene may be replaced by —O— or —CH=CH—, but —O— and —O— or —O— and SiH$_3$ are not adjacent; Y$^2$ is halogen, —CN, —C≡C—CN, or alkyl having 1 to 10 carbon, in which any —CH$_2$— in the alkyl may be replaced by —O—, but —O— and —O— are not adjacent, and at least one hydrogen is replaced by halogen; and A$^1$, A$^2$, A$^3$, and A$^4$ each are independently 1,4-cyclohexylene in which one or more non-adjacent —CH$_2$— are replaced by —O—, 1,4-phenylene, 1,4-phenylene in which at least one hydrogen is replaced by halogen, or pirimidine-2,5-diyl.

7. The silicon compound defined in claim 1, wherein in formula (1) described in claim 1, Y$^1$ is alkylene having 1 to 10 carbon, in which any —CH$_2$— in the alkylene may be replaced by —O— or —CH=CH—, but —O— and —O— or —O— and SiH$_3$ are not adjacent; Y$^1$ is alkyl having 1 to 10 carbon, in which any —CH$_2$— in the alkyl may be replaced by —O—, —S— or —CH=CH—, but —O— and —O—, —S— and —S— or —O— and —S— are not adjacent; A$^1$, A$^2$, A$^3$ and A$^4$ each are independently 1,4-cyclohexylene, 1,4-cyclohexylene in which one or more non-adjacent —CH$_2$— are replaced by —O—, 1,4-phenylene in which a 2-position is replaced by halogen, 1,4-phenylene in which a 3-position is replaced by halogen, or 1,4-phenylene in which a 2-position and a 3-position are replaced by halogen, and one of A$^1$, A$^2$, A$^3$, and A$^4$ is always 1,4-phenylene in which a 2-position or a 3-position is replaced by halogen or 1,4-phenylene in which a 2-position and a 3-position are replaced by halogen.

8. A liquid crystal composition comprising at least one silicon compound defined in any one of claims 1 to 7.

9. A liquid crystal composition comprising at least one silicon compound described in any one of claims 1 to 7 as a first component and at least one compound selected from the group of compounds represented by formulas (2), (3) and (4) as a second component:

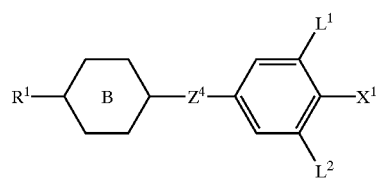

(2)

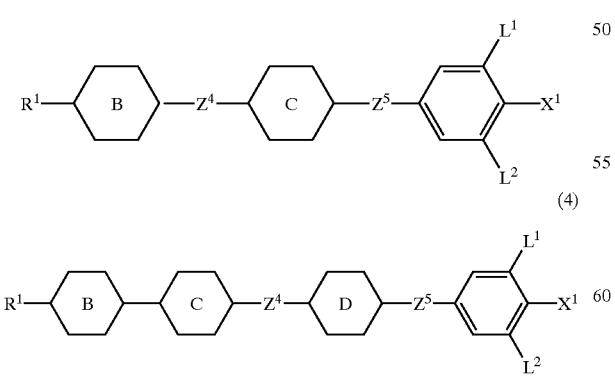

(3)

(4)

wherein R$^1$ is alkyl having 1 to 10 carbon, in which any —CH$_2$— in the alkyl may be replaced by —O— or —CH=CH—, but —O— and —O— are not adjacent, and any hydrogen in the group may be replaced by fluorine; X$^1$ is fluorine, chlorine, —OCF$_3$, —OCF$_2$H, —CF$_3$, —CF$_2$H, —CFH$_2$, —OCF$_2$CF$_2$H, or —OCF$_2$CFHCF$_3$; L$^1$ and L$^2$ each are independently hydrogen or fluorine; Z$^4$ and Z$^5$ each are independently —(CH$_2$)$_2$—, —(CH$_2$)$_4$—, —COO—, —CF$_2$O—, —OCF$_2$—, —CH=CH—, or a single bond; a ring B and a ring C each are independently 1,4-cyclohexylene, 1,3-dioxane-2,5-diyl, 1,4-phenylene, or 1,4-phenylene in which at least one hydrogen is replaced by fluorine; and a ring D is 1,4-cyclohexylene, 1,4-phenylene or 1,4-phenylene in which at least one hydrogen is replaced by fluorine.

10. A liquid crystal composition comprising at least one silicon compound described in any one of claims 1 to 7 as the first component and at least one compound selected from the group of compounds represented by formulas (5) and (6) as a second component:

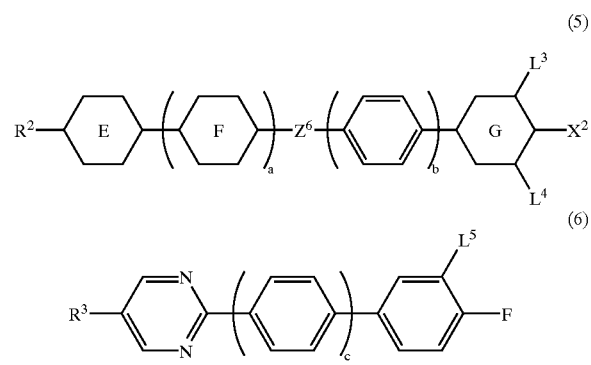

(5)

(6)

wherein R$^2$ and R$^3$ each are independently alkyl having 1 to 10 carbon, in which any —CH$_2$— in the alkyl may be replaced by —O— or —CH=CH—, but —O— and —O— are not adjacent, and any hydrogen in the alkyl may be replaced by fluorine; X$^2$ is —CN or —C≡C—CN; a ring E is 1,4-cyclohexylene, 1,4-phenylene, 1,3-dioxane-2,5-diyl, or pyrimidine-2,5-diyl; a ring F is 1,4-cyclohexylene, 1,4-phenylene, 1,4-phenylene in which hydrogen is replaced by fluorine, or pyrimidine-2,5-diyl; a ring G is 1,4-cyclohexylene or 1,4-phenylene; Z$^6$ is —(CH$_2$)$_2$—, —COO—, —CF$_2$O—, —OCF$_2$—, or a single bond; L$^3$, L$^4$ and L$^5$ each are independently hydrogen or fluorine; and a, b and c each are independently 0 or 1.

11. A liquid crystal composition comprising at least one silicon compound described in any one of claims 1 to 7 as the first component and at least one compound selected from the group of compounds represented by formulas (7), (8) and (9) as a second component:

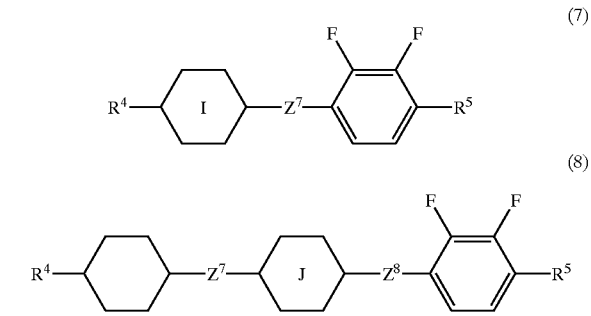

(7)

(8)

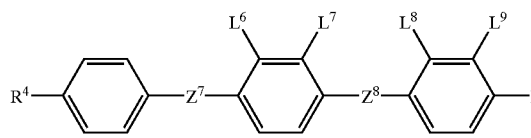

(9)

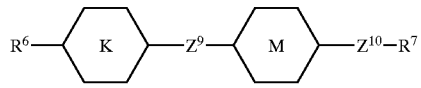

(10)

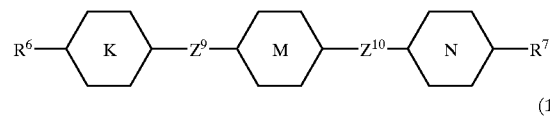

(11)

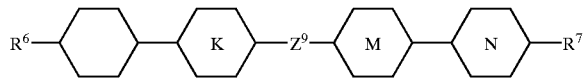

(12)

wherein $R^4$ and $R^5$ each are independently alkyl having 1 to 10 carbon, in which any —$CH_2$— in the alkyl may be replaced by —O— or —CH═CH—, but —O— and —O— are not adjacent, and any hydrogen in the alkyl may be replaced by fluorine; a ring I and a ring J each are independently 1,4-cyclohexylene or 1,4-phenylene; $L^6$, $L^7$, $L^8$, and $L^9$ each are independently hydrogen or fluorine, and all of them are not hydrogen simultaneously; and $Z^7$ and $Z^8$ each are independently —$(CH_2)_2$—, —COO— or a single bond.

12. A liquid crystal composition comprising at least one silicon compound described in any one of claims 1 to 7 as the first component, at least one compound selected from the group of the compounds represented by formulas (2), (3) and (4) as the second component, and at least one compound selected from the group of compounds represented by formulas (10), (11) and (12) as a third component:

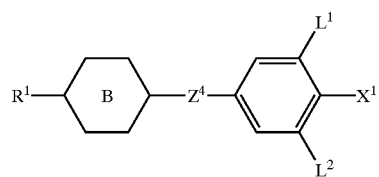

(2)

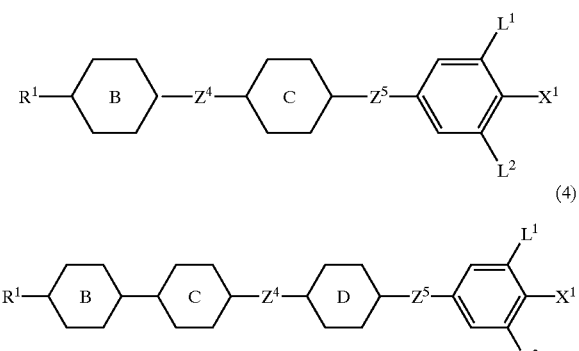

(3)

(4)

wherein $R^1$ is alkyl having 1 to 10 carbon, in which any —$CH_2$— in the alkyl may be replaced by —O— or —CH═CH—, but —O— and —O— are not adjacent, and any hydrogen in the group may be replaced by fluorine; $X^1$ is fluorine, chlorine, —$OCF_3$, —$OCF_2H$, —$CF_3$, —$CF_2H$, —$CFH_2$, —$OCF_2CF_2H$, or —$OCF_2CFHCF_3$; $L^1$ and $L^2$ each are independently hydrogen or fluorine; $Z^4$ and $Z^5$ each are independently —$(CH_2)_2$—, —$(CH_2)_4$—, —COO—, —$CF_2O$—, —$OCF_2$—, —CH═CH—, or a single bond; a ring B and a ring C each are independently 1,4-cyclohexylene, 1,3-dioxane-2,5-diyl, 1,4-phenylene, or 1,4-phenylene in which at least one hydrogen is replaced by fluorine; and a ring D is 1,4-cyclohexylene, 1,4-phenylene or 1,4-phenylene in which at least one hydrogen is replaced by fluorine, wherein $R^6$ and $R^7$ each are independently alkyl having 1 to 10 carbon, in which any —$CH_2$— in the alkyl may be replaced by —O— or —CH═CH—, but —O—and —O— are not adjacent, and any hydrogen in the alkyl may be replaced by fluorine; a ring K, a ring M and a ring N each are independently 1,4-cyclohexylene, pyrimidine-2,5-diyl, 1,4-phenylene, or 1,4-phenylene in which hydrogen is replaced by fluorine; and $Z^9$ and $Z^{10}$ each are independently —C≡C—, —COO—, —$(CH_2)_2$—, —CH═CH—, or a single bond.

13. A liquid crystal composition comprising at least one silicon compound described in any one of claims 1 to 7 as the first component, at least one compound selected from the group of the compounds represented by formulas (5) and (6) as the second component, and at least one compound selected from the group of the compounds represented by formulas (10), (11) and (12) as the third component:

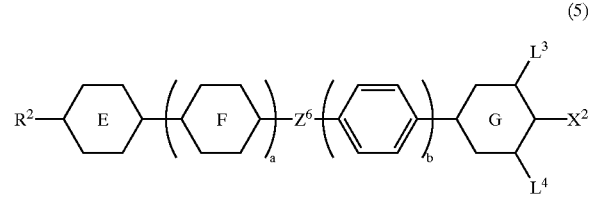

(5)

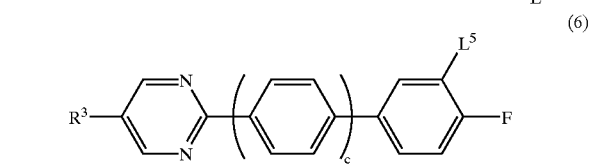

(6)

wherein $R^2$ and $R^3$ each are independently alkyl having 1 to 10 carbon, in which any —$CH_2$— in the alkyl may be replaced by —O— or —CH═CH—, but —O— and —O— are not adjacent, and any hydrogen in the alkyl may be replaced by fluorine; $X^2$ is —CN or —C≡C—CN; a ring E is 1,4-cyclohexylene, 1,4-phenylene, 1,3-dioxane-2,5-diyl, or pyrimidine-2,5-diyl; a ring F is 1,4-cyclohexylene, 1,4-phenylene, 1,4-phenylene in which hydrogen is replaced by fluorine, or pyrimidine-2,5-diyl; a ring G is 1,4-cyclohexylene or 1,4-phenylene; $Z^6$ is —$(CH_2)_2$—, —COO—, —$CF_2O$—, —$OCF_2$—, or a single bond; $L^3$, $L^4$ and $L^5$ each are independently hydrogen or fluorine; and a, b and c each are independently 0 or 1,

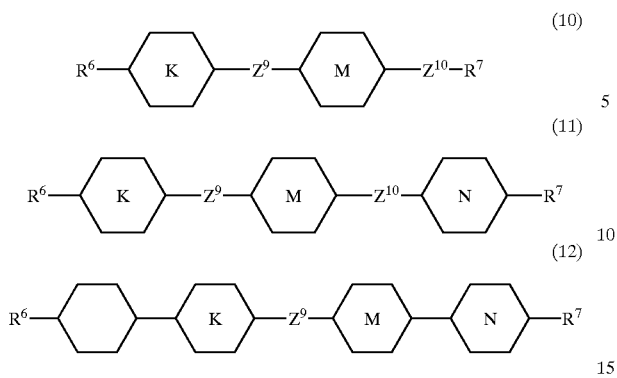

(10)

(11)

(12)

wherein R⁶ and R⁷ each are independently alkyl having 1 to 10 carbon, in which any —CH₂— in the alkyl may be replaced by —O— or —CH=CH—, but —O— and —O— are not adjacent, and any hydrogen in the alkyl may be replaced by fluorine; a ring K, a ring M and a ring N each are independently 1,4-cyclohexylene, pyrimidine-2,5-diyl, 1,4-phenylene, or 1,4-phenylene in which hydrogen is replaced by fluorine; and $Z^9$ and $Z^{10}$ each are independently —C≡C—, —COO—, —(CH₂)₂—, —CH=CH—, or a single bond.

14. A liquid crystal composition comprising at least one silicon compound described in any one of claims 1 to 7 as the first component, at least one compound selected from the group of the compounds represented by formulas (7), (8) and (9) as the second component and at least one compound selected from the group of the compounds represented by formulas (10), (11) and (12) as the third component:

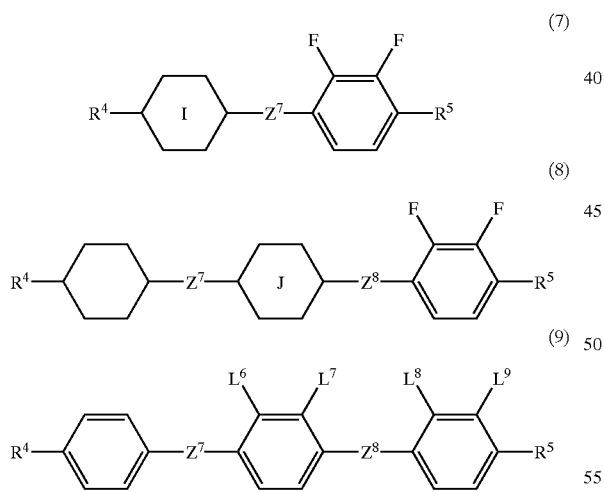

(7)

(8)

(9)

wherein R⁴ and R⁵ each are independently alkyl having 1 to 10 carbon, in which any —CH₂— in the alkyl may be replaced by —O— or —CH=CH—, but —O— and —O— are not adjacent, and any hydrogen in the alkyl may be replaced by fluorine; a ring I and a ring J each are independently 1,4-cyclohexylene or 1,4-phenylene; L⁶, L⁷, L⁸, and L⁹ each are independently hydrogen or fluorine, and all of them are not hydrogen simultaneously; and $Z^7$ and $Z^8$ each are independently —(CH₂)₂—, —COO— or a single bond,

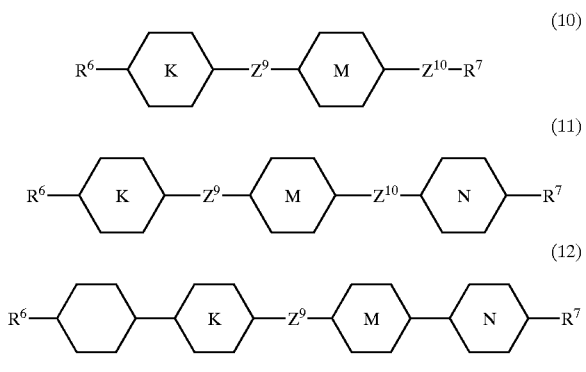

(10)

(11)

(12)

wherein R⁶ and R⁷ each are independently alkyl having 1 to 10 carbon, in which any —CH₂— in the alkyl may be replaced by —O— or —CH=CH—, but —O— and —O— are not adjacent, and any hydrogen in the alkyl may be replaced by fluorine; a ring K, a ring M and a ring N each are independently 1,4-cyclohexylene, pyrimidine-2,5-diyl, 1,4-phenylene, or 1,4-phenylene in which hydrogen is replaced by fluorine; and $Z^9$ and $Z^{10}$ each are independently —C≡C—, —COO—, —(CH₂)₂—, —CH=CH—, or a single bond.

15. A liquid crystal composition comprising at least one silicon compound described in any one of claims 1 to 7 as the first component, at least one compound selected from the group of the compounds represented by formulas (2), (3) and (4) as the second component, at least one compound selected from the group of the compounds represented by formulas (5) and (6) as the third component, and at least one compound selected from the group of the compounds represented by formulas (10), (11) and (12) as a fourth component:

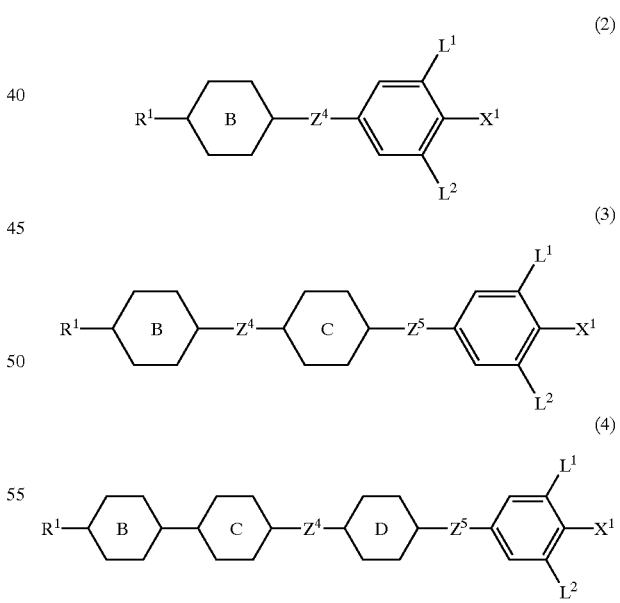

(2)

(3)

(4)

wherein R¹ is alkyl having 1 to 10 carbon, in which any —CH₂— in the alkyl may be replaced by —O— or —CH=CH—, but —O— and —O— are not adjacent, and any hydrogen in the group may be replaced by fluorine; X¹ is fluorine, chlorine, —OCF₃, —OCF₂H, —CF₃, —CF₂H, —CFH₂, —OCF₂CF₂H, or —OCF₂CFHCF₃; L¹ and L² each are independently hydrogen or fluorine; $Z^4$ and $Z^5$ each are independently —(CH$_2$)$_2$—, —(CH$_2$)$_4$—, —COO—, —CF$_2$O—, —OCF$_2$—, —CH=CH—, or a single bond; a ring B and a ring C each are independently 1,4-cyclohexylene, 1,3-dioxane-2,5-diyl, 1,4-phenylene, or 1,4-phenylene in which at least one hydrogen is replaced by fluorine; and a ring D is 1,4-cyclohexylene, 1,4-phenylene or 1,4-phenylene in which at least one hydrogen is replaced by fluorine, (5)

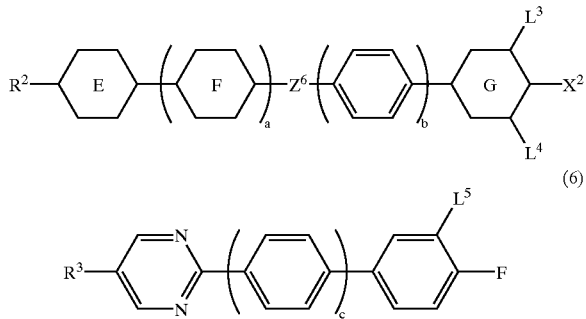

(6)

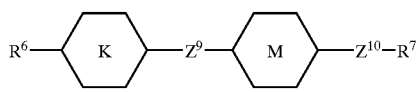

wherein R$^2$ and R$^3$ each are independently alkyl having 1 to 10 carbon, in which any —CH$_2$— in the alkyl may be replaced by —O— or —CH=CH—, but —O— and —O— are not adjacent, and any hydrogen in the alkyl may be replaced by fluorine; X$^2$ is —CN or —C≡C—CN; a ring E is 1,4-cyclohexylene, 1,4-phenylene, 1,3-dioxane-2,5-diyl, or pyrimidine-2,5-diyl; a ring F is 1,4-cyclohexylene, 1,4-phenylene, 1,4-phenylene in which hydrogen is replaced by fluorine, or pyrimidine-2,5-diyl; a ring G is 1,4-cyclohexylene or 1,4-phenylene; Z$^6$ is —(CH$_2$)$_2$—, —COO—, —CF$_2$O—, —OCF$_2$—, or a single bond; L$^3$, L$^4$ and L$^5$ each are independently hydrogen or fluorine; and a, b and c each are independently 0 or 1, (10)

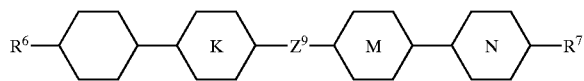

(11)

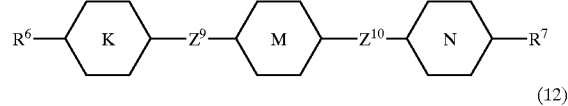

(12)

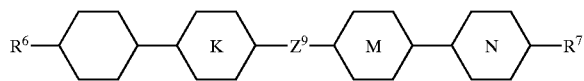

wherein R$^6$ and R$^7$ each are independently alkyl having 1 to 10 carbon, in which any —CH$_2$— in the alkyl may be replaced by —O— or —CH=CH—, but —O— and —O— are not adjacent, and any hydrogen in the alkyl may be replaced by fluorine; a ring K, a ring M and a ring N each are independently 1,4-cyclohexylene, pyrimidine-2,5-diyl, 1,4-phenylene, or 1,4-phenylene in which hydrogen is replaced by fluorine; and Z$^9$ and Z$^{10}$ each are independently —C≡C—, —COO—, —(CH$_2$)—, —CH=CH—, or a single bond.

16. A liquid crystal composition comprising the liquid crystal composition defined in claim 8 and further comprising at least one optically active compound.

17. A liquid crystal display comprising the liquid crystal composition defined in claim 8.

18. A liquid crystal display comprising the liquid crystal composition defined in claim 9.

19. A liquid crystal display comprising the liquid crystal composition defined in claim 10.

20. A liquid crystal display comprising the liquid crystal composition defined in claim 11.

21. A liquid crystal display comprising the liquid crystal composition defined in claim 12.

22. A liquid crystal display comprising the liquid crystal composition defined in claim 13.

23. A liquid crystal display comprising the liquid crystal composition defined in claim 14.

24. A liquid crystal display comprising the liquid crystal composition defined in claim 15.

* * * * *